US012667844B2

(12) United States Patent　　　　(10) Patent No.: US 12,667,844 B2
　Klein et al.　　　　　　　　　　　 (45) Date of Patent:　Jun. 30, 2026

(54) SYSTEMS AND METHODS FOR SENSING ANALYTES IN GMR-BASED DETECTION OF BIOMARKERS

(71) Applicant: Zepto Life Technology, Inc., St. Paul, MN (US)

(72) Inventors: Todd Michael Klein, Wayzata, MN (US); Wei Wang, St. Paul, MN (US); Yi-Hsuan Su, Maplewood, MN (US); Gemma Mendonsa, Edina, MN (US); Ian Stuyvenberg, Minneapolis, MN (US)

(73) Assignee: Zepto Life Technology, Inc., St. Paul, MN (US)

( * ) Notice: Subject to any disclaimer, the term of this patent is extended or adjusted under 35 U.S.C. 154(b) by 989 days.

(21) Appl. No.: 17/793,136

(22) PCT Filed: Jan. 17, 2020

(86) PCT No.: PCT/US2020/014068

§ 371 (c)(1),
　(2) Date: Jul. 15, 2022

(87) PCT Pub. No.: WO2021/145889

PCT Pub. Date: Jul. 22, 2021

(65) Prior Publication Data

US 2023/0085052 A1　　Mar. 16, 2023

(51) Int. Cl.
　*B01L 3/00*　　　　　(2006.01)
　*G01N 27/72*　　　　(2006.01)
　　　　(Continued)

(52) U.S. Cl.
　CPC ........ *B01L 3/502738* (2013.01); *G01N 27/72* (2013.01); *G01N 33/18* (2013.01);
　　　　(Continued)

(58) Field of Classification Search
　CPC ......... B01L 3/502738; B01L 2200/027; B01L 2300/024; B01L 2300/025;
　　　　(Continued)

(56) References Cited

U.S. PATENT DOCUMENTS 5,371,469 A　12/1994　Anderson
5,646,001 A　　7/1997　Terstappen et al.
　　　　(Continued)

FOREIGN PATENT DOCUMENTS

CN　　101632018 A　　1/2010
CN　　101855366 A　　10/2010
　　　　(Continued)

OTHER PUBLICATIONS

Doyle et al., "Catalytic Carbene Insertion into C—H Bonds", Chemical Reviews, 2010, pp. 704-724, vol. 110, No. 2, American Chemical Society.
　　　　(Continued)

*Primary Examiner* — Lee E Rodak
*Assistant Examiner* — Zannatul Ferdous
(74) *Attorney, Agent, or Firm* — Schwegman Lundberg & Woessner, P.A.

(57)　　　　ABSTRACT

Methods of, inter alia, detecting the presence of one or more analytes in one or more query samples include providing one or more sensor that each include biomolecules disposed on a functionalized surface of one or more giant magnetoresistance (GMR) sensors. Modes of operation remove or add magnetic beads from the vicinity of sensor surfaces by interactions with the biomolecules. The methods feature, inter alia, detecting the presence of one or more analytes in one or more query samples by measuring magnetoresistance change of the one or more GMR sensors based on deter- (Continued)

<u>100</u> mining magnetoresistance before and after passing magnetic particles over the one or more sensors.

20 Claims, 53 Drawing Sheets

Specification includes a Sequence Listing.

(51) Int. Cl.

| | |
|---|---|
| *G01N 33/18* | (2006.01) |
| *G01N 33/543* | (2006.01) |
| *G01N 33/84* | (2006.01) |

(52) U.S. Cl.
CPC ....... *G01N 33/54326* (2013.01); *G01N 33/84* (2013.01); *B01L 2200/027* (2013.01); *B01L 2300/024* (2013.01); *B01L 2300/025* (2013.01); *B01L 2300/0663* (2013.01); *B01L 2400/0487* (2013.01); *G01N 2333/91177* (2013.01)

(58) Field of Classification Search
CPC ..... B01L 2300/0663; B01L 2400/0487; G01N 27/72; G01N 33/18; G01N 33/54326; G01N 33/84; G01N 2333/91177; G01N 27/745; G01N 33/6854; B82Y 5/00; B82Y 25/00; H01F 1/0054; C12N 2310/127; G01R 33/0094; G01R 33/1269; G01R 33/091

See application file for complete search history.

(56) References Cited

U.S. PATENT DOCUMENTS

| | | | |
|---|---|---|---|
| 5,981,297 A | 11/1999 | Baselt | |
| 6,426,043 B1 | 7/2002 | Cohen et al. | |
| 6,437,563 B1 | 8/2002 | Simmonds et al. | |
| 8,889,760 B2 | 11/2014 | Kurdyumov et al. | |
| 8,937,174 B2 * | 1/2015 | Rothmann ............. | C12M 47/06 |
| | | | 536/25.4 |
| 9,487,663 B2 | 11/2016 | Kurdyumov et al. | |
| 9,994,721 B2 | 6/2018 | Kurdyumov et al. | |
| 10,072,258 B2 * | 9/2018 | Faltin ...................... | C12N 1/08 |
| 10,253,193 B2 | 4/2019 | Kurdyumov et al. | |
| 10,315,987 B2 | 6/2019 | Kurdyumov | |
| 10,688,493 B2 | 6/2020 | Kim et al. | |
| 2002/0119470 A1 | 8/2002 | Nerenberg et al. | |
| 2003/0044323 A1 | 3/2003 | Diamond et al. | |
| 2003/0153092 A1 | 8/2003 | Skinner | |
| 2005/0085619 A1 | 4/2005 | Wilson | |
| 2006/0115514 A1 | 6/2006 | Gengrinovitch | |
| 2008/0129286 A1 | 6/2008 | Kahlman et al. | |
| 2008/0190735 A1 | 8/2008 | Luoma | |
| 2008/0246471 A1 | 10/2008 | Kahlman et al. | |
| 2008/0278156 A1 | 11/2008 | De Boer | |
| 2008/0284419 A1 | 11/2008 | Ikeda | |
| 2008/0309329 A1 | 12/2008 | Kahlman et al. | |
| 2009/0066318 A1 | 3/2009 | Kahlman et al. | |
| 2009/0163785 A1 | 6/2009 | Nelson | |
| 2009/0184706 A1 | 7/2009 | Duric et al. | |
| 2010/0259250 A1 | 10/2010 | Kahlman | |
| 2010/0267169 A1 | 10/2010 | Hajimiri et al. | |
| 2010/0323355 A1 | 12/2010 | Dittmer | |
| 2010/0324828 A1 | 12/2010 | Kahlman et al. | |
| 2011/0117676 A1 | 5/2011 | Ikeda et al. | |
| 2011/0241664 A1 | 10/2011 | Zhang | |
| 2012/0115214 A1 | 5/2012 | Battrell et al. | |
| 2012/0231971 A1 | 9/2012 | Choi et al. | |
| 2012/0315621 A1 | 12/2012 | Lu et al. | |
| 2013/0102489 A1 | 4/2013 | Osterfeld et al. | |
| 2013/0130262 A1 | 5/2013 | Battrell et al. | |
| 2013/0331298 A1 | 12/2013 | Rea | |
| 2013/0343966 A1 | 12/2013 | Medoro et al. | |

| | | | |
|---|---|---|---|
| 2014/0120523 A1 | 5/2014 | Lowery, Jr. et al. | |
| 2014/0178900 A1 | 6/2014 | Jung et al. | |
| 2014/0248612 A1 | 9/2014 | Princen et al. | |
| 2014/0292318 A1 | 10/2014 | Wang et al. | |
| 2015/0197784 A1 | 7/2015 | Williams et al. | |
| 2015/0198594 A1 | 7/2015 | Williams et al. | |
| 2015/0338427 A1 | 11/2015 | Pollack et al. | |
| 2016/0011182 A1 | 1/2016 | Qiu | |
| 2016/0025756 A1 | 1/2016 | Pollack et al. | |
| 2016/0090633 A1 | 3/2016 | Platero et al. | |
| 2016/0187240 A1 * | 6/2016 | Ismagilov ........... | G05D 7/0694 |
| | | | 436/180 |
| 2016/0193603 A1 | 7/2016 | Battrell et al. | |
| 2016/0194691 A1 | 7/2016 | Powell et al. | |
| 2016/0209405 A1 * | 7/2016 | Wang .................... | G01N 33/84 |
| 2017/0097337 A1 | 4/2017 | Shultz et al. | |
| 2017/0113221 A1 | 4/2017 | Hoffman et al. | |
| 2017/0241971 A1 | 8/2017 | Liu et al. | |
| 2017/0260567 A1 | 9/2017 | Selden et al. | |
| 2017/0312751 A1 | 11/2017 | Glezer et al. | |
| 2017/0356056 A1 | 12/2017 | Powell et al. | |
| 2018/0021783 A1 | 1/2018 | Arlett et al. | |
| 2018/0067094 A1 | 3/2018 | Sinha et al. | |
| 2018/0099278 A1 | 4/2018 | Niemeyer et al. | |
| 2018/0299407 A1 | 10/2018 | Haratani et al. | |
| 2018/0314046 A1 | 11/2018 | Sakurai et al. | |
| 2019/0283025 A1 | 9/2019 | Brenk et al. | |

FOREIGN PATENT DOCUMENTS

| | | |
|---|---|---|
| CN | 103597344 | 2/2014 |
| CN | 103698320 A | 4/2014 |
| CN | 104530413 A | 4/2015 |
| CN | 107513577 A | 12/2017 |
| CN | 107690581 A | 2/2018 |
| CN | 108474779 | 8/2018 |
| CN | 109563199 A | 4/2019 |
| CN | 115335701 | 11/2022 |
| CN | 115427826 | 12/2022 |
| EP | 1936350 A1 | 6/2008 |
| EP | 3324189 A1 | 5/2018 |
| EP | 4090987 | 11/2022 |
| JP | 2005180921 A | 7/2005 |
| JP | 2008511842 A | 4/2008 |
| JP | 2008522151 A | 6/2008 |
| JP | 2008544246 A | 12/2008 |
| JP | 2009008475 A | 1/2009 |
| JP | 2009511860 A | 3/2009 |
| JP | 2009511895 A | 3/2009 |
| JP | 2009530602 A | 8/2009 |
| JP | 2009236933 A | 10/2009 |
| JP | 2009249512 A | 10/2009 |
| JP | 2009250926 A | 10/2009 |
| JP | 2009539098 A | 11/2009 |
| JP | 2010500547 A | 1/2010 |
| JP | 2011503585 A | 1/2011 |
| JP | 2011221017 A | 11/2011 |
| JP | 2012516455 A | 7/2012 |
| JP | 2013518289 A | 5/2013 |
| JP | 2016509206 A | 3/2016 |
| JP | 2016534333 A | 11/2016 |
| JP | 2017082227 A | 5/2017 |
| JP | 2017520239 A | 7/2017 |
| JP | 2018507403 A | 3/2018 |
| JP | 2018525980 A | 9/2018 |
| KR | 101304323 B1 | 9/2013 |
| KR | 20160080112 A | 7/2016 |
| WO | 03054523 A2 | 7/2003 |
| WO | 2005016115 A2 | 2/2005 |
| WO | 2006059270 A2 | 6/2006 |
| WO | 2007042959 A2 | 4/2007 |
| WO | 2007092909 A2 | 8/2007 |
| WO | 2008047533 A1 | 4/2008 |
| WO | 2008101196 A1 | 8/2008 |
| WO | 2009024922 A2 | 2/2009 |
| WO | 2009039437 A1 | 3/2009 |
| WO | 2012085884 A1 | 6/2012 |
| WO | 2016035197 A1 | 3/2016 |
| WO | 2016124907 A1 | 8/2016 |

(56) References Cited

FOREIGN PATENT DOCUMENTS

| WO | 2017030999 A1 | 2/2017 |
| WO | 2017082227 A1 | 5/2017 |
| WO | 2018053501 A1 | 3/2018 |
| WO | 2018057647 A1 | 3/2018 |
| WO | 2017170238 A1 | 2/2019 |
| WO | 2021145889 | 7/2021 |

OTHER PUBLICATIONS

Bayley, "Photogenerated reactive intermediates and their properties", Laboratory Techniques in Biochemistry and Molecular Biology, 1983, Chapter 2, pp. 8-24, vol. 12, Elsevier.

Extended European Search Report issued Aug. 30, 2023 in EP Application No. 20864198.5.

Supplementary Partial European Search Report issued Sep. 14, 2023 in EP Application No. 20913973.2.

Hulme et al., "Incorporation of prefabricated screw, pneumatic, and solenoid valves into microfluidic devices", The Royal Society of Chemistry, Lab Chip, 2009, pp. 79-86, vol. 9, Department of Chemistry and Chemical Biology, Harvard University, Cambridge, MA, USA.

Osterberg et al., "Bead Capture on Magnetic Sensors in a Microfluidic System", IEEE Sensors Journal, Jun. 2009, pp. 682-688, vol. 9, No. 6, Denmark.

Rizzi et al.,"Denaturation strategies for detection of double stranded PCR products on GMR magnetic biosensor array", Biosensors and Bioelectronics, 2017, pp. 155-160, Issue 93, Elsevier B.V., Denmark.

Son et al., "Preparation and properties of PEG-modified PHEMA hydro gel and the morphological effect", Macromolecular Research, 2006, pp. 394-399, vol. 14, No. 3, Department of Chemical Engineering, Polymer Technology Institute, Sungkyunkwan University, Suwon, Gyeonggi, Korea.

Sun et al., "Separable detecting of *Escherichia coli* O157H:H7by a giant magneto-resistance-based bio-sensing system", Sensors and Actuators B; Chemical, 2016, pp. 485-492, Elsevier B.V., Shanghai, China.

Teramura et al., "Surface plasmon resonance-based highly sensitive immunosensing for brain natriuretic peptide using nanobeads for signal amplification" Analytical Biochemistry, 2006, pp. 208-215, No. 357, Elsevier Inc., Japan.

Bajpai, "Blood protein adsorption onto macroporous semi-interpenetrating polymer networks (IPNs) of poly(ethylene glycol) (PEG) and poly(2-hydroxyethyl methacrylate) (PH EMA) and assessment of in vitro blood compatibility", Polymer International, Oct. 31, 2006, pp. 1-2, vol. 56, Iss. 2, Abstract.

Capanema et al., "Superabsorbent crosslinked carboxymethyl cellulose-PEG hydrogels for potential wound dressing applications" International Journal of Biological Macromolecules, Aug. 26, 2017, pp. 1218-1234, vol. 106, Elsevier Science B.V.

Chu et al., "Bioconjugated Magnetic Nanoparticles for the Detection of Bacteria", Journal of Biomedical Nanotechnology, Dec. 2013, pp. 1951-1961, vol. 9, No. 12, American Scientific Publishers.

Edelstein et al., "The BARC biosensor applied to the detection of biological warfare agents," Biosensors and Bioelectronics, 2000, pp. 805-813, vol. 14, Elsevier Science B.V.

Extended European Search Report dated Mar. 14, 2018 in European Application 15818539.7.

Extended European Search Report issued Apr. 21, 2021 in European Application 19816193.7.

Extended European Search Report issued Mar. 15, 2021 in European Application 19816192.9.

Gaster et al., "Matrix-insensitive protein assays push the limits of biosensors in medicine", Nature Medicine, Technical Reports, Oct. 11, 2009, pp. 1-7.

Graham et al., "Magnetic field-assisted DNA hybridisation and simultaneous detection using micron-sized spin-valve sensors and magnetic nanoparticles", Sensors and Actuators B: Chemical, Feb. 2005, pp. 936-944, vol. 107, Elsevier Science B.V.

Graham et al., "Magnetoresistive-based biosensors and biochips", Trends in Biotechnology, Sep. 2004, pp. 455-462, vol. 22, No. 9, Elsevier Ltd.

Han et al., "A Novel Zero-Drift Detection Method for Highly Sensitive GMR Biochips", IEEE Transactions on Magnetics, IEEE, USA, vol. 42, No. 10, Oct. 1, 2006, pp. 3560-3562.

Han et al., "CMOS Integrated DNA Microarray Based on GMR Sensors", Electron Devices Meeting, 2006. IEDM '06. International, IEEE, PI, Dec. 2006, pp. 1-4.

Han et al., "Magnetic Nanotechnology for Biodetection", Journal of the Association for Laboratory Automation, Apr. 2010, pp. 93-98, vol. 15, No. 2, Elsevier.

Huo et al., "A Novel High-Sensitivity Cardiac Multibiomarker Detection System Based on Microfluidic Chip and GMR Sensors", IEEE Transactions on Magnetics, vol. 51, No. 11, Nov. 2015, pp. 1-4.

International Search Report and Written Opinion mailed Jun. 16, 2020 in International Application PCT/US2020/014068.

International Search Report and Written Opinion mailed May 27, 2021 in International Patent Application PCT/US2021/012131.

International Search Report and Written Opinion mailed Nov. 13, 2019 in International Application PCT/US2019/043791.

International Preliminary Report on Patentability issued on Jan. 19, 2017 in International Application PCT/US2015/039747.

International Preliminary Report on Patentability issued Sep. 22, 2020 in International Application PCT/US2019/021837.

International Preliminary Report on Patentability mailed Feb. 11, 2021 in International Application PCT/US2019/043720.

International Preliminary Report on Patentability mailed Feb. 11, 2021 in International Application PCT/US2019/043753.

International preliminary Report on Patentability mailed Feb. 11, 2021 in International Application PCT/US2019/043766.

International Preliminary Report on Patentability mailed Feb. 11, 2021 in International Application PCT/US2019/043791.

International Search Report and Written Opinion mailed May 8, 2019 in International Application PCT/US2019/021837.

International Search Report and Written Opinion mailed Nov. 13, 2019 in International Application PCT/US2019/043720.

International Search Report and Written Opinion mailed Nov. 13, 2019 in International Application PCT/US2019/043753.

International Search Report and Written Opinion mailed Nov. 15, 2019 in International Application PCT/US2019/043766.

International Search Report and Written Opinion mailed on Dec. 11, 2015 in International Application PCT/US2015/039747.

International Search Report and Written Opinion mailed on Jul. 6, 2020 in International Application PCT/US2020/014570.

Klein et al., "Development of a multiplexed giant magnetoresistive biosensor array prototype to quantify ovarian cancer biomarkers", Biosensors and Bioelectronics, Oct. 23, 2018, pp. 301-307, vol. 126, Elsevier B.V.

Koets et al., "Rapid DNA multi-analyte immunoassay on a magneto-resistance biosensor," Biosensors and Bioelectronics, Oct. 8, 2008, pp. 1893-1898, vol. 24, Elsevier B.V.

Litwin et al., "Single molecule FRET methods to study Glutamate receptors", Methods Mol Biol., Author manuscript; Jan. 1, 2020, pp. 1-17.

Liu et al., "Functional Nucleic Acid Sensors," Chem. Rev., Author Manuscript, May 2009, 109(5), pp. 1948-1998.

Lu et al., "New highly sensitive and selective catalytic DNA biosensors for metal ions", Biosensors and Bioelectronics; 2003; pp. 529-540; vol. 18; Elsevier Science B.V.

Martins et al., "Femtomolar limit of detection with a magnetoresistive biochip," Biosensors and Bioelectronics, Feb. 6, 2008, pp. 2690-2695, vol. 24, Elsevier B.V.

Mcghee et al., "DNAzyme sensors for detection of metal ions in the environment and imaging them in living cells", ScienceDirect, Current Opinion in Biotechnology, Apr. 28, 2017, pp. 191-201, vol. 45, Elsevier Ltd.

Quinn et al., "Photo-crosslinked copolymers of 2-hydroxyethyl methacrylate, poly(ethylene glycol) tetra-acrylate and ethylene dimethacrylate for improving biocompatibility of biosensors", Biomaterials, 1995, pp. 1-6, vol. 16, Issue 5, Abstract.

(56) References Cited

OTHER PUBLICATIONS

Supplementary European Search Report issued Jan. 5, 2022 in EP Application No. 19816194.5.

Teh et al., "Highly sensitive and selective detection of Pb 2+ ions using a novel and simple DNAzyme-based quartz crystal microbalance with dissipation biosensor", Analyst, Jul. 18, 2014, pp. 5170-5175, vol. 139, The Royal Society of Chemistry.

Tian et al., "Rapid Newcastle Disease Virus Detection Based on Loop-Mediated Isothermal Amplification and Optomagnetic Read-out", ACS Sensors, 2016, pp. 1228-1234, vol. 1, ACS Publications.

Wang et al., "Surface Modification for Protein and DNA Immobilization onto GMR Biosensor", IEEE Transactions on Magnetics, Jan. 2013, pp. 296-299, vol. 49, No. 1, IEEE.

Wernette et al., "Incorporation of a DNAzyme into AU-coated nanocapillary array membranes with an internal standard for Pb(II) sensing", The Analyst, , Nov. 24, 2005, pp. 41-47, Issue 131, The Royal Society of Chemistry.

Wu et al., "Comparison of Hydroxylated Print Additives on Antibody Microarray Performance", Journal of Proteome Research, Oct. 19, 2006, pp. 2956-2965, vol. 5, American Chemical Society.

Xu et al., "Giant magnetoresistive biochip for DNA detection and HPV genotyping", Biosensors and Bioelectronics; Apr. 8, 2008; pp. 99-103; vol. 24, Elsevier Science B.V.

Zhu et al., "Functional Nucleic Acid-Based Sensors for Heavy Metal ion Assays," The Analyst, 2014, pp. 6326-6342, vol. 139, No. 4, The Royal Society of Chemistry.

Baselt et al., "A biosensor based on magnetoresistance technology", Biosensors and Bioelectronics, 1998, pp. 731-739, vol. 13, Issues 7-8, Elsevier Science LTD.

Supplementary European Search Report issued Feb. 7, 2022 in EP Application No. 19840618.3.

Extended European Search Report dated Dec. 5, 2022 in European Application No. 22182712.4.

Yu et al., "Giant Magnetoresistive Biosensors for Molecular Diagnosis: Surface Chemistry and Assay Development", SPIE, vol. 7035, Aug. 2008, pp. 1-9.

Cha et al., "Immobilization of oriented protein molecules on poly-(ethylene glycol)-coated Si(111)", Proteomics, 2004, pp. 1965-1976, vol. 4, WILEY-VCH Verlag Gmbh & Co., Minneapolis, MN.

Zellander et al., "Characterization of Pore Structure in Biologically Functional Poly(2-Hydroxyethyl Methacrylate)—Poly(Ethylene Glycol) Diacrylate (Phema-Pegda)", PLoS One, May 9, 2014, pp. 1-8, vol. 9, Issue 5, Chicago, Illinois.

"European Application Serial No. 20913973.2, Extended European Search Report mailed Dec. 15, 2023", 13 pgs.

"International Application Serial No. PCT US2020 014068, International Preliminary Report on Patentability mailed Jul. 28, 2022", 16 pgs.

"European Application Serial No. 20913973.2, Response Filed Jul. 2, 2024 to Extended European Search Report mailed Dec. 15, 2023", 17 pgs.

"European Application Serial No. 20913973.2, Response to Communication pursuant to Rules 161(2) and 162 EPC filed Mar. 1, 2023", 49 pgs.

"Chinese Application Serial No. 202080098583.X, Notification to Make Rectification mailed Oct. 13, 2022", W English Translation, 2 pgs.

"Chinese Application Serial No. 202080098583.X, Office Action mailed Apr. 30, 2025", w Machine English Translation, 34 pgs.

"European Application Serial No. 20913973.2, Communication Pursuant to Article 94(3) EPC mailed May 26, 2025", 5 pgs.

Klein, T., "Development of a multiplexed giant magnetoresistive biosensor array prototype to quantify ovarian cancer biomarkers", Biosensors and Bioelectronics, vol. 126, Elsevier B.V, (Oct. 23, 2018), 14 pgs.

* cited by examiner

200

1301a

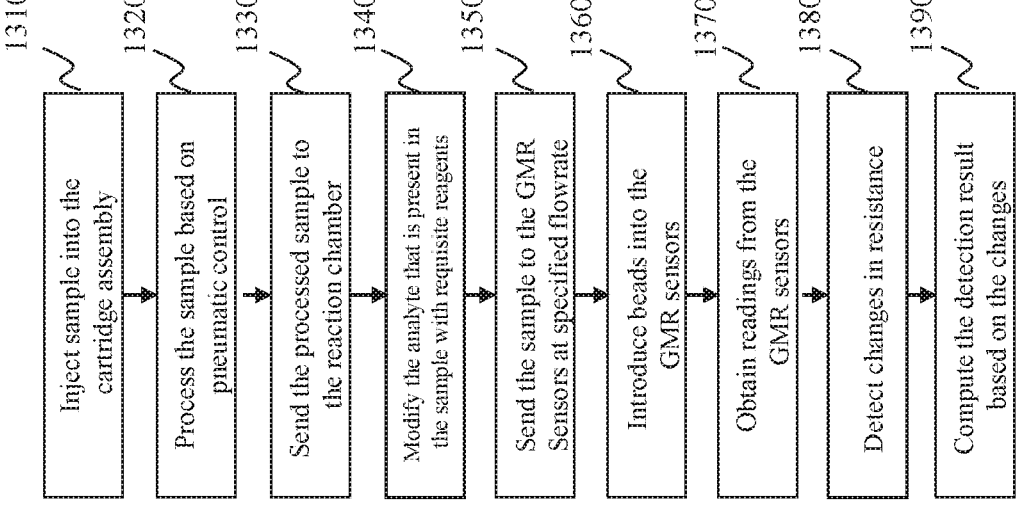

1310 Inject sample into the cartridge assembly

1320 Process the sample based on pneumatic control

1330 Send the processed sample to the reaction chamber

1340 Modify the analyte that is present in the sample with requisite reagents

1350 Send the sample to the GMR Sensors at specified flowrate

1360 Introduce beads into the GMR sensors

1370 Obtain readings from the GMR sensors

1380 Detect changes in resistance

1390 Compute the detection result based on the changes

Fig. 13B

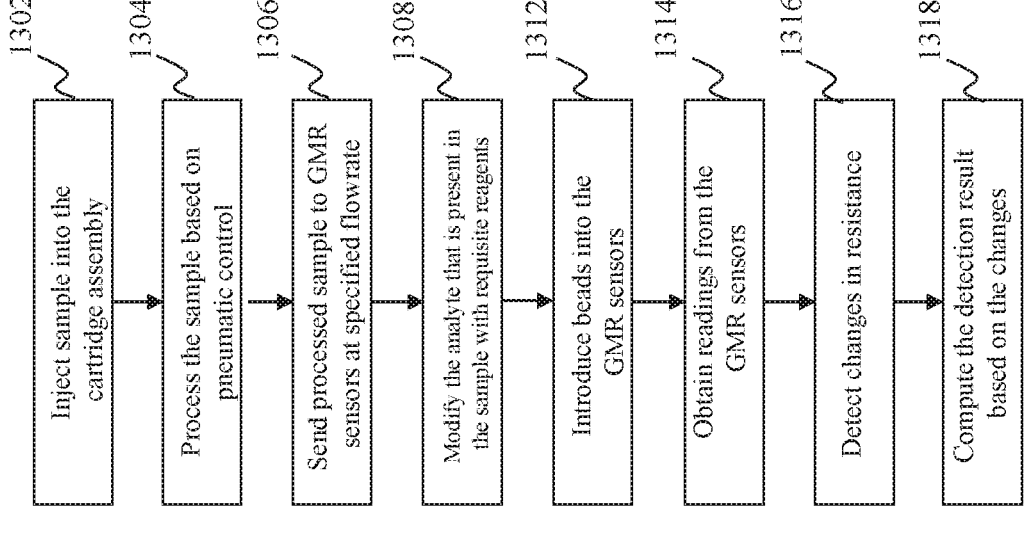

1302 — Inject sample into the cartridge assembly

1304 — Process the sample based on pneumatic control

1306 — Send processed sample to GMR sensors at specified flowrate

1308 — Modify the analyte that is present in the sample with requisite reagents

1312 — Introduce beads into the GMR sensors

1314 — Obtain readings from the GMR sensors

1316 — Detect changes in resistance

1318 — Compute the detection result based on the changes

1420 — Inject sample into the cartridge assembly

1430 — Process the sample based on pneumatic control

1440 — Send processed sample to GMR sensors at specified flowrate

1450 — Introduce beads in to the GMR sensing unit, beads bind where analyte altered receptor 1460 — Obtain readings from the GMR sensors 1470 — Detect changes in resistance 1480 — Compute the detection result based on the changes

1510

1520

1530

1540

1550

1560

1570

Inject sample into the cartridge assembly

Process the sample based on pneumatic control

Send processed sample to GMR sensors at specified flowrate

Introduce beads in to the GMR sensors, beads bind where analyte did not alter receptor Obtain readings from the GMR sensors Detect changes in resistance Compute the detection result based on the changes

1501

1610 — Inject sample into the cartridge assembly

1620 — Process the sample based on pneumatic control

1630 — Send processed sample to GMR sensors at specified flowrate

1640 — Introduce biotinylated Ab to the GMR sensors

1650 — Introduce beads in to the GMR sensors

1660 — Obtain readings from the GMR sensors

1670 — Detect changes in resistance

1680 — Compute the detection result based on the changes

1601

500nM PolyT Substrate ——— 250nM PolyT Substrate ——— 250nM DNA + Substrate

Δ MR 3000
2500
2000
1500
1000
500
0

0nM Pb  10nM Pb  25nM Pb  100nM Pb  250nM Pb  500nM Pb

SEQUENCE LISTING

<160> NUMBER OF SEQ ID NOS: 24

<210> SEQ ID NO 1
<211> LENGTH: 117
<212> TYPE: PRT

```
<213> ORGANISM: Unknown
<220> FEATURE:
<223> OTHER INFORMATION: Description of Unknown:
      arsR sequence

<400> SEQUENCE: 1

Met Ser Phe Leu Leu Pro Ile Gln Leu Phe Lys Ile Leu Ala Asp Glu
1               5                   10                  15

Thr Arg Leu Gly Ile Val Leu Leu Leu Ser Glu Leu Gly Glu Leu Cys
            20                  25                  30

Val Cys Asp Leu Cys Thr Ala Leu Asp Gln Ser Gln Pro Lys Ile Ser
            35                  40                  45

Arg His Leu Ala Leu Leu Arg Glu Ser Gly Leu Leu Leu Asp Arg Lys
        50                  55                  60

Gln Gly Lys Trp Val His Tyr Arg Leu Ser Pro His Ile Pro Ala Trp
65                  70                  75                  80

Ala Ala Lys Ile Ile Asp Glu Ala Trp Arg Cys Glu Gln Glu Lys Val
                85                  90                  95

Gln Ala Ile Val Arg Asn Leu Ala Arg Gln Asn Cys Ser Gly Asp Ser
                100                 105                 110

Lys Asn Ile Cys Ser
        115

<210> SEQ ID NO 2
<211> LENGTH: 122
<212> TYPE: PRT
<213> ORGANISM: Unknown
<220> FEATURE:
<223> OTHER INFORMATION: Description of Unknown:
      cadC sequence

<400> SEQUENCE: 2

Met Lys Lys Lys Asp Thr Cys Glu Ile Phe Cys Tyr Asp Glu Glu Lys
1               5                   10                  15

Val Asn Arg Ile Gln Gly Asp Leu Gln Thr Val Asp Ile Ser Gly Val
            20                  25                  30

Ser Gln Ile Leu Lys Ala Ile Ala Asp Glu Asn Arg Ala Lys Ile Thr
            35                  40                  45

Tyr Ala Leu Cys Gln Asp Glu Glu Leu Cys Val Cys Asp Ile Ala Asn
        50                  55                  60

Ile Leu Gly Val Thr Ile Ala Asn Ala Ser His His Leu Arg Thr Leu
65                  70                  75                  80

Tyr Lys Gln Gly Val Val Asn Phe Arg Lys Glu Gly Lys Leu Ala Leu
                85                  90                  95

Tyr Ser Leu Gly Asp Glu His Ile Arg Gln Ile Met Met Ile Ala Leu
                100                 105                 110

Ala His Lys Lys Glu Val Lys Val Asn Val
        115                 120

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cattcgttaa gtcatatatg tttttgac                                        28
```

-continued

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cttacacatt cgttaagtca tatatgtttt tgac                                34

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tctgcactta cacattcgtt aagtcatata tgtttttgac                          40

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cattcgttaa gtcatatatg tttttgactt                                    30

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cattcgttaa gtcatatatg tttttgactt atccgcttcg aaga                    44

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cttacacatt cgttaagtca tatatgtttt tgacttatcc gcttcgaaga              50

<210> SEQ ID NO 9
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tctgcactta cacattcgtt aagtcatata tgtttttgac ttatccgctt cgaaga        56

-continued

```
<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ataatacact caaataaata tttgaatgaa gatg                                 34

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cctacacatt cgttaagtca tatatgtttt tgacttatcc gcttcgaaga               50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcttcgaagc ggataagtca aaaacatata tgacttaacg aatgtgtaag               50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgagtcgaaa atggttataa tacactcaaa taaatatttg aatgaagatg               50

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctcactatag gaagagatga tgtctgtaaa tt                                  32

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acagacatca tctctgaagt agcgccgccg tatagtgag                           39

<210> SEQ ID NO 16
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
actcactata ggaagagatg                                                                      20

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gaagtagcgc cgccg                                                                           15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tccgagccgg tcgaa                                                                           15

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
catctcttct ccgagccggt cgaaatagtg agt                                                       33

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cttacacatt cgttaagtca tatatgtttt atgacttatc cgcttcgaag a                                   51

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgagtcgaaa atggttataa tacactcaaa taaatatttg aatgaagatg                                     50

<210> SEQ ID NO 22
<211> LENGTH: 50
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
catcttcatt caaatattta tttgagtgta ttataaccat tttcgactca                    50

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctcactatag gaagagatga tgtctg                                             26

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctcactatag gaagagatga tgtctgtttt tttttt                                  36
```

SYSTEMS AND METHODS FOR SENSING ANALYTES IN GMR-BASED DETECTION OF BIOMARKERS

The instant application contains a Sequence Listing which has been submitted electronically in ASCII format and is hereby incorporated by reference in its entirety. Said ASCII copy, created on Dec. 23, 2019, is named 026462-0509389_SL.txt and is 7,786 bytes in size.

INTRODUCTION

The present disclosure is generally related to systems and methods for sensing analytes in water and biological samples. In particular, the present disclosure relates to analyte sensing using methods of detection based on Giant Magneto-Resistive (GMR) sensors.

GMR sensors enable development of multiplex assays and multiples detection schemes, for example for, performing multiplex assays for detecting more than one analyte in the same query sample or in difference query samples, with high sensitivity and low cost in a compact system, and therefore have the potential to provide a platform suitable for a wide variety of applications. Reliable analyte sensing remains a challenge. The present disclosure provides exemplary solutions.

Certain analytes, such as metals, are present throughout the environment; therefore, all living things, including mammals, such as humans, risk unhealthy exposure to such analytes. Metals contamination in, for example, water and water supplies, food and food supplies, air, buildings, living and working spaces, and the like, can have adverse effects on human health, especially in children. Provided herein are novel devices and method for efficient detection of metals, such as, for example, cadmium, arsenic, mercury, and/or lead, in environmental and subject, such as patient, samples. Devices and methods presented herein offer significant advances and improvements to current metal detection techniques. Such advances and improvements described herein can help expedite screening for metals in a sample by methods that are low cost and highly sensitive.

The present disclosure is generally related to a microfluidic device and uses thereof to detect metals in a sample. The devices and methods presented herein also utilize, in some embodiments, DNAzymes and magnetic sensors. The devices and methods presented herein also utilize, in some embodiments, DNA binding proteins and magnetic sensors. In some embodiments, the present disclosure relates to a microfluidic device comprising a Giant MagnetoResistance (GMR) sensor.

SUMMARY

In some aspects, embodiments herein relate to methods of detecting the presence of an analyte in a query sample comprising providing a sensor comprising a biomolecule disposed on a functionalized surface of a giant magnetoresistance (GMR) sensor, the biomolecule comprising a cleavable portion covalently bound to the biomolecule, cleavage being catalyzed by the presence of the analyte in the query sample and a receptor associated with the cleavable portion of the biomolecule, the receptor being capable of binding a magnetic nanoparticle, passing the query sample over the sensor, thereby allowing cleavage and removal of the cleavable portion with the associated receptor from the biomolecule if the analyte is present, passing magnetic particles over the sensor after passing the query sample over the sensor, and detecting the presence of the analyte in the query sample by measuring magnetoresistance change of the GMR sensor based on determining magnetoresistance before and after passing magnetic particles over the sensor.

In some aspects, embodiments herein relate to methods of amplifying a signal, such as a magnetoresistance change of a GMR sensor, the methods comprising detecting the presence of an analyte in a query sample comprising providing a sensor comprising a biomolecule disposed on a functionalized surface of a giant magnetoresistance (GMR) sensor, the biomolecule comprising a cleavable portion covalently bound to the biomolecule, cleavage being catalyzed by the presence of the analyte in the query sample and a receptor associated with the cleavable portion of the biomolecule, the receptor being capable of binding a magnetic nanoparticle, passing the query sample over the sensor, thereby allowing cleavage and removal of the cleavable portion with the associated receptor from the biomolecule if the analyte is present, passing a plurality of magnetic particles comprising a first member of a binding pair over the sensor after passing the reporter protein configured to bind to the first plurality of magnetic particles comprising a first member of a binding pair over the sensor, then passing a plurality of magnetic particles comprising a second member of the binding pair over the sensor and detecting the presence of the analyte by measuring an amplified magnetoresistance change of the GMR sensor based on determining magnetoresistance before and after passing magnetic particles over the GMR sensor. In some embodiments, such methods further comprise passing a second plurality of magnetic particles comprising the first member of a binding pair over the sensor after passing the plurality of magnetic particles comprising the second member of the binding pair over the sensor. In some embodiments, such methods further comprise passing a second plurality of magnetic particles comprising the second member of the binding pair over the sensor after passing the second plurality of magnetic particles comprising first second member of the binding pair over the GMR sensor. In some embodiments, such methods further comprise passing one or more subsequent pluralities of magnetic particles comprising the first member of the binding pair, and one or more subsequent pluralities of magnetic nanoparticles comprising the second member of the binding pair, over the GMR sensor. In some embodiments, the binding pair comprises streptavidin and biotin. In some embodiments, the first member of the binding pair comprises streptavidin. In some embodiments, the second member of the binding pair comprises biotin.

In other aspects, embodiments herein relate to methods of detecting the presence of an analyte in a query sample comprising providing a sensor comprising a biomolecule disposed on a functionalized surface of a giant magnetoresistance (GMR) sensor, the biomolecule comprising an antigenic portion that binds an antibody at an antigen binding site, the antibody further comprising a portion separate from the antigen binding site configured to bind a magnetic nanoparticle, passing a mixture of the query sample and the antibody over the sensor, wherein the antigen binding site of the antibody binds the analyte if present in the query sample, thereby preventing binding of the antibody to the antigenic portion of the biomolecule, passing magnetic particles over the sensor after passing the mixture over the sensor, and detecting the presence of the analyte in the query sample by measuring a magnetoresistance change of the GMR sensor based on determining magnetoresistance before and after passing magnetic particles over the sensor.

In other aspects, embodiments herein relate to method of detecting the presence of an analyte in a query sample comprising providing a sensor comprising a biomolecule disposed on a functionalized surface of a giant magnetoresistance (GMR) sensor, the biomolecule comprising a binding region configured to bind a detection protein, the detection protein also being capable of binding the analyte, wherein when the detection protein binds the analyte, it prevents binding of the detection protein to the binding region of the biomolecule, passing the detection protein over the sensor, passing the query sample over the sensor, passing a reporter protein over the sensor after passing the query sample over the sensor, the reporter protein capable of binding the detection protein and the reporter protein configured to bind to magnetic particles, passing magnetic particles over the sensor after passing the reporter protein over the sensor, and detecting the presence of the metal ion by measuring magnetoresistance change of the GMR sensor based on determining magnetoresistance before and after passing magnetic particles over the sensor.

In yet other aspects, embodiments herein relate to methods of detecting the presence of an analyte in a query sample comprising providing a sensor comprising a biomolecule disposed on a functionalized surface of a giant magnetoresistance (GMR) sensor, the biomolecule comprising an associated magnetic particle, passing the query sample over the sensor, thereby causing removal of the associated magnetic particle from the biomolecule if the analyte is present, and detecting the presence of the analyte in the query sample by measuring magnetoresistance change of the GMR sensor based on determining magnetoresistance before and after passing the query sample over the sensor, wherein determining magnetoresistance change of the GMR sensor comprises using at least one reference resistor to perform phase-sensitive solution of magnetoresistance change of the GMR sensor.

In still other aspects, embodiments herein relate to methods of detecting the presence of an analyte in a query sample comprising providing a sensor comprising a first biomolecule disposed on a functionalized surface of a giant magnetoresistance (GMR) sensor, the first biomolecule comprising a conditional binding site for a second biomolecule comprising a binding site for a magnetic particle, passing the query sample over the sensor, passing the second biomolecule over the sensor, passing magnetic particles over the sensor after passing the query sample over the sensor, and detecting the presence of the analyte in the query sample by measuring magnetoresistance change of the GMR sensor based on determining magnetoresistance before and after passing magnetic particles over the sensor, wherein determining magnetoresistance change of the GMR sensor comprises using at least one reference resistor to perform phase-sensitive solution of magnetoresistance change of the GMR sensor.

In yet still further aspects, embodiments herein relate to methods of detecting the presence of an analyte in a query sample comprising providing a sensor comprising a first biomolecule disposed on a functionalized surface of a giant magnetoresistance (GMR) sensor, the biomolecule comprising a binding site for a magnetic particle when the analyte is present, passing the query sample over the sensor, passing magnetic particles over the sensor after passing the query sample over the sensor, and detecting the presence of the analyte in the query sample by measuring magnetoresistance change of the GMR sensor based on determining magnetoresistance before and after passing magnetic particles over the sensor, wherein determining magnetoresistance change of the GMR sensor comprises using at least one reference resistor to perform phase-sensitive solution of magnetoresistance change of the GMR sensor.

In some aspects, embodiments herein relate to methods of detecting a presence of a metal in a query sample comprising providing a sensor comprising a biomolecule disposed on a functionalized surface of a giant magnetoresistance (GMR) sensor, the biomolecule comprising a cleavable portion covalently bound to the biomolecule, cleavage being catalyzed by the presence of the metal in the query sample and a receptor associated with the cleavable portion of the biomolecule, the receptor being capable of binding a magnetic nanoparticle, passing the query sample over the sensor, thereby allowing cleavage and removal of the cleavable portion with the associated receptor from the biomolecule if the metal is present, passing magnetic particles over the sensor after passing the query sample over the sensor, and detecting the presence of the metal in the query sample by measuring magnetoresistance change of the GMR sensor based on determining magnetoresistance before and after passing magnetic particles over the sensor.

In some aspects, embodiments herein relate to methods of detecting a presence of a metal in a query sample comprising providing a sensor comprising a biomolecule disposed on a functionalized surface of a giant magnetoresistance (GMR) sensor, the biomolecule comprising a cleavable portion covalently bound to the biomolecule, cleavage being catalyzed by the absence of the metal in the query sample and a receptor associated with the cleavable portion of the biomolecule, the receptor being capable of binding a magnetic nanoparticle, passing the query sample over the sensor, thereby allowing cleavage and removal of the cleavable portion with the associated receptor from the biomolecule if the metal is absent, passing magnetic particles over the sensor after passing the query sample over the sensor, and detecting the presence of the metal in the query sample by measuring magnetoresistance change of the GMR sensor based on determining magnetoresistance before and after passing magnetic particles over the sensor.

In some aspects, embodiments herein relate to methods of amplifying a detection signal for detecting the presence of an analyte in a query sample, the method comprising: providing a sensor comprising a biomolecule disposed on a functionalized surface of a giant magnetoresistance (GMR) sensor, the biomolecule comprising: a cleavable portion covalently bound to the biomolecule, cleavage being catalyzed by the presence of the analyte in the query sample; and a receptor associated with the cleavable portion of the biomolecule, the receptor being capable of binding a magnetic nanoparticle; (a) passing the query sample over the sensor, thereby allowing cleavage and removal of the cleavable portion with the associated receptor from the biomolecule if the analyte is present; (b) passing a plurality of magnetic particles comprising a first member of a binding pair over the sensor after passing the query sample over the sensor, then passing a plurality of magnetic particles comprising a second member of the binding pair over the sensor; and (c) detecting the presence of the analyte in the query sample by measuring magnetoresistance change of the GMR sensor based on determining magnetoresistance before and after passing magnetic particles over the sensor; thereby amplifying the detection signal.

In some aspects, embodiments herein relate to methods of amplifying a detection signal for detecting the presence of an analyte in a query sample comprising: (a) providing a sensor comprising a biomolecule disposed on a functionalized surface of a giant magnetoresistance (GMR) sensor, the ized surface of a giant magnetoresistance (GMR) sensor, the biomolecule comprising: an antigenic portion that binds an antibody at an antigen binding site, the antibody further comprising a portion separate from the antigen binding site configured to bind a magnetic nanoparticle; (b) passing a mixture of the query sample and the antibody over the sensor, wherein the antigen binding site of the antibody binds the analyte if present in the query sample, thereby preventing binding of the antibody to the antigenic portion of the biomolecule; (c) passing a plurality of magnetic particles comprising a first member of a binding pair over the sensor after passing the query sample over the sensor, then passing a plurality of magnetic particles comprising a second member of the binding pair over the sensor; and (d) detecting the presence of the analyte in the query sample by measuring magnetoresistance change of the GMR sensor based on determining magnetoresistance before and after passing magnetic particles over the sensor; thereby amplifying the detection signal.

In some aspects, embodiments herein relate to methods of amplifying a detection signal for detecting the presence of an analyte in a query sample comprising: (a) providing a sensor comprising a biomolecule disposed on a functionalized surface of a giant magnetoresistance (GMR) sensor, the biomolecule comprising: a binding region configured to bind a detection protein, the detection protein also being capable of binding the analyte; wherein when the detection protein binds the analyte, it prevents binding of the detection protein to the binding region of the biomolecule; (b) passing the detection protein over the sensor; (c) passing the query sample over the sensor; (d) passing a reporter protein over the sensor after passing the query sample over the sensor, the reporter protein capable of binding the detection protein and the reporter protein configured to bind to magnetic nanoparticles; (e) passing a plurality of magnetic particles comprising a first member of a binding pair over the sensor after passing the query sample over the sensor, then passing a plurality of magnetic particles comprising a second member of the binding pair over the sensor; and (f) detecting the presence of the metal ion by measuring amplified magnetoresistance change of the GMR sensor based on determining magnetoresistance before and after passing magnetic particles over the sensor; thereby amplifying the detection signal.

In some aspects, embodiments herein relate to methods amplifying a detection signal for detecting the presence of an analyte in a query sample comprising: (a) providing a sensor comprising a first biomolecule disposed on a functionalized surface of a giant magnetoresistance (GMR) sensor, the first biomolecule comprising a conditional binding site for a second biomolecule comprising a binding site for a magnetic particle; (b) passing the query sample over the sensor; (c) passing the second biomolecule over the sensor; (d) passing a plurality of magnetic particles comprising a first member of a binding pair over the sensor after passing the query sample over the sensor, then passing a plurality of magnetic particles comprising a second member of the binding pair over the sensor; and (e) detecting the presence of the analyte in the query sample by measuring magnetoresistance change of the GMR sensor based on determining magnetoresistance before and after passing magnetic particles over the sensor, wherein determining magnetoresistance change of the GMR sensor comprises using at least one reference resistor to perform phase-sensitive solution of magnetoresistance change of the GMR sensor; thereby amplifying the detection signal.

In some aspects, embodiments herein relate to methods of amplifying a detection signal for detecting the presence of an analyte in a query sample comprising: (a) providing a sensor comprising a first biomolecule disposed on a functionalized surface of a giant magnetoresistance (GMR) sensor, the biomolecule comprising a binding site for a magnetic particle when the analyte is present; (b) passing the query sample over the sensor; (c) passing a plurality of magnetic particles comprising a first member of a binding pair over the sensor after passing the query sample over the sensor, then passing a plurality of magnetic particles comprising a second member of the binding pair over the sensor; and (e) detecting the presence of the analyte in the query sample by measuring magnetoresistance change of the GMR sensor based on determining magnetoresistance before and after passing magnetic particles over the sensor, wherein determining magnetoresistance change of the GMR sensor comprises using at least one reference resistor to perform phase-sensitive solution of magnetoresistance change of the GMR sensor; thereby amplifying the detection signal.

In some aspects the first member of the binding pair comprises streptavidin and the second member of the binding pair comprises biotin.

In some aspects the first member first member of the binding pair comprises biotin and the second member of the binding pair comprises streptavidin.

In some aspects the first member the magnetoresistance change of the GMR sensor comprises an amplified magnetoresistance change.

In some aspects, embodiments herein relate to methods of detecting the presence of one or more analytes in one or more query samples in a multiplex detection scheme, the method comprising: providing spacially disposed giant magnetoresistance (GMR) sensors, wherein at least two of the GMR sensors comprise at least two different biomolecules disposed on a functionalized surface of the at least two (GMR) sensors, each different biomolecule comprising: a cleavable portion covalently bound to the at least two biomolecules, cleavage being catalyzed by the presence of at least one of the one or more analytes in the one or more query samples; and a receptor associated with the cleavable portion of the biomolecule, the receptor being capable of binding a magnetic nanoparticle; (a) passing the one or more query samples over the sensors, thereby allowing cleavage and removal of the cleavable portion with the associated receptor from at least two biomolecules if at least one of the one or more analytes is present; (b) passing magnetic particles over the sensors after passing the one or more query samples over the sensors; and (c) detecting the presence of at least one of the one or more analytes in the one or more query samples by measuring magnetoresistance change of at least one of the at least two GMR sensors based on determining magnetoresistance before and after passing magnetic particles over the sensors.

In some aspects, embodiments herein relate to methods of detecting the presence of one or more analytes in one or more query samples comprising in a multiplex detection scheme: (a) providing at least two spacially disposed giant magnetoresistance (GMR) sensors, wherein at least two of the GMR sensors comprise at least two different biomolecules disposed on a functionalized surface of the at least two (GMR) sensors, each different biomolecule comprising: an antigenic portion that binds an antibody at an antigen binding site, the antibody further comprising a portion separate from the antigen binding site configured to bind a magnetic nanoparticle; (b) passing a mixture of the one or more query samples and the antibody over the sensors, wherein the antigen binding site of the antibody binds the one or more analytes if present in the one or more query samples, thereby preventing binding of the antibody to the antigenic portion of at least one of the at least two biomolecules; (c) passing magnetic particles over the sensors after passing the mixture over the sensors; and (d) detecting the presence of the analyte in the query sample by measuring a magnetoresistance change of at least one of the at least two GMR sensors based on determining magnetoresistance before and after passing magnetic particles over the sensors.

In some aspects, embodiments herein relate to methods of detecting the presence of one or more analytes in one or more query samples comprising in a multiplex detection scheme comprising: (a) providing at least two spacially disposed giant magnetoresistance (GMR) sensors, wherein at least two of the GMR sensors comprise at least two different biomolecules disposed on a functionalized surface of a GMR sensor, each different biomolecule comprising: a binding region configured to bind one of at least two different detection proteins, the at least two different detection proteins also being capable of binding one of the one or more analytes; wherein when one of the at least two different detection proteins binds one of the analytes, it prevents binding of said one of the at least two detection proteins to the binding region of the biomolecule; (b) passing the at least two different detection proteins over the sensors; (c) passing the one or more query samples over the sensors; (d) passing at least one reporter protein over the sensors after passing the one or more query samples over the sensor, the at least one reporter protein capable of binding the at least two detections proteins and the at least one reporter protein configured to bind to magnetic particles; (e) passing magnetic particles over the sensors after passing the at least one reporter protein over the sensors; and (f) detecting the presence of one or more analyte by measuring magnetoresistance change of the at least two GMR sensors based on determining magnetoresistance before and after passing magnetic particles over the sensors.

In some aspects, the least two spacially disposed GMR sensors are disposed in the channel of a GMR sensor chip, wherein the GMR sensor chip comprises at least one channel.

In some aspects, the least two spacially disposed GMR sensors are disposed in the channel of a GMR sensor chip, wherein the GMR sensor chip comprises a plurality of channels.

In some aspects, the least two spacially disposed GMR sensors are each disposed different channels of a GMR sensor chip, wherein the GMR sensor chip comprises a plurality of channels.

In some aspects, wherein passing magnetic particles over the sensors comprises passing a plurality of magnetic particles comprising a first member of a binding pair over the sensor after passing the reporter protein over the sensor, and subsequently passing a plurality of magnetic particles comprising a second member of the binding pair over the sensor, and wherein magnetoresistance change of the GMR sensors comprises an amplified magnetoresistance change of the GMR sensors.

In some aspects, embodiments herein relate to methods of amplifying a signal, such as a magnetoresistance change of a GMR sensor comprising detecting a presence of a metal in a sample comprising (a) providing a sensor comprising a surface, and a metal-dependent DNAzyme attached to the surface, wherein the DNAzyme comprises (i) a substrate strand comprising a first member of a binding pair, and (ii) an enzyme strand comprising a metal-dependent catalytic domain, wherein a portion of the substrate strand is complementary to a portion of the enzyme strand; (b) contacting the sensor with a liquid sample suspected of comprising a metal; (c) contacting the sensor with a detectable label comprising a second member of the binding pair; and (d) detecting a presence, absence, or amount of the detectable label associated with the surface of the sensor. In some embodiments, the metal is lead and the metal-dependent DNAzyme is activated by the presence of lead. In some embodiments, the sensor is a magnetic sensor (e.g., a giant magnetoresistance (GMR) sensor) and the detectable label comprises a magnetic particle. In certain embodiments, the first member of a binding pair comprises biotin and the second member of the binding pair comprises streptavidin. Further, in certain embodiments, the contacting of (b) is performed before or after the contacting of (c). Accordingly, in some aspects, presented herein is a method of detecting a presence, absence of amount of lead in a liquid sample comprising (a) providing a magnetic sensor comprising a surface, and a lead-dependent DNAzyme attached to the surface, wherein the DNAzyme comprises (i) a substrate strand comprising biotin, and (ii) an enzyme strand comprising a metal-dependent catalytic domain, wherein a portion of the substrate strand is complementary to a portion of the enzyme strand; (b) contacting the magnetic sensor with a liquid sample suspected of comprising lead; (c) contacting the magnetic sensor with a plurality of magnetic particles comprising streptavidin; and (d) detecting a presence, absence, or amount of the magnetic particles associated with the surface of the magnetic sensor.

In some aspects, the presence, absence or amount of lead in the sample is determined according to the presence, absence, or amount of magnetic particles that are detected at, on or near the surface of the magnetic sensor. In some embodiments, the detecting of (d) comprises detecting a presence, absence, or amount of magnetic particles at or near the surface of the sensor. Accordingly, in some embodiments, the presence, absence, or amount of magnetic particles associated with the surface of the magnetic sensor is determined according to the change of magnetoresistance of the sensor.

In some aspects, some or all of the steps of a method described herein are conducted in a microfluidic device comprising the sensor, and a plurality of valves, chambers, microfluidic channels and ports that are configured to direct flow of the sample, the magnetic particles and optionally, one or more wash buffers, over the surface of the sensor.

In some aspects, the substrate strand of a lead-dependent DNAzyme comprises the nucleotide sequence of SEQ ID NO:1 (5'-CTCACTAT$\underline{A}$GGAAGAGAT-GATGTCTGTAAATT-3') and the enzyme strand comprises the nucleotide sequence of SEQ ID NO:2 (5'-ACAGACAT-CATCTCTGAAGTAGCGCCGCCGTATAGTGAG-3'). In certain embodiments, the 5'-end of the substrate strand is attached to the surface of the sensor, the 3'-end of the substrate strand is attached to biotin, and the underlined and bolded $\underline{A}$ residue indicates the target cleavage site. In certain embodiments, after a DNAzyme is contacted with streptavidin coated magnetic particles, the particles bind to biotin on the 3'-end of the substrate strand, and the presence of the magnetic particles at the surface of the magnetic sensor is detected, thereby providing a base-line magnetoresistance at the surface of the sensor. In some embodiments, when lead is present, the enzyme strand cleaves the substrate strand and releases the 3'-arm of the substrate strand and associated magnetic particles from the surface, which can be detected as a change of magnetoresistance of the sensor (e.g., see FIG. 21).

In some aspects, presented herein is a microfluidic device comprising: (a) a magnetic sensor comprising a surface; (b) a metal-dependent DNAzyme attached to the surface; (c) one or more microfluidic channels; (d) one or more chambers; and (e) one or more valves or pumps; wherein the one or more microfluidic channels are operably connected and/or fluidically connected with the sensor, the one or more chambers and the one or more valves and/or pumps. In some embodiments, the one or more chambers comprise a sample chamber, one or more wash chambers, and a reagent chamber comprising a suspension of magnetic particles. In certain embodiments, the sample chamber, wash chambers and reagent chamber are proximal (i.e., upstream) of the sensor. In some embodiments, the device comprises a waste chamber located distal to the sensor (i.e., downstream).

In some aspects, presented herein are devices and method for detecting the presence, absence or amount of mercury in a sample (e.g., a water sample). In some aspects, presented herein is a microfluidic device comprising (a) a magnetic sensor comprising a surface, and a plurality of mercury binding proteins attached to the surface, wherein each of the mercury binding protein comprises, or is bound to a mercury ion, (b) one or more microfluidic channels, (d) one or more chambers and (e) one or more valves or pumps, where the one or more microfluidic channels are operably connected and/or fluidically connected with the sensor, the one or more chambers and the one or more valves or pumps. In some embodiments, the mercury binding protein is serum albumin. In some embodiments, the microfluidic device comprises a chamber comprising a plurality of mercury binding agents (e.g., antibodies configured to bind to mercury) and another chamber comprising a plurality of magnetic particles, each configured to bind to a mercury binding agent of the device. In some embodiments, each of the mercury binding agents comprises biotin and each of the magnetic particles comprises streptavidin. In some embodiments, the microfluidic device is configured for integration with a controller and or a computer. For example, in some embodiments, the microfluidic device is in the form of a removable card or cartridge.

In some aspects, presented herein is a method of detecting the presence, absence, or amount of mercury in a sample, the method comprising (a) providing a magnetic sensor comprising a surface comprising a plurality of mercury-binding proteins (e.g., a modified serum albumin configured to bind to mercury), wherein each mercury binding protein comprises at least one mercury ion bound thereto, (b) contacting the magnetic sensor with a mercury binding agent (e.g., an antibody that binds to mercury) comprising a first member of a binding pair (e.g., biotin), (c) contacting the magnetic sensor with a liquid sample suspected of comprising mercury, (d) contacting the magnetic sensor with a plurality of magnetic particles, wherein each of the magnetic particles comprises a second member of the binding pair (e.g., streptavidin) and (e) detecting a presence, absence, or amount of the mercury binding agent or magnetic particles associated with the surface of the magnetic sensor. In some embodiments, the presence, absence, or amount of mercury in the sample is determined according to the presence, absence, or amount of magnetic particles that are associated with the surface of the magnetic sensor. In some embodiments, the presence, absence or amount of mercury in a sample is determined by an amount of magnetoresistance, or a change in magnetoresistance, where the amount of magnetoresistance or change is magnetoresistance is caused by the presence, absence or amount of magnetic particles that are attached to, or associated with, the surface of the sensor.

In some aspects, presented herein is a method of detecting the presence, absence, or amount of mercury in a sample, the method comprising (a) providing a magnetic sensor comprising a surface comprising a plurality of mercury-binding proteins, wherein each mercury binding protein comprises at least one mercury ion, (b) contacting the magnetic sensor with a plurality of mercury binding agents (e.g., antibodies configured to bind to mercury), each comprising a magnetic particle, (c) contacting the magnetic sensor with a liquid sample suspected of comprising mercury and (d) detecting a presence, absence, or amount of the mercury binding agent or magnetic particles associated with the surface of the magnetic sensor. In some embodiments, the presence, absence, or amount of mercury in the sample is determined according to the presence, absence or amount of magnetic particles that are associated with the surface of the sensor. In some embodiments, the presence, absence, or amount of mercury in the sample is determined according to a magnetoresistance, or change in magnetoresistance, detected or measured by the sensor, where the magnetoresistance, or change in magnetoresistance, correlates with the presence, absence or amount of magnetic particles that are associated with the surface of the sensor.

In some aspects, presented herein is a method of detecting the presence or absence of a heavy metal in a sample, the method comprising: (a) providing a magnetic sensor comprising a surface, and a nucleic acid attached to the surface, and a metalloregulatory repressor protein (MRP), wherein (i) the nucleic acid comprises a repressor binding site for the MRP, and (ii) the MRP is bound to the repressor binding site; (b) contacting the magnetic sensor with a liquid sample suspected of comprising a heavy metal; and (c) detecting a presence, or absence of the heavy metal in the sample. In some embodiments, the MRP is bound to (directly or indirectly) magnetic particles and the detecting comprises detecting the presence, absence or amount of magnetic particles on, at, near or associated with the surface of the sensor. In some embodiments, detecting the presence of a heavy metal in a sample comprises detecting an amount of a heavy metal in a sample.

In some aspects, presented herein is a method of detecting the presence of a heavy metal in a sample, the method comprising: (a) providing a magnetic sensor comprising a surface, a nucleic acid attached to the surface, and a metalloregulatory repressor protein (MRP), wherein (i) the nucleic acid comprises a repressor binding site for the MRP, and (ii) the MRP is bound to the repressor binding site of the nucleic acid; (b) contacting the magnetic sensor with a liquid sample suspected of comprising a heavy metal; (c) contacting the magnetic sensor with a plurality of magnetic particles; and (d) detecting a presence, absence, or amount of the magnetic particles associated with the surface of the magnetic sensor. In certain embodiments, the MRP is a cadmium resistance operon repressor (cadC) and the heavy metal is cadmium. In certain embodiments, the MRP is an arsenical resistance operon repressor (arsR) and the heavy metal is arsenic. In some embodiments, the magnetic sensor is a giant magnetoresistance (GMR) sensor.

In some embodiments, the MRP comprises a first member of a binding pair, and the magnetic particles comprises a second member of the binding pair. In some embodiments, the first member of the binding pair comprises biotin and the second member of the binding pair comprises streptavidin.

In some embodiments, the methods disclosed herein are performed in a microfluidic device.

In some aspects, presented herein is a microfluidic device comprising (a) a magnetic sensor comprising a surface, a nucleic acid attached to the surface, and an MRP, wherein (i) the nucleic acid comprises a repressor binding site for the MRP, and (ii) the MRP is bound to the repressor binding site of the nucleic acid; (b) one or more microfluidic channels; (d) one or more chambers; and (e) one or more valves or pumps; wherein the one or more microfluidic channels are operably connected and/or fluidically connected with the sensor, the one or more chambers and the one or more valves or pumps. In some embodiments, the magnetic sensor is a giant magnetoresistance (GMR) sensor.

In some embodiments, the microfluidic device is configured for integration with a controller and or computer. For example, in some embodiments, the microfluidic device is in the form of a removable card or cartridge.

In yet still further aspects, embodiments relate to the systems configured to carry out the foregoing methods.

Other aspects, features, and advantages of the present disclosure will become apparent from the following detailed description, the accompanying drawings, and the appended claims.

BRIEF DESCRIPTION OF THE DRAWINGS

Various embodiments of the present disclosure will be described herein below with reference to the Figures wherein:

FIG. 13B shows a process flow diagram for the GMR sensing process of FIG. 13A.

FIG. 13C shows an alternative flow diagram for the GMR sensing process of FIG. 13A.

DETAILED DESCRIPTION

As evident by the drawings and below description, this disclosure relates to a sample handling system (or "system" as noted throughout this disclosure) which may be used for detecting presence of an analyte (or analytes) in a sample. In an embodiment, this system, depicted as system 300 in FIG. 3, may include (1) a sample handling system or "cartridge assembly" that includes sample preparation microfluidic channel(s) and at least one sensing device (or sensor) for sensing biomarkers in a test sample, and (2) a data processing and display device or "cartridge reader unit" that includes a processor or controller for processing any sensed data of the sensing device of the cartridge assembly and a display for displaying a detection event. Together these two components make up the system. In an embodiment, these components may include variable features including, without limitation, one or more reagent cartridges, a cartridge for waste, and a flow control system which may be, for example, a pneumatic flow controller.

Generally, the process for preparing a sample in the cartridge assembly, in order for detection of analytes, biomarkers, etc. to happen by the assembly and output via the cartridge reader unit, is as-follows: A raw patient sample is loaded onto a card, optionally filtered via a filter membrane, after which a negative pressure generated by off-card pneumatics filters the sample into a separated test sample (e.g., plasma). This separated test sample is quantitated on-card through channel geometry. The sample is prepared on card by interaction with mixing materials (e.g., reagent(s) (which may be dry or wet), buffer and/or wash buffer, beads and/or beads solution, etc.) from a mixing material source (e.g., blister pack, storage chamber, cartridge, well, etc.) prior to flow over the sensor/sensing device. The sample preparation channels may be designed so that any number of channels may be stacked vertically in a card, allowing multiple patient samples to be used. The same goes for sensing microfluidic devices, which may also be stacked vertically. A sample preparation card, which is part of the cartridge assembly, includes one or more structures providing functionalities selected from filtering, heating, cooling, mixing, diluting, adding reagent, chromatographic separation and combinations thereof, and a means for moving a sample throughout the sample preparation card. Further description regarding these features is provided later below.

Figure 1:
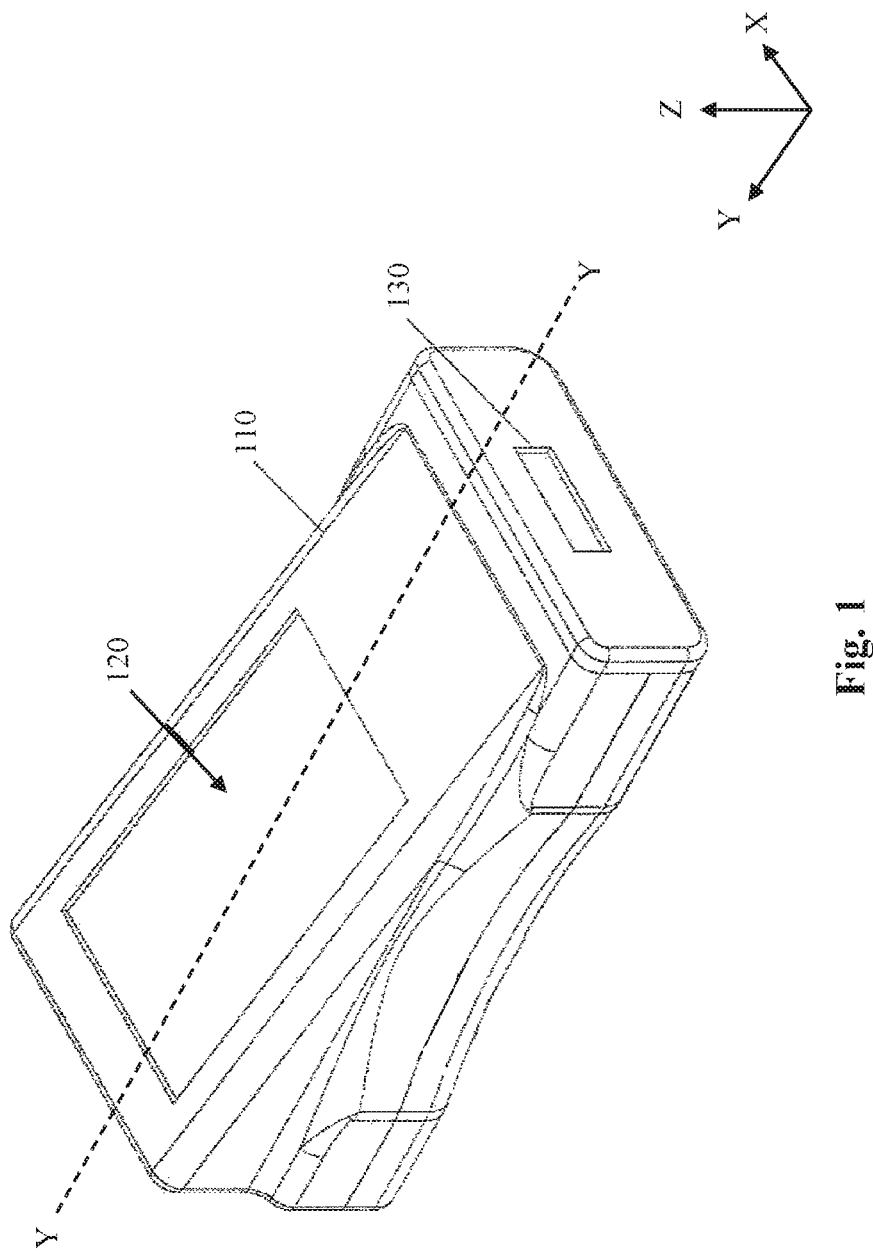
FIG. 1 is a perspective view of an exemplary cartridge reader unit used in a system in accordance with an embodiment of the present disclosure.

FIG. 1 shows an example of a cartridge reader unit 100, used in system 300 (see FIG. 3) in accordance with an embodiment. The cartridge reader unit 100 may be configured to be compact and/or small enough to be a hand-held, mobile instrument, for example. The cartridge reader unit 100 includes a body or housing 110 that has a display 120 and a cartridge receiver 130 for receiving a cartridge assembly. The housing 110 may have an ergonomic design to allow greater comfort if the reader unit 100 is held in an operator's hand. The shape and design of the housing 110 is not intended to be limited, however.

The cartridge reader unit 100 may include an interface 140 and a display 120 for prompting a user to input and/or connect the cartridge assembly 200 with the unit and/or sample, for example. In accordance with an embodiment, in combination with the disclosed cartridge assembly 200, the system 300 may process, detect, analyze, and generate a report of the results, e.g., regarding multiple detected biomarkers in a test sample, e.g., five cardiac biomarkers, using sensor (GMR) technology, and further display the biomarker results, as part of one process.

The display 120 may be configured to display information to an operator or a user, for example. The display 120 may be provided in the form of an integrated display screen or touch screen (e.g., with haptics or tactile feedback), e.g., an LCD screen or LED screen or any other flat panel display, provided on the housing 110, and (optionally) provides an input surface that may be designed for acting as end user interface (UI) 140 that an operator may use to input commands and/or settings to the unit 100, e.g., via touching a finger to the display 120 itself. The size of the display 120 may vary. More specifically, in one embodiment, the display 120 may be configured to display a control panel with keys, buttons, menus, and/or keyboard functions thereon for inputting commands and/or settings for the system 300 as part of the end user interface. In an embodiment, the control panel includes function keys, start and stop buttons, return or enter buttons, and settings buttons. Additionally, and/or alternatively, although not shown in FIG. 1, the cartridge reader 100 may include, in an embodiment, any number of physical input devices, including, but not limited to, buttons and a keyboard. In another embodiment, the cartridge reader 100 may be configured to receive input via another device, e.g., via a direct or wired connection (e.g., using a plug and cord to connect to a computer (PC or CPU) or a processor) or via wireless connection. In yet another embodiment, display 120 may be to an integrated screen, or may be to an external display system, or may be to both. Via the display control unit 120, the test results (e.g., from a cartridge reader 310, described with reference to FIG. 3, for example) may be displayed on the integrated or external display. In still yet another embodiment, the user interface 140 may be provided separate from the display 120. For example, if a touch screen UI is not used for display 120, other input devices may be utilized as user interface 140 (e.g., remote, keyboard, mouse, buttons, joystick, etc.) and may be associated with the cartridge reader 100 and/or system 300. Accordingly, it should be understood that the devices and/or methods used for input into the cartridge reader 100 are not intended to be limiting. All functions of the cartridge reader 100 and/or system 300 may, in one embodiment, be managed via the display 120 and/or input device(s), including, but not limited to: starting a method of processing (e.g., via a start button), selecting and/or altering settings for an assay and/or cartridge assembly 200, selecting and/or settings related to pneumatics, confirming any prompts for input, viewing steps in a method of processing a test sample, and/or viewing (e.g., via display 120 and/or user interface 140) test results and values calculated by the GMR sensor and control unit/cartridge reader. The display 120 may visually show information related to analyte detection in a sample. The display 120 may be configured to display generated test results from the control unit/cartridge reader. In an embodiment, real-time feedback regarding test results that have been determined/processed by the cartridge reader unit/ controller (by receiving measurements from the sensing device, the measurements being determined as a result of the detected analytes or biomarkers), may be displayed on the display 120.

Optionally, a speaker (not shown) may also be provided as part of the cartridge reader unit 100 for providing an audio output. Any number of sounds may be output, including, but not limited to speech and/or alarms. The cartridge reader unit 100 may also or alternatively optionally include any number of connectors, e.g., a LAN connector and USB connector, and/or other input/output devices associated therewith. The LAN connector and/or USB connector may be used to connect input devices and/or output devices to the cartridge reader unit 100, including removable storage or a drive or another system.

In accordance with an embodiment, the cartridge receiver 130 may be an opening (such as shown in FIG. 1) within the housing 110 in which a cartridge assembly (e.g., cartridge assembly 200 of FIG. 2) may be inserted. In another embodiment, the cartridge receiver 130 may include a tray that is configured to receive a cartridge assembly therein. Such a tray may move relative to the housing 110, e.g., out of and into an opening therein, and to thereby receive the cartridge assembly 200 and move the cartridge assembly into (and out of) the housing 110. In one embodiment, the tray may be a spring-loaded tray that is configured to releasably lock with respect to the housing 110. Additional details associated with the cartridge reader unit 100 are described later with respect to FIG. 3.

Figure 2A:
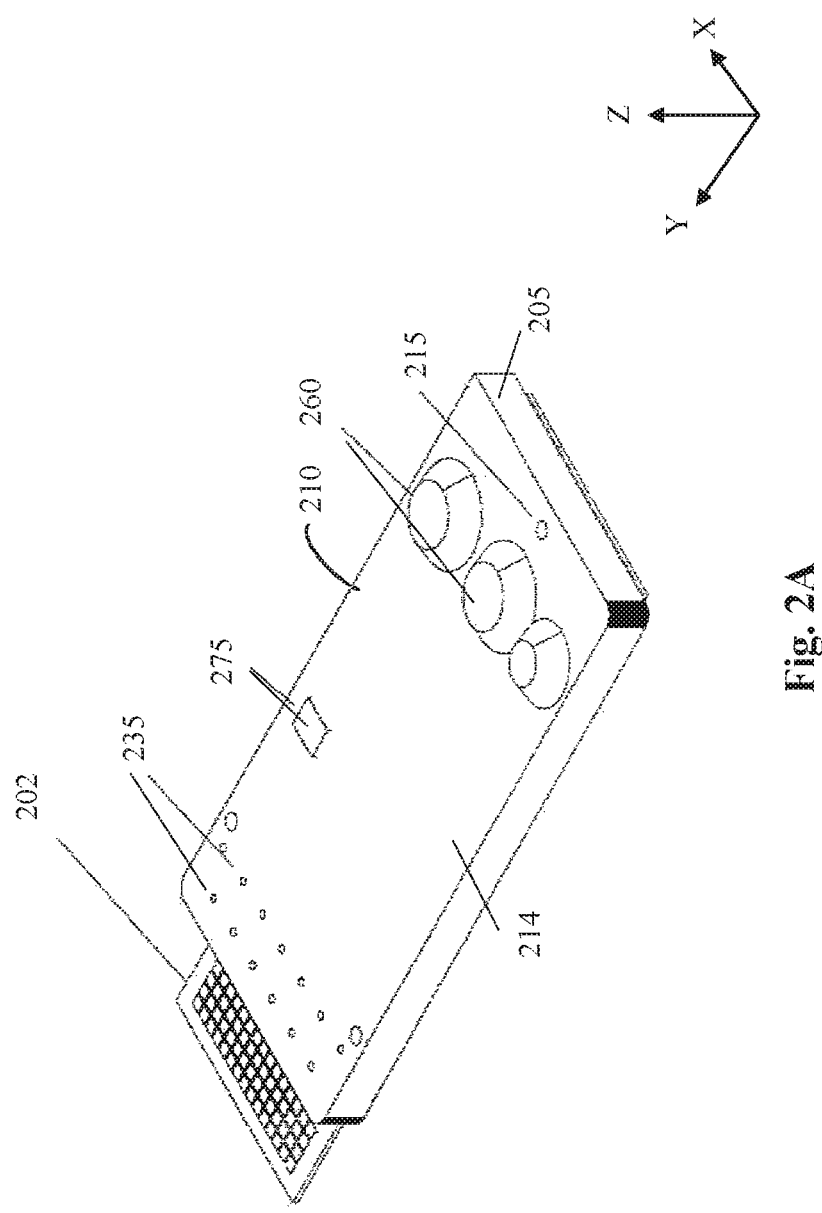
FIG. 2A is a perspective view of an exemplary cartridge assembly used in the system, in accordance with an embodiment of the present disclosure.
Figure 2B:
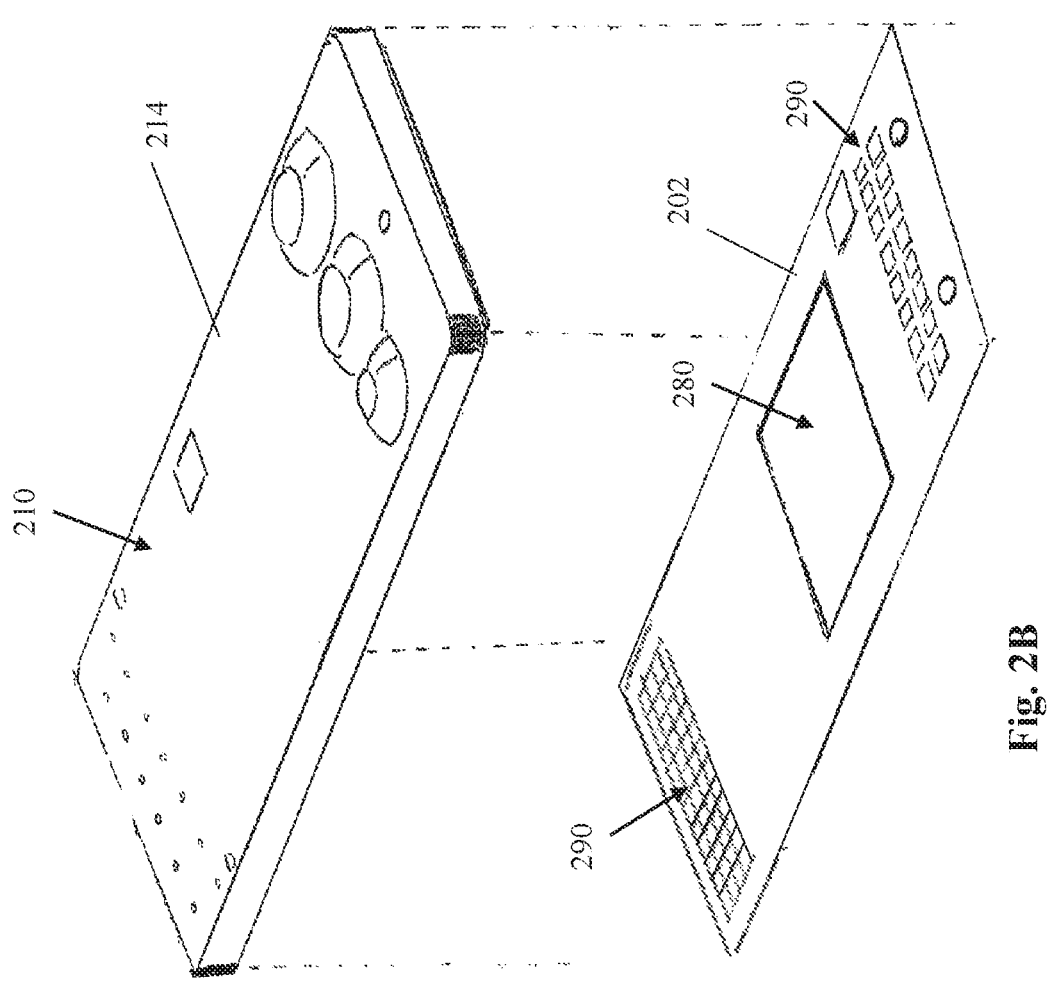
FIG. 2B is an exploded view of the cartridge assembly of FIG. 2A, in accordance with an embodiment herein.
Figure 2C:
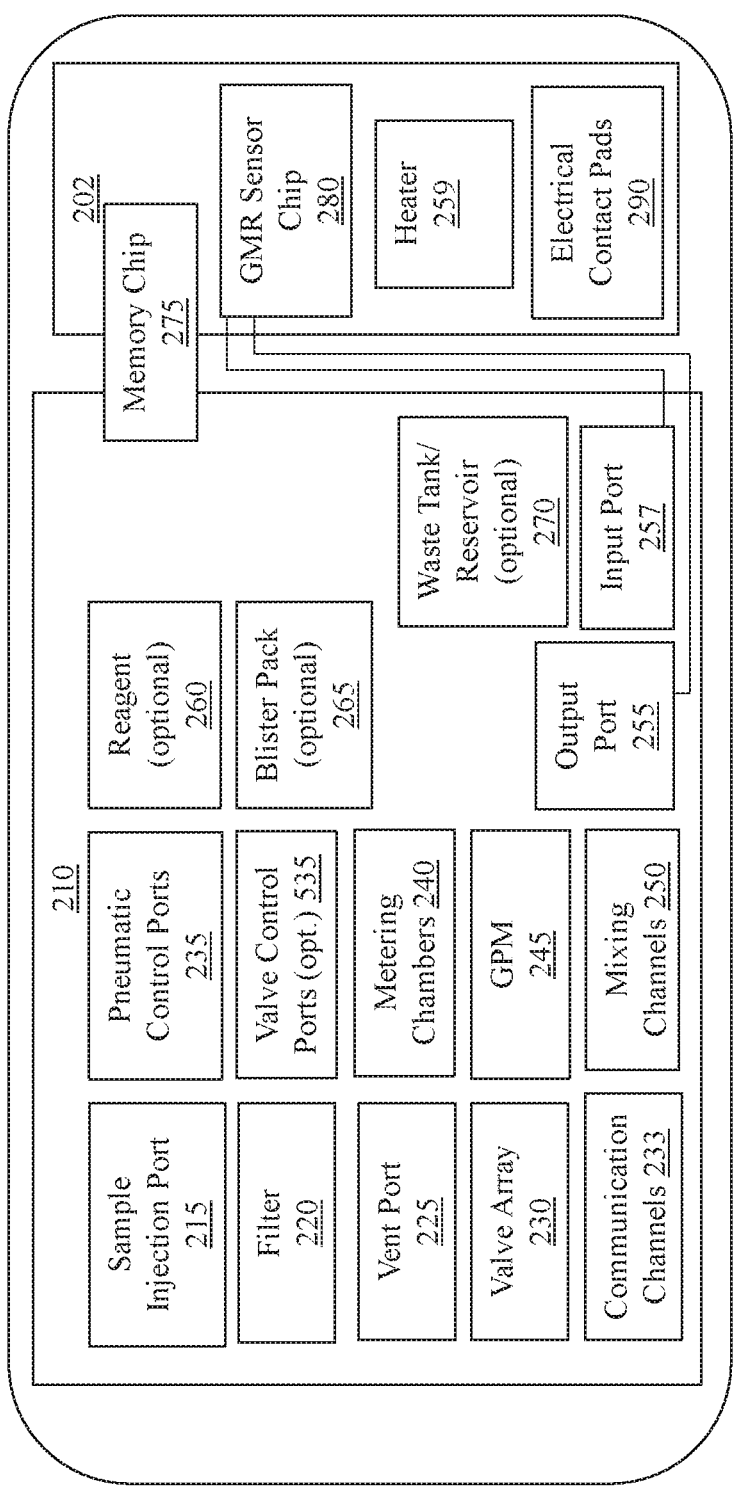
FIG. 2C is a schematic drawing of the cartridge assembly of FIGS. 2A, in accordance with an embodiment herein.

As previously noted, cartridge assembly 200 may be designed for insertion into the cartridge reader unit 100, such that a sample (e.g., blood, urine) may be prepared, processed, and analyzed. FIGS. 2A-2C illustrate an exemplary embodiment of a cartridge assembly 200 in accordance with embodiments herein. Some general features associated with the disclosed cartridge assembly 200 are described with reference to these figures. However, as described in greater detail later, several different types of cartridge cards and thus cartridge assemblies may be utilized with the cartridge reader unit 100 and thus provided as part of system 300. In embodiments, the sampling handling system or cartridge assembly 200 may take the form of disposable assemblies for conducting individual tests. That is, as will be further understood by the description herein, depending on a type of sample and/or analytes being tested, a different cartridge card configuration(s) and/or cartridge assembly(ies) may be utilized. FIG. 2A shows a top, angled view of a cartridge assembly 200, in accordance with an embodiment herein. The cartridge assembly 200 includes a sample processing card 210 and a sensing and communication substrate 202 (see also FIG. 2B). Generally, the sample processing card 210 is configured to receive the sample (e.g., via a sample port such as injection port, also described below) and, once inserted into the cartridge reader unit 100, process the sample and direct flow of the sample to produce a prepared sample. Card 210 may also store waste from a sample and/or fluid used for preparing the test sample in an internal waste chamber(s) (not shown in FIG. 2A, but further described below). Memory chip 275 may be read and/or written to and is used to store information relative to the cartridge application, sensor calibration, and sample processing required, for example. In an embodiment, the memory chip 275 is configured to store a pneumatic system protocol that includes steps and settings for selectively applying pressure to the card 210 of the cartridge assembly 200, and thus implementing a method for preparation of sample for delivery to a sensor (e.g., GMR sensor chip 280). The memory chip may be used to mistake-proof each cartridge assembly 200 inserted into the unit 100, as it includes the automation recipe for each assay. The memory chip 275 also contain traceability to the manufacturing of each card 210 and/or cartridge assembly 200. The sensing and communication substrate 202 may be configured to establish and maintain communication with the cartridge reader unit 100, as well as receive, process, and sense features of the prepared sample. The substrate 202 establishes communication with a controller in the cartridge reader unit 100 such that analyte(s) may be detected in a prepared sample. The sample processing card 210 and the sensing and communication substrate 202 (see, e.g., FIG. 2B) are assembled or combined together to form the cartridge assembly 200. In an embodiment, adhesive material (see, e.g., FIG. 2D) may optionally be used to adhere the card 210 and substrate 202 to one another. In an embodiment, the substrate 202 may be a laminated layer applied to the sample processing card 210. In one embodiment, the substrate 202 may be designed as a flexible circuit that is laminated to sample processing card 210. In another embodiment, the sample processing card 210 may be fabricated from a ceramic material, with the circuit, sensor (sensor chip 280) and fluid channels integrated thereon. Alternatively, the card 210 and substrate 202 may be mechanically aligned and connected together. In one embodiment, a portion of the substrate 202 may extend from an edge or an end of the card 210, such as shown in FIG. 2A. In another embodiment, such as shown in FIG. 2B, the substrate 202 may be aligned and/or sized such that it has similar or smaller edges than the card 210.

Figure 3:
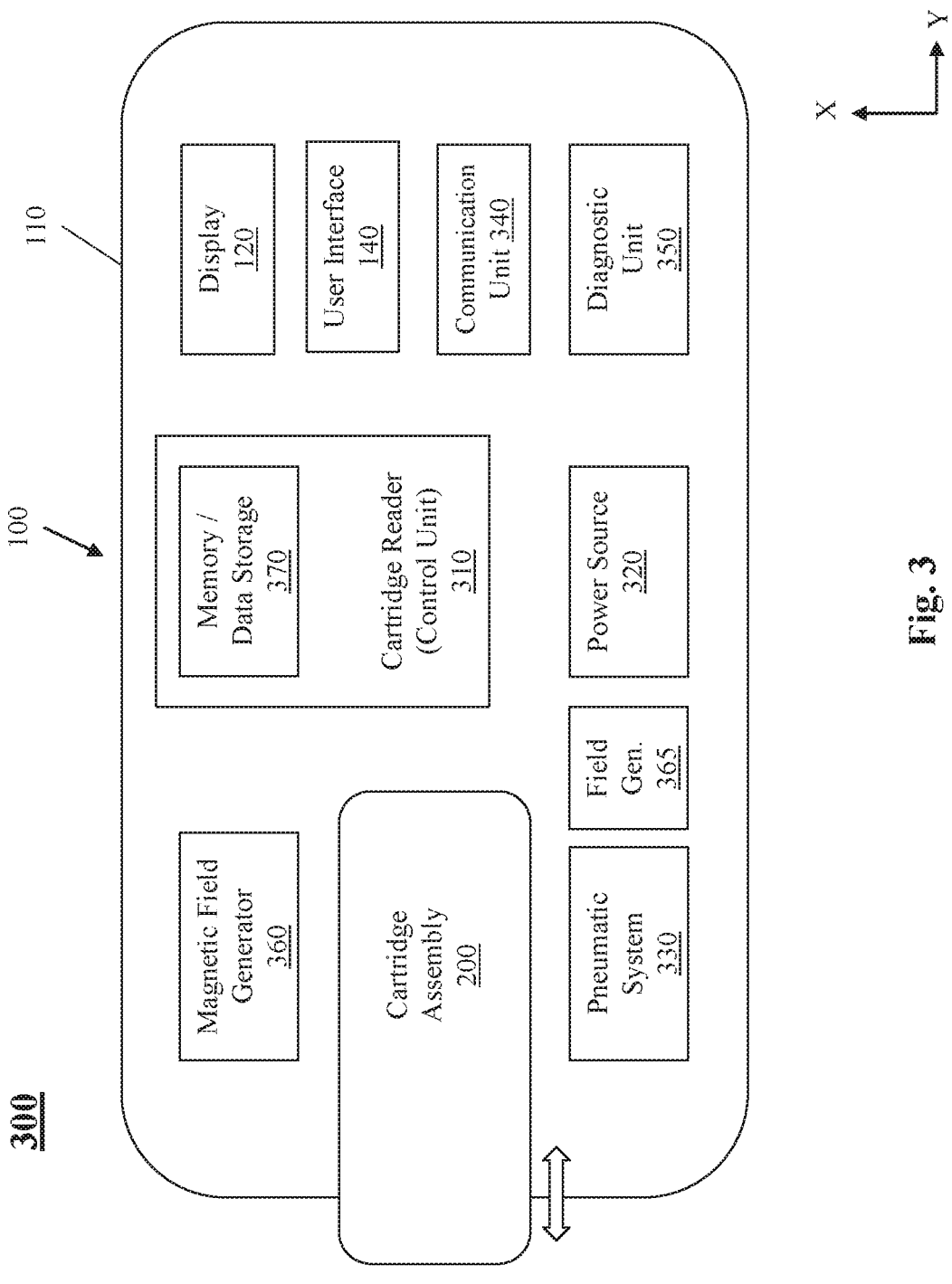
FIG. 3 is a schematic diagram of the system in accordance with an embodiment of the present disclosure.

FIG. 2C schematically illustrates features of the cartridge assembly 200, in accordance with an embodiment. As shown, some of the features may be provided on the sample processing card 210, while other may be associated with the substrate 202. Generally, to receive a test sample (e.g., blood, urine) (within a body of the card), the cartridge assembly 200 includes a sample injection port 215, which may be provided on a top of the card 210. Also optionally provided as part of the card 210 are filter 220 (also referred to herein as a filtration membrane), vent port 225, valve array 230 (or valve array zone 230), and pneumatic control ports 235. Communication channels 233 are provided within the card 210 to fluidly connect such features of the card 210. Pneumatic control ports 235 are part of a pneumatic interface on the cartridge assembly 200 for selectively applying pressurized fluid (air) to the communication channels 233 of the card, for directing flow of fluids (air, liquids, test sample, etc.) therein and/or valve array 230. Optionally, the card 210 may include distinct valve control ports 535 connected to designated communication channels 233 for controlling the valves in the valve array 230. The card 210 may also have one or more metering chambers 240, gas permeable membranes 245, and mixing channels 250 that are fluidly connected via communication channels 233. Metering chamber (s) are designed to receive at least the test sample (either directly or filtered) therein via communication channels 233. Generally, a sample may be injected into the cartridge assembly 200 through port 215 and processed by means of filtering with filter (e.g., filter 220), metering in metering chamber(s) 240, mixing in mixing channel(s) 250, heating and/or cooling (optional), and directing and changing the flow rate via communication channels 233, pneumatic control ports 235, and valve array 230. For example, flow of the fluid may be controlled using internal micro fluidic channels (also generally referred to as communication channels 233 throughout this disclosure) and valves via a connection of a pneumatic system (e.g., system 330 in the cartridge reader unit 100, as shown in FIG. 3) and a pneumatic interface e.g., on the card 210 that has pneumatic control ports 235 or a similar connection section. Optional heating of the test sample and/or mixing materials/fluids within the card 210 may be implemented, in accordance with an embodiment, via a heater 259 which may be in the form of a wire trace provided on a top side of a PCB/substrate 202 with a thermistor. Optional cooling of the test sample and/or mixing materials/fluids within the card 210 may be implemented, in accordance with an embodiment, via a TEC module integrated in the cartridge assembly 200 (e.g., on the substrate 202), or, in another embodiment, via a module integrated inside of the cartridge reader unit 100. For example, if the cooling module is provided in the unit 100, it may be pressed against the cartridge assembly 200 should cooling be required. Processing may also optionally include introduction of reagents via optional reagent sections 260 (and/or blister packs) on the card 210 and/or via reagent cartridges in the housing 110 the cartridge reader unit 100. Reagents may be released or mixed as required by the process for that sample and the cartridge assembly 200 being analyzed. Further, optional blister packs 265 may be provided on the card 210 to introduce materials such as reagents, eluants, wash buffers, magnetic nanoparticles, bead solution, or other buffers to the sample via communication channels 233 during processing. One or more internal waste chambers (also referred to herein as waste tanks for waste reservoirs) 270 may also be optionally provided on the card 210 to store waste from the sample and reagents. An output port 255—also referred to as a sensor delivery port, or input port to the sensor—is provided to output a prepared sample from the card 210 to a GMR sensor chip 280, as discussed below, for detecting analytes in the test sample. The output port 255 may be fluidly connected to a metering chamber for delivering the test sample and one or more mixing materials to the sensor. Accordingly, the sensor may be configured to receive the test sample and the one or more mixing materials via the at least one output port 255. In embodiments, an input port 257—also referred to as a waste delivery port, or output port from the sensor—is provided to output any fluid or sample from the GMR sensor chip 280 to a waste chamber 270. Waste chamber(s) 270 may be fluidly connected to other features of the card 210 (including, for example, metering chamber(s) 240, an input port 257, or both) via communication channels 233.

The cartridge assembly 200 has the ability to store, read, and/or write data on a memory chip 275, which may be associated with the card 210 or the substrate 202. As noted previously, the memory chip 275 may be used to store information related and/or relative to the cartridge application, sensor calibration, and required sample processing (within the sample processing card), as well as receive additional information based on a prepared and processed sample. The memory chip 275 may be positioned on the sample processing card 210 or on the substrate 200.

As previously noted, a magnetoresistive sensor may be utilized, in accordance with embodiments herein, to determine analytes (such as biomarkers) within a test sample using the herein disclosed system. While the description and Figures note use of a particular type of magnetoresistance sensor, i.e., a giant magnetoresistance (GMR) sensor, it should be understood that this disclosure is not limited to a GMR sensor platform. In accordance with some embodiments, the sensor may be an anisotropic magnetoresistive (AMR) sensor and/or magnetic tunnel junction (MTJ) sensors, for example. In embodiments, other types of magnetoresistive sensor technologies may be utilized. Nonetheless, for explanatory purposes only, the description and Figures reference use of a GMR sensor as a magnetoresistive sensor.

The substrate 202 of cartridge assembly 200 may be or include an electronic interface and/or a circuit interface such as a PCB (printed circuit board) that may have a giant magnetoresistance (GMR) sensor chip 280 and electrical contact pads 290 (or electrical contact portions) associated therewith. Other components may also be provided on the substrate 202. The GMR sensor chip 280 is attached at least to the substrate 202, in accordance with an embodiment. The GMR sensor chip 280 may be placed on and attached to the substrate 202 using adhesive, for example. In an embodiment, a liquid adhesive or a tape adhesive may be used between the GMR sensor 280 and the PCB substrate 202. Such a design may require a bond to the PCB at the bottom and a bond to the processing card at the top, for example. Alternatively, other approaches for attaching the GMR sensor chip 280 to the substrate 202 include, but are not limited to: friction fitting the GMR sensor to the PCB, and connecting a top of the GMR sensor chip 280 directly to the sample processing card 210 (e.g., in particular when the substrate 202 is provided in the form of a flexible circuit that is laminated (to the back) of sample processing card 210. The GMR sensor chip 280 may be designed to receive a prepared sample from the output port 255 of the sample processing card 210. Accordingly, placement of the GMR sensor chip 280 on the substrate may be changed or altered based on a position of the output port 255 on card 210 (thus, the illustration shown in FIG. 2B is not intended to be limiting)—or vice versa. In an embodiment, the GMR sensor chip 280 is positioned on a first side of the substrate 202 (e.g., a top side that faces an underside of the card 210, as shown in FIG. 2B), e.g., so as to receive the prepared sample from an output port that outputs on an underside of the card 210, and the contact pads 290 are positioned on an opposite, second side of the substrate (e.g., on a bottom side or underside of the substrate 202, such that the contact pads 290 are exposed on a bottom side of the cartridge assembly 200 when fully assembled for insertion into the cartridge reader unit 100). The GMR sensor chip 280 may include its own associated contact pads (e.g., metal strips or pins) that are electrically connected via electronic connections on the PCB/substrate 202 to the electrical contact pads 290 provided on the underside thereof. Accordingly, when the cartridge assembly 200 is inserted into the cartridge reader 100, the electrical contact pads 290 are configured to act as an electronic interface and establish an electrical connection and thus electrically connect with electronics (e.g., cartridge reader 310) in the cartridge reader unit 100. Thus, any sensors in the sensor chip 280 are connected to the electronics in the cartridge reader unit 100 through the electrical contact pads 290 and contact pads of the GMR sensor chip 280.

Figure 2D:
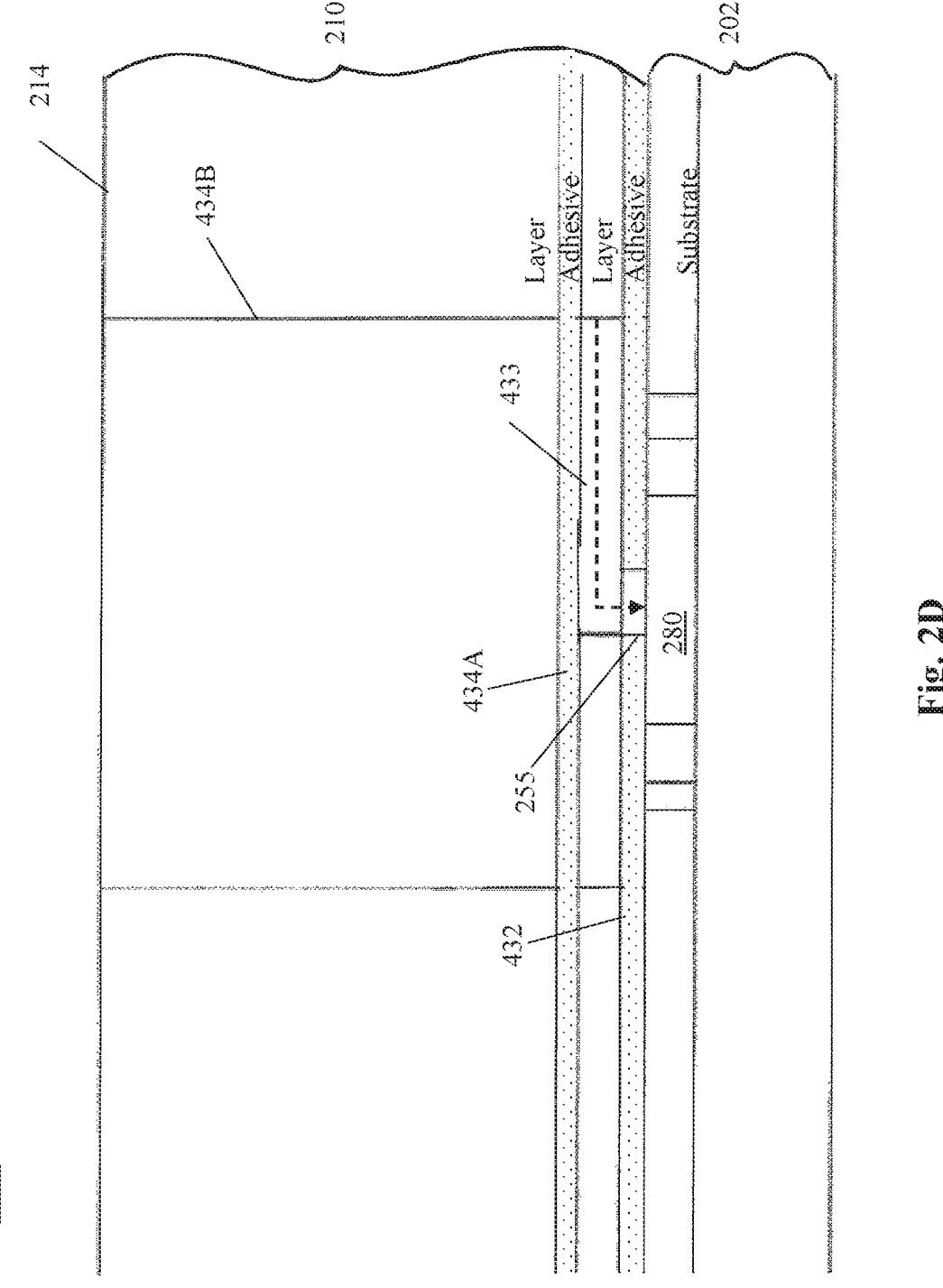
FIG. 2D shows a cross section of the cartridge assembly of FIG. 2A, illustrating a connection interface between a sample processing card and a sensing and communication substrate thereof.

FIG. 2D shows a view of an exemplary cross section of a mating or connection interface of card 210 and substrate 202. More specifically, FIG. 2D illustrates an interface, in accordance with one embodiment, between an output port 255 on the card 210 and GMR sensor chip 280 of the substrate 202. For example, shown is a PCB substrate 202 positioned below and adjacent to a card 210 according to any of the herein disclosed embodiments. The substrate 202 may be attached to bottom surface of the card 210. The card 210 has a channel feature, labeled here as microfluidic channel 433 (which is one of many communication channels within the card 210), in at least one layer thereof, designed to direct a test sample that is processed within the card 210 to an output port 255 directed to GMR sensor 280. Optionally, adhesive material may be provided between layers of the card 210, e.g., adhesive 434A may be provided between a layer in the card that has reagent ports 434B and a layer with the channel 433. The substrate 202 includes a GMR sensor chip 280 that is positioned adjacent to the channel 433 and output port 255 of the card 210.

Magnetic field (from a magnetic coil 365 that is different than magnetic field generator 360, described below with reference to FIG. 3) may be used to excite the nanoparticle magnetic particles located near sensors.

GMR sensors have sensitivities that exceed those of anisotropic magnetoresistance (AMR) or Hall sensors. This characteristic enables detection of stray fields from magnetic materials at nanometer scales. For example, stray fields from magnetic nanoparticles that bound on sensor surface will alter the magnetization in the magnetic layers, and thus change the magnetoresistance of the GMR sensor. Accordingly, changes in the number of magnetic nanoparticles bound to the GMR sensor per unit area can be reflected in changes of the magnetoresistance value of the GMR sensor.

For such reasons, the sensor utilized in cartridge assembly 200, in accordance with the embodiments described herein, is a GMR sensor chip 280.

Referring now to FIG. 3, an overview of features provided in the system are shown. In particular, some additional features of the cartridge reader unit 100 are schematically shown to further describe how the cartridge reader unit 100 and cartridge assembly 200 are configured to work together to provide the system 300 for detecting analyte(s) in a sample. As depicted, the cartridge assembly 200 may be inserted into the housing 110 of the cartridge reader unit 100. Generally, the housing 110 of the cartridge reader unit 100 may further include or contain a processor or control unit 310, also called a "controller" and/or a "cartridge reader" 310 herethroughout, a power source 320, a pneumatic system 330, a communications unit 340, a (optional) diagnostic unit 350, a magnetic field generator 360, and a memory 370 (or data storage), along with its user interface 140 and/or display 120. Optionally, a reagent opener (e.g., puncture system 533 in FIG. 6), e.g., for opening a reagent source on an inserted cartridge assembly or for introducing reagent into the cartridge assembly (e.g., if the reagent is not contained in the assembly in a particular reagent section), may also be provided as part of the cartridge reader unit 100. Once a cartridge assembly 200 is inserted into the housing 110 of the cartridge reader unit 100, and the electrical and pneumatics system(s) are connected, and the cartridge memory chip 275 may be read from the cartridge assembly 200 (e.g., read by cartridge reader 310/control unit, or PCB assembly, in the unit 100) to determine the pneumatic system protocol that includes steps and settings for selectively applying pressure to the card 210 of the cartridge assembly 200, and thus implementing a method for preparation of sample for delivery to a sensor (e.g., GMR sensor chip 280), and thus the sample placed in the assembly 200 may be prepped, processed, and analyzed. The control unit or cartridge reader 310 may control inputs and outputs required for automation of the process for detecting the analyte(s) in a sample. The cartridge reader 310 may be a real-time controller that is configured to control, among other things, the giant magnetoresistance (GMR) sensor chip 280 and/or memory chip 275 associated with the cartridge assembly 200 and the pneumatic system 330 within the housing 110, as well as the controls from user interface, driving the magnetic field generator 360, and receiving and/or sending signals from/to sensor chip and/or memory associated with the cartridge assembly 200, for example. In an embodiment, the cartridge reader 310 is provided in the form of a PCB (printed circuit board) which may include additional chips, memory, devices, therein. The cartridge reader 310 may be configured to communicate with and/or control an internal memory unit, a system operation initializer, a signal preparing unit, a signal preparing unit, a signal processing unit, and/or data storage (none of which are shown in the Figures), for example. The cartridge reader 310 may also be configured to send and receive signals with respect to the communications unit 340 such that network connectivity and telemetry (e.g., with a cloud server) may be established, and non-volatile recipes may be implemented, for example. Generally, the communications unit 340 allows the cartridge reader unit 100 to transmit and receive data using wireless or wired technology. Power can be supplied to the cartridge reader unit 100 via power source 320 in the form of an internal battery or in the form of a connector that receives power via an external source that is connected thereto (e.g., via a cord and a plug). The pneumatic system 330 is used to process and prepare a sample (e.g., blood, urine) placed into the cartridge assembly 200 by means of moving and directing fluids inside and along the sample processing card 210 (e.g., via pneumatic connection 235, through its channels and connecting to direct elastomeric valves). The pneumatic system 330 may be a system and/or device for moving fluid, which could use, for example, plungers and/or pistons in contact with fluids (further described later below). The magnetic field generator 360 may be an external magnetic coil or other field generating device that is mounted in the unit 100 or integrated in some fashion with one or more of the chips (e.g., sensor chip 280) provided on the cartridge assembly 200 or provided on the circuit board of the cartridge reader unit 100. The magnetic field generator 360 is used to stimulate magnetic nanoparticles near the GMR sensor chip 280 while reading the signal. In accordance with embodiments, a second magnetic field generator 365, which may be a coil or other field generating device, may be provided as part of the cartridge reader unit 100 and in the housing 110. For example, in accordance with an embodiment, the second magnetic field generator 365 may be separate and distinct from magnetic field generator 360. This second magnetic field generator 365 may be configured to generate a non-uniform magnetic field such that it may apply such a magnetic field to a part (e.g., top, bottom, sides) of the sample processing card 210 during preparation and processing of a sample, e.g., when moving mixing material(s), such as a buffer and/or magnetic beads from a mixing material source, and test sample within the card. In an embodiment, the second magnetic field generator 365 is provided on an opposite end or side of the cartridge reader unit (e.g., located in a top of the housing 110 of unit 100), i.e. away from the magnetic field generator 360, which is used for GMR sensing. In one embodiment, the second magnetic field generator 365 is provided on an opposite end of the cartridge reader unit as compared to the magnetic field generator 360 (e.g., second magnetic field generator is located in a top of the housing 110 of unit 100 and magnetic field generator 360 is provided at a bottom end of the unit 100 (e.g., near cartridge receiver 130)). In an embodiment, the total magnetic field for sensing biomarkers/analytes includes an applied field from magnetic field generator 360 (either external or integrated with the sensor chip) along with any disturbance from magnetic nanoparticles near the GMR sensor chip 280. The reagent opener is optionally used to introduce reagents during the sample processing and reading of the GMR sensor chip 280 (e.g., if the reagent is not contained in the card in a particular reagent section). As described previously, the user interface 140/display 120 allows an operator to input information, control the process, provide system feedback, and display (via an output display screen, which may be a touch screen) the test results.

Figure 4:
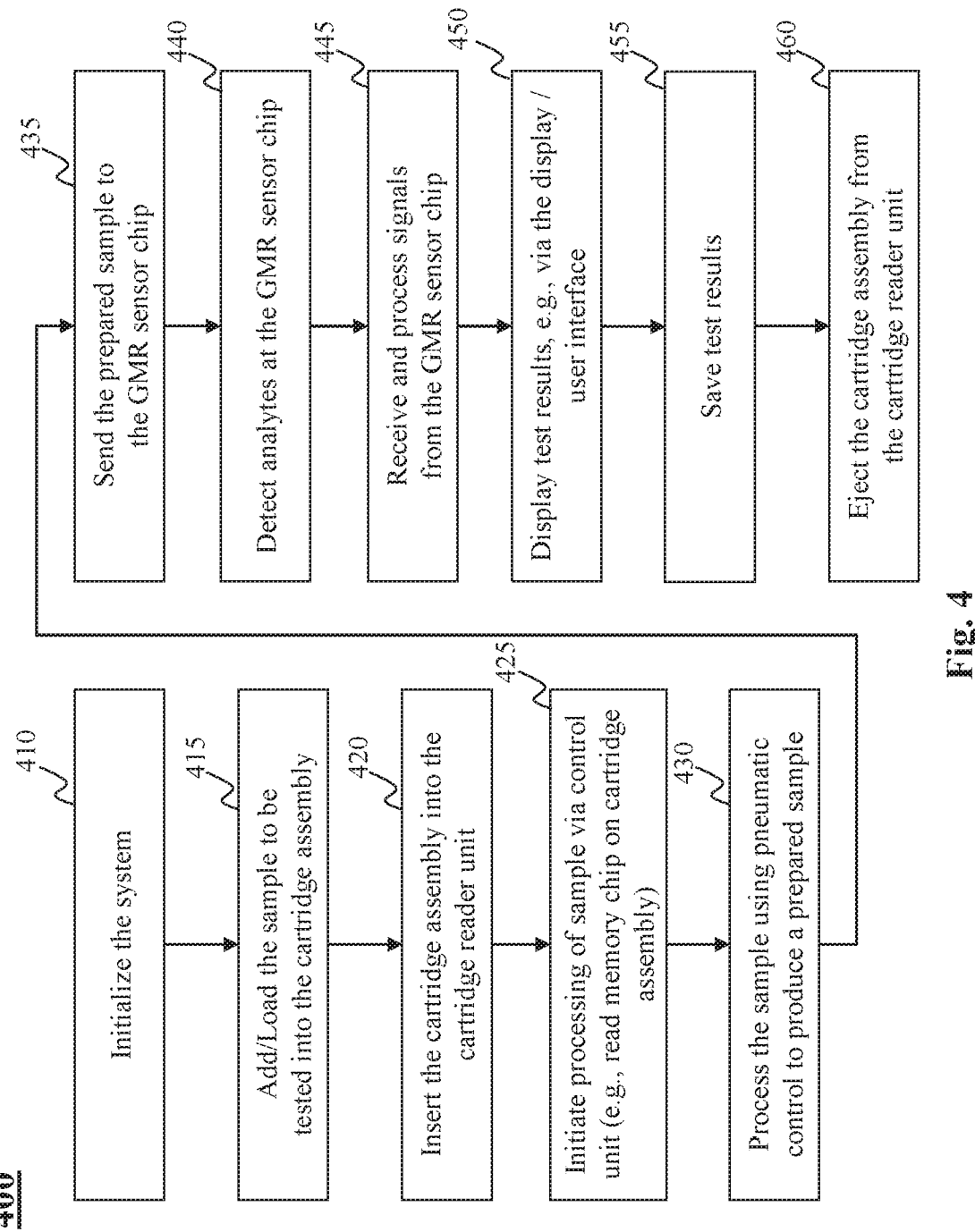
FIG. 4 shows steps of a method for performing analyte detection in a sample when using features of the herein disclosed system of FIG. 3, in accordance with an embodiment.

FIG. 4 shows general steps of a method 400 for performing analyte detection in a sample using the herein disclosed system 300. At step 410, the system is initialized. For example, initialization of the system may include: applying power to the system 300 (including cartridge reader unit 100), determining configuration information for the system, reading computations, determining that features (e.g., magnetic coil and carrier signals) are online and ready, etc. At step 415, a whole test sample is added or loaded into the cartridge assembly 200 (e.g., sample is injected into the injection port 215, as shown in FIG. 2C). The order of steps 410 and 415 may be changed; i.e., the addition of the whole test sample to the assembly 200 may be before or after the system is initialized. At step 420, the cartridge assembly 200 is inserted into the cartridge reader unit 100. Optionally, as part of method 400, user instruction may be input to the cartridge reader unit 100 and/or system 300 via the user interface/display 120. Then, at step 425, the processing of sample is initiated via the control unit 310. This initiation may include, for example, receiving input via an operator or user through the user interface/display 120 and/or a system that is connected to the reader unit 100. In another embodiment, processing may be initiated automatically via insertion of the cartridge assembly 200 into the cartridge reader unit 100 and detecting presence of the cartridge assembly 200 therein (e.g., via electrical connection between electrical contact pads 290 on the assembly 200 with the control unit 310, and automatically reading instructions from memory chip 275). The sample is processed at step 425 using pneumatic control instructions (e.g., obtained from memory chip 275) in order to produce a prepared sample. As generally described above (and further later below), the processing of the sample may be dependent upon the type of sample and/or the type of cartridge assembly 200 inserted into the reader unit 100. In some cases, the processing may include a number of steps, including mixing, introduction of buffers or reagents, etc., before the sample is prepared. Once the sample is prepared, the prepared sample is sent (e.g., through channels in the card 210 and to output port 255, via pneumatic control through pneumatic system 330 and control unit 310) to the GMR sensor chip 280. At step 440, analytes in the prepared sample are detected at the GMR sensor chip 280. Then, at step 445, signals from the GMR sensor chip 280 are received and processed, e.g., via cartridge reader 310 (control unit; which may include one or more processors, for example). Once the signals are processed, test results may be displayed at 450, e.g., via the display 120/user interface. At 455, test results are saved. For example, test results may be saved in a cloud server and/or memory chip 275 on board the cartridge assembly 200. In embodiments, any fluids or sample may be directed from the GMR sensor chip 280 through an input port 257 to waste chamber 270. Thereafter, once all tests are preformed and read by the sensing device/GMR sensor chip 280, the cartridge assembly 200 may be ejected from the cartridge reader unit 100. In accordance with an embodiment, this may be automatically performed, e.g., mechanics within the housing 110 of the cartridge reader unit 100 may push the assembly 200 out of the housing 110, or performed manually (by way of a button or force) by the operator, for example.

In an embodiment, the system 300 described herein may utilize a pneumatic control system as disclosed in International Patent Application No. PCT/US2019/043720, entitled "SYSTEM AND METHOD FOR GMR-BASED DETECTION OF BIOMARKERS" and filed on the same day, which is hereby incorporated by reference herein in its entirety.

In an embodiment, the system 300 described herein may utilize a cartridge assembly (e.g., for sample preparation and delivery to the sensor(s)) as disclosed in International Patent Application No. PCT/US2019/043753, entitled "SYSTEM AND METHOD FOR SAMPLE PREPARATION IN GMR-BASED DETECTION OF BIOMARKERS" and filed on the same day, which is hereby incorporated by reference herein in its entirety.

In an embodiment, the system 300 described herein may sense, detect, and/or measure analytes at the GMR sensor as disclosed in International Patent Application No. PCT/US2019/043766, entitled "SYSTEM AND METHOD FOR SENSING ANALYTES IN GMR-BASED DETECTION OF BIOMARKERS and filed on the same day, which is hereby incorporated by reference herein in its entirety.

In an embodiment, the system 300 described herein may process signals at the GMR sensor as disclosed in International Patent Application No. PCT/US2019/043791, entitled "SYSTEM AND METHOD FOR PROCESSING ANALYTE SIGNALS IN GMR-BASED DETECTION OF BIOMARKERS and filed on the same day, which is hereby incorporated by reference herein in its entirety. For example, as noted above, at step 445, signals from the GMR sensor chip 280 are received and processed, e.g., via cartridge reader 310. In an embodiment, cartridge reader 310 is configured to perform the function of processing results from the GMR sensor chip 280 using a sample preparation control part having a memory reader unit and a sample preparation control unit (e.g., used to receive signals indicating that a cartridge assembly 200 has been inserted into the cartridge reader unit 100, read information stored in the memory chip 275, and generate pneumatic control signals and send them to the pneumatic system 330) and a signal processing part adapted to control electrical elements, prepare and collect signals, and process, display, store, and/or relay detection results to external systems, including processing measurements signals to obtain test results of the analyte detection, as described in detail in the –0504850 application. Additional features relating to the cartridge reader 310 and signal processor of the unit 100 are provided in greater detail later in this disclosure.

It should be understood that, with regards to FIGS. 1 and 2A-2D, the features shown are representative schematics of a cartridge reader unit 100 and cartridge assembly 200 that are part of the herein disclosed system 300 for detecting the analyte(s) in a sample. Accordingly, the illustrations are explanatory only and not intended to be limiting.

Turning back to the features of the sample processing card 210 and cartridge assembly 200 as previously discussed with reference to FIG. 2C, the arrangement, placement, inclusion, and number of features provided on a sample processing card 210 in the cartridge assembly 200 may be based on the test sample being analyzed and/or the test being performed (e.g., detection of biomarkers, detection of metal, etc.), for example. Further, the card 210 may be arranged, in some embodiments, such that there are zones on the card, and/or such that features are provided in different layers (however, such layers do not need to be distinct layers with a body thereof, rather, layered relative to one another at a depth or height (in the Z-direction)). In accordance with embodiments herein, the sample processing card 210 may be formed using parts that are laser cut to form inlets, channels, valve areas, etc. and sandwiched and connected/sealed together. In other embodiments, one or more layers of the sample processing card may be laser cut, laminated, molded, etc. or formed from a combination of processes. The method of forming the sample processing card 210 is not intended to be limiting. For illustrative purposes herein, some of the Figures include a depiction of layers to show positioning of parts of the sample processing card 210 relative to one another (e.g., positioning within the card relative to other features that are placed above and/or below). Such illustrations are provided to show exemplary depths or placement of the features (channels, valves, etc.) within a body of the sample processing card 210, without being limiting.

Generally, each card 210 has body 214 extending in a longitudinal direction along a longitudinal centerline A-A (provided in the Y-direction) when viewed overhead or from the top. In an embodiment, each card 210 may have dimensions defined by a length extending in the longitudinal direction (i.e., along or relative to centerline A-A), a width extend laterally to the length (e.g., in the X-direction), and a height (or depth or thickness) in the Z-direction, or vertical direction. In a non-limiting embodiment, the body 214 of the card 210 may be of a substantially rectangular configuration. In one embodiment, the cartridge receiver 130 (and/or any related tray) in the cartridge reader unit 100 is sized to accommodate the dimensions of the sample processing card 210, such that the card 210 may be inserted into the housing of the unit 100.

The illustrated structural features shown in the Figures of this disclosure are not intended to be limiting. For example, the numbers of sets, valves, metering chambers, membranes, mixing channels, and/or ports are not intended to be limited with regards to those shown. In some embodiments, more channels may be provided. In some embodiments, less channels may be provided. The number of valves is also not intended to be limiting.

Although the cartridge assembly 200 and sample processing card 210 may be described herein as being used with a reagent and a patient or medical blood sample, it should be noted that the herein disclosed cartridge assembly 200 is not limited to use with blood or solely in medical practices. Other fluids that may be separable and combined with a reagent or reactionary material may be employed in the herein disclosed cartridge for assaying. Other samples may derive from saliva, urine, fecal samples, epithelial swabs, ocular fluids, biopsies (both solid and liquid) such as from the mouth, water samples, such as from municipal drinking water, tap water, sewage waste, ocean water, lake water, and the like.

Figure 5A:
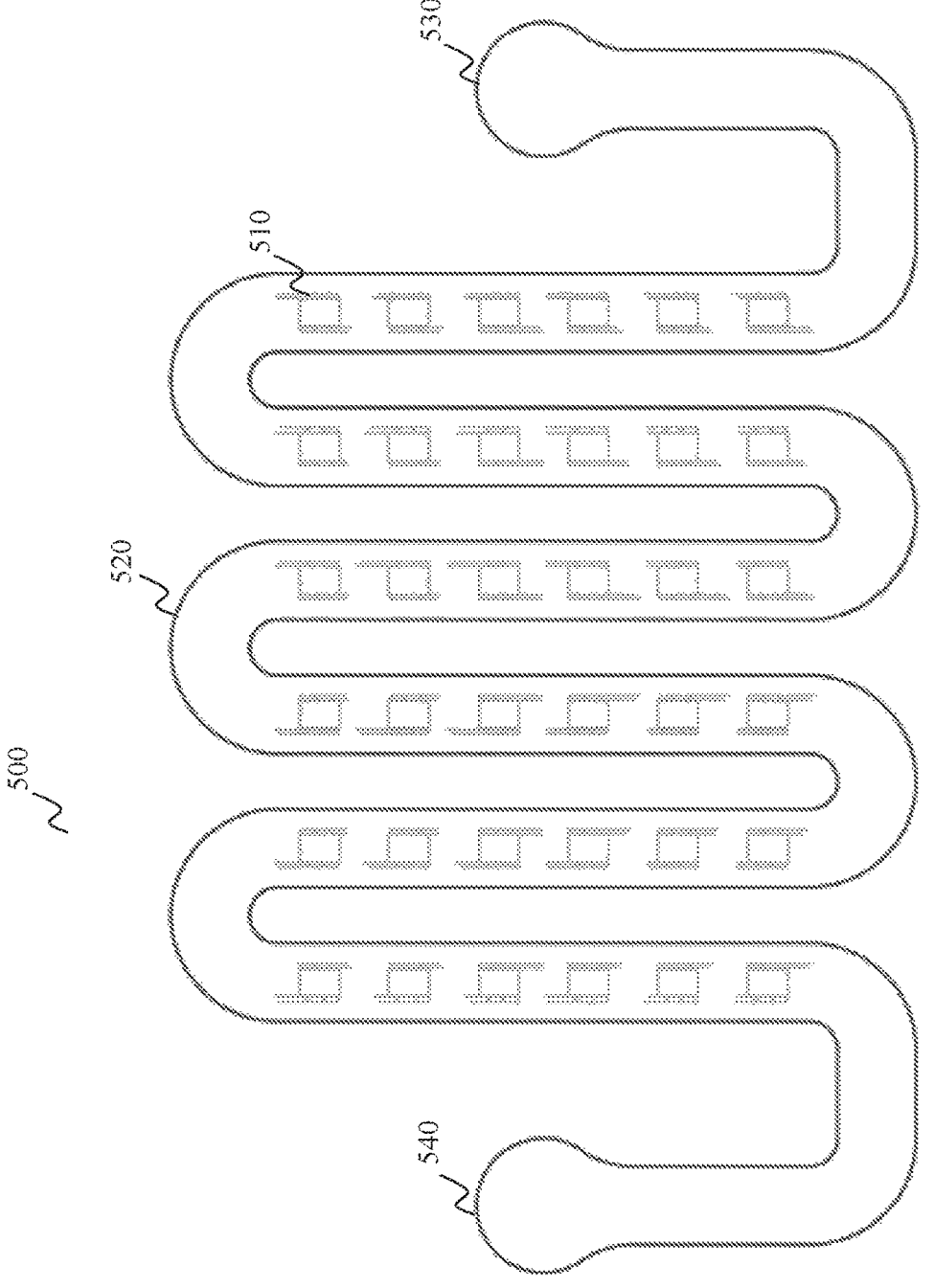
FIG. 5A shows a serpentine channel comprising a plurality of GMR sensors, in accordance with an embodiment.

A sensing microfluidic device comprises one or more microfluidic channels and a plurality of sensor pads disposed within the one or more microfluidic channels. Referring now to FIG. 5A there is shown an exemplary channel 500 in accordance with some embodiments. Channel 500 is shown as serpentine in structure, but it need not be so limited in geometry. Channel 500 comprises a plurality of GMR sensors 510 disposed within the channel body 520. GMR sensors 510 may be all identically configured to detect a single analyte, the redundancy allowing for enhanced detection. GMR sensors 510 may also be all configured differently to detect a myriad of analytes or a combination of differently configured sensors with some redundancies. Channel 500 further comprises a channel entrance 530 where any samples, reagents, bead suspensions, or the like enter channel body 520. Flow through channel body 520 may be mediated under positive pressure at channel entrance 530 or under vacuum applied at channel exit 540.

Figure 5B:
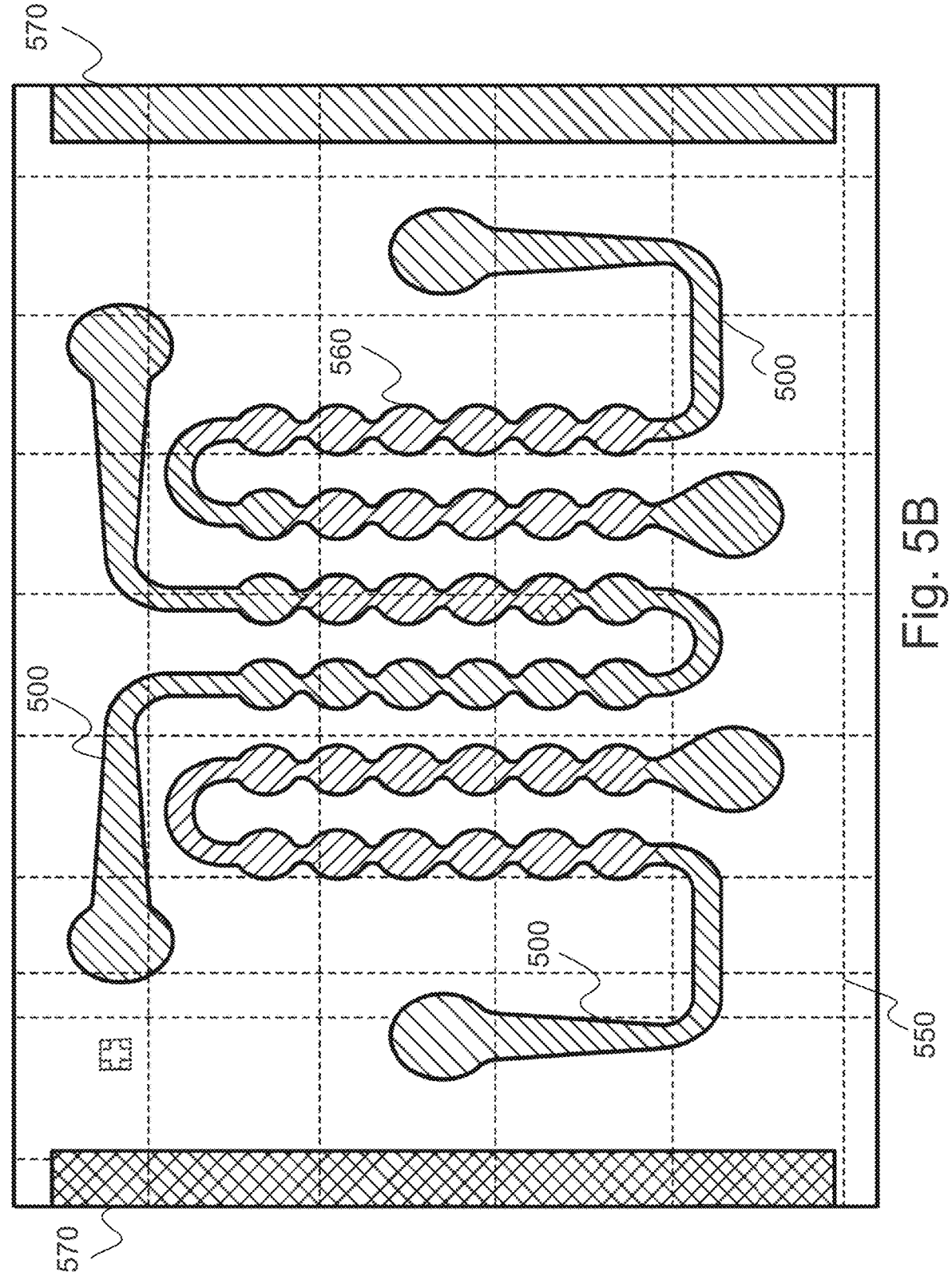
FIG. 5B shows an arrangement of a plurality of channels on a substrate for GMR sensing, in accordance with an embodiment.

FIG. 5B shows a plurality of channels 500 disposed within base 550. Each channel 500 features channel expansions 560 which is an expanded area surrounding each GMR sensor 510 (FIG. 5A; not shown in FIG. 5B for clarity). Without being bound by theory, it is postulated that channel expansions 560 provide a means for better mixing of materials as they pass over the GMR sensors. At the periphery of base 550 are disposed a pair of contact pads 570 which serve as an electrical conduit between the GMR sensors located in channel expansions 560 and the rest of the circuitry. GMR sensors 510 are electronically linked via wiring (not shown) to contact pads 570.

Figure 6A:
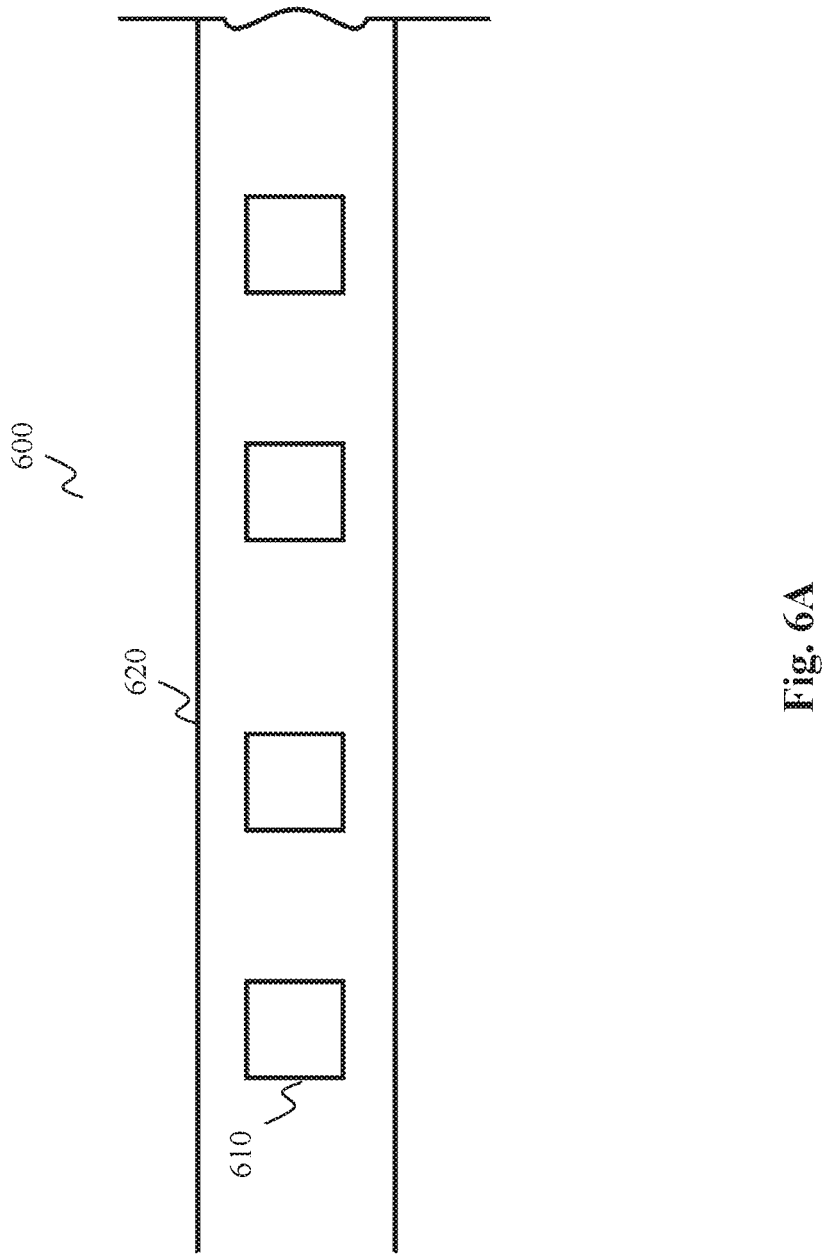
FIG. 6A shows a cross-section of a linear length of channel with GMR sensors disposed therein, in accordance with an embodiment.
Figure 6B:
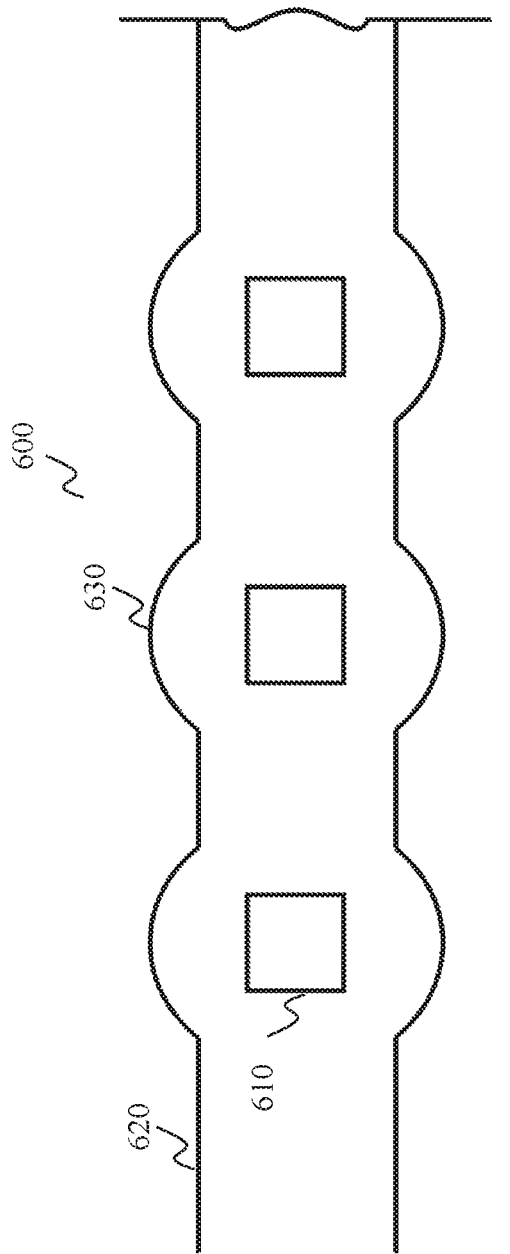
FIG. 6B shows a cross-section of a linear length of channel having circular channel expansions where GMR sensors reside, in accordance with an embodiment.
Figure 6C:
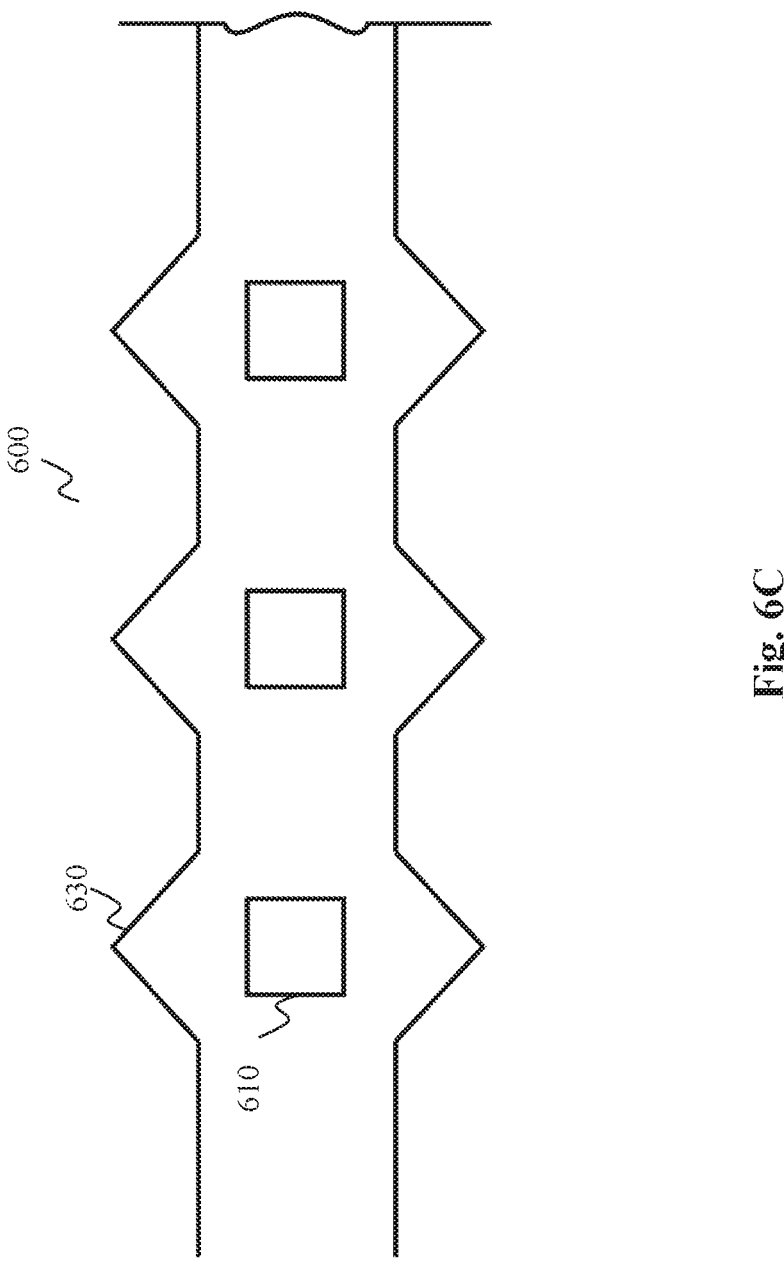
FIG. 6C shows a cross-section of a linear length of channel having square channel expansions where GMR sensors reside, in accordance with an embodiment.

FIG. 6A shows a cross-section of a channel 600 comprising a plurality of GMR sensors 610 in a channel body 620 having a straight configuration. In such embodiments, the flow direction of materials can be from either direction. In other embodiments, as indicated in FIG. 6B, channel 600 can comprise a similar plurality of GMR sensors 610 incorporated within channel body 620 at channel expansions 630 that are shaped roughly circular or oval. In still further embodiments, as indicated in FIG. 6C, channel 600 can have GMR sensors 610 disposed in channel expansions 630 that are roughly square or rectangular. Although not shown such square or rectangular channel expansions can also be disposed so that the sides, rather than the points of the square or rectangle are part of channel expansion 630 rather than the vertices. Other configures of channel expansions 1030 are possible, including that shown in FIG. 6D where channel 600 has GMR sensors 610 disposed in triangular (or trapezoidal)-shaped. Channel expansions 630 can have any geometry and can be selected for desired flow and mixing properties, as well as residence times over GMR sensors 610.

Figure 6D:
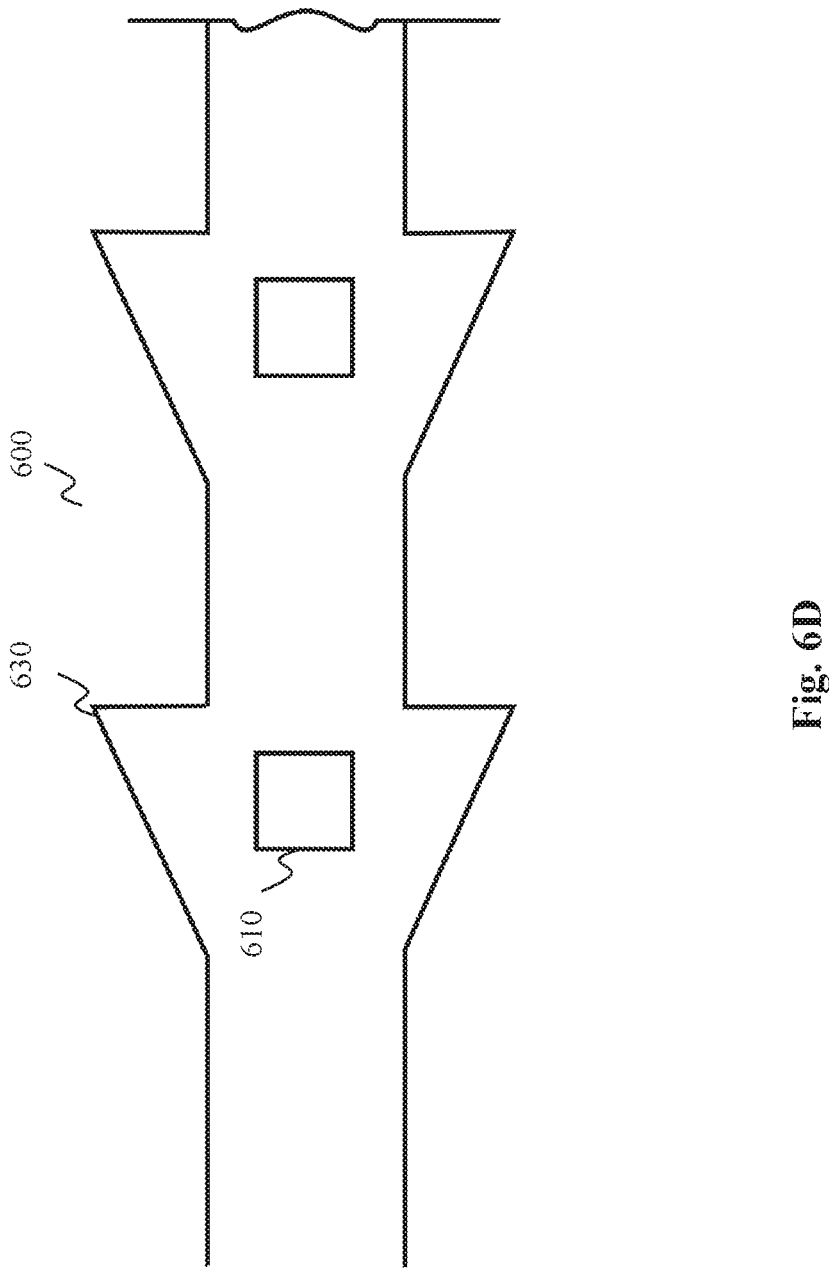
FIG. 6D shows a cross-section of a linear length of channel having triangular channel expansions where GMR sensors reside, in accordance with an embodiment.
Figure 6E:
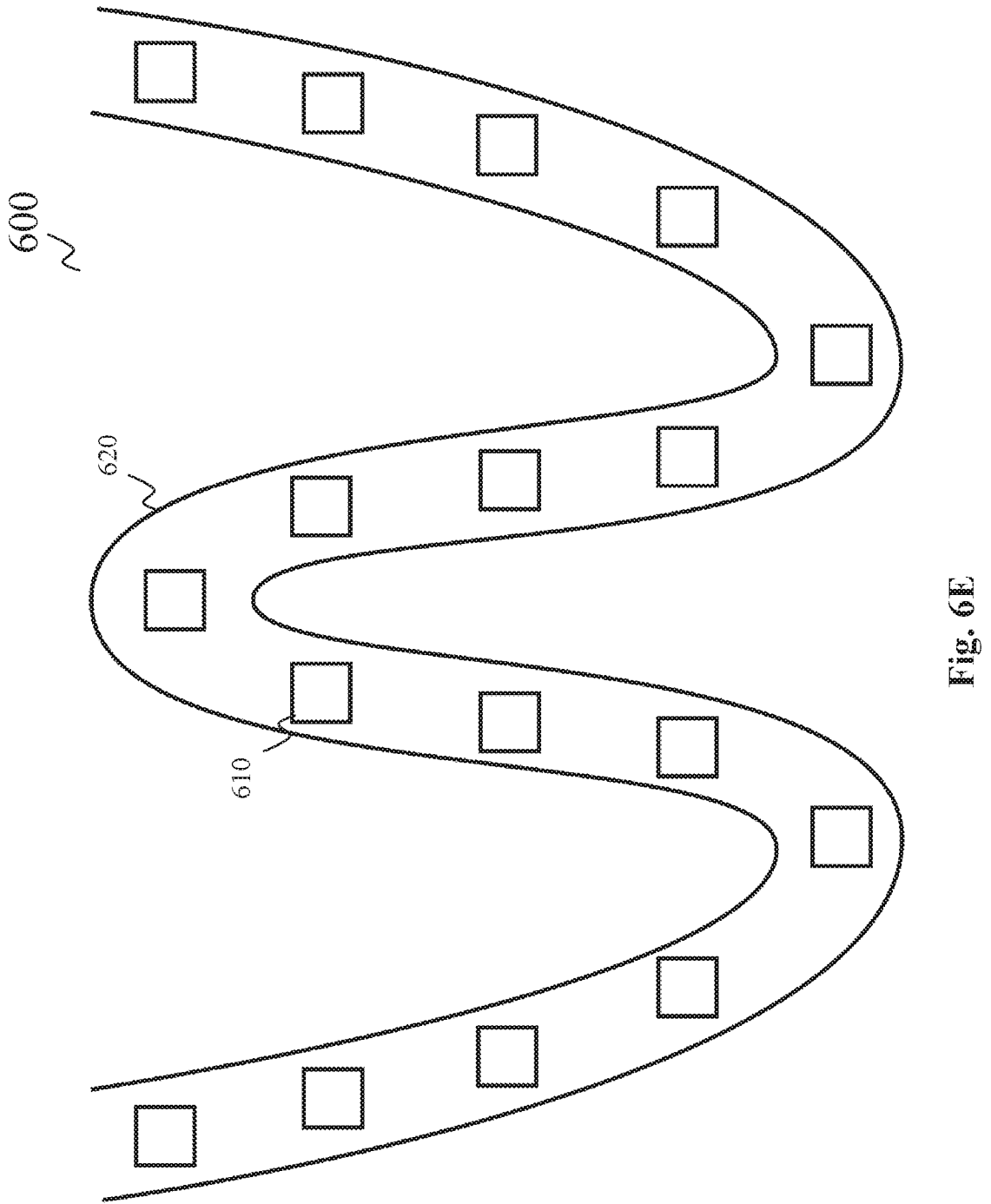
FIG. 6E shows a section of a serpentine channel with GMR sensors disposed therein, in accordance with an embodiment.
Figure 6F:
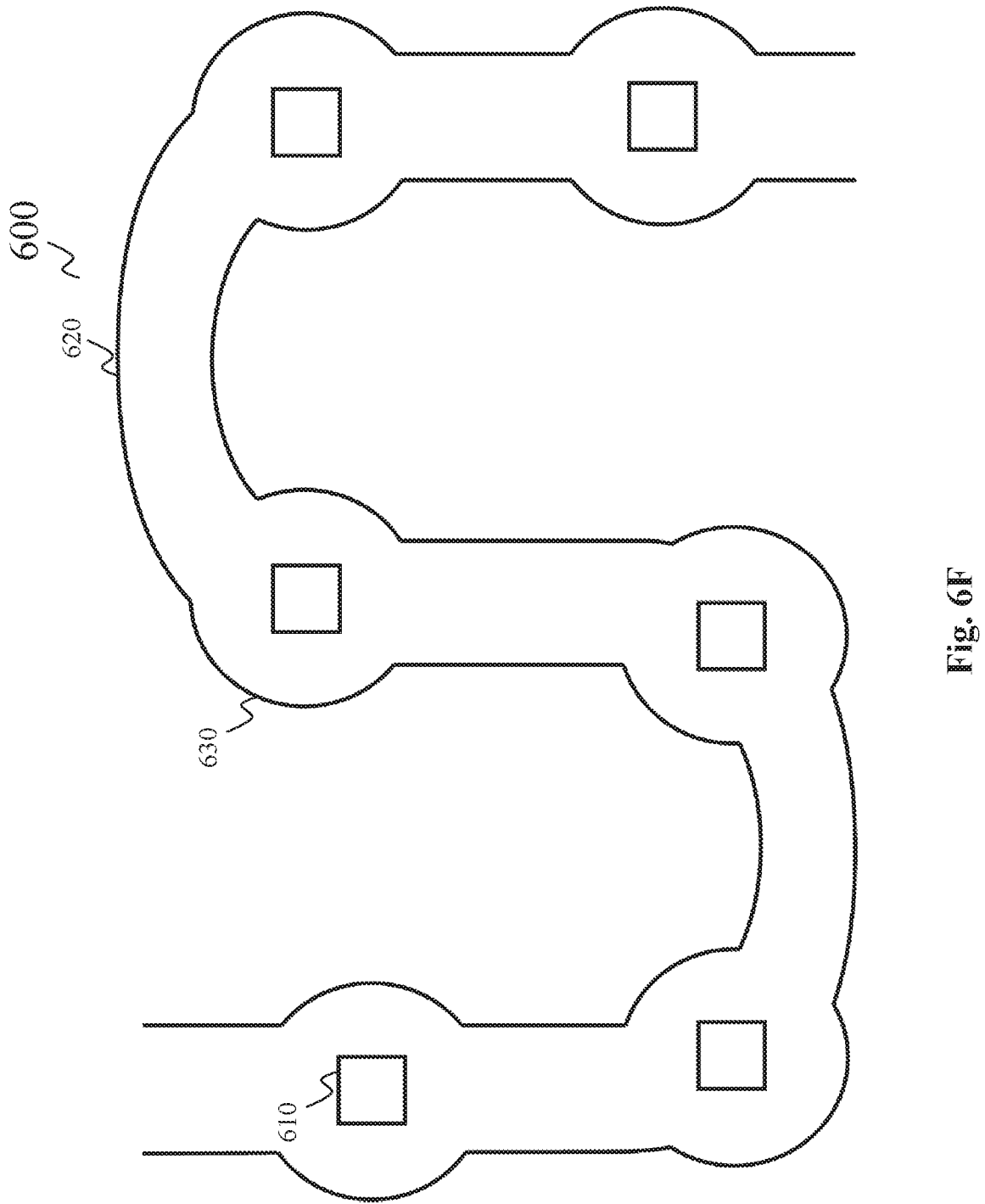
FIG. 6F shows a section of a serpentine channel with GMR sensors disposed circular channel expansions, in accordance with an embodiment.
Figure 6G:
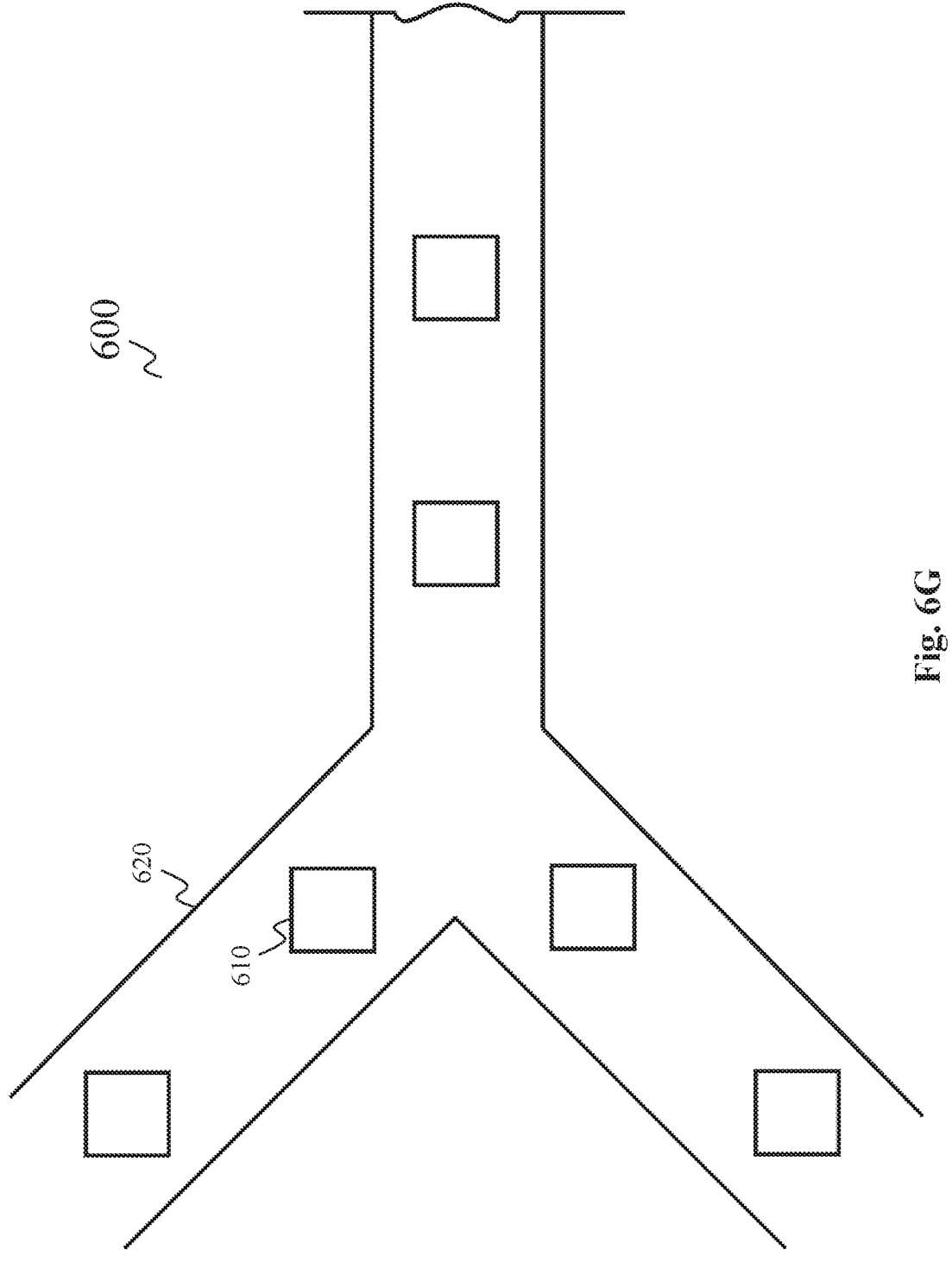
FIG. 6G shows a section of a channel having a bifurcation and with GMR sensors disposed therein, in accordance with an embodiment.

As indicated in FIG. 6D, channel 600 may have a channel body 620 that is serpentine in shape, with GMR sensors 610 disposed along the length of the serpentine path. In some embodiments, such serpentine structures may allow for more sensors to packed into a small area compared to a linear channel 600. As shown FIG. 6F, channel 600 can incorporate both a body 620 that is serpentine in structure as well as having channel expansions 630 wherein GMR sensors 610 reside. Further optional structural features of channel 1000 are shown in FIG. 6G which shows channel 600 with GMR sensors disposed therein and which has a channel body 620 that incorporates a bifurcation. In some such embodiments, the flow direction can be modulated in either direction, depending on the exact application. For example, when flowing to the left in the drawing, materials can be split into two different pathways. This may represent, for example, the use of different GMR sensors 610 along the two bifurcation arms. The width of channel body 620 can vary before and after the bifurcation and can be selected for specific flow characteristics.

In some embodiments, referring as non-limiting examples to FIGS. 6A, 6B, 6C, 6D, 6F, and 6G, multiplex detection schemes are provided, for example, for performing multiplex assays for detecting more than one analyte in the same query sample or in difference query samples, may be achieved by spatially disposing different GMR sensors 610 within channel 620, wherein each different GMR sensor 610 is configured with differential tagging and/or coating such that each differentially tagged and/or coated GMR sensor 610 interacts with different molecules, such as different reporter proteins, different detection proteins, different members of binding pairs, and/or the like described herein and throughout, thereby allowing for the detection of different analytes in the same sample, or different analytes in different samples, to be detected.

Figure 7:
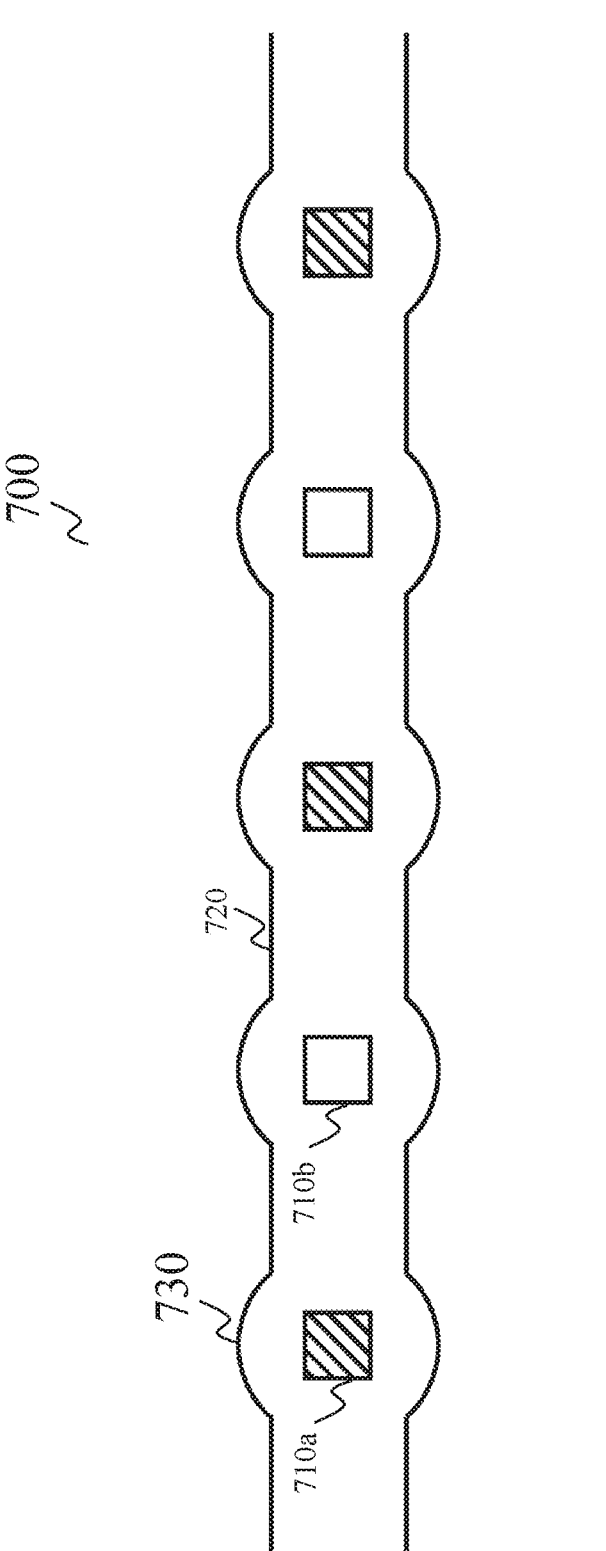
FIG. 7 shows a cross-section of a linear length of channel having circular channel expansions where differing GMR sensors reside, in accordance with an embodiment.

Referring now to FIG. 7, there is shown channel 700 which incorporates within channel body 720, channel expansions 730 in which different GMR sensors 710a and 710b are disposed. Although FIG. 7 shows different GMR sensors 710a and 710b alternating, it need not follow this pattern. For example, all of one type of GMR sensors 710a may be clustered together adjacent to each other and likewise all of the other type of GMR sensors 710b may be clustered together. In some embodiments, such alternating GMR sensors 710a and 710b Referring back to FIG. 6G, different sensors may also appear along the separated lines of a bifurcation.

In some embodiments, referring as a non-limiting example to FIG. 7, multiplex detection schemes are provided, for example, for performing multiplex assays for detecting more than one analyte in the same query sample or in difference query samples, may be achieved by spatially disposing different GMR sensors 710a and 710b within channel 720, wherein each different GMR sensor 710a and 710b is configured with differential tagging and/or coating such that each differentially tagged and/or coated GMR sensor 710a and 710b interacts with different a molecule, such as a different reporter protein, a different detection protein, a different members of binding pair, and/or the like described herein and throughout, thereby allowing for the detection of different analytes in the same sample, or different analytes in different samples, to be detected.

Figure 8A:
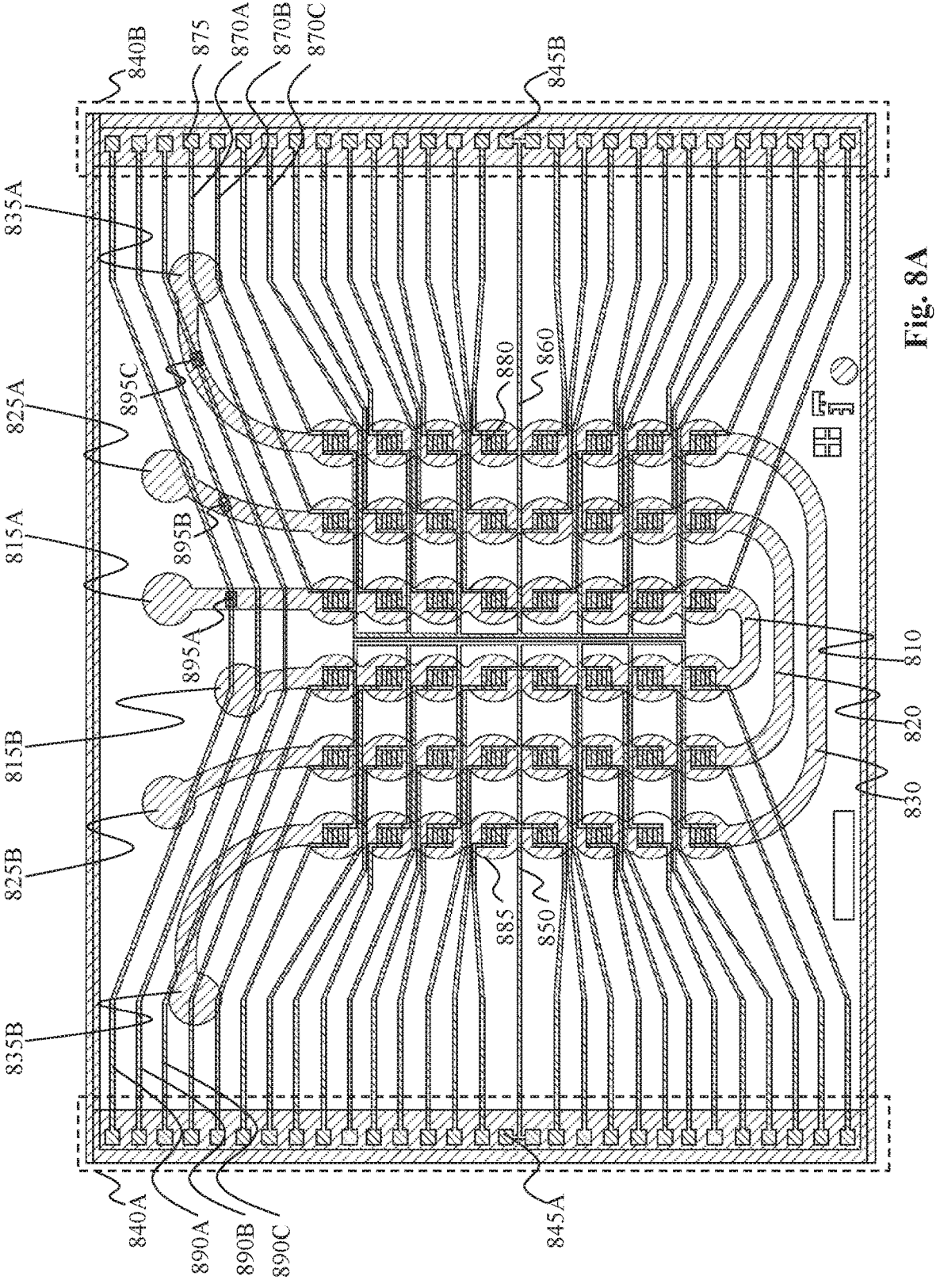
FIG. 8A shows a GMR sensor chip having a plurality of channels with GMR sensors incorporated at circular expansions and the connectivity of the GMR sensors to contact pads via wiring, in accordance with an embodiment.
Figure 8B:
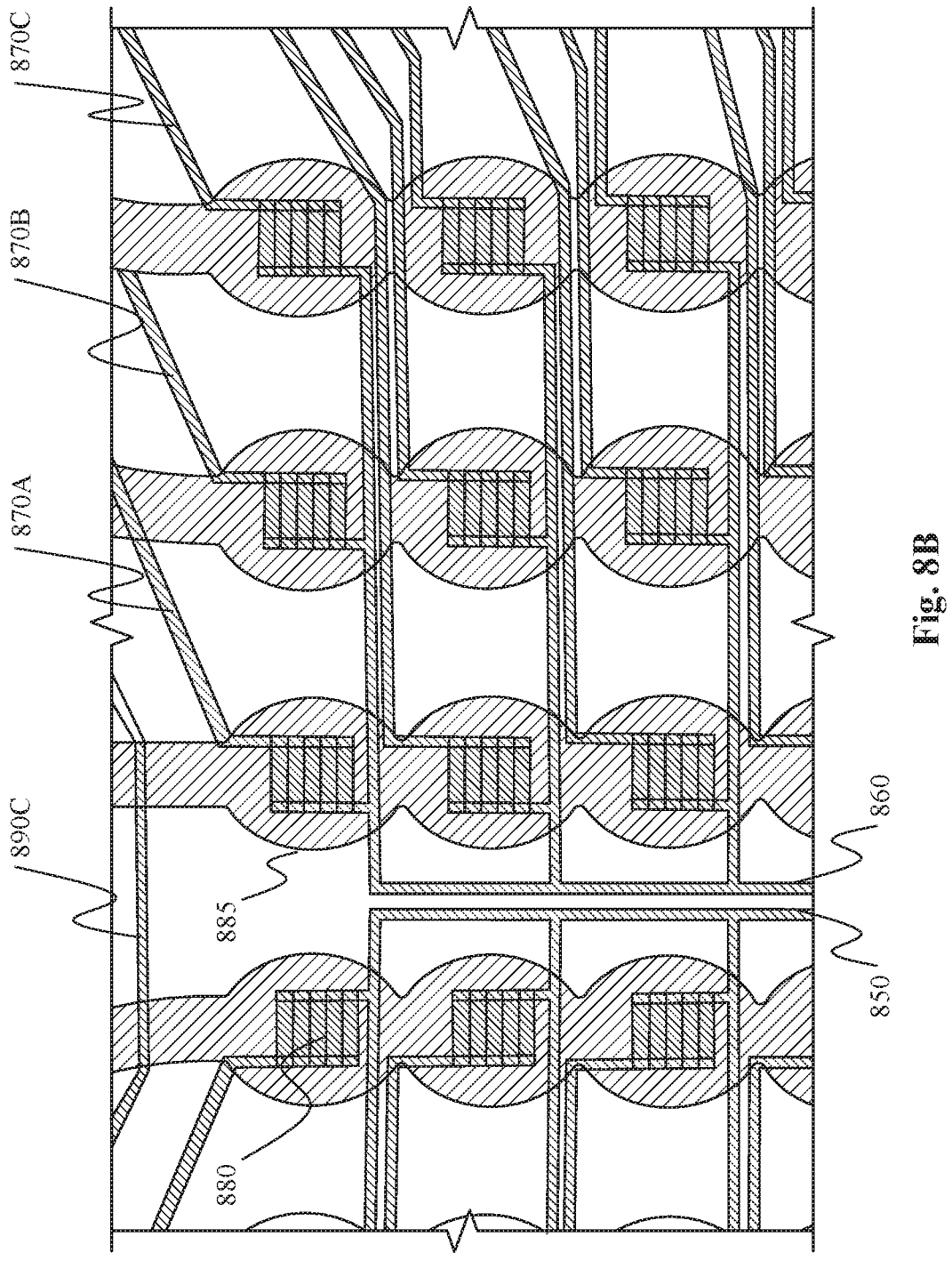
FIG. 8B shows an expansion of the area around the GMR sensors in the circular channel expansions showing the wiring network, in accordance with an embodiment.
Figure 8C:
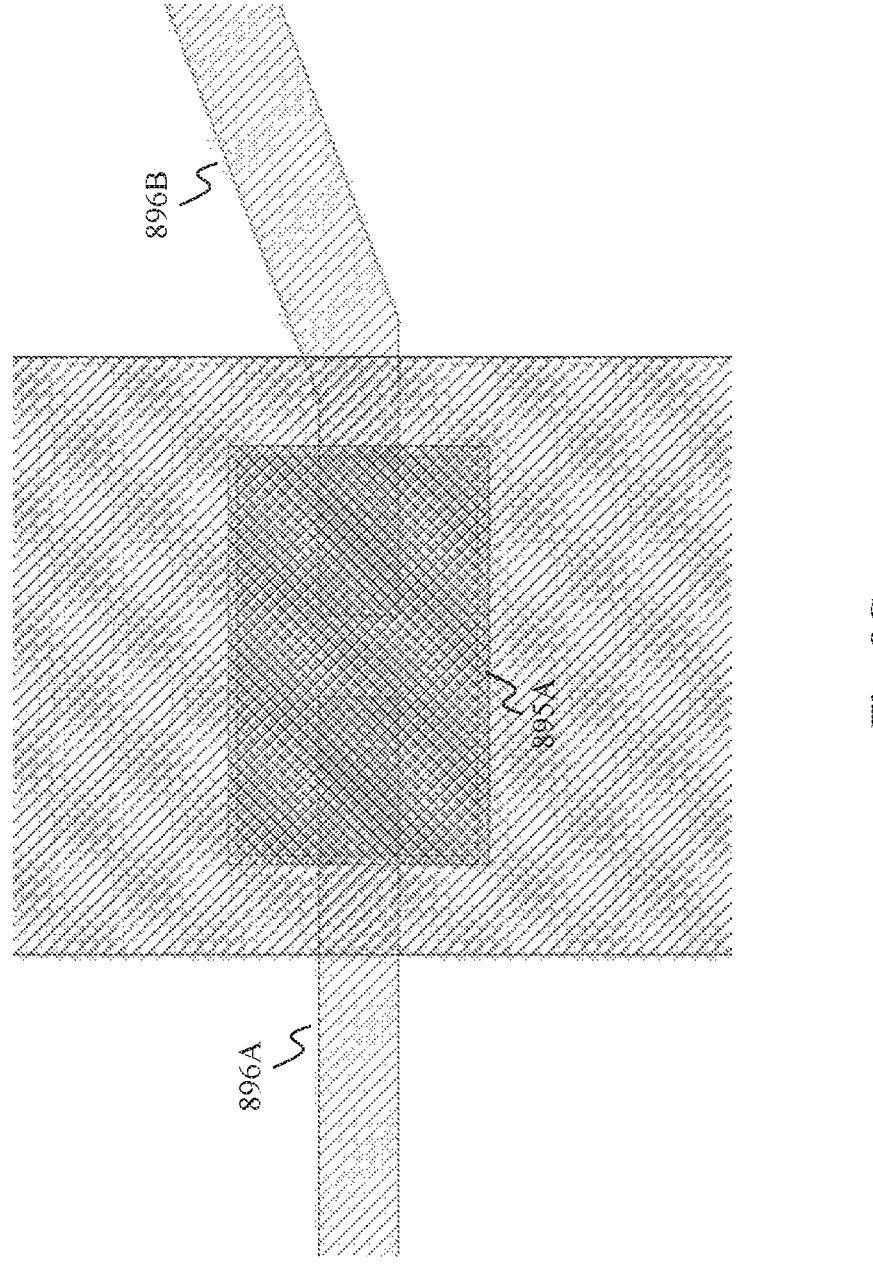
FIG. 8C shows the structure of a switch, in accordance with an embodiment.

FIGS. 8A, 8B and 8C schematically illustrate the structure of a GMR sensor chip 280 which can be mounted on the cartridge assembly 200 according to an embodiment of the present disclosure. As shown in FIG. 8A, the GMR sensor chip 280 includes: at least one of channels 810, 820 and 830 arranged approximately in the center of the chip; a plurality of GMR sensors 880 disposed within the channels; electric contact pads 840A, 840B arranged on two opposing ends of the GMR sensor chip; and metal wires 850, 860, 870A, 870B, 870C, 890A, 890B, 890C coupled to the electric contact pads 840A, 840B.

The channels 810, 820 and 830 each can have a serpentine shape to allow for more sensors to be packed inside. A plurality of channel expansions 885 can be arranged along the channels to receive the plurality of GMR sensors. Fluid to be tested flows into and out of the channels 810, 820, 830 via channel entrances 815A, 825A, 835A and channel exits 815B, 825B, 835B, respectively. Although FIG. 8A shows that the GMR sensors 880 are arranged in an 8×6 sensor array, with 16 sensors received in each of three channels 810, 820, 830, other combinations can be used to satisfy the specific needs of the analyte to be sensed.

In some embodiments, referring as non-limiting examples to FIGS. 8A and 8B, multiplex detection schemes, for example, for performing multiplex assays for detecting more than one analyte in the same query sample or in difference query samples, may be achieved by spatially disposing one or more different GMR sensors 880, or one or more different sets of GMR sensors 880, within one or more of channels 810, 820, and 830, wherein each different GMR sensor 880 or each different set of GMR sensors 880 is configured with differential tagging and/or coating such that each differentially tagged and/or coated GMR sensor 880 or sets of GMR sensor 880 set interacts with different molecules, such as different reporter proteins, different detection proteins, different members of binding pairs, and/or the like described herein and throughout, thereby allowing for the detection of different analytes in the same sample, or different analytes in different samples, to be detected. In some embodiments, a different analyte for the same query sample or from different query samples is detected from each channel 810, 820, and/or 830.

The electric contact pads 840A, 840B comprise a plurality of electric contact pins. The metal wires 850, 860, 870A, 870B, 870C connect the GMR sensors to corresponding electric contact pins 845A, 845B, 875. The electric contact pads 840A, 840B are in turn connected to the electrical contact pads 290 provided on the cartridge assembly 200. When the cartridge assembly 200 is inserted to the cartridge reader 310, electric connection is formed between the GMR sensor chip 280 and the cartridge reader 310 to enable sending of measurement signals from the GMR sensors to the cartridge reader 310.

FIG. 8B shows more details of the GMR sensors. For example, each GMR sensor can be comprised of five GMR strips which are connected in parallel. At one end, each GMR sensor is connected by one of two main metal wires (i.e., either wire 850 or 860) to one of two common pins (i.e., either pin 845A or 845B). The other ends of the GMR sensors are connected by separate metal wires 870A, 870B, 870C to distinct pins 875 on the electric contact pads 840A or 840B.

FIG. 8A also shows fluid detection metal wires 890A, 890B, 890C which are arranged in the proximity of the channel entrances and/or exits, each corresponding to one of the channels. The fluid detection function is carried out by switches 895A, 895B, 895C arranged in the respective fluid detection metal wires. FIG. 8C shows the structure of the switch 895A in detail. In response to recognition that conductive fluid (for example, plasma) flows over it, the switch 895A can couple the wire 896A on one side to the wire 896B on the other side, generating a fluid detection signal.

Figure 9:
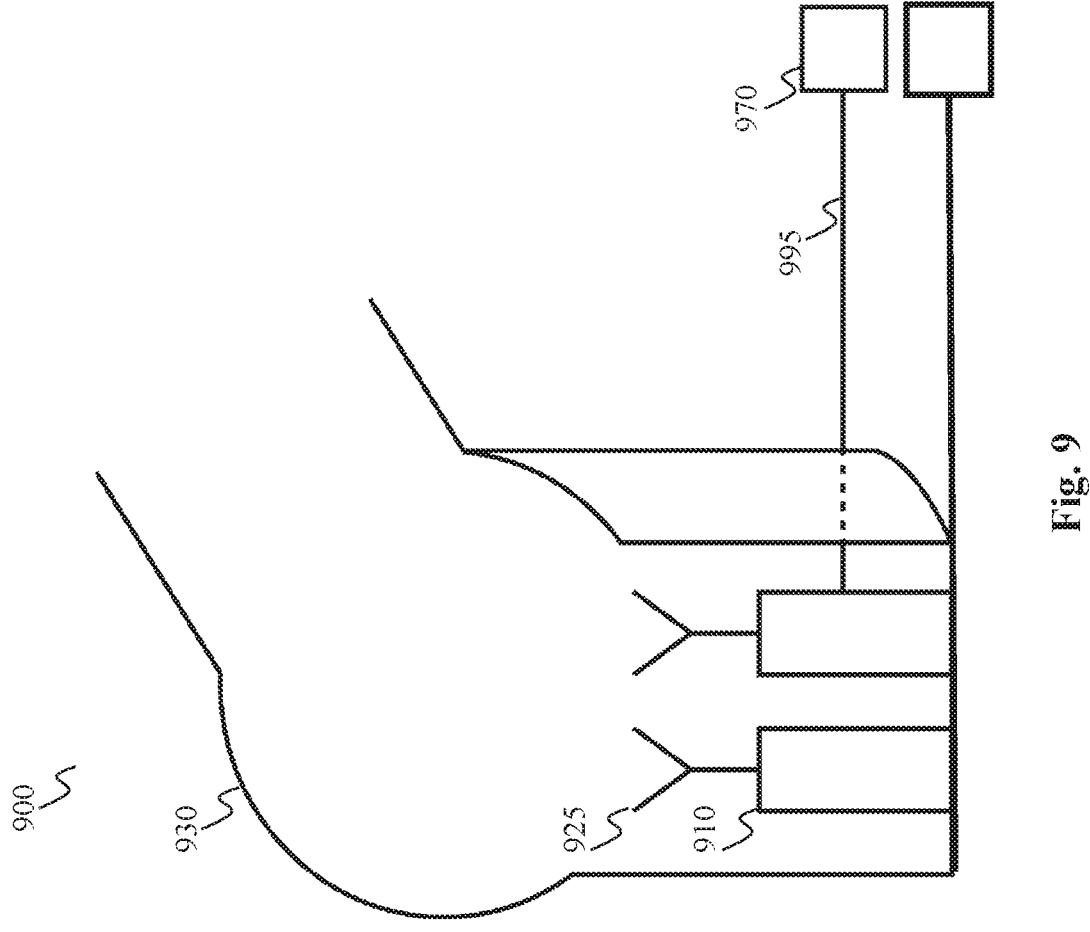
FIG. 9 shows a cross-section representation of a circular channel expansion and the GMR residing therein along with attachment to a contact pad via a wire, in accordance with an embodiment.

The structure and wiring of the GMR sensor chip shown in FIGS. 8A-C are only exemplary in nature, it will be apparent to those skilled in the art that other structures and wirings are feasible to achieve the same or similar functions. Referring now to FIG. 9, there is shown a cross-sectional view of channel 900 at a channel expansion 930. Disposed within channel expansion 930 is GMR sensor 910 on which is immobilized one or more biomolecules 925. Immobilization of biomolecule 925 to GMR sensor 910 is via conventional surface chemistry (shown in some further detail in FIG. 14). Biomolecule 925 may be a peptide or protein, DNA, RNA, oligosaccharide, hormone, antibody, glycoprotein or the like, depending on the nature of the specific assay being conducted. Each GMR sensor 910 is connected by wire 995 to a contact pad 970 located outside of channel 900. In some embodiments, wire 995 is connect to GMR sensor 910 at the bottom of the sensor.

Figure 10A:
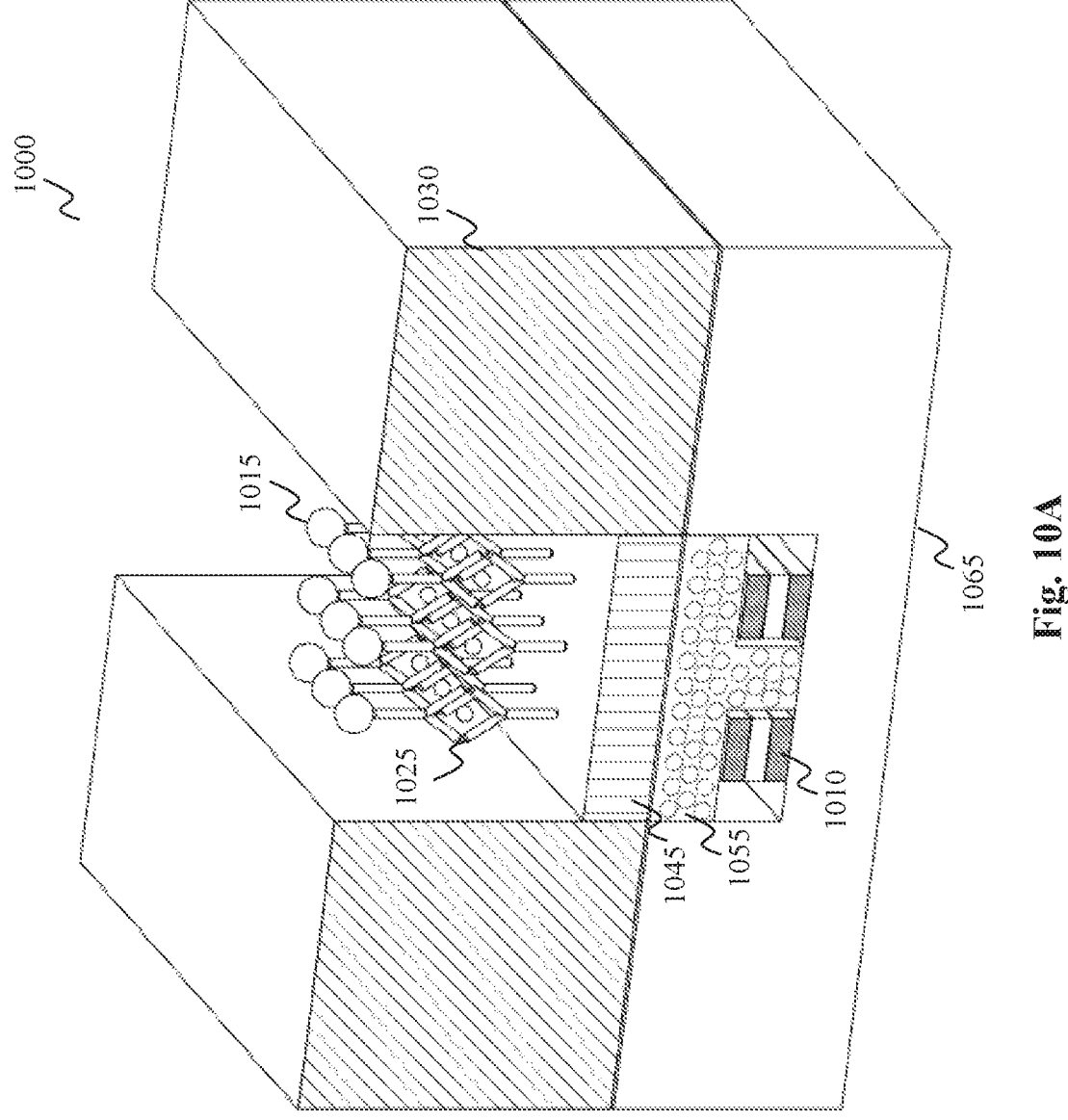
FIG. 10A shows a cross-section representation of a channel with no expansion and the GMR residing therein along with a biosurface layer disposed over the GMR sensor, in accordance with an embodiment.

Referring now to FIG. 10A, there is shown a more detailed cross-sectional view of a channel 1000 having a channel body 1030 lacking a channel expansion at the location of a GMR sensor 1010. Biomolecule 1025 is immobilized with respect to the sensor via attachment to a biosurface 1045. Such biosurface immobilization chemistry is known in the art. See, for example, Cha et al. "Immobilization of oriented protein molecules on poly(ethylene glycol)-coated Si(111)," *Proteomics* 4:1965-1976, (2004); Zellander et al. "Characterization of Pore Structure in Biologically Functional Poly(2-hydroxyethyl methacrylate)-Poly(ethylene glycol) Diacrylate (PHEMA-PEGDA)," *PLOS ONE* 9(5):e96709, (2014).

In some embodiments, biosurface 1045 comprises polymer composition comprising at least two hydrophilic polymers crosslinked with a crosslinking reagent. Such polymer compositions comprising at least two hydrophilic polymers and a crosslinking reagent, comprising such polymer compositions, polymer compositions and/or biosurfaces further comprising a biomolecule, such as a nucleic acid, a protein, and antibody, and the like, and methods of crosslinking and/or preparing such polymer compositions and/or biosurfaces are described in U.S. Provisional Patent Application No. 62/958,510, entitled "POLYMER COMPOSITIONS AND BIOSURFACES COMPRISING THEM ON SENSORS," filed on Jan. 8, 2020, which is hereby incorporated by reference in its entirety.

In some embodiments, biosurface 1045 comprises a polymer composition comprising a PEG polymer crosslinked with PHEMA.

In some embodiments, the crosslinking reagent is represented by Formula (I):

$$PA\text{-}L\text{-}PA \qquad\qquad (I)$$

wherein each PA is a photo- or metal-activated or activated group, and L is a linking group. In some embodiments, each PA is independently selected from a photo-activated group or a metal-activated group, and L is a linking group. In some embodiments, each PA is the same and in other embodiments each PA is different. In some embodiments, each PA independently comprises an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone. In some embodiments, each PA independently comprises an azide ($-N_3$), or a diazo ($-N_2$) group. In some embodiments, such polymer compositions do not comprise a block co-polymer of a PEG polymer and a PHEMA polymer.

In some embodiments PA is photo- or metal-activated to form a nitrene intermediate capable of C—H and/or O—H insertion. See, for example, "Photogenerated reactive intermediates and their properties," Chapter 2 in *Laboratory Techniques in Biochemistry and Molecular Biology*, Elsevier Press, 12:8-24 (1983). In some embodiments, PA is metal activated to form a carbene or carbenoid intermediate capable of C—H and/or O—H insertion. See, for example, Doyle et al. "Catalytic Carbene Insertion into C—H Bonds," *Chem. Rev.* 2:704-724 (2010).

In some embodiments, each PA is an azide ($-N_3$) moiety and photoactivation generates nitrene intermediates capable of C—H and/or O—H insertion thereby mediating crosslinking of at least to hydrophilic polymers, such as PEG and PHEMA polymers. In some embodiments, each PA is a diazo ($-N_2$) and metal catalyzed decomposition reaction forms a carbene or carbenoid intermediate capable of C—H and/or O—H insertion thereby mediating crosslinking of PEG and PHEMA polymers. Both azide and diazo preparations are well known in the art, and in the case of azide are readily prepared by $S_N{}^2$ displacement reaction of azide anion, $N_3{}^-$ with an appropriate organic moiety possessing a leaving group.

In some embodiments, L comprises at least one Y and one or more X, wherein: (a) each at least one Y is independently selected from the group consisting of: an optionally substituted divalent alkylene; an optionally substituted arylene; and optionally substituted divalent heteroaromatic ring moiety; having from 1 to 20 atoms; an alkylene, $-(CR_2)_p-$, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl; and/or a divalent heteroaromatic ring having from 4 to 20 carbon atoms and contains at least one heteroatom selected from the group consisting of O, N, and S; and (b) each X is independently selected from the group consisting of alkylene, $-NR_1-$, $-O-$, $-S-$, $-S-S-$, $-CO-NR_1-$, $-NR_1-CO-$, $-CO-O-$, $-O-CO-$, $-CO-$, and a bond, wherein $R_1$ is independently selected from the group consisting of H and lower alkyl.

In some embodiments, the crosslinking reagent is represented by Formula (II):

$$PA-Y_1-X_1-X_2-X_3-X_4-X_5-X_6-X_7-X_8-X_9-Y_2-PA \qquad (II)$$

wherein each PA is a photo-activated group or a metal-activated group, and $Y_1-X_1-X_2-X_3-X_4-X_5-X_6-X_7-X_8-X_9-Y_2$ is a linking group. In some embodiments, each PA independently comprises an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone. In some embodiments, each PA independently comprises an azide ($-N_3$), or a diazo ($-N_2$) group. In some embodiments, $Y_1-X_1-X_2-X_3-X_4-X_5-X_6-X_7-X_8-X_9-Y_2$ is a linking group. In some embodiments, each of $X_1$, $X_2$, $X_3$, $X_4$, $X_5$, $X_6$, $X_7$, $X_8$, and $X_9$ is independently selected from the group consisting of alkylene, $-NR_1-$, $-O-$, $-S-$, $-S-S-$, $-CO-NR_1-$, $-NR_1-CO-$, $-CO-O-$, $-O-CO-$, $-CO-$, and a bond, wherein $R_1$ is independently selected from the group consisting of H and lower alkyl. In some embodiments, each of $Y_1$ and $Y_2$ are each, independently, selected from the group consisting of: an optionally substituted divalent alkylene; an optionally substituted arylene; and optionally substituted divalent heteroaromatic ring moiety; having from 1 to 20 atoms; an alkylene, $-(CR_2)_p-$, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl; and/or a divalent heteroaromatic ring having from 4 to 20 carbon atoms and contains at least one heteroatom selected from the group consisting of O, N, and S.

The term "alkyl," as used herein, alone or in combination, refers to a straight-chain or branched-chain alkyl radical containing from 2 to 20 carbon atoms. In some embodiments, the alkyl may comprise from 2 to 10 carbon atoms. In further embodiments, the alkyl group may comprise from 2 to 6 carbon atoms. Alkyl groups may be optionally substituted as defined herein below. Examples of alkyl group (given as radicals) include, without limitation methyl, ethyl, n-propyl, isopropyl, n-butyl, isobutyl, sec-butyl, tert-butyl, pentyl, iso-amyl, hexyl, octyl, nonyl and the like.

The term "alkenyl," as used herein, alone or in combination, refers to a straight-chain or branched-chain hydrocarbon radical having one or more double bonds and containing from 2 to 20 carbon atoms. In some embodiments, the alkenyl group may comprise from 2 to 6 carbon atoms.

The term "alkenylene" refers to a carbon-carbon double bond system attached at two or more positions such as ethenylene [($-CH=CH-$), ($-C::C-$)]. Examples of suitable alkenyl radicals include propenyl, 2-methylpropenyl, 1,4-butadienyl and the like.

The term "alkynyl," as used herein, alone or in combination, refers to a straight-chain or branched chain hydrocarbon radical having one or more triple bonds and containing from 4 to 20 carbon atoms. In certain embodiments, said alkynyl comprises from 4 to 6 carbon atoms. Examples of alkynyl groups include butyn-1-yl, butyn-2-yl, pentyn-1-yl, 3-methylbutyn-1-yl, hexyn-2-yl, and the like.

The term "aryl," as used herein, alone or in combination, means a carbocyclic aromatic system containing one, two or three rings wherein such rings may be attached together in a pendent manner or may be fused. In some embodiments, "Aryl" groups include groups having one or more 5- or 6-member aromatic rings. Aryl groups contain no heteroatoms in the aryl rings. Aryl groups are optionally substituted with one or more non-hydrogen substituents.

The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylene," refers to a divalent aromatic radical which consists of the elements carbon and hydrogen. The divalent aromatic radical may include only one benzene ring, or a plurality of benzene rings as in diphenyl, naphthyl, oranthracyl.

The term "aralkyl," as used herein, alone or in combination, refers to an aryl group attached to the parent molecular moiety through an alkyl group.

The term "heteroaryl" and "heteroaromatic rings", as used herein, refer to and include groups having one or more aromatic rings in which at least one ring contains a heteroatom (a non-carbon ring atom). Heteroaryl groups include those having one or two heteroaromatic rings carrying 1, 2 or 3 heteroatoms. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyridinyl, pyrazinyl, pyrimidinyl, quinolinyl, and purinyl groups.

The term "lower alkyl" refers to, for example, $C_1$-$C_9$ alkyl, $C_1$-$C_8$ alkyl, $C_1$-$C_7$ alkyl, $C_1$-$C_6$ alkyl, $C_1$-$C_6$ alkyl, $C_1$-$C_5$ alkyl, $C_1$-$C_4$ alkyl, $C_1$-$C_3$ alkyl, or $C_1$-$C_2$ alkyl.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $-CH_2CH_3$), fully substituted (e.g., $-CF_2CF_3$), monosubstituted (e.g., $-CH_2CH_2F$) or substituted at a level anywhere in-between fully substituted and monosubstituted (e.g., $-CH_2CF_3$). Where substituents are recited without qualification as to substitution, both substituted and unsubstituted forms are encompassed.

Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." The term "lower," as used herein, alone or in combination, means containing from 1 to and including 6 carbon atoms.

In some embodiments, the crosslinking reagent comprises bis[2-(4-azidosalicylamido)ethyl]disulfide or dithiobis(phenylazide).

In some embodiments, L in Formula (I) can be any organic fragment that will support the presence of each PA moiety. It can be a simple $C_2$-$C_{20}$ hydrocarbon chain that is straight chained or branched. Such hydrocarbons can include fluorinated variants with any degree of fluorine substitution. In some embodiments, LG can include aromatic hydrocarbons including, without limitation, benzene, naphthalene, biphenyl, binaphthyl, or combinations of aromatic structures with $C_2$-$C_{20}$ hydrocarbon chains. Thus, in some embodiments, LG can be alkyl, aryl, or aralkyl in structure. In some embodiments, alkyl linking groups may have one or more carbons in their chains substituted with oxygen (O), or an amine (NR), where R is H or $C_1$-$C_6$ alkyl.

In accordance with the foregoing embodiments, a crosslinked PEG-PHEMA structure may be given by Formula (III):

PEG-A-L-A-PHEMA wherein PEG is the polyethylene glycol moiety, each A is an attachment atom from the catalytic reaction of azide or diazo, i.e., $CH_2$ or NH, and LG is the linking group as described above.

In some embodiments, each A in Formula (I), Formula (II), and/or Formula (III) represents an attachment atom derived from the decomposition reaction of an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, or an anthrone.

In FIG. 10A, a magnetic bead-bound entity 1015 is configured to interact with biomolecule 1025 or an analyte of interest, such as in a sandwich complex of antibody-analyte-magnetic bead-bound antibody. Below biosurface 1045 is a further insulating layer 1055. Insulating layer 1055 may be in direct contact with GMR sensors 1010 and may comprise, for example, a metal oxide layer. Biosurface layer 1045 is in direct contact with insulating layer 1045. A base 1065 serves as the scaffold for each component above it, the GMR sensors 1010, insulating layer 1055, and biosurface layer 1045. In some embodiments, base 1065 is made from silicon wafer.

Figure 10B:
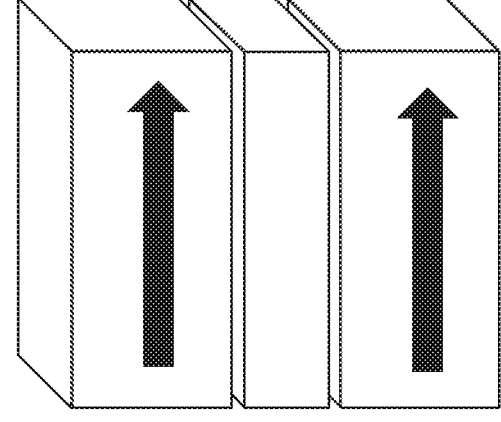
FIG. 10B shows the basic structure and operating principle of GMR sensors, in accordance with an embodiment.
Figure 10B:
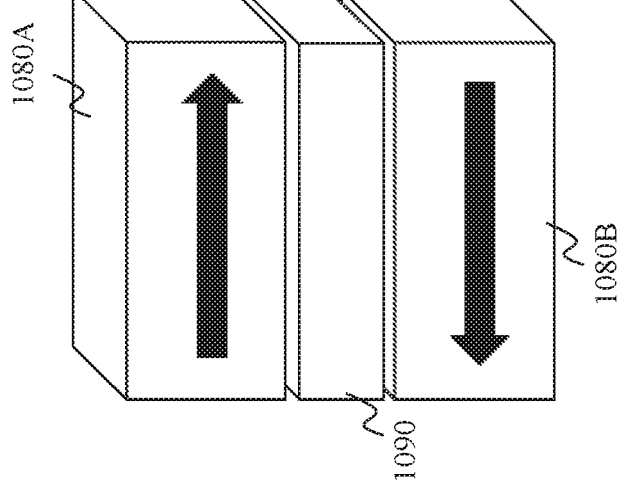

FIG. 10B schematically illustrates the basic structure and principle of GMR sensors. A typical GMR sensor consists of a metallic multi-layered structure with a non-magnetic conductive interlayer 1090 sandwiched between two magnetic layers 1080A and 1080B. The non-magnetic conductive interlayer 1490 is often a thin copper film. The magnetic layers 1080A and 1080B can be made of ferromagnetic alloy material.

The electrical resistance of the metallic multi-layered structure changes depending on the relative magnetization direction of the magnetic layers 1080A and 1080B. Parallel magnetization (as shown in the right half of FIG. 10B)

results in lower resistance, while anti-parallel magnetization (as shown in the left half of FIG. 10B) results in higher resistance. The magnetization direction can be controlled by a magnetic field applied externally. As a result, the metallic multi-layered structure displays a change in its electrical resistance as a function of the external magnetic field.

GMR sensors have sensitivities that exceed those of anisotropic magnetoresistance (AMR) or Hall sensors. This characteristic enables detection of stray fields from magnetic materials at nanometer scales. For example, stray fields from magnetic nanoparticles that bound on sensor surface will alter the magnetization in the magnetic layers, and thus change the magnetoresistance of the GMR sensor. Accordingly, changes in the number of magnetic nanoparticles bound to the GMR sensor per unit area can be reflected in changes of the magnetoresistance value of the GMR sensor.

Figure 11A:
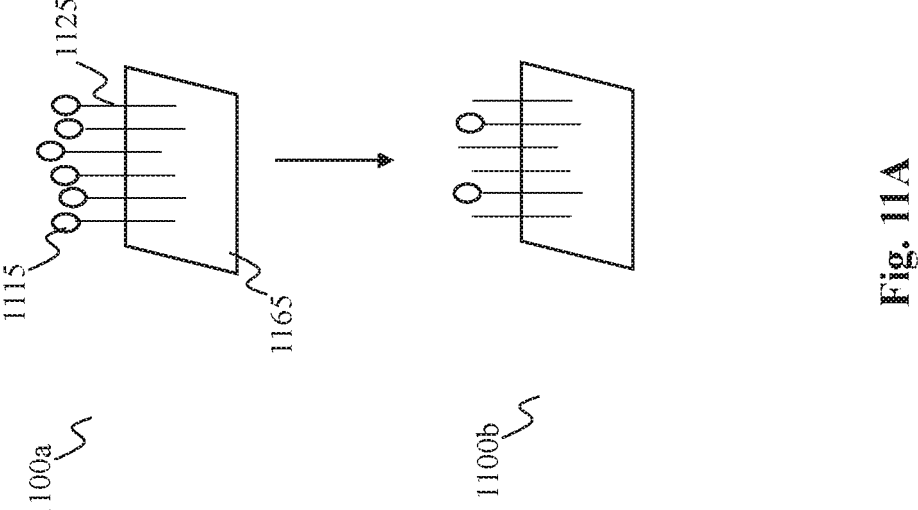
FIG. 11A shows a structure state diagram of a subtractive GMR sensing process, in accordance with an embodiment.
Figure 12A:
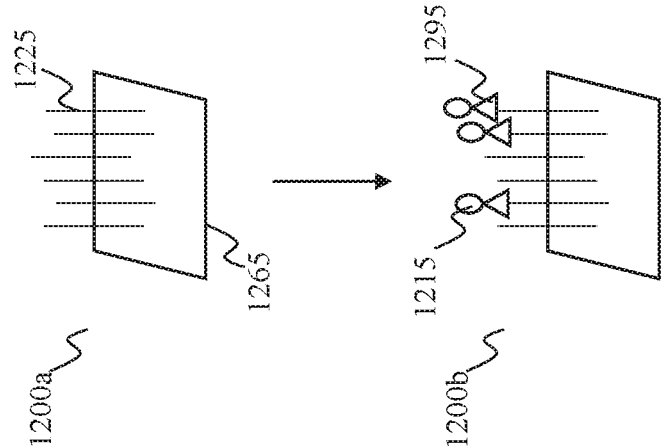
FIG. 12A shows a structure state diagram of an additive GMR sensing process, in accordance with an embodiment.

Referring now to FIGS. 11A and 12A, there are shown two exemplary basic modes by which GMR sensors operate in accordance with various assay applications described herein. In the first mode, exemplified in FIG. 11A, magnetic beads 1115 are loaded proximal to a GMR sensor (see FIG. 11A, 1010) via biosurface 1165 at the start of the assay. During the assay the presence of a query analyte results in magnetic beads 1115 being displaced from biosurface 1165 (and thus, displaced away from the GMR sensor); this mode is the so-called subtractive mode because magnetic beads are being taken away from the proximity of the sensor surface. The second main mode operation, typified in FIG. 12A, is the additive mode. In such assays, there is a net addition of magnetic beads 1215 in the vicinity of the GMR sensor (see FIG. 10A, 1010) when a query analyte is present. Either mode, subtractive or additive, relies on the changed state in the number of beads (1115, 1215) proximal to the sensor surface thereby altering the magnetoresistance in the GMR sensor system. The change in magnetoresistance is measured and query analyte concentrations can be determined quantitatively.

Referring back to FIG. 11A, there is shown a sensor structure diagram illustrating the sensor structures throughout an exemplary subtractive process. At the start of the process the system is in state 1100a in which the GMR sensor has disposed on its biosurface 1165 a plurality of molecules (typically biomolecules) 1125 with associated magnetic beads 1115. The volume above biosurface 1165 may begin dry or with a solvent present. When dry, the detection process may include a solvent priming step with, for example, a buffer solution. After introduction of analyte, the system takes the form of state 1100b in which some of magnetic beads 1115 have been removed from the molecules 1125 in proportion to the concentration of analyte. The change in states 1100a and 1100b provide a measurable change in magnetoresistance that allows quantitation of the analyte of interest. In some embodiments, the analyte may simply displace beads directly from molecules 1125. In other embodiments, the analyte may chemically react with molecules 1125 to cleave a portion of the molecule attached to beads 1115, thereby releasing beads 1115 along with the cleaved portion of molecule 1125.

In embodiments, biosurface 1165 comprises a polymer. The specific polymer may be chosen to facilitate covalent attachment of molecules 1125 to biosurface 1165. In other embodiments, molecules 1125 may be associated with biosurface 1165 via electrostatic interactions. Polymer coatings may be selected for or modified to use conventional linking chemistries for covalently anchoring biomolecules, for example. Linking chemistries include any chemical moieties comprising an organic functional group handle including, without limitation, amines, alcohols, carboxylic acids, and thiol groups. Covalent attachment chemistry includes, without limitation, the formation of esters, amides, thioesters, and imines (which can be subsequently subjected to reduction, i.e., reductive amination). Biosurface 1165 may include surface modifiers, such as surfactants, including without limitation, anionic surfactants, cationic surfactants, and zwitterionic surfactants.

Molecules 1125 can include any number of receptor/ ligand entities which can be attached to biosurface 1165. In some embodiments molecules 1125 include any of a variety of biomolecules. Biomolecules include DNA, RNA, and proteins that contains free amine groups can be covalently immobilized on GMR sensor surface with functional NHS groups. For the immunoassays, primary antibody (mouse monoclonal IgG) specific to analyte is attached onto GMR surface. All primary antibodies have multiple free amine groups and most proteins have lysine and/or alpha-amino groups. As long as lysine free primary amines are present, antibodies will be covalently immobilized on GMR sensor. To immobilize antibody on sensors surface, 1.2 nL of primary antibody (1 mg/mL in PBS buffer) are injected onto sensors surface using a printer system (sciFLEXARRAYER, Scienion, Germany). All printed surfaces are incubated overnight at 4° C. under a relative humidity of ~85%. The surfaces will be washed three times with blocking buffer (50 mM ethanolamine in Tris buffer), and are further blocked with the same buffer for 30 min.

In embodiments, magnetic beads 1115 may be nanoparticulate, including spheroidal nanoparticles. In some embodiments, such nanoparticles have effective diameters in a range from about 1 to about 1000 nanometers (nm), 1 nm to about 500 nm, about 5 nm to about 1000 nm, about 10 nm to about 1000 nm, about 5 nm to about 500 nm, about 5 nm to about 400 nm, about 5 nm to about 300 nm, about 5 nm to about 300 nm, about 5 nm to about 200 nm, about 5 nm to about 100 nm, about 2 to about 50 nm, about 5 to about 20 nm, or about 5 to about 10 nm, and/or ranges in between. In some embodiments such nanoparticles may have effective diameters in a range from about 2 to about 50 nm, or about 5 to about 20 nm, or about 5 to about 10 nm. In embodiments, magnetic beads 1115 may be coated to facilitate covalent attachment to molecules 1125. In other embodiments magnetic beads 1115 may be coated to facilitate electrostatic association with molecules 1125. Magnetic beads 1115 may be differentially tagged and/or coated to facilitate multiplex detection schemes, for example, for performing multiplex assays for detecting more than one analyte in the same query sample or in difference query samples. In such embodiments, the differential tagging and/ or coating is configured such that the different beads interact with different molecules disposed on different GMR sensors or on a single sensor in which different molecules are spatially organized to create addressable signals.

In some embodiments, referring as a non-limiting example to FIG. 5A multiplex detection schemes, for example, for performing multiplex assays for detecting more than one analyte in the same query sample or in difference query samples, may be achieved by spatially disposing different GMR sensors 510 within serpentine channel 540, wherein each different GMR sensor 510 is configured to with differential tagging and/or coating such that each differentially tagged and/or coated GMR sensor 510 interacts with different molecules, such as different reporter proteins, different detection proteins, different members of binding pairs, and/or the like described herein and throughout, thereby allowing for the detection of different analytes in the same sample, or different analytes in different samples, to be detected.

In some embodiments, referring as a non-limiting example to FIG. 5B, multiplex detection schemes for example, for performing multiplex assays detecting more than one analyte in the same query sample or in difference query samples, may be achieved by spatially disposing GMR sensors tagged and/or coated with one tag or coating within one of channel 500, and disposing one or more different GMR sensors tagged and/or coated with a different tag or coating in a different channels 500, such GMR sensors in the one channel 500 interact with different molecules, such as different reporter proteins, different detection proteins, different members of binding pairs, and/or the like described herein and throughout, than GMR sensors in the one or more different channels 500, thereby allowing for different samples to be flowed though different channels 500 and thereby allowing for either the same analyte to be measures from different samples or for different analytes to be measured from different samples.

Figure 11B:
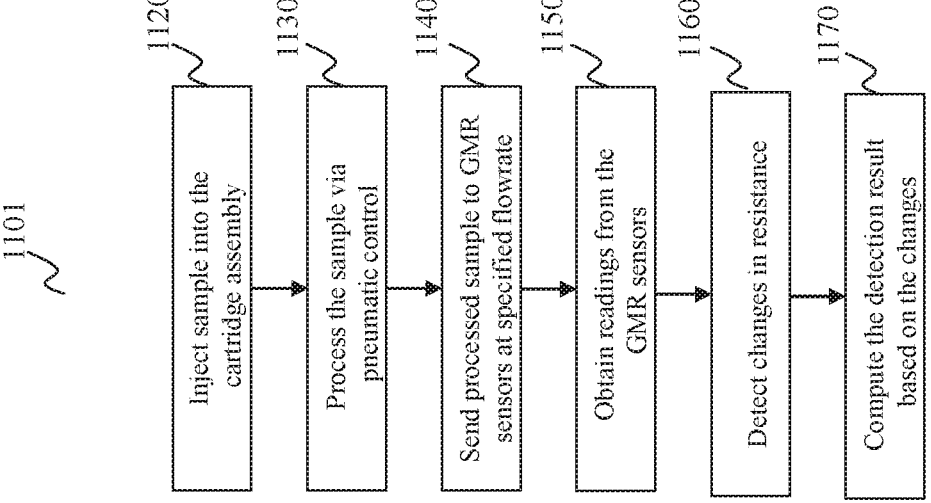
FIG. 11B shows a process flow diagram for the GMR sensing process of FIG. 11A.

Referring back to FIG. 11B, shown is a process flow 1101 associated with the sensor structure scheme of FIG. 11A. The process commences at 1120 by injecting a sample into a cartridge assembly. The sample may then undergo processing at step 1130 through any necessary steps such as filtration, dilution, and/or chemical modification. The sequencing of these pre-process steps will depend on the nature of the sample and query analyte to be detected. Movement through the system may be controlled pneumatically. Step 1140 involves sending the processed sample to the GMR sensor at a target specified flow rate. Such flow rate may be selected to reflect the kinetics of the chemistry on the GMR sensor surface. Step 1150 provides obtaining readings from the GMR sensors that reflect changes in the concentration of magnetic beads at the surface of the GMR sensor. These readings allow detecting changes in magnetoresistance at step 1160. Finally, step 1170 provides computing the detect result based on the changes in magnetoresistance.

Referring now to FIG. 12A, there is shown a sensor structure diagram illustrating the sensor structures throughout an exemplary additive process. At the start of the process the system is in state 1200*a* in which the GMR sensor has disposed on its biosurface 1265 a plurality of molecules (typically biomolecules) 1225. The plurality of molecules 1225 is selected to bind a query analyte 1290, as indicated in second state 1200*b*. Query analyte 1295 is configured to bind magnetic beads 1215. In some embodiments, query analyte 1295 is associated with the bead prior to passing over biosurface 1265. For example, this may take place during pre-processing of the sample being tested. (In other embodiments, query analyte 1295 may pass over the biosurface first, then query analyte 1295 may be modified with magnetic beads 1215 after the analyte is bound to biosurface 1265, as described below with reference to FIG. 13A). In some embodiments, a given query analyte 1295 may require chemical modification prior to binding magnetic particles 1215. In some embodiments, magnetic beads 1215 may be modified to interact with query analyte 1295. The ability to quantitate analyte is provided by changes in measured magnetoresistance from state 1200*a*, where no magnetic beads 1215 are present, to state 1200*b*, where magnetic beads 1215 are associated with biosurface 1265.

Figure 12B:
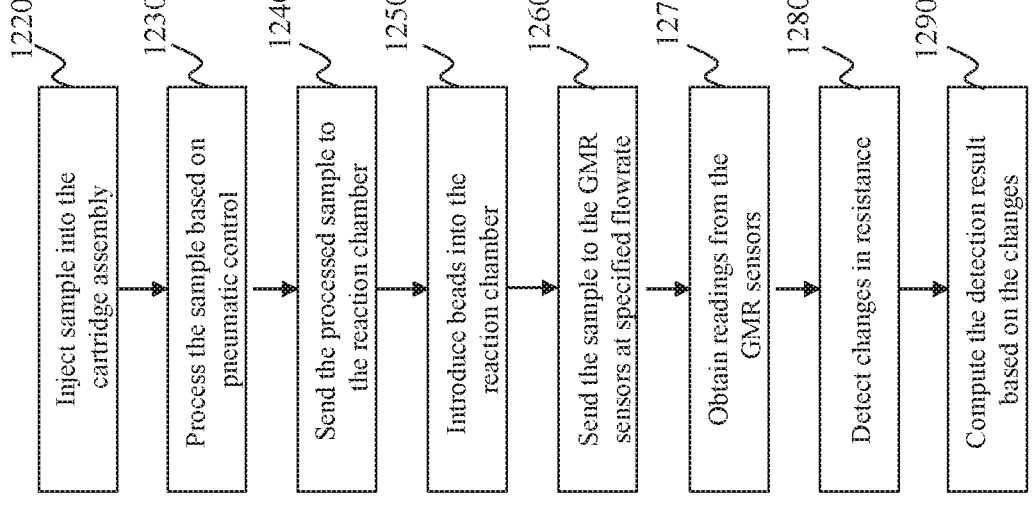
FIG. 12B shows a process flow diagram for the GMR sensing process of FIG. 12A.

FIG. 12B shows an exemplary process flow 1201 associated with the sensor structure scheme of FIG. 12A. The process commences at 1220 by injecting a sample into a cartridge assembly. The sample may then undergo processing at step 1230 through any necessary steps such as filtration, dilution, and/or chemical modification. The sequencing of these pre-process steps will depend on the nature of the sample and query analyte to be detected. Movement through the system may be controlled pneumatically. Step 1240 involves sending the processed sample to a reaction chamber and then in step 1250 beads are introduced into the reaction chamber to modify the query analyte. As described above, such modification may be performed directly on the sensor surface rather than in the reaction chamber. In step 1260, the modified sample is sent to the GMR sensors at a target flow rate. Such flow rate may be selected to reflect the kinetics of the chemistry on the GMR sensor surface. Step 1270 provides obtaining readings from the GMR sensors that reflect changes in the concentration of magnetic beads at the surface of the GMR sensor. These readings allow detecting changes in magnetoresistance at step 1280. Finally, step 1290 provides computing the detect result based on the changes in magnetoresistance.

Figure 13A:
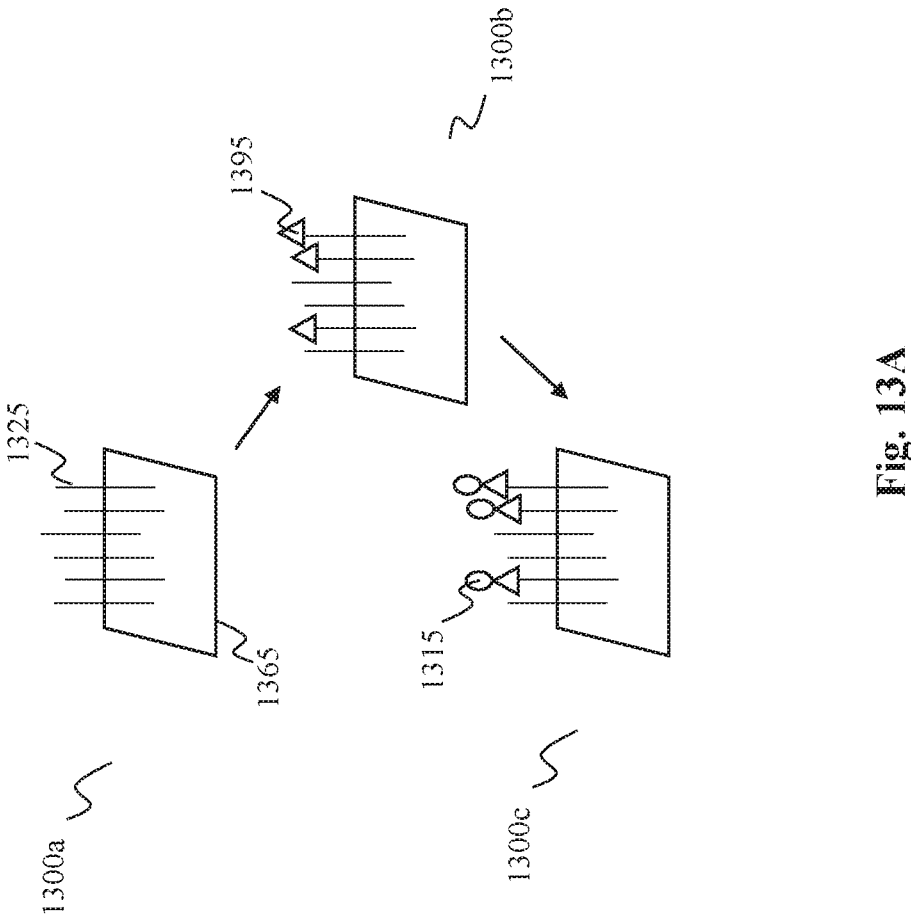
FIG. 13A shows another structure state diagram of an additive GMR sensing process, in accordance with an embodiment.

Referring now to FIG. 13A, there is shown a sensor structure diagram illustrating the sensor structures states 1300a-c throughout an exemplary additive process. At the start of the process the system is in state 1300a in which the GMR sensor has disposed on its biosurface 1365 a plurality of molecules (typically biomolecules) 1325. The plurality of molecules 1325 is selected to bind a query analyte 1395, as indicated in second state 1300b. Query analyte 1395 is configured to bind magnetic beads 1315, as indicated in state 1300c. In some embodiments, a given query analyte 1395 may require chemical modification prior to binding magnetic particles 1315. In other embodiments, query analyte 1395 may bind magnetic nanoparticles 1315 without chemical modification. In some embodiments, magnetic beads 1315 are coated or otherwise modified to interact with query analyte 1395. The ability to quantitate query analyte 1395 is provided by changes in measured magnetoresistance from state 1300a, where no magnetic beads 1315 are present, to state 1300c, where magnetic beads 1315 are associated with biosurface 1365.

FIG. 13B shows an exemplary process flow 1301a associated with the sensor structure scheme of FIG. 13A. The process commences at 1310 by injecting a sample into a cartridge assembly. The sample may then undergo processing at step 1320 through any necessary steps such as filtration, dilution, and/or the like. The sequencing of these pre-process steps will depend on the nature of the sample and query analyte to be detected. At 1330, the process sample is sent to a reaction chamber. Movement through the system may be controlled pneumatically. Step 1340 involves modifying the analyte present in the sample chamber with reagents to allow it to interact with magnetic particles. At step 1350, the modified sample is sent to the GMR sensors at a target flow rate. Such flow rate may be selected to reflect the kinetics of the chemistry on the GMR sensor surface. Next, step 1360 introduces beads into the GMR sensors, which can now interact with the modified analyte. In some embodiments, the beads may be modified as well, such as with a coating or some other linking molecule that will enable interaction with the modified analyte. Step 1370 provides obtaining readings from the GMR sensors that reflect changes in the concentration of magnetic beads at the surface of the GMR sensor. These readings allow detecting changes in magnetoresistance at step 1380. Finally, step 1390 provides computing the detect result based on the changes in magnetoresistance.

FIG. 13C shows an alternative exemplary process flow 1301b associated with the sensor structure scheme of FIG. 13A. The process commences at 1302 by injecting a sample into a cartridge assembly. The sample may then undergo processing at step 1304 through any necessary steps such as filtration, dilution, and/or the like. The sequencing of these pre-process steps will depend on the nature of the sample and query analyte to be detected. Movement through the system may be controlled pneumatically. At step 1306, the modified sample is sent to the GMR sensors at a target flow rate. Such flow rate may be selected to reflect the kinetics of the chemistry on the GMR sensor surface. Step 1308 involves modifying the analyte present in the sample with reagents to allow it to interact with magnetic particles. Next, step 1312 introduces beads into the GMR sensors, which can now interact with the modified analyte. In some embodiments, the beads may be modified as well, such as with a coating or some other linking molecule that will enable interaction with the modified analyte. Step 1314 provides obtaining readings from the GMR sensors that reflect changes in the concentration of magnetic beads at the surface of the GMR sensor. These readings allow detecting changes in magnetoresistance at step 1316. Finally, step 1318 provides computing the detect result based on the changes in magnetoresistance.

Figure 14A:
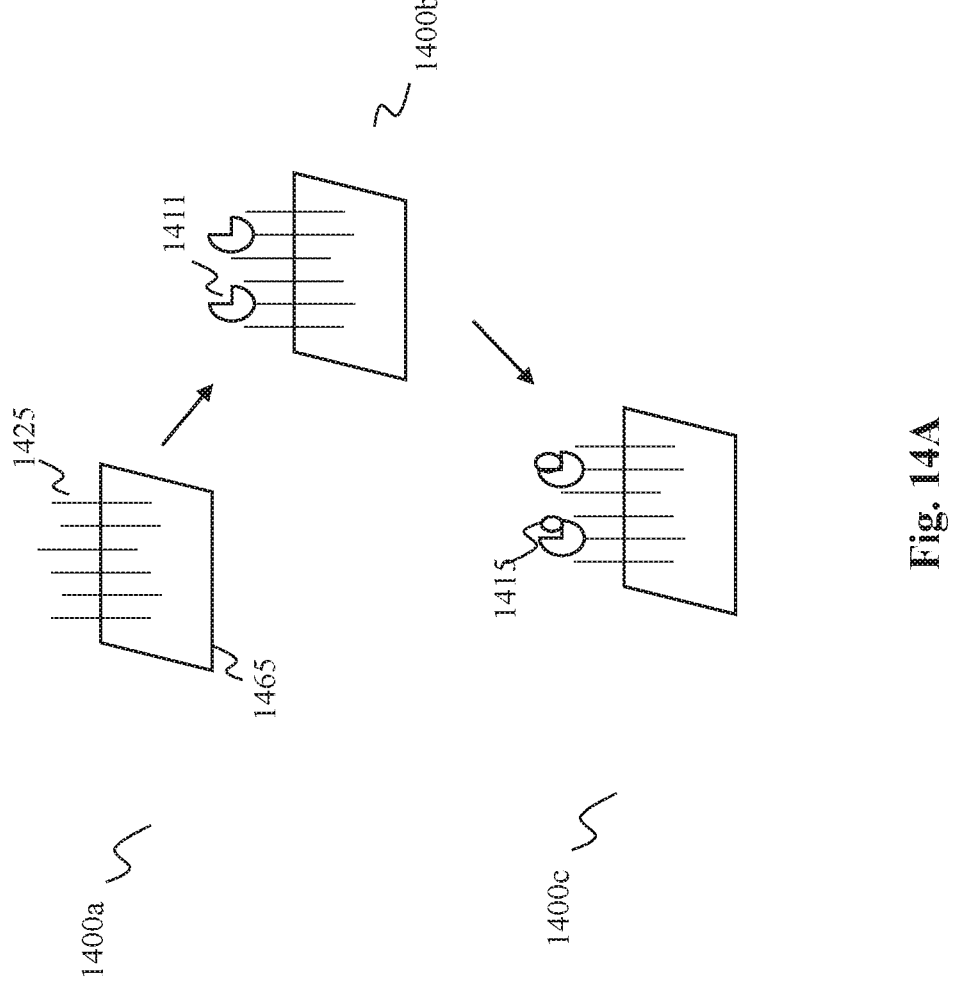
FIG. 14A shows a structure state diagram of an additive GMR sensing process in which an analyte modifies a molecule bound to a biosurface, in accordance with an embodiment.

Referring now to FIG. 14A, there is shown a sensor structure diagram illustrating the sensor structures states 1400a-c throughout an exemplary additive process. At the start of the process the system is in state 1400a in which the GMR sensor has disposed on its biosurface 1465 a plurality of molecules (typically biomolecules) 1425. The plurality of molecules 1425 is selected to interact (chemically react) with a query analyte. Such interaction modifies molecules 1425 (in proportion to analyte concentration) to provide modified molecules 1411, as indicated in second state 1400b. Modified molecules 1411 are configured to bind magnetic beads 1415, as indicated in state 1300c. In some embodiments, modified molecules 1411 may require further chemical modification prior to binding magnetic particles 1415. In other embodiments, modified molecules 1411 may bind magnetic nanoparticles 1415 without chemical modification. In some embodiments, magnetic beads 1415 are coated or otherwise modified to interact with modified molecules 1411. The ability to quantitate query analyte is provided by changes in measured magnetoresistance from state 1400a, where no magnetic beads 1415 are present, to state 1400c, where magnetic beads 1415 are associated with biosurface 1465 via modified molecules 1411. Note, in the overall process, the query analyte is merely serving as a reagent to chemically modify the plurality of molecules 1425 and does not otherwise remain a part of the process once it has performed this function.

Figure 14B:
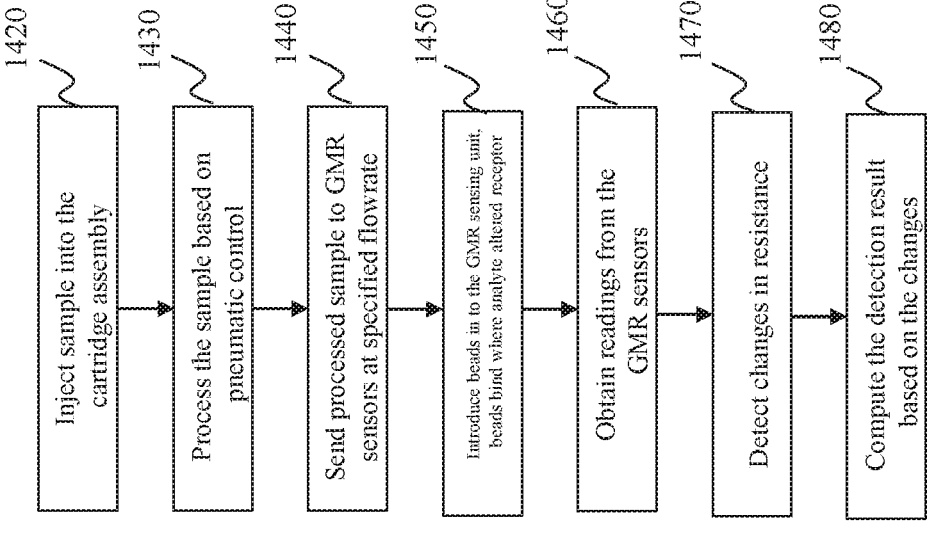
FIG. 14B shows a process flow diagram for the GMR sensing process of FIG. 14A.

FIG. 14B shows an exemplary process flow 1401 associated with the sensor structure scheme of FIG. 14A. The process commences at 1420 by injecting a sample into a cartridge assembly. The sample may then undergo processing at step 1430 through any necessary steps such as filtration, dilution, and/or the like. The sequencing of these pre-process steps will depend on the nature of the sample and query analyte to be detected. Movement through the system may be controlled pneumatically. At 1440, the process sample is sent to GMR sensors at a specified flowrate. Such flow rate may be selected to reflect the kinetics of the chemistry on the GMR sensor surface. Next, step 1450 introduces beads into the GMR sensors, which can now interact with the modified molecules on the biosurface. In some embodiments, the beads may be modified as well, such as with a coating or some other linking molecule that will enable interaction with the modified molecules on the biosurface. Step 1460 provides obtaining readings from the GMR sensors that reflect changes in the concentration of magnetic beads at the surface of the GMR sensor. These readings allow detecting changes in magnetoresistance at step 1470. Finally, step 1480 provides computing the detect result based on the changes in magnetoresistance.

Figure 15A:
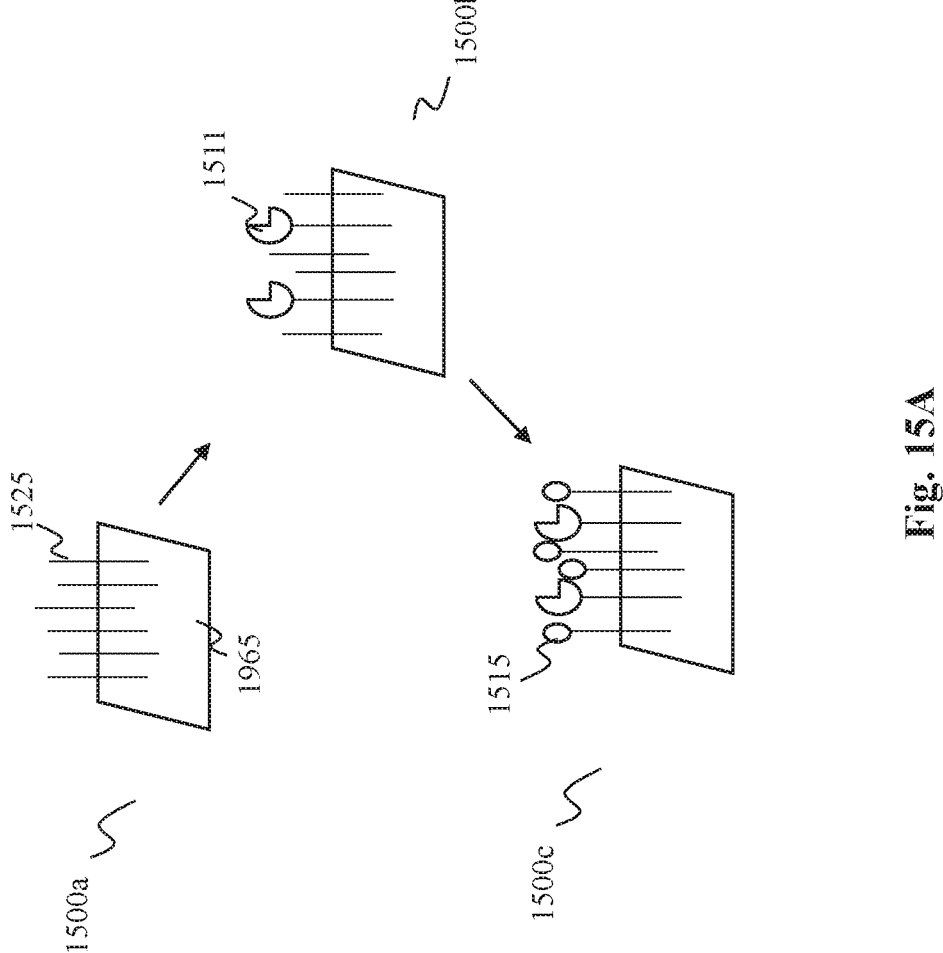
FIG. 15A shows an alternative structure state diagram of an additive GMR sensing process in which an analyte modifies a molecule bound to a biosurface, in accordance with an embodiment.

Referring now to FIG. 15A, there is shown a sensor structure diagram illustrating the sensor structures states 1500*a*-*c* throughout an exemplary additive process. At the start of the process the system is in state 1500*a* in which the GMR sensor has disposed on its biosurface 1565 a plurality of molecules (typically biomolecules) 1525. The plurality of molecules 1525 is selected to interact (chemically react) with a query analyte. Such interaction modifies molecules 1525 (in proportion to analyte concentration) to provide modified molecules 1511, as indicated in second state 1500*b*. Modified molecules 1511 are configured to prevent binding of magnetic beads 1515, as indicated in state 1500*c*, in which magnetic beads only bind to molecules 1525 that were not modified by the analyte. In some embodiments, magnetic beads 1515 are coated or otherwise modified to interact with molecules 1525. The ability to quantitate query analyte is provided by changes in measured magnetoresistance from state 1500*a*, where no magnetic beads 1515 are present, to state 1500*c*, where magnetic beads 1515 are associated with biosurface 1565 via molecules 1525. Note, in the overall process, the query analyte is merely serving as a reagent to chemically modify the plurality of molecules 1525 and does not otherwise remain a part of the process once it has performed this function.

Figure 15B:
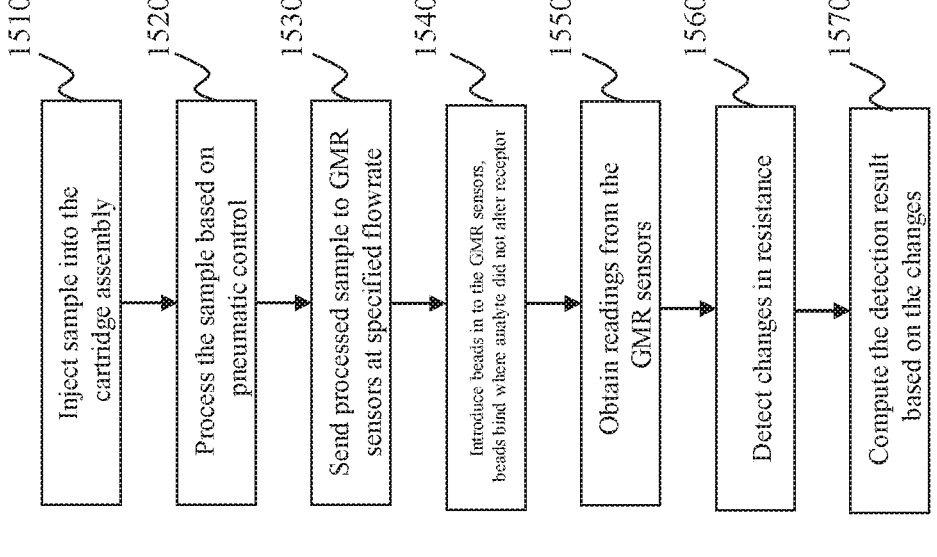
FIG. 15B shows a process flow diagram for the GMR sensing process of FIG. 15A.

FIG. 15B shows an exemplary process flow 1501 associated with the sensor structure scheme of FIG. 15A. The process commences at 1510 by injecting a sample into a cartridge assembly. The sample may then undergo processing at step 1520 through any necessary steps such as filtration, dilution, and/or the like. The sequencing of these pre-process steps will depend on the nature of the sample and query analyte to be detected. Movement through the system may be controlled pneumatically. At step 1530, the processed sample is sent to GMR sensors at a specified flowrate. Such flow rate may be selected to reflect the kinetics of the chemistry on the GMR sensor surface. Next, step 1540 introduces beads into the GMR sensors, which can now interact with the unmodified molecules on the biosurface. In some embodiments, the beads may be modified, such as with a coating or some other linking molecule that will enable interaction with the unmodified molecules. Step 1550 provides obtaining readings from the GMR sensors that reflect changes in the concentration of magnetic beads at the surface of the GMR sensor. These readings allow detecting changes in magnetoresistance at step 1560. Finally, step 1570 provides computing the detect result based on the changes in magnetoresistance.

Figure 16A:
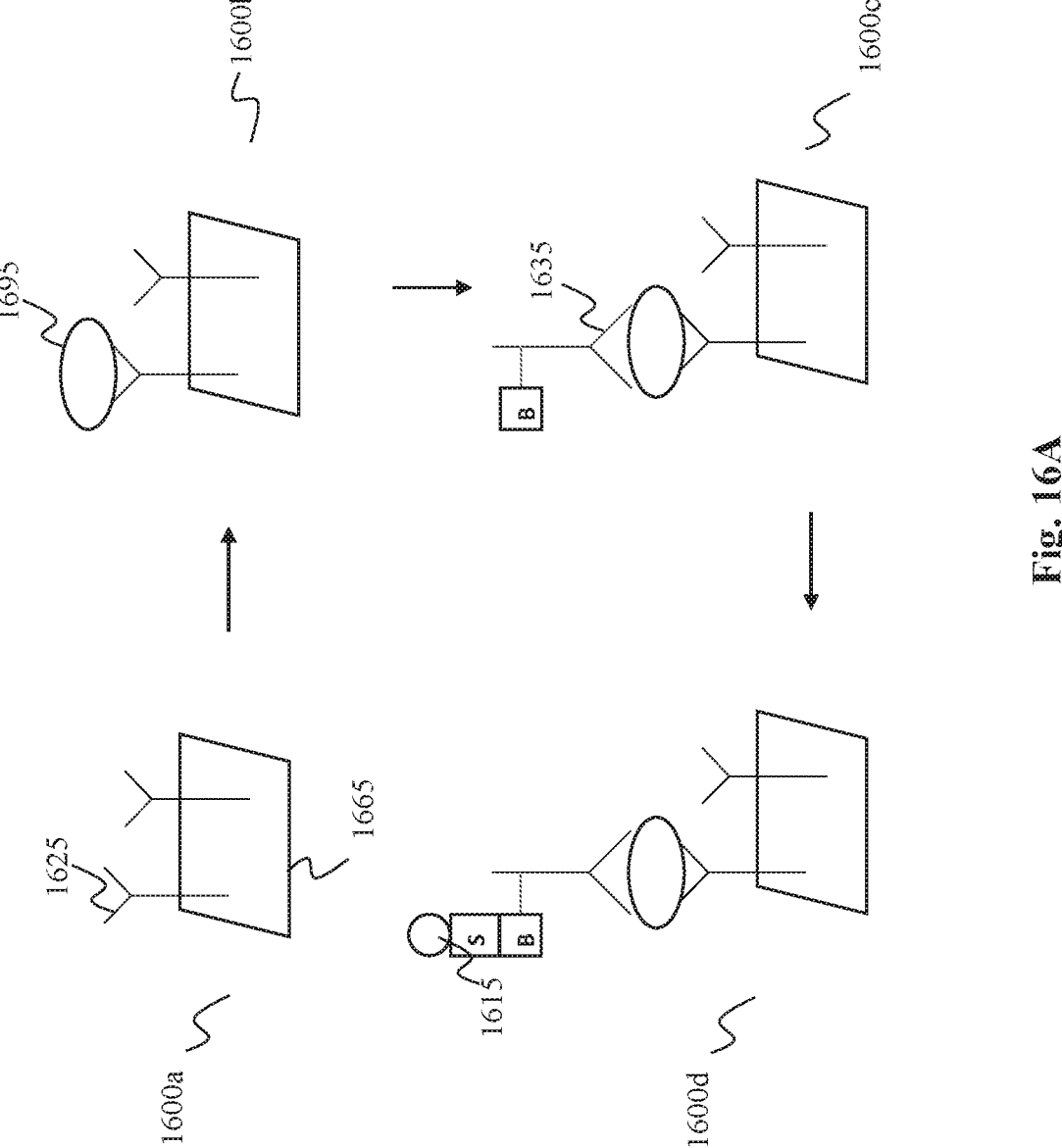
FIG. 16A shows a structure state diagram of an additive GMR sensing process employing an exemplary "sandwich" antibody process.

Referring now to FIG. 16A, there is shown a sensor structure diagram illustrating the sensor structure states 1600*a*-*d* throughout an exemplary additive process that employs a sandwich antibody strategy for detection of analyte 1695 (state 1600*b*). At the start of the process the system is in state 1600*a* in which the GMR sensor has disposed on its biosurface 1665 a plurality of antibodies 1625. Analyte 1695 is then passed over biosurface 1665, allowing binding of analyte 1695 to antibody 1625, as indicated in state 1600*b*. Analyte 1695 is then modified by binding to a second antibody 1635 to which a covalently linked biotin moiety (B) is provided, as indicated in state

1600*c*. Magnetic beads 1615 modified with streptavidin (S) are then added, thereby allowing the strong biotin-streptavidin association to provide state 1600*d*. In some embodiments, streptavidin is provided as a coating on magnetic beads 1615.

Figure 16B:
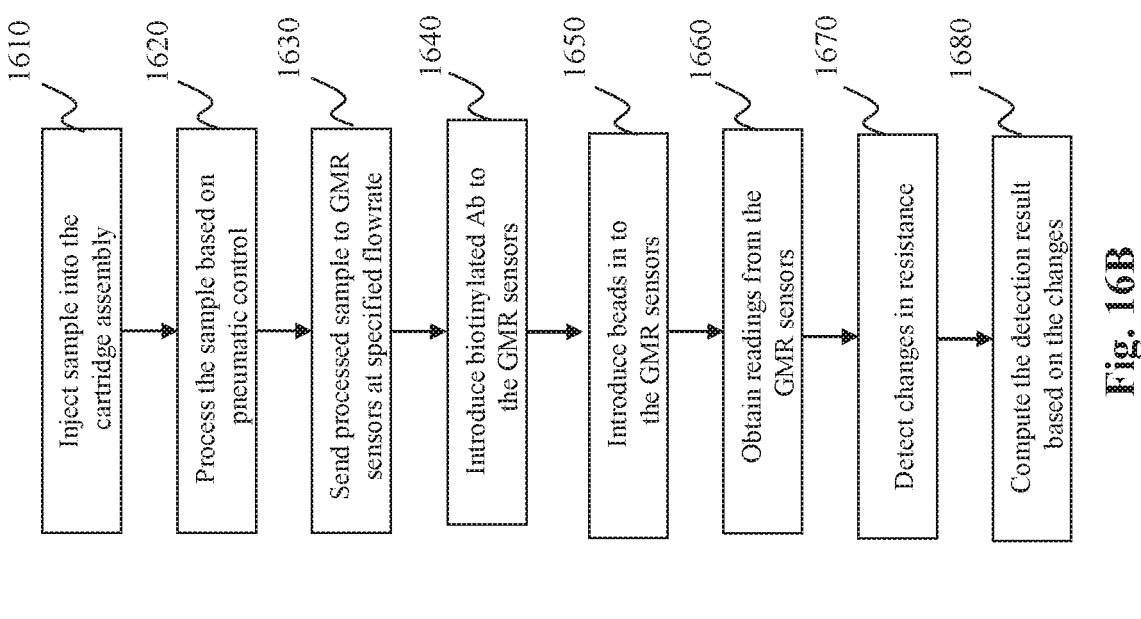
FIG. 16B shows a process flow diagram for the GMR sensing process of FIG. 16A.

FIG. 16B shows an exemplary process flow 1601 associated with the sensor structure scheme of FIG. 16A. The process commences at 1610 by injecting a sample into a cartridge assembly. The sample may then undergo processing at step 1620 through any necessary steps such as filtration, dilution, and/or the like. The sequencing of these pre-process steps will depend on the nature of the sample and query analyte to be detected. Movement through the system may be controlled pneumatically. At step 1630, the processed sample is sent to GMR sensors at a specified flowrate. Such flow rate may be selected to reflect the kinetics of the chemistry on the GMR sensor surface between biosurface-bound antibody and the analyte. Next, step 1640 introduces biotinylated antibody (Ab) to the GMR sensors. This creates the "sandwich" structure of the analyte between two antibodies. At step 1650 streptavidin coated beads are introduced into the GMR sensors, which can now interact with the biotin-bound antibody. Step 1660 provides obtaining readings from the GMR sensors that reflect changes in the concentration of magnetic beads at the surface of the GMR sensor. These readings allow detecting changes in magnetoresistance at step 1670. Finally, step 1680 provides computing the detect result based on the changes in magnetoresistance.

Figure 17A:
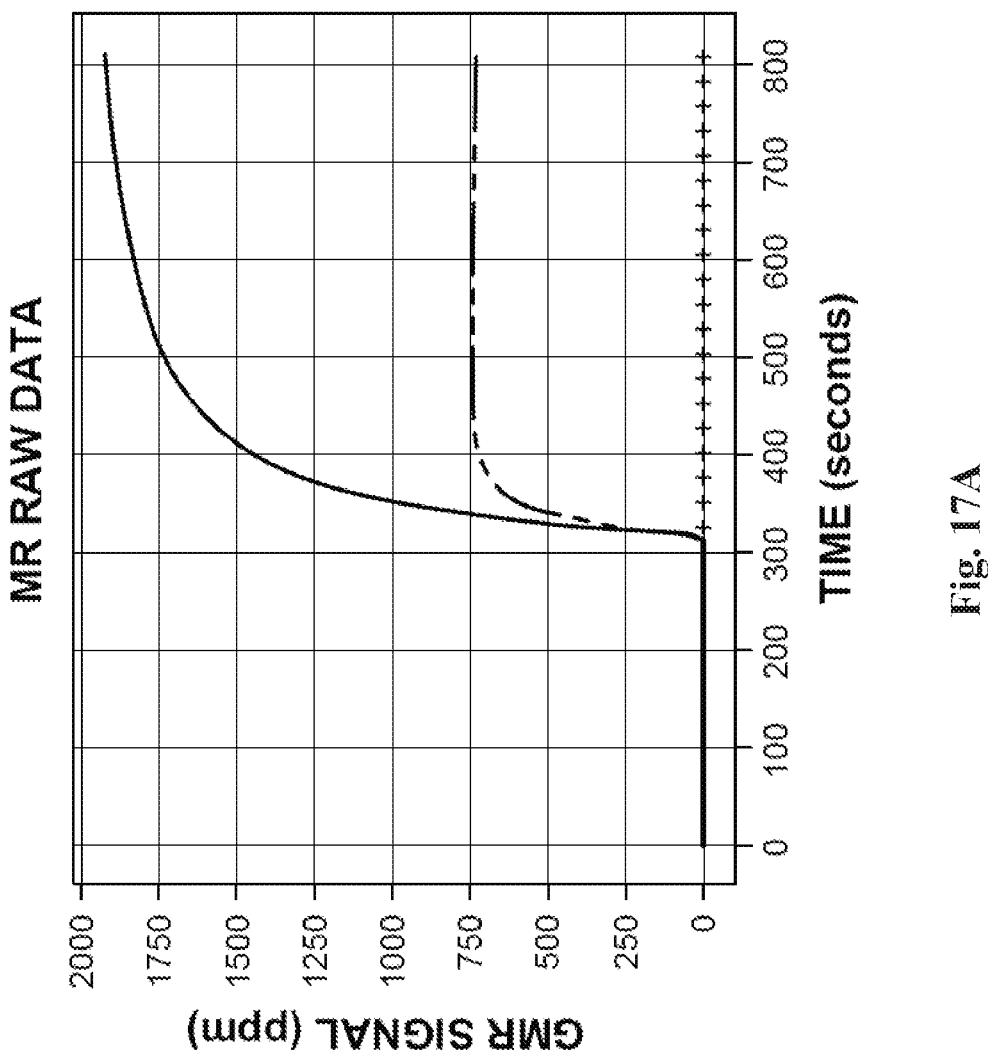
FIG. 17A shows a plot of data generated with a GMR sensor for detecting D-dimer cardiac biomarker: solid line is a positive control; dashed line is a sample run; line indicated with "+" is a negative control.
Figure 17B:
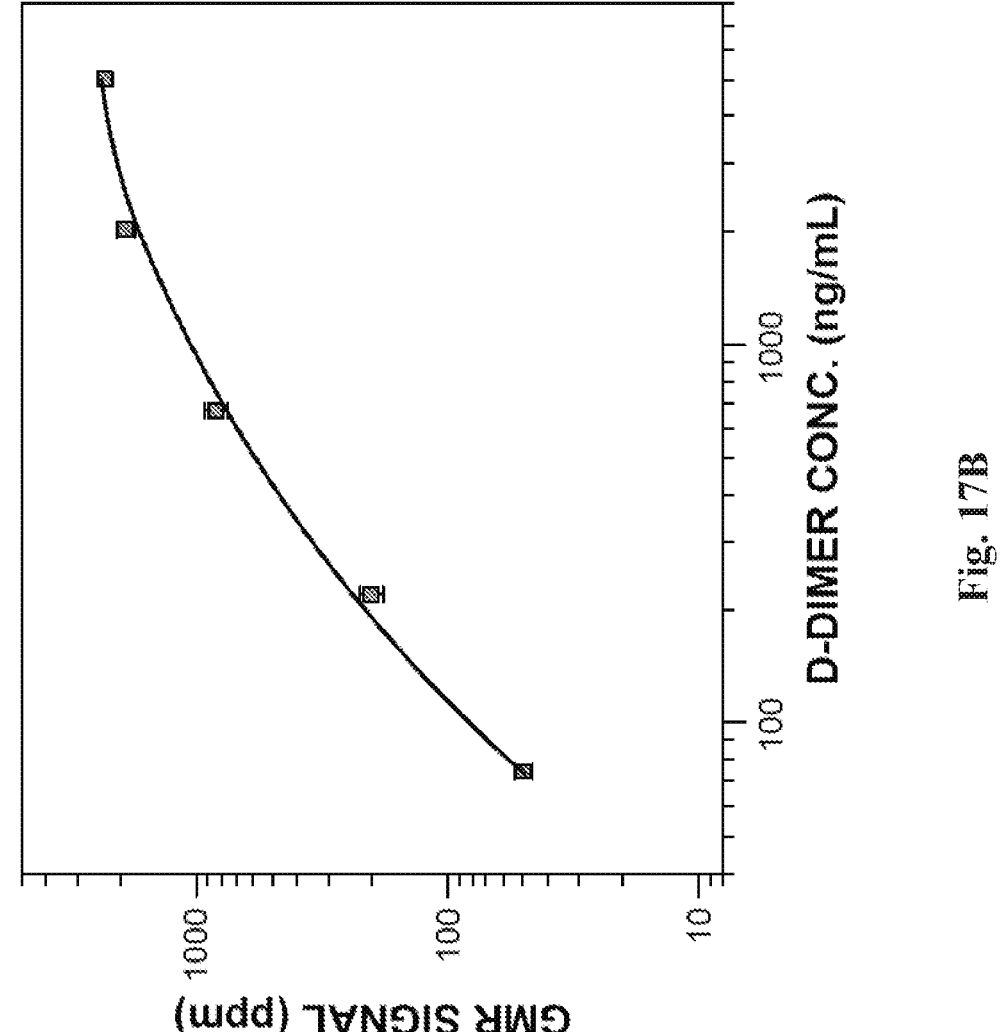
FIG. 17B shows a calibration curve for D-dimer using a GMR sensor for detecting D-dimer cardiac biomarker.
Figure 17C:
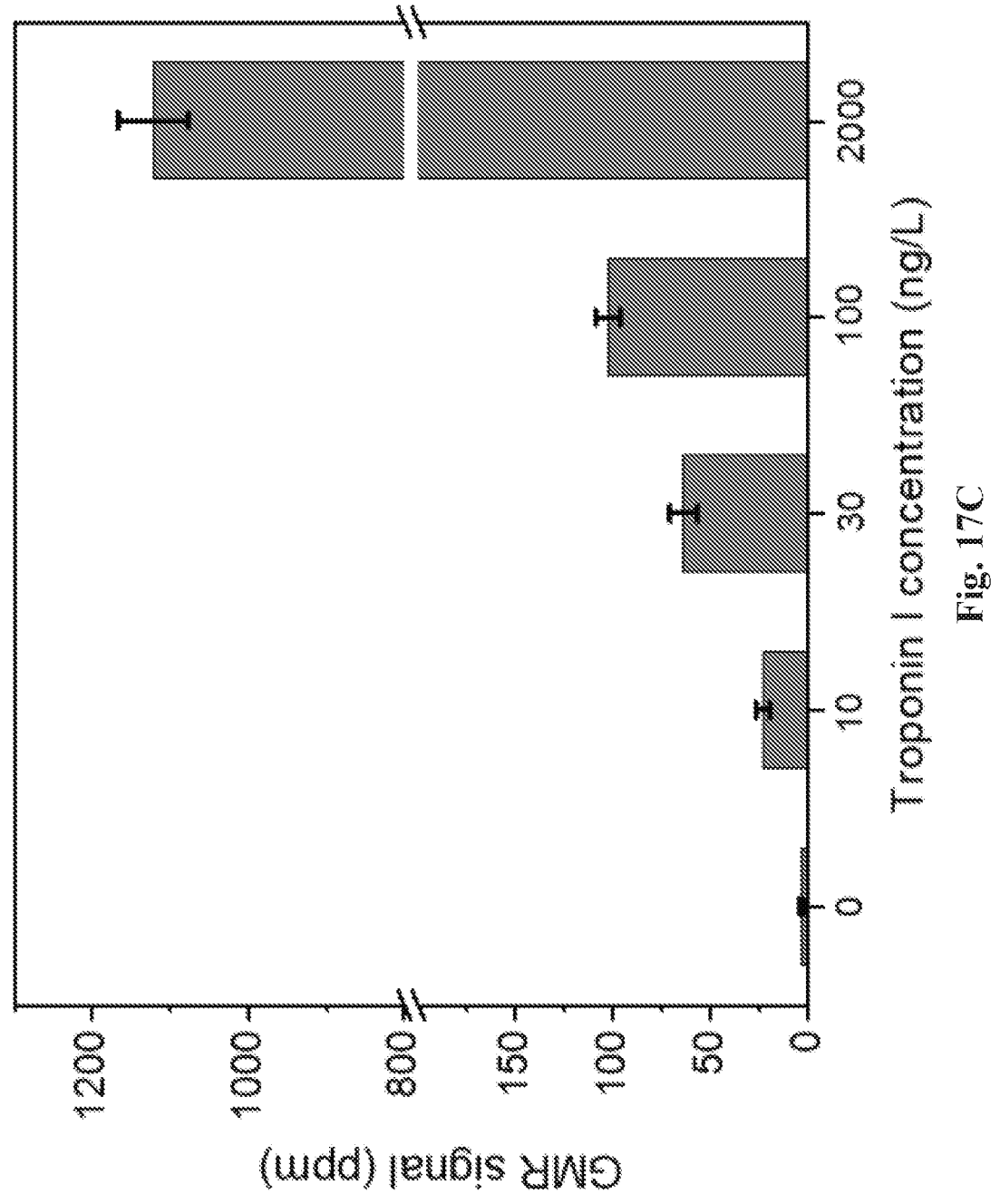
FIG. 17C shows a graph of data generated with a GMR sensor for detecting troponin cardiac biomarker.

The schemes of FIGS. 16A and 16B were put into practice with cardiac biomarkers and proof of concept results are shown in FIGS. 17A-C. FIG. 17A shows a plot of GMR signal (in ppm) over time (in seconds) in a test run designed to detect cardiac biomarker D-dimer. To generate this data, a biosurface was prepared by printing a D-dimer capture antibody using 2 nL of a 1 mg/mL of D-dimer antibody in PBS buffer with 0.05% sodium azide. For testing potential cross reactivity, the biosurface was also functionalized with troponin I capture antibody by printing two combined capture antibodies using 2 nL of a solution of 1 mg/mL troponin I antibody in PBS buffer with 0.05% sodium azide. Additionally, two other controls were printed on the biosurface. The first is a negative control prepared by printing 2 nL of a solution of 0.5% BSA in PBS buffer with 0.05% sodium azide and the second is a positive control prepared by pringint 2 nL of 1 mg/mL of biotin conjugated to mouse IgG in PBS buffer with 0.05% sodium azide. The printed sensors were incorporated into a cardiac test cartridge and is configured to use the "sandwich" assay described above in FIGS. 16A and 16B.

In the sample test 120 microliters of plasma or whole blood was loaded into a sample well in the cartridge. A membrane filter serves to remove blood cells as the sample is pulled into the flow channel from the sample well. 40 microliters of plasma (or plasma portion of whole blood) is flowed into a metering channel and deposited powder including antibody/biotin conjugates, blockers, and mouse IgG in the channel dissolve into the sample solution. While flowing over the sensor area, the analytes, antibody/biotin conjugates and antibodies immobilized on the sensor surface form a sandwich of antibody-analyte-biotinylated antibody. Flow rates are modulated depending on the test. For troponin I, the sample is flowed over the sensor for 20 minutes at a flow rate of 1 microliter/minute. For D-dimer, the sample is flowed for 5 minutes at a flow rate of 4 microliters/minute. Following flow of the sample streptavidin-coated magnetic beads were introduced which allow binding to the sensor surface wherever there is a biotinylated antibody bound. The GMR sensor measure bound magnetic beads, which is proportional to the concentration of analytes with the sample. The bead solution is flowed over the sensor for 5 minutes at a flow rate of 4 to 10 microliters/minute. The signals were read from the peak value within 300 seconds after beads started to bind.

As indicated in the plot of FIG. 17A, a negative control with just printed BSA did not bind D-Dimer and thus, the signal remained near baseline as expected. The positive control with biotinylated mouse IgG showed competent bead binding, as expected. A plot of the actual sample of 666.6 ng/mL of human D-dimer appears with a peak detection signal of about 750 ppm indicating successful detection of the D-dimer in an actual sample. There was virtually no cross reactivity with the two bound troponin I capture antibodies (not shown for clarity because these lines were very close to the line with the negative control).

FIG. 17B shows a calibration curve (GMR signal in ppm vs. D-dimer concentration) for D-dimer by running samples with varied, fixed concentrations of D-dimer. The calibration curve allows concentrations to be computed for a future unknown sample containing the D-dimer as the query analyte. A similar plot in FIG. 17C is provided for the cardiac biomarker troponin I. Together, these results establish the viability of detecting D-dimer and troponin I in, blood or plasma samples of a subject.

Metal Detection Applications

Figure 18:
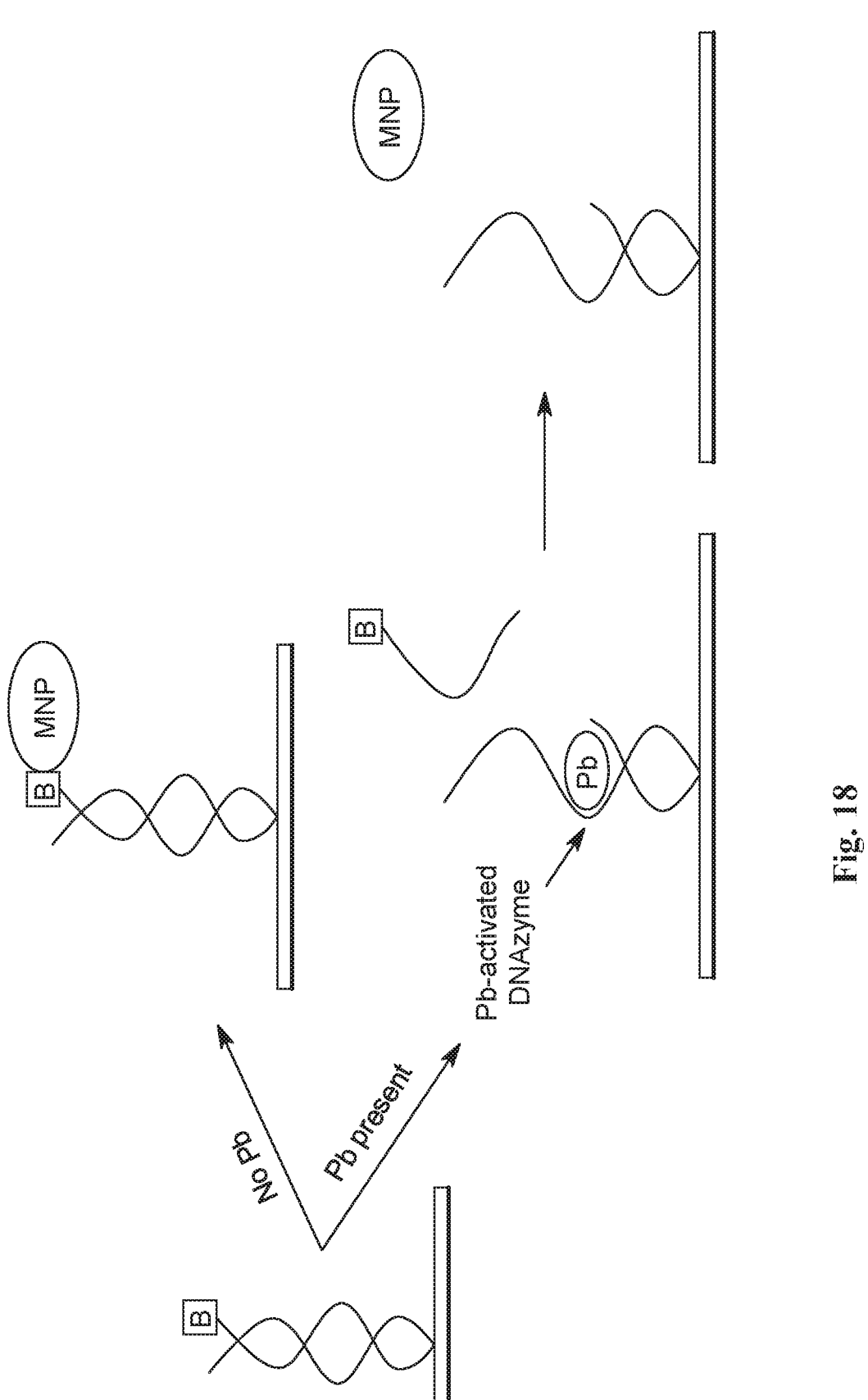
FIG. 18 shows a reaction scheme for the GMR-based detection of lead ion, in accordance with an embodiment.

FIG. 18 shows an application, in accordance with embodiments above, to a lead detection scheme using a GMR sensor platform. Double stranded DNA is printed on the biosurface of the sensor, with one strand being biotinylated (B). If lead is not present, streptavidin-tagged (or coated) magnetic nanoparticles (MNP) can bind to biotin (B), which is part of the DNA substrate strand. When lead is present, a Pb-activated DNAzyme cleaves the biotin-containing substrate strand. When cleaved, the streptavidin-tagged MNP's cannot bind to the via the DNA strand because the biotinylated portion of the strand is no longer present. Thus, MNP's only bind to the GMR surface if lead is not present in the sample. The more lead that is present, the fewer MNPs bind to the DNA at the biosurface. Such a scheme can be used for the detection of lead in water, blood, or other fluids of interest.

Figure 19:
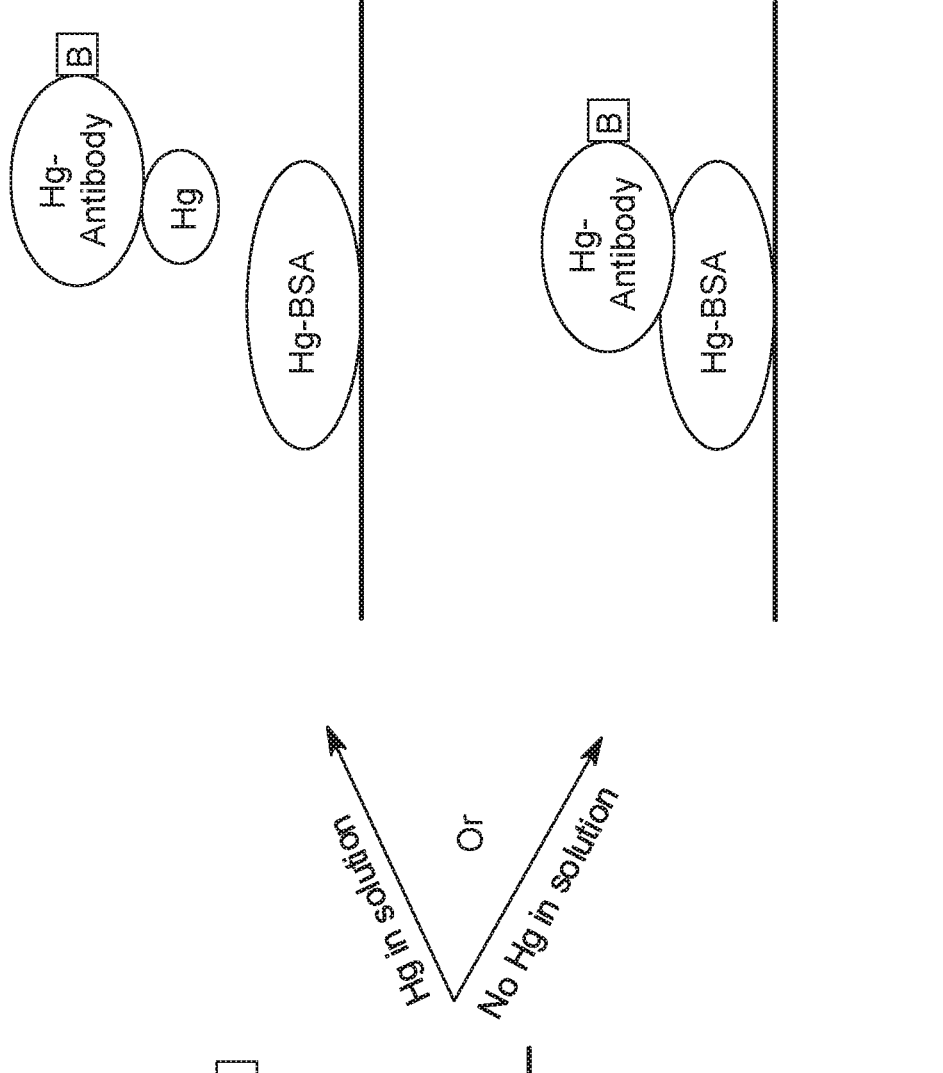
FIG. 19 shows a reaction scheme for the GMR-based detection of mercury ion, in accordance with an embodiment.

FIG. 19 shows an application, in accordance with embodiments above, to a mercury detection scheme using a GMR sensor platform. A Hg-BSA substrate is immobilized on the a biosurface. In the absence of mercury (Hg) ion (I or II or both), a biotinylated (B) Hg-antibody can bind to the biosurface bound Hg-BSA. In the presence of Hg ion, the ion blocks the biotinylated Hg-antibody's binding site to Hg-BSA, preventing Hg-antibody from binding to Hg-BSA. As described above, streptavidin tagged (or coated) magnetic nanoparticles can bind to biotin. Thus, the more mercury ion present in solution, the fewer magnetic beads will end up bound to the sensor at the biosurface due to the interfering binding of mercury to biotinylated Hg-antibody.

Figure 20:
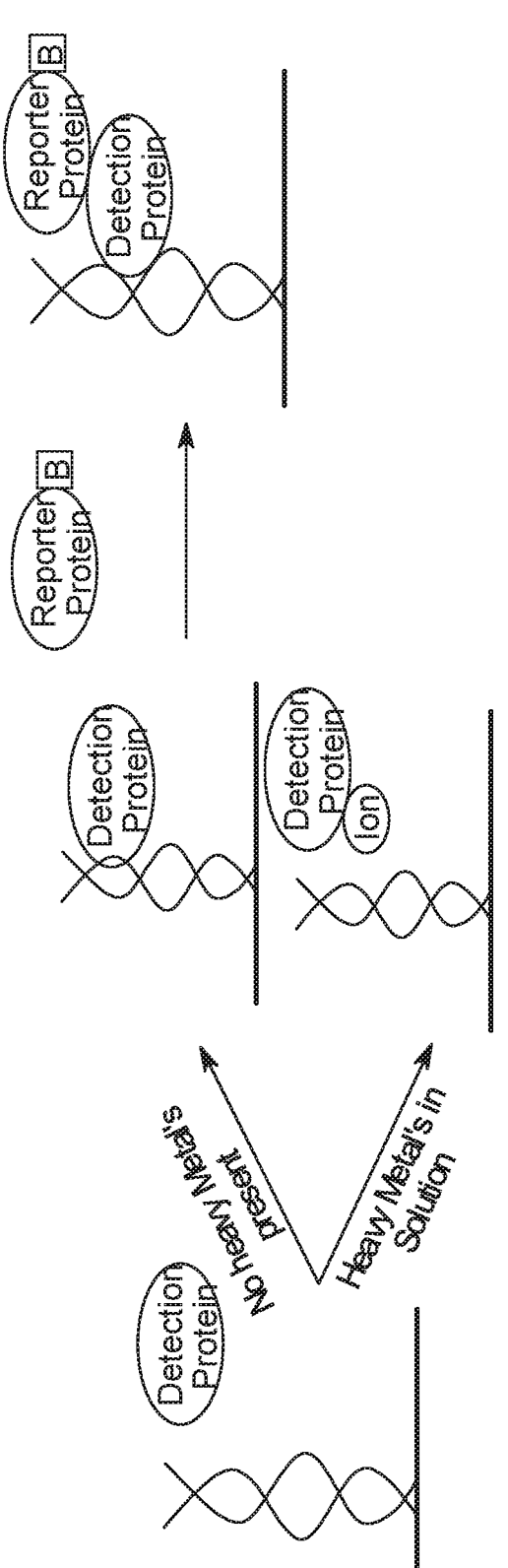
FIG. 20 shows a reaction scheme for the GMR-based detection of cadmium or arsenic ion, in accordance with an embodiment.

FIG. 20 shows an application, in accordance with embodiments above, to a cadmium or arsenic detection scheme using a GMR sensor platform. A double stranded DNA is printed on the biosurface of the sensor which can bind a detection protein. The detection protein arsR (for arsenate III detection) or Pcad (for cadmium detection) is added in the presence of a sample that may contain the query metal analyte. The detection protein is unable to bind to the DNA double-strand in the presence of their respective heavy metal ion, so DNA-protein binding occurs in proportion to the absence of heavy metal ions in the sample. This is a similar competitive binding event much like the mercury assay described above. A biotinylated (B) reporter protein is then added. This protein can bind to the detection protein. If the detection protein is bound to the DNA double-strand, the biotinylated reporter is immobilized to the DNA-protein complex. Once again, streptavidin tagged magnetic nanoparticles will bind to the biotinylated reporter protein that is bound to the biosurface. Thus, the smaller the concentration of cadmium or arsenic, the more beads will be bound to the biosurface.

The following is a non-limiting list of applications of analyte sensing that may be accomplished, in accordance with the principles detailed herein.

(1) Blood samples can include analytes such as proteins or other substance, such as DNA, that can be measured by immunoassay employing the GMR device. Exemplary disease states associated with analytes that may be detected are summarized in Table 1 below.

TABLE 1

| Diseases | Analytes |
| --- | --- |
| Cardiac | Apolipoprotein A1, Apolipoprotein B, CK-MB, hsCRP, Cystatin C, D-Dimer, GDF-15, Myoglobin, NT-proBNP, BNP, Troponin I, Troponin T |
| Cancer | AFP, CA 125, CA 15-3, CA 19-9, CA 72-4, CEA, Cyfra 21-1, hCG plus beta, HE4, NSE, proGRP, PSA free, PSA total, SCC, S-100, Thyreoglobulin (TG II), Thyreoglobulin confirmatory, b2-Microglobulin |
| Drugs of Abuse | Acetaminophen/Paracetamol (APAP), Amphetamines (AMP), Methamphetamines (mAMP), Barbiturates (BAR), Benzodiazepines (BZO), Cocaine (COC), Methadone (MTD), Opiates (OPI), Phencyclidine (PCP), THC, and Tricyclic Antidepressants (TCA). |
| Infectious | Anti-HAV, Anti-HAV IgM, Anti-HBc, Anti-HBc IgM, Anti-Hbe, HBeAg, Anti-HBs, HBsAg, HBsAg confirmatory, HBsAg quantitative, Anti-HCV, Chagas4, CMV IgG, CMV IgG Avidity, CMV IgM, HIV combi PT, HIV-Ag, HIV-Ag confirmatory, HSV-1 IgG, HSV-2 IgG, HTLV-I/II, Rubella IgG, Rubella IgM, Syphilis, Toxo IgG, Toxo IgG Avidity, Toxo IgM, TPLA (Syphilis) |
| Inflammation | Anti-CCP, ASLO, C3c, Ceruloplasmin, CRP, Haptoglobin, IgA, IgE, IgG, IgM, Immunglobulin A CSF, Immunglobulin M CSF, Interleukin 6, Kappa light chains, Kappa light chains free, Lambda |

TABLE 1-continued

| Diseases | Analytes |
|---|---|
| | light chains, Lambda light chains free, Prealbumin, Procalcitonin, Rheumatoid factor, a1-Acid Glycoprotein, a1-Antitrypsin, SSA |

(2) GMR systems described herein may be use in urine analyte detection. Any protein, DNA, metal or other substance in urine can be measured and/or detected by the GMR devices described herein. Urine associated protein biomarkers include, without limitation preeclampsia, human chorionic gonadotropin (hCG), kidney injury molecule-1 (KIM-1), neutrophil gelatinase-associated lipocalin (NGAL), interleukin (IL)-18, and fatty-acid binding proteins (FABPs), nuclear matrix protein 22 (NMP22), BLCA-4, and epidermal growth factor receptor (EGFR), etc. Drugs and/or their major urinary metabolites include Acetaminophen/Paracetamol (APAP), Amphetamines (AMP), Methamphetamines (mAMP), Barbiturates (BAR), Benzodiazepines (BZO), Cocaine (COC), Methadone (MTD), Opiates (OPI), Phencyclidine (PCP), THC, and Tricyclic Antidepressants (TCA), etc.

(3) GMR systems described herein may be use in saliva analyte detection. Any protein, DNA, metal or other substance in saliva or mouth epithelium can be measured and/or detected by the GMR devices described herein. Exemplary biomarkers include, without limitation, matrix metalloproteinases (i.e., MMP1, MMP3, MMP9), cytokines (i.e., interleukin-6, interleukin-8, vascular endothelial growth factor A (VEGF-A), tumor necrosis factor (TNF), transferrins, and fibroblast growth factors, myeloid-related protein 14 (MRP14), profilin, cluster of differentiation 59 (CD59), catalase, and Mac-2-binding protein (M2BP), etc. Drugs include Amphetamines (AMP), Barbiturates (BAR), Benzodiazepines (BZO), Buprenorphine (BUP), Cocaine (COC), Cotinine (COT), Fentanyl (FYL), K2/Spice (K2), Ketamine (KET), Methamphetamine (MET), Methadone (MTD), Opiates (OPI), Oxycodone (OXY), Phencyclidine (PCP), Marijuana (THC), and Tramadol (TML).

(4) GMR systems described herein may be use in ocular fluid analyte detection. Any protein, DNA, metal or other substance in ocular fluid can be measured and/or detected by the GMR devices described herein. Ocular fluid protein biomarkers include, without limitation α-enolase, α-1 acid glycoprotein 1, S100 A8/calgranulin A, S100 A9/calgranulin B, S100 A4 and S100 A11 (calgizzarin), prolactin-inducible protein (PIP), lipocalin-1 (LCN-1), lactoferrin and lysozyme, b-amyloid 1-40, Neutrophil defensins NP-1 and NP-2, etc, can be measured by sandwich assay in the system.

(5) Embodiments disclosed herein may employ a liquid biopsy as a sample for query analytes, such as biomarkers. In some such embodiments, there may be provided methods for identifying cancer in patients' blood. Methods described below may be used to detect "rare" mutations in DNA found in the blood. DNA from cancer cells frequently enter the blood stream, however most of the blood borne DNA (>99%) will be from healthy cells. The methods disclosed herein provide for detecting these "rare" mutations and verifying the results. Methods disclosed herein provide for a multistep process to be captured in a single assay using a GMR detection platform.

Methods disclosed herein comprise extracting DNA from blood, which in accordance with embodiments herein, are automated in cartridge which can perform the requisite extract and purification of DNA from the blood. In some embodiments, a silica membrane is employed as part of the extraction process, but methods herein are not so limited. After extraction and purification, the methods provide for selectively amplifying the query biomarker of interest. In some embodiments, methods for amplifying just the cancer DNA involves the use of locked nucleic acids to act as a blocker to prevent normal DNA from being amplified. Other selective amplification methods are known in the art. The next step in the methods is detecting whether the cancer DNA biomarker of interest is present in the patient sample. In some embodiments, this is achieved using exonuclease to convert double-stranded DNA (dsDNA) to single-stranded DNA (ssDNA). Other ways to convert dsDNA to ssDNA are known in the art. The methods continue with capturing the ssDNA by using a complimentary segment of DNA printed on the biosurface. In some embodiments, the ssDNA has a biotin attached to the end, and this biotin captures a streptavidin tagged magnetic bead. In some embodiments, methods include verifying whether the ssDNA (from the patient) is perfectly complimentary to the printed probe (synthetic segment of DNA). Verification can be accomplished using heat to denature the binding between two pieces of DNA. Imperfect binding will denature (or separate) at a lower temperature, than the perfect binding. This allows for verification of the signal, determining if the signal is caused by a true-positive or a false-positive. By using this verification step one can achieve a higher level of accuracy in diagnosing patients. There are other methods besides heating to denature DNA are known in the art.

Provided herein are methods and compositions for analyzing nucleic acids. In some embodiments, nucleic acid fragments in a mixture of nucleic acid fragments are analyzed. Nucleic acid may be isolated from any type of suitable biological specimen or sample (e.g., a test sample). In some embodiments, a sample comprises nucleic acids. A sample or test sample can be any specimen that is isolated or obtained from a subject (e.g., a mammal, a human). Non-limiting examples of specimens include fluid or tissue from a subject, including, without limitation, blood, amniotic fluid, cerebrospinal fluid, spinal fluid, lavage fluid (e.g., bronchoalveolar, gastric, peritoneal, ductal, ear, arthroscopic), a biopsy sample, urine, feces, sputum, saliva, nasal mucous, prostate fluid, lavage, semen, lymphatic fluid, bile, tears, sweat, breast milk, the like or combination thereof. In some embodiments, a biological sample is blood, or a blood product (e.g., plasma or serum). Nucleic acid may be derived from one or more samples or sources.

In some embodiments, a sample is contacted with one or more suitable cell lysis reagents. Lysis reagents are often configured to lyse whole cells, and/or separate nucleic acids from contaminants (e.g., proteins, carbohydrates and fatty acids). Non-limiting examples of cell lysis reagents include detergents, hypotonic solutions, high salt solutions, alkaline solutions, organic solvents (e.g., phenol, chloroform), chaotropic salts, enzymes, the like, or combination thereof. Any suitable lysis procedure can be utilized for a method described herein.

The term "nucleic acid" refers deoxyribonucleic acid (DNA, e.g., complementary DNA (cDNA), genomic DNA (gDNA) and the like) and/or ribonucleic acid (RNA, e.g., mRNA, short inhibitory RNA (siRNA)), DNA or RNA analogs (e.g., containing base analogs, sugar analogs and/or a non-native backbone and the like), RNA/DNA hybrids and polyamide nucleic acids (PNAs), the like and combinations thereof. Nucleic acids can be single- or double-stranded. In some embodiments, a nucleic acid is a primer. In some embodiments, a nucleic acid is a target nucleic acid. A target nucleic acid is often a nucleic acid of interest.

Nucleic acid may be provided for conducting methods described herein without processing of a sample containing the nucleic acid, in certain embodiments. In some embodiments, nucleic acid is provided for conducting methods described herein after processing of a sample containing the nucleic acid. For example, a nucleic acid can be extracted, isolated, purified, partially purified or amplified from a sample prior to, during or after a method described herein.

In some embodiments, a nucleic acid is amplified by a process comprising nucleic acid amplification wherein one or both strands of a nucleic acid are enzymatically replicated such that copies or complimentary copies of a nucleic acid strand are generated. Copies of a nucleic acid that are generated by an amplification process are often referred to as amplicons. A nucleic acid amplification process can linearly or exponentially generates amplicons having the same or substantially the same nucleotide sequence as a template or target nucleic acid, or segment thereof. A nucleic acid may be amplified by a suitable nucleic acid amplification process non-limiting examples of which include polymerase chain reaction (PCR), nested (n) PCR, quantitative (q) PCR, real-time PCR, reverse transcription (RT) PCR, isothermal amplification (e.g., loop mediated isothermal amplification (LAMP)), quantitative nucleic acid sequence-based amplification (QT-NASBA), the like, variations thereof, and combinations thereof. In some embodiments, an amplification process comprises a polymerase chain reaction. In some embodiments, an amplification process comprises an isothermal amplification process.

In some embodiments, a nucleic acid amplification process comprises the use of one or more primers (e.g., a short oligonucleotide that can hybridize specifically to a nucleic acid template or target). A hybridized primer can often be extended by a polymerase during a nucleic acid amplification process). In some embodiments, a sample comprising nucleic acids is contacted with one or more primers. In some embodiments, a nucleic acid is contacted with one or more primers. A primer can be attached to a solid substrate or may be free in solution.

In some embodiments a nucleic acid or primer, comprises one or more distinguishable identifiers. Any suitable distinguishable identifier and/or detectable identifier can be used for a composition or method described herein. In certain embodiments a distinguishable identifier can be directly or indirectly associated with (e.g., bound to) a nucleic acid. For example, a distinguishable identifier can be covalently or non-covalently bound to a nucleic acid. In some embodiments a distinguishable identifier is attached to a member of binding pair that is covalently or non-covalently bound to a nucleic acid. In some embodiments a distinguishable identifier is reversibly associated with a nucleic acid. In certain embodiments a distinguishable identifier that is reversibly associated with a nucleic acid can be removed from a nucleic acid using a suitable method (e.g., by increasing salt concentration, denaturing, washing, adding a suitable solvent and/or by heating).

In some embodiments a distinguishable identifier is a label. In some embodiments a nucleic acid comprises a detectable label, non-limiting examples of which include a radiolabel (e.g., an isotope), a metallic label, a fluorescent label, a chromophore, a chemiluminescent label, an electro-chemiluminescent label (e.g., Origen™), a phosphorescent label, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an enzyme substrate, a small molecule, a mass tag, quantum dots, the like or combinations thereof. Any suitable fluorophore can be used as a label. A light emitting label can be detected and/or quantitated by a variety of suitable methods such as, for example, by a photocell, digital camera, flow cytometry, gel electrophoresis, exposure to film, mass spectrometry, cytofluorimetric analysis, fluorescence microscopy, confocal laser scanning microscopy, laser scanning cytometry, the like and combinations thereof.

In some embodiments a distinguishable identifier is a barcode. In some embodiments a nucleic acid comprises a nucleic acid barcode (e.g., indexing nucleotides, sequence tags or "barcode" nucleotides). In certain embodiments a nucleic acid barcode comprises a distinguishable sequence of nucleotides usable as an identifier to allow unambiguous identification of one or more nucleic acids (e.g., a subset of nucleic acids) within a sample, method or assay. In certain embodiments a nucleic acid barcode is specific and/or unique to a certain sample, sample source, a particular nucleic acid genus or nucleic acid species, chromosome or gene, for example.

In some embodiments a nucleic acid or primer comprises one or more binding pairs. In some embodiments a nucleic acid or primer comprises one or more members of a binding pair. In some embodiments a binding pair comprises at least two members (e.g., molecules) that bind non-covalently and specifically to each other. Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair includes antibody/antigen, antibody/antibody receptor, antibody/protein A or protein G, hapten/anti-hapten, sulfhydryl/maleimide, sulfhydryl/haloacetyl derivative, amine/isotriocyanate, amine/succinimidyl ester, amine/sulfonyl halides, biotin/avidin, biotin/streptavidin, folic acid/folate binding protein, receptor/ligand, vitamin B12/intrinsic factor, analogues thereof, derivatives thereof, binding portions thereof, the like or combinations thereof. Non-limiting examples of a member of a binding pair include an antibody or antibody fragment, antibody receptor, an antigen, hapten, a peptide, protein, a fatty acid, a glyceryl moiety (e.g., a lipid), a phosphoryl moiety, a glycosyl moiety, a ubiquitin moiety, lectin, aptamer, receptor, ligand, metal ion, avidin, neutravidin, biotin, B12, intrinsic factor, analogues thereof, derivatives thereof, binding portions thereof, the like or combinations thereof. In some embodiments, a nucleic acid or primer comprises biotin. In some embodiments, a nucleic acid or primer is covalently attached to biotin.

In some embodiments a nucleic acid or primer is attached non-covalently or covalently to a suitable solid substrate. In some embodiments, a capture oligonucleotide and/or a member of a binding pair is attached to a solid substrate. A capture oligonucleotide is often a nucleic acid configured to hybridize specifically to a target nucleic acid. In some embodiments a capture nucleic acid is a primer that is attached to a solid substrate. Non-limiting examples of a solid substrate include surfaces provided by microarrays and particles such as beads (e.g., paramagnetic beads, magnetic beads, microbeads, nanobeads), microparticles, and nanoparticles. Solid substrates also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), poly-formaldehyde, cellulose, cellulose acetate, paper, ceramics, metals, metalloids, semi-conductive materials, quantum dots, coated beads or particles, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In some embodiments, a solid substrate is coated using passive or chemically-derivatized coatings with any number of materials, including polymers, such as dextrans, acrylamides, gelatins or agarose. Beads and/or particles may be free or in connection with one another (e.g., sintered). In some embodiments, a solid substrate refers to a collection of particles. In some embodiments, particles comprise an agent that confers a paramagnetic property to the particles. In some embodiments a first solid substrate (e.g., a plurality of magnetic particles) is non-covalently and/or reversibly attached to a second solid substrate (e.g., a surface). In some embodiments, a second substrate or surface can be magnetized electronically such that magnetic particles are reversibly attached to the second substrate when the surface is magnetized, and the magnetic particles can be released when the second substrate is demagnetized or where the magnetic polarity of the second substrate is changed.

In some embodiments, a nucleic acid is a capture oligonucleotide. In some embodiments, a capture oligonucleotide is a nucleic acid that is attached covalently or non-covalently to a solid substrate. A capture oligonucleotide typically comprises a nucleotide sequence capable of hybridizing or annealing specifically to a nucleic acid of interest (e.g. target nucleic acid) or a portion thereof. In some embodiments, a capture nucleic acid comprises a nucleic acid sequence that is substantially complimentary to a target nucleic acid, or portion thereof. In some embodiments, a capture oligonucleotide is a primer that is attached to a solid substrate. A capture oligonucleotide may be naturally occurring or synthetic and may be DNA or RNA based. Capture oligonucleotides can allow for specific separation of, for example, a target nucleic acid from other nucleic acids or contaminants in a sample.

In some embodiments, a method described herein comprises contacting a plurality of nucleic acids (e.g., nucleic acids in a sample) with at least one primer comprising a member of a binding pair. In some embodiments, a member of a binding pair comprise biotin. In some embodiments, the plurality of nucleic acids is contacted with a first primer and a second primer, where one of the first or second primers comprise biotin. In some embodiments, a plurality of nucleic acids comprises a target nucleic acid (e.g., a target RNA or DNA molecule). A target nucleic acid is often a nucleic acid of interested (e.g., a gene, a transcript or portion thereof). In some embodiments, a target nucleic comprises RNA. In some embodiments a target nucleic acid is amplified by a nucleic acid amplification process. In some embodiments, the nucleic amplification process comprises contacting a sample, nucleic acids of a sample and/or a target nucleic acid with a first primer, a second primer that is biotinylated and a polymerase under suitable conditions that promote nucleic acid amplification (e.g., conditions conducive to PCR or isothermal amplification). In some embodiments, a nucleic acid amplification process results in the production of amplicons. In some embodiments, amplicons comprise DNA amplicons, RNA amplicons, or a combination thereof. In some embodiments, amplicons comprise biotinylated DNA amplicons, RNA amplicons, or a combination thereof. In some embodiments, amplicons comprising RNA and biotinylated DNA (e.g., RNA/DNA duplexes) are contacted with a nuclease (e.g., an RNA exonuclease). In some embodiments, DNA amplicons are non-covalently attached to a solid substrate comprising a capture oligonucleotide, where the DNA amplicons, or a portion thereof, hybridize specifically to the capture oligonucleotide. In some embodiments, biotinylated amplicons are contacted with, and/or are attached to magnetic beads comprising streptavidin, or a variant thereof.

Accordingly, in some embodiments, there are provided methods of detecting the presence of an analyte in a query sample comprising providing a sensor comprising a biomolecule disposed on a functionalized surface of a giant magnetoresistance (GMR) sensor, the biomolecule comprising a cleavable portion covalently bound to the biomolecule, cleavage being catalyzed by the presence of the analyte in the query sample and a receptor associated with the cleavable portion of the biomolecule, the receptor being capable of binding a magnetic nanoparticle, passing the query sample over the sensor, thereby allowing cleavage and removal of the cleavable portion with the associated receptor from the biomolecule if the analyte is present, passing magnetic particles over the sensor after passing the query sample over the sensor, and detecting the presence of the analyte in the query sample by measuring magnetoresistance change of the GMR sensor based on determining magnetoresistance before and after passing magnetic particles over the sensor.

In some embodiments, there are provided methods of amplifying a signal, such as a change in magnetoresistance of a GMR sensor that detects the presence of an analyte in a query sample, comprising providing a sensor comprising a biomolecule disposed on a functionalized surface of a giant magnetoresistance (GMR) sensor, the biomolecule comprising a cleavable portion covalently bound to the biomolecule, cleavage being catalyzed by the presence of the analyte in the query sample and a receptor associated with the cleavable portion of the biomolecule, the receptor being capable of binding a magnetic nanoparticle, passing the query sample over the sensor, thereby allowing cleavage and removal of the cleavable portion with the associated receptor from the biomolecule if the analyte is present, passing a plurality of magnetic particles comprising a first member of a binding pair over the sensor after passing the query sample over the sensor, then passing a plurality of magnetic particles comprising a second member of the binding pair over the sensor, and detecting the presence of the analyte in the query sample by measuring magnetoresistance change of the GMR sensor based on determining magnetoresistance before and after passing magnetic particles over the sensor. In some embodiments, such methods further comprise passing a second plurality of magnetic particles comprising the second member of the binding pair over the sensor after passing the second plurality of magnetic particles comprising first second member of the binding pair over the GMR sensor. In some embodiments, such methods further comprise passing one or more subsequent pluralities of magnetic particles comprising the first member of the binding pair, and one or more subsequent pluralities of magnetic particles comprising the second member of the binding pair, over the GMR sensor. In some embodiments, the binding pair comprises streptavidin and biotin. In some embodiments, the first member of the binding pair comprises streptavidin. In some embodiments, the second member of the binding pair comprises biotin.

In some embodiments, the methods further comprise calculating a concentration of analyte in the query sample based on the magnetoresistance change of the GMR sensor.

In one or more of the preceding embodiments, methods include performing a buffer wash over the sensor prior to passing the query sample over the sensor.

In one or more of the preceding embodiments, methods include performing a buffer wash over the sensor after passing the query sample over the sensor but before passing the magnetic particles over the sensor.

In one or more of the preceding embodiments, methods include performing a buffer wash over the sensor after passing the magnetic particles over the sensor.

In one or more of the preceding embodiments, the analyte is a metal ion.

In one or more of the preceding embodiments, the query sample is water.

In one or more of the preceding embodiments, the query sample is derived from the blood of a subject.

In one or more of the preceding embodiments, the biomolecule is double stranded DNA (dsDNA).

In one or more of the preceding embodiments, the receptor is covalently bound to one of the two strands of the dsDNA.

In one or more of the preceding embodiments, the dsDNA comprises a DNAzyme, the DNAzyme activated by the metal ion.

In one or more of the preceding embodiments, methods include determining magnetoresistance change of the GMR sensor comprises using at least one reference resistor to perform phase-sensitive solution of magnetoresistance change of the GMR sensor.

In one or more of the preceding embodiments, a plurality of biomolecules are attached on the surface of the sensor in a density of about $1\times10^9$ to about $5\times10^{10}$ biomolecules per/mm$^2$.

In one or more of the preceding embodiments, a sensitivity limit of detection is in a range from about 1 nanomolar to about 10 nanomolar in the analyte.

In one or more of the preceding embodiments, passing the query sample over the detector comprises a flow rate of the query sample over the sensor at a rate of about 1 microL/min to about 20 microL/min.

In some embodiments, there are provided methods of detecting the presence of an analyte in a query sample comprising providing a sensor comprising a biomolecule disposed on a functionalized surface of a giant magnetoresistance (GMR) sensor, the biomolecule comprising an antigenic portion that binds an antibody at an antigen binding site, the antibody further comprising a portion separate from the antigen binding site configured to bind a magnetic nanoparticle, passing a mixture of the query sample and the antibody over the sensor, wherein the antigen binding site of the antibody binds the analyte if present in the query sample, thereby preventing binding of the antibody to the antigenic portion of the biomolecule, passing magnetic particles over the sensor after passing the mixture over the sensor, and detecting the presence of the analyte in the query sample by measuring a magnetoresistance change of the GMR sensor based on determining magnetoresistance before and after passing magnetic particles over the sensor.

In some embodiments, there are provided methods of amplifying a signal, such as a change in magnetoresistance of a GMR sensor, comprising detecting the presence of an analyte in a query sample by a method comprising providing a sensor comprising a biomolecule disposed on a functionalized surface of a giant magnetoresistance (GMR) sensor, the biomolecule comprising an antigenic portion that binds an antibody at an antigen binding site, the antibody further comprising a portion separate from the antigen binding site configured to bind a magnetic nanoparticle, passing a mixture of the query sample and the antibody over the sensor, wherein the antigen binding site of the antibody binds the analyte if present in the query sample, thereby preventing binding of the antibody to the antigenic portion of the biomolecule, passing a plurality of magnetic particles comprising a first member of a binding pair over the sensor after passing the mixture of the query sample and the antibody over the sensor, then passing a plurality of magnetic particles comprising a second member of the binding pair over the sensor, and detecting the presence of the analyte by measuring an amplified magnetoresistance change of the GMR sensor based on determining magnetoresistance before and after passing magnetic particles over the GMR sensor. In some embodiments, such methods further comprise passing a second plurality of magnetic particles comprising the first member of a binding pair over the sensor after passing the plurality of magnetic particles comprising the second member of the binding pair over the sensor. In some embodiments, such methods further comprise passing a second plurality of magnetic particles comprising the second member of the binding pair over the sensor after passing the second plurality of magnetic particles comprising first second member of the binding pair over the GMR sensor. In some embodiments, such methods further comprise passing one or more subsequent pluralities of magnetic particles comprising the first member of the binding pair, and one or more subsequent pluralities of magnetic particles comprising the second member of the binding pair, over the GMR sensor. In some embodiments, the binding pair comprises streptavidin and biotin. In some embodiments, the first member of the binding pair comprises streptavidin. In some embodiments, the second member of the binding pair comprises biotin.

In some embodiments, the methods further comprise calculating a concentration of the analyte in the query sample based on the magnetoresistance change of the GMR sensor.

In one or more of the preceding embodiments, methods may further comprise performing a buffer wash over the sensor prior to passing the mixture over the sensor.

In one or more of the preceding embodiments, methods may further comprise performing a buffer wash over the sensor after passing the mixture over the sensor but before passing the magnetic particles over the sensor.

In one or more of the preceding embodiments, methods may further comprise performing a buffer wash over the sensor after passing the magnetic particles over the sensor.

In one or more of the preceding embodiments, the analyte is a metal ion.

In one or more of the preceding embodiments, the query sample is water.

In one or more of the preceding embodiments, the query sample is derived from the blood of a subject.

In one or more of the preceding embodiments, the biomolecule is a protein.

In one or more of the preceding embodiments, the protein is a bovine serum albumin.

In one or more of the preceding embodiments, determining magnetoresistance change of the GMR sensor comprises using at least one reference resistor to perform phase-sensitive solution of magnetoresistance change of the GMR sensor.

In one or more of the preceding embodiments, a plurality of biomolecules are attached on the surface of the sensor in a density of about $1\times10^9$ to about $5\times10^{10}$ biomolecules per/mm$^2$.

In one or more of the preceding embodiments, a sensitivity limit of detection is in a range from about 1 nanomolar to about 10 nanomolar in the metal ion.

In one or more of the preceding embodiments, passing the mixture over the detector comprises a flow rate of the mixture over the sensor at a rate of about 1 uL/min to about 20 uL/min.

In some embodiments, there are provided methods of detecting the presence of an analyte in a query sample comprising providing a sensor comprising a biomolecule disposed on a functionalized surface of a giant magnetoresistance (GMR) sensor, the biomolecule comprising a binding region configured to bind a detection protein, the detection protein also being capable of binding the analyte, wherein when the detection protein binds the analyte, it prevents binding of the detection protein to the binding region of the biomolecule, passing the detection protein over the sensor, passing the query sample over the sensor, passing a reporter protein over the sensor after passing the query sample over the sensor, the reporter protein capable of binding the detection protein and the reporter protein configured to bind to magnetic particles, passing magnetic particles over the sensor after passing the reporter protein over the sensor, and detecting the presence of the metal ion by measuring magnetoresistance change of the GMR sensor based on determining magnetoresistance before and after passing magnetic particles over the sensor.

In some embodiments, there are provided methods of amplifying a signal, such as a change in magnetoresistance, of a GMR sensor comprising of detecting the presence of an analyte in a query sample comprising providing a sensor comprising a biomolecule disposed on a functionalized surface of a giant magnetoresistance (GMR) sensor, the biomolecule comprising a binding region configured to bind a detection protein, the detection protein also being capable of binding the analyte, wherein when the detection protein binds the analyte, it prevents binding of the detection protein to the binding region of the biomolecule, passing the detection protein over the sensor, passing the query sample over the sensor, passing a reporter protein over the sensor after passing the query sample over the sensor, the reporter protein capable of binding the detection protein and the reporter protein configured to bind to magnetic particles, passing a plurality of magnetic particles comprising a first member of a binding pair over the sensor after passing the reporter protein configured to bind to the first plurality of magnetic particles comprising a first member of a binding pair over the sensor, then passing a plurality of magnetic particles comprising a second member of the binding pair over the sensor and detecting the presence of the analyte by measuring an amplified magnetoresistance change of the GMR sensor based on determining magnetoresistance before and after passing magnetic particles over the GMR sensor. In some embodiments, such methods further comprise passing a second plurality of magnetic particles comprising the first member of a binding pair over the sensor after passing the plurality of magnetic particles comprising the second member of the binding pair over the sensor. In some embodiments, such methods further comprise passing a second plurality of magnetic particles comprising the second member of the binding pair over the sensor after passing the second plurality of magnetic particles comprising first second member of the binding pair over the GMR sensor. In some embodiments, such methods further comprise passing one or more subsequent pluralities of magnetic particles comprising the first member of the binding pair, and one or more subsequent pluralities of magnetic particles comprising the second member of the binding pair, over the GMR sensor. In some embodiments, the binding pair comprises streptavidin and biotin. In some embodiments, the first member of the binding pair comprises streptavidin. In some embodiments, the second member of the binding pair comprises biotin.

In some embodiments, methods may further comprise calculating a concentration of the analyte in the query sample based on the magnetoresistance change.

In one or more of the preceding embodiments, methods may further comprise performing one or more buffer washes.

In one or more of the preceding embodiments, the detection protein and query sample are mixed prior to passing them over the sensor.

In one or more of the preceding embodiments, the query sample is passed over the sensor after the detection protein is passed over the sensor.

In one or more of the preceding embodiments, the analyte is a metal ion.

In one or more of the preceding embodiments, the query sample is water.

In one or more of the preceding embodiments, the query sample is derived from the blood of a subject.

In one or more of the preceding embodiments, the biomolecule is double stranded DNA (dsDNA).

In one or more of the preceding embodiments, the detection protein is an arsenic-binding regulatory protein comprising a tag.

In one or more of the preceding embodiments, the detection protein is a cadmium-binding regulatory protein comprising a tag.

In one or more of the preceding embodiments, the tag is glutathione S-transferase.

In one or more of the preceding embodiments, the tag is a poly-histidine.

In one or more of the preceding embodiments, the reporter protein is a biotinylated antibody.

In one or more of the preceding embodiments, the magnetic particles comprise streptavidin-linked particles.

In one or more of the preceding embodiments, determining magnetoresistance change of the GMR sensor comprises using at least one reference resistor to perform phase-sensitive solution of magnetoresistance change of the GMR sensor.

In one or more of the preceding embodiments, a plurality of biomolecules are attached on the surface of the sensor in a density $1\times10^9$ to about $5\times10^{10}$ biomolecules per/mm2.

In one or more of the preceding embodiments, a sensitivity limit of detection is in a range from about 1 nanomolar to about 10 nanomolar in the metal ion.

In one or more of the preceding embodiments, passing the query sample over the detector comprises a flow rate of the query sample over the sensor at a rate of about 1 uL/min to about 20 uL/min.

In some embodiments, there are provided methods of detecting the presence of an analyte in a query sample comprising providing a sensor comprising a biomolecule disposed on a functionalized surface of a giant magnetoresistance (GMR) sensor, the biomolecule comprising an associated magnetic particle, passing the query sample over the sensor, thereby causing removal of the associated magnetic particle from the biomolecule if the analyte is present, detecting the presence of the analyte in the query sample by measuring magnetoresistance change of the GMR sensor based on determining magnetoresistance before and after passing the query sample over the sensor, wherein determining magnetoresistance change of the GMR sensor comprises using at least one reference resistor to perform phase-sensitive solution of magnetoresistance change of the GMR sensor.

In some embodiments, there are provided methods of detecting the presence of an analyte in a query sample comprising providing a sensor comprising a first biomolecule disposed on a functionalized surface of a giant magnetoresistance (GMR) sensor, the first biomolecule comprising a conditional binding site for a second biomolecule comprising a binding site for a magnetic particle, passing the query sample over the sensor, passing the second biomolecule over the sensor, passing magnetic particles over the sensor after passing the query sample over the sensor, and detecting the presence of the analyte in the query sample by measuring magnetoresistance change of the GMR sensor based on determining magnetoresistance before and after passing magnetic particles over the sensor, wherein determining magnetoresistance change of the GMR sensor comprises using at least one reference resistor to perform phase-sensitive solution of magnetoresistance change of the GMR sensor.

In some embodiments, there are provided methods of detecting the presence of an analyte in a query sample comprising providing a sensor comprising a first biomolecule disposed on a functionalized surface of a giant magnetoresistance (GMR) sensor, the first biomolecule comprising a conditional binding site for a second biomolecule comprising a binding site for a magnetic particle, passing the query sample over the sensor, passing the second biomolecule over the sensor, passing a plurality of magnetic nanoparticles comprising a first member of a binding pair over the sensor after passing the second biomolecule over the sensor, then passing a plurality of magnetic nanoparticles comprising a second member of the binding pair over the sensor and detecting the presence of the analyte by measuring an amplified magnetoresistance change of the GMR sensor based on determining magnetoresistance before and after passing magnetic particles over the GMR sensor. In some embodiments, such methods further comprise passing a second plurality of magnetic nanoparticles comprising the first member of a binding pair over the sensor after passing the plurality of magnetic nanoparticles comprising the second member of the binding pair over the sensor. In some embodiments, such methods further comprise passing a second plurality of magnetic nanoparticles comprising the second member of the binding pair over the sensor after passing the second plurality of magnetic nanoparticles comprising first second member of the binding pair over the GMR sensor. In some embodiments, such methods further comprise passing one or more subsequent pluralities of magnetic nanoparticles comprising the first member of the binding pair, and one or more subsequent pluralities of magnetic nanoparticles comprising the second member of the binding pair, over the GMR sensor. In some embodiments, the binding pair comprises streptavidin and biotin. In some embodiments, the first member of the binding pair comprises streptavidin. In some embodiments, the second member of the binding pair comprises biotin.

In one or more of the preceding embodiments, the presence of the analyte prevents the binding of the second biomolecule.

In one or more of the preceding embodiments, the presence of the analyte enables the binding of the second molecule to the first biomolecule.

In some embodiments, there are provided methods of detecting the presence of an analyte in a query sample comprising providing a sensor comprising a first biomolecule disposed on a functionalized surface of a giant magnetoresistance (GMR) sensor, the biomolecule comprising a binding site for a magnetic particle when the analyte is present, passing the query sample over the sensor, passing magnetic particles over the sensor after passing the query sample over the sensor, and detecting the presence of the analyte in the query sample by measuring magnetoresistance change of the GMR sensor based on determining magnetoresistance before and after passing magnetic particles over the sensor, wherein determining magnetoresistance change of the GMR sensor comprises using at least one reference resistor to perform phase-sensitive solution of magnetoresistance change of the GMR sensor.

In one or more of the preceding embodiments, methods may further comprise calculating a concentration of analyte in the query sample based on the magnetoresistance change of the GMR sensor.

In one or more of the preceding embodiments, the biomolecule comprises DNA.

In one or more of the preceding embodiments, the biomolecule comprises a protein.

In some embodiments, there are provided systems configured to carry out the methods disclosed herein comprising, the system comprising a sample processing subsystem, a sensor subsystem comprising a microfluidics network comprising a GMR sensor having disposed on a functionalized surface of the sensor a biomolecule, a plurality of wires connected to a plurality of contact pads to carry a signal to a processor, a processor, and a pneumatic control subsystem for moving samples, reagents, and solvents throughout the sample processing subsystem and the sensor subsystem.

In some embodiments, there are provided methods of detecting the presence of a metal ion in a query sample comprising providing a sensor comprising a biomolecule disposed on a functionalized surface of a giant magnetoresistance (GMR) sensor, the biomolecule comprising a cleavable portion covalently bound to the biomolecule, cleavage being catalyzed by the presence of the metal ion in the query sample, and a receptor associated with the cleavable portion of the biomolecule, the receptor being capable of binding a magnetic nanoparticle, passing the query sample over the sensor, thereby allowing cleavage and removal of the cleavable portion with the associated receptor from the biomolecule if the metal ion is present, passing magnetic particles over the sensor after passing the query sample over the sensor, and detecting the presence of the metal ion in the query sample by measuring a magnetoresistance change of the GMR sensor based on determining magnetoresistance before and after passing magnetic particles over the GMR sensor.

In some embodiments, such methods may further comprise calculating a concentration of metal ion in the query sample based on the magnetoresistance change of the GMR sensor.

In one or more of the preceding embodiments, methods may further comprise performing a buffer wash over the sensor prior to passing the query sample over the sensor.

In one or more of the preceding embodiments, methods may further comprise performing a buffer wash over the sensor after passing the query sample over the sensor but before passing the magnetic particles over the sensor.

In one or more of the preceding embodiments, methods may further comprise performing a buffer wash over the sensor after passing the magnetic particles over the sensor.

In one or more of the preceding embodiments, the metal ion is lead.

In one or more of the preceding embodiments, the query sample is water.

In one or more of the preceding embodiments, the query sample is derived from the blood of a subject.

In one or more of the preceding embodiments, the biomolecule is double stranded DNA (dsDNA).

In one or more of the preceding embodiments, the receptor is covalently bound to one of the two strands of the dsDNA.

In one or more of the preceding embodiments, the dsDNA comprises a DNAzyme, the DNAzyme activated by the metal ion.

In one or more of the preceding embodiments, determining magnetoresistance change of the GMR sensor comprises using at least one reference resistor to perform phase-sensitive solution of magnetoresistance change of the GMR sensor.

In one or more of the preceding embodiments, a plurality of biomolecules are attached on the surface of the sensor in a density of about $1 \times 10^9$ to about $5 \times 10^{10}$ biomolecules per/mm$^2$.

In one or more of the preceding embodiments, a sensitivity limit of detection is in a range from about 10 nanomolar to about 1 micromolar in the metal ion.

In one or more of the preceding embodiments, passing the query sample over the detector comprises a flow rate of the query sample over the sensor at a rate of about 0.5 uL/min to about 5 uL/min. The sample is flowed over the sensor in a constant supply of fresh sample. This ensures maximum exposure of the dsDNA to metal ion present in the sample solution. For example, for lead ion, the sample is flowed over the sensor for 30 minutes.

In some embodiments, there are provided methods of detecting the presence of lead ion in a query sample comprising providing a sensor comprising double stranded DNA (dsDNA) disposed on a functionalized surface of a giant magnetoresistance (GMR) sensor, the dsDNA comprising a cleavable portion of one strand of the dsDNA, cleavage being catalyzed by the presence of lead ion in the query sample, and a receptor associated with the cleavable portion, the receptor being capable of binding a magnetic nanoparticle, passing the query sample over the sensor, thereby allowing cleavage and removal of the cleavable portion with the associated receptor from the dsDNA if lead ion is present, passing magnetic particles over the sensor after passing the query sample over the sensor, and detecting the presence of lead ion in the query sample by measuring magnetoresistance change of the GMR sensor based on determining magnetoresistance before and after passing magnetic particles over the GMR sensor.

In some such embodiments, methods may further comprise calculating a concentration of lead ion in the query sample based on the magnetoresistance change of the GMR sensor.

In one or more of the preceding embodiments, methods may further comprise performing a buffer wash over the sensor prior to passing the query sample over the sensor.

In one or more of the preceding embodiments, methods may further comprise performing a buffer wash over the sensor after passing the query sample over the sensor but before passing the magnetic particles over the sensor.

In one or more of the preceding embodiments, may further comprise performing a buffer wash over the sensor after passing the magnetic particles over the sensor.

In one or more of the preceding embodiments, the query sample is water.

In one or more of the preceding embodiments, the query sample is derived from the blood of a subject.

In one or more of the preceding embodiments, the receptor is covalently bound.

In one or more of the preceding embodiments, the dsDNA comprises a DNAzyme, the DNAzyme activated by the lead ion.

In one or more of the preceding embodiments, determining magnetoresistance change of the GMR sensor comprises using at least one reference resistor to perform phase-sensitive solution of magnetoresistance change of the GMR sensor In one or more of the preceding embodiments, a plurality of dsDNAs are attached on the surface of the sensor in a density of about $1 \times 10^9$ to about $5 \times 10^{10}$ biomolecules per/mm$^2$.

In one or more of the preceding embodiments, a sensitivity limit of detection is in a range from about 1 nanomolar to about 10 nanomolar in lead ion.

In one or more of the preceding embodiments, passing the query sample over the detector comprises a flow rate of the query sample over the sensor at a rate of about 0.5 uL/min to about 5 uL/min.

In some embodiments, there are provided sensors comprising a biomolecule disposed on a functionalized surface of the giant magnetoresistance (GMR) sensor, the biomolecule comprising a cleavable portion covalently bound to the biomolecule, cleavage being catalyzed by the presence of a metal ion and a receptor associated with the cleavable portion, the receptor being capable of binding a magnetic nanoparticle; wherein when the cleavable portion is cleaved, the cleavable portion with the receptor is no longer covalently bound to the biomolecule.

In some such embodiments, the biomolecule is double stranded DNA (dsDNA).

In one or more of the preceding embodiments, the receptor is covalently bound to one of the two strands of the dsDNA.

In one or more of the preceding embodiments, the dsDNA comprises a DNAzyme, the DNAzyme activated by the metal ion.

In one or more of the preceding embodiments, a plurality of biomolecules are attached on the surface of the sensor in a density of about $1 \times 10^9$ to about $5 \times 10^{10}$ biomolecules per/mm$^2$.

In one or more of the preceding embodiments, the surface of the GMR sensor comprises a crosslinked PEG-PHEMA polymer.

In one or more of the preceding embodiments, the polymer is coated with a surfactant.

In one or more of the preceding embodiments, the surfactant is cetyl trimethylammonium bromide.

In one or more of the preceding embodiments, sensors may further comprise a plurality of wires connected to a plurality of contact pads configured to carry an electronic signal from the sensor to a processor.

In some embodiments, there are provided sensors comprising double stranded DNA (dsDNA) disposed on a functionalized surface of the giant magnetoresistance (GMR) sensor, the dsDNA comprising a cleavable portion, cleavage being catalyzed by the presence of a lead ion and a receptor associated with the cleavable portion, the receptor being capable of binding a magnetic nanoparticle, wherein when the cleavable portion is cleaved, the cleavable portion with the receptor is no longer covalently bound to the dsDNA.

In some such embodiments, the receptor is covalently bound to one of the two strands of the dsDNA.

In one or more of the preceding embodiments, the dsDNA comprises a DNAzyme, the DNAzyme activated by the lead ion.

In one or more of the preceding embodiments, a plurality of dsDNAs are attached on the surface of the sensor in a density of about $1 \times 10^9$ to about $5 \times 10^{10}$ biomolecules per/ mm$^2$.

In one or more of the preceding embodiments, the surface of the GMR sensor comprises a crosslinked PEG-PHEMA polymer.

In one or more of the preceding embodiments, the polymer is coated with a surfactant.

In one or more of the preceding embodiments, the surfactant is cetyl trimethylammonium bromide.

In one or more of the preceding embodiments, sensor may further comprise a plurality of wires connect to a plurality of contact pads configured to carry an electronic signal from the sensor to a processor.

In some embodiments, there are provided cartridges for use in detecting metal ions in a query sample, the cartridge comprising (a) a sensor comprising a biomolecule disposed on a functionalized surface of a giant magnetoresistance (GMR) sensor, the biomolecule comprising a cleavable portion covalently bound to the biomolecule, cleavage being catalyzed by the presence of metal ions in the query sample and a receptor associated with the cleavable portion, the receptor being capable of binding a magnetic nanoparticle; wherein when the cleavable portion is cleaved, the cleavable portion with the receptor is no longer covalently bound to the biomolecule; (b) one or more ports to introduce a query sample, magnetic nanoparticles, and optional wash buffers into the cartridge; and (c) a microfluidics system for moving the query sample, magnetic nanoparticles, and optional wash buffers from the one or more ports to the sensor.

In some such embodiments, such cartridges may further comprise a waste collection area.

In one or more of the preceding embodiments, the biomolecule is double stranded DNA (dsDNA).

In one or more of the preceding embodiments, the receptor is covalently bound to one of the two strands of the dsDNA.

In one or more of the preceding embodiments, the dsDNA comprises a DNAzyme, the DNAzyme activated by the metal ion.

In one or more of the preceding embodiments, a plurality of biomolecules are attached on the surface of the sensor in a density of about $1 \times 10^9$ to about $5 \times 10^{10}$ biomolecules per/mm$^2$.

In one or more of the preceding embodiments, the surface of the GMR sensor comprises a crosslinked PEG-PHEMA polymer.

In one or more of the preceding embodiments, the polymer is coated with a surfactant.

In one or more of the preceding embodiments, the surfactant is cetyl trimethylammonium bromide.

In one or more of the preceding embodiments, cartridges may further comprise a plurality of wires connect to a plurality of contact pads configured to carry an electronic signal from the sensor to a processor.

In one or more of the preceding embodiments, cartridges may further comprise one or more filters to filter the query sample.

In one or more of the preceding embodiments, the metal ions are lead ions.

In one or more of the preceding embodiments, the microfluidics system is pneumatically controlled.

In one or more of the preceding embodiments, the cartridge further comprises one or more hardware chips to control flowrate throughout the microfluidics system.

In some embodiments, there are provided cartridges for use in detecting lead ions in a query sample, the cartridge comprising (a) a sensor comprising double stranded DNA (dsDNA) disposed on a functionalized surface of a giant magnetoresistance (GMR) sensor, the dsDNA comprising a cleavable portion on one strand of the dsDNA, cleavage being catalyzed by the presence of lead ions in the query sample and a receptor associated with the cleavable portion, the receptor being capable of binding a magnetic nanoparticle; wherein when the cleavable portion is cleaved, the cleavable portion with the receptor is no longer covalently bound to the dsDNA; (b) one or more ports to introduce a query sample, magnetic nanoparticles, and optional wash buffers into the cartridge; and (c) a microfluidics system for moving the query sample, magnetic nanoparticles, and optional wash buffers from the one or more ports to the sensor.

In some such embodiments, the cartridge may further comprise a waste collection area.

In one or more of the preceding embodiments, the dsDNA comprises a DNAzyme, the DNAzyme activated by the metal ion.

In one or more of the preceding embodiments, a plurality of dsDNAs are attached on the surface of the sensor in a density of about $1 \times 10^9$ to about $5 \times 10^{10}$ biomolecules per/ mm$^2$.

In one or more of the preceding embodiments, the surface of the GMR sensor comprises a crosslinked PEG-PHEMA polymer.

In one or more of the preceding embodiments, the polymer is coated with a surfactant.

In one or more of the preceding embodiments, the surfactant is cetyl trimethylammonium bromide.

In one or more of the preceding embodiments, cartridges may further comprise a plurality of wires connected to a plurality of contact pads configured to carry an electronic signal from the sensor to a processor.

In one or more of the preceding embodiments, cartridges may further comprise one or more filters to filter the query sample.

In one or more of the preceding embodiments, the microfluidics system is pneumatically controlled.

In one or more of the preceding embodiments, the cartridge further comprises one or more hardware chips to control flowrate throughout the microfluidics system.

In some embodiments, there are provided methods of making a sensor for the detection of lead ions in a query sample comprising (a) printing double stranded DNA (dsDNA) on a surface of a giant magnetoresistance (GMR) sensor; the dsDNA comprising a cleavable portion on one strand of the dsDNA, cleavage being catalyzed by the presence of lead ions in the query sample; and a receptor associated with the cleavable portion, the receptor being capable of binding a magnetic nanoparticle; wherein when the cleavable portion is cleaved, the cleavable portion with the receptor is no longer covalently bound to the dsDNA; the GMR sensor comprising a polymer coating onto which the dsDNA is printed; and (b) modifying the surface of the polymer coating by adding one or more blocking agents to the polymer coating after the printing step; adding a surfactant to the polymer coating after adding the one or more blocking agents.

In some such embodiments, the dsDNA comprises a DNAzyme.

In one or more of the preceding embodiments, the polymer coating comprises a crosslinked PEG-PHEMA polymer.

In one or more of the preceding embodiments, methods may further comprise one or more washing steps with a buffer wash.

In one or more of the preceding embodiments, buffer wash is a HEPES buffer.

In one or more of the preceding embodiments, HEPES buffer has a concentration of 25 mM.

In one or more of the preceding embodiments, the surfactant is acetyl trimethylammonium bromide (CTAB).

In one or more of the preceding embodiments, CTAB has a concentration of 1% by weight in 25 mM HEPES.

In some embodiments, there are provided methods of detecting the presence of a metal ion in a query sample comprising providing a sensor comprising a biomolecule disposed on a functionalized surface of a giant magnetoresistance (GMR) sensor, the biomolecule comprising an antigenic portion that binds an antibody at an antigen binding site, the antibody further comprising a portion separate from the antigen binding site configured to bind a magnetic nanoparticle; passing a mixture of the query sample and the antibody over the sensor, wherein the antigen binding site of the antibody binds the metal ion if present in the query sample, thereby preventing binding of the antibody to the antigenic portion of the biomolecule; passing magnetic particles over the sensor after passing the mixture over the sensor; and detecting the presence of the metal ion in the query sample by measuring a magnetoresistance change of the GMR sensor based on determining magnetoresistance before and after passing magnetic particles over the GMR sensor.

In some such embodiments, methods may further comprise calculating a concentration of metal ion in the query sample based on the magnetoresistance change of the GMR sensor.

In one or more of the preceding embodiments, methods may further comprise performing a buffer wash over the sensor prior to passing the mixture over the sensor.

In one or more of the preceding embodiments, methods may further comprise performing a buffer wash over the sensor after passing the mixture over the sensor but before passing the magnetic particles over the sensor.

In one or more of the preceding embodiments, methods may further comprise performing a buffer wash over the sensor after passing the magnetic particles over the sensor.

In one or more of the preceding embodiments, the metal ion is mercury.

In one or more of the preceding embodiments, the query sample is water.

In one or more of the preceding embodiments, the query sample is derived from the blood of a subject.

In one or more of the preceding embodiments, the biomolecule is a protein.

In one or more of the preceding embodiments, the protein is a modified bovine serum albumin. In embodiments, the modified bovine serum albumin is HgBSA and has the Product Name: $Hg^{2+}$ [BSA] (Cat. No: DAGA-007B) Creative Diagnostics at Ramsey Road Shirley, NY 11967, USA. In embodiments, the antibody paired with HgBSA is HgAb and has Product Name: RHA anti-$Hg^{2+}$ monoclonal antibody, clone Hg2 (Cat. No: HMABPY007) also available from Creative Diagnostics.

In one or more of the preceding embodiments, determining magnetoresistance change of the GMR sensor comprises using at least one reference resistor to perform phase-sensitive solution of magnetoresistance change of the GMR sensor.

In one or more of the preceding embodiments, a sensitivity limit of detection is in a range from about 1 nanomolar to about 10 nanomolar in the metal ion.

In one or more of the preceding embodiments, the sample is flowed over the sensor in a loop. In one or more of the preceding embodiments, the sample is flowed over the sensor providing a constant supply of fresh sample. In one or more of the preceding embodiments, B-HgAb (detection antibody) is added to mercury ion containing query sample at a working concentration of about 0.1 ug/mL. Mercury ion (II) in solution competes with HgBSA substrate for the binding site of HgAb. In solutions that have a high concentration of Hg, very little HgAb can bind to HgBSA. This incubation occurs while flowing of the GMR sensor at a flowrate between 1 ul/min and 5 ul/min. A fresh supply of the sample may be continuously being introduced over the sensor to ensure ample binding time of any non-Hg-bound HgAb. In one or more of the preceding embodiments, the query sample may be reacted for about 30 minutes.

In some embodiments, there are provided methods of detecting the presence of mercury ion in a query sample comprising providing a sensor comprising a protein disposed on a functionalized surface of a giant magnetoresistance (GMR) sensor, the protein comprising an antigenic portion capable of binding to an antibody at an antigen binding site, the antibody further comprising a portion separate from the antigen binding site configured to bind a magnetic nanoparticle; and passing a mixture of the query sample and the antibody over the sensor, wherein the antigen binding site of the antibody binds mercury ion if present in the query sample, thereby preventing binding of the antibody to the antigenic portion of the protein; passing magnetic particles over the sensor after passing the mixture over the sensor; and detecting the presence of the mercury ion in the query sample by measuring a magnetoresistance change of the GMR sensor based on determining magnetoresistance before and after passing magnetic particles over the sensor. In some such embodiments, such methods are sued to detect $Hg^{2+}$ ion.

In some such embodiments, methods may further comprise calculating a concentration of mercury ion in the query sample based on the magnetoresistance change of the GMR sensor.

In one or more of the preceding embodiments, the methods may comprise performing a buffer wash over the sensor prior to passing the mixture over the sensor.

In one or more of the preceding embodiments, the methods may further comprise performing a buffer wash over the sensor after passing the mixture over the sensor but before passing the magnetic particles over the sensor.

In one or more of the preceding embodiments, the methods may further comprise performing a buffer wash over the sensor after passing the magnetic particles over the sensor.

In one or more of the preceding embodiments, the query sample is water.

In one or more of the preceding embodiments, the query sample is derived from the blood of a subject.

In one or more of the preceding embodiments, the protein is a modified bovine serum albumin. In embodiments, the modified bovine serum albumin is HgBSA and has the Product Name: $Hg^{2+}$ [BSA] (Cat. No: DAGA-007B) Creative Diagnostics at Ramsey Road Shirley, NY 11967, USA. In embodiments, the antibody paired with HgBSA is HgAb and has Product Name: RHA anti-$Hg^{2+}$ monoclonal antibody, clone Hg2 (Cat. No: HMABPY007) also available from Creative Diagnostics.

In one or more of the preceding embodiments, determining magnetoresistance change of the GMR sensor comprises using at least one reference resistor to perform phase-sensitive solution of magnetoresistance change of the GMR sensor.

In one or more of the preceding embodiments, the sample is flowed over the sensor in a loop. In one or more of the preceding embodiments, the sample is flowed over the sensor providing a constant supply of fresh sample. In one or more of the preceding embodiments, B-HgAb (detection antibody) is added to mercury ion containing query sample at a working concentration of about 0.1 ug/mL. Mercury ion (II) in solution competes with HgBSA substrate for the binding site of HgAb. In solutions that have a high concentration of Hg, very little HgAb can bind to HgBSA. This incubation occurs while flowing of the GMR sensor at a flowrate between 1 ul/min and 5 ul/min. A fresh supply of the sample may be continuously being introduced over the sensor to ensure ample binding time of any non-Hg-bound HgAb. In one or more of the preceding embodiments, the query sample may be reacted for about 30 minutes.

In one or more of the preceding embodiments, a sensitivity limit of detection is in a range from about 1 nanomolar to about 10 nanomolar in the mercury ion.

In some embodiments, there are provided sensors comprising a protein disposed on a functionalized surface of a giant magnetoresistance (GMR) sensor, the protein comprising an antigenic portion. In some such embodiments, the protein is a modified bovine serum albumin. In embodiments, the modified bovine serum albumin is HgBSA and has the Product Name: $Hg^{2+}$ [BSA] (Cat. No: DAGA-007B) Creative Diagnostics at Ramsey Road Shirley, NY 11967, USA. In embodiments, the antibody paired with HgBSA is HgAb and has Product Name: RHA anti-$Hg^{2+}$ monoclonal antibody, clone Hg2 (Cat. No: HMABPY007) also available from Creative Diagnostics.

In one or more of the preceding embodiments, a surfactant may be disposed on the functionalized surface of the GMR sensor. In some such embodiments, the surfactant is cationic. In some such embodiments, the surfactant is cetyl trimethylammonium bromide.

In one or more of the preceding embodiments, the protein is spatially organized on the GMR sensor via printing.

In some embodiments, there are provided sensors comprising a modified bovine serum albumin (BSA) disposed on a functionalized surface of a giant magnetoresistance (GMR) sensor, the modified bovine serum albumin comprising an antigenic portion that binds an antibody at an antigen binding site. In embodiments, the modified bovine serum albumin is HgBSA and has the Product Name: $Hg^{2+}$ [BSA] (Cat. No: DAGA-007B) Creative Diagnostics at Ramsey Road Shirley, NY 11967, USA. In embodiments, the antibody paired with HgBSA is HgAb and has Product Name: RHA anti-$Hg^{2+}$ monoclonal antibody, clone Hg2 (Cat. No: HMABPY007) also available from Creative Diagnostics.

In one or more of the preceding embodiments, the sensors may further comprise a surfactant disposed on the functionalized surface of the GMR sensor. In some such embodiments, the surfactant is cationic. In some such embodiments, the surfactant is cetyl trimethylammonium bromide.

In one or more of the preceding embodiments, the modified BSA is spatially organized on the GMR sensor via printing.

In some embodiments, there are provided cartridges for use in detecting metal ions in a query sample, the cartridge comprising (a) a sensor comprising a protein disposed on a functionalized surface of a giant magnetoresistance (GMR) sensor, the protein comprising an antigenic portion; (b) a port to introduce a query sample; (c) a storage source of magnetic nanoparticles; (d) a storage source of antibody, the antibody comprising an antigen binding site capable of binding the antigenic portion and a portion separate from the antigen binding site configured to bind the magnetic nanoparticles; and (e) a pneumatically-controlled microfluidics system for moving the query sample, magnetic nanoparticles, and antibody.

In some such embodiments, the cartridge further comprises a waste collection area.

In one or more of the preceding embodiments, the protein is a modified bovine serum albumin. In embodiments, the modified bovine serum albumin is HgBSA and has the Product Name: $Hg^{2+}$ [BSA] (Cat. No: DAGA-007B) Creative Diagnostics at Ramsey Road Shirley, NY 11967, USA. In embodiments, the antibody paired with HgBSA is HgAb and has Product Name: RHA anti-$Hg^{2+}$ monoclonal antibody, clone Hg2 (Cat. No: HMABPY007) also available from Creative Diagnostics.

In one or more of the preceding embodiments, a surfactant is disposed on the functionalized GMR sensor. In some such embodiments, the surfactant is cetyl trimethylammonium bromide.

In one or more of the preceding embodiments, the sensor is configured to be in electronic communication with a plurality of contact pins to carry an electronic signal from the sensor to a processor.

In one or more of the preceding embodiments, the cartridge may comprise one or more filters to filter the query sample.

In one or more of the preceding embodiments, the cartridge may further comprise one or more hardware chips to control the pneumatically-controlled microfluidics system.

In some embodiments, there are provided cartridges for use in detecting mercury ions in a query sample, the cartridges comprising (a) a sensor comprising a modified bovine serum albumin (BSA) disposed on a functionalized surface of a giant magnetoresistance (GMR) sensor, the modified BSA comprising an antigenic portion; (b) a port to introduce a query sample; (c) a storage source of magnetic nanoparticles; (d) a storage source of antibody, the antibody comprising an antigen binding site capable of binding the antigenic portion and a portion separate from the antigen binding site configured to bind the magnetic nanoparticles; and (e) a pneumatically-controlled microfluidics system for moving the query sample, magnetic nanoparticles, and antibody. In embodiments, the modified bovine serum albumin is HgBSA and has the Product Name: $Hg^{2+}$ [BSA] (Cat. No: DAGA-007B) Creative Diagnostics at Ramsey Road Shirley, NY 11967, USA. In embodiments, the antibody paired with HgBSA is HgAb and has Product Name: RHA anti-$Hg^{2+}$ monoclonal antibody, clone Hg2 (Cat. No: HMABPY007) also available from Creative Diagnostics.

In some such embodiments, the cartridge may further comprise a waste collection area.

In one or more of the preceding embodiments, a surfactant may be disposed on the functionalized GMR sensor. In some such embodiments, the surfactant may be cetyl trimethyl-ammonium bromide.

In one or more of the preceding embodiments, the sensor is configured to be in electronic communication with a plurality of contact pins to carry an electronic signal from the sensor to a processor.

In one or more of the preceding embodiments, the cartridge may comprise one or more filters to filter the query sample.

In one or more of the preceding embodiments, the cartridge further comprises one or more hardware chips to control the pneumatically-controlled microfluidics system.

In some embodiments, there are provided methods of making a sensor for the detection of mercury ions in a query sample comprising printing a protein comprising an antigenic portion of on a functionalized GMR sensor. In embodiments, the protein is a modified bovine serum albumin. In embodiments, the modified bovine serum albumin is HgBSA and has the Product Name: $Hg^{2+}$ [BSA] (Cat. No: DAGA-007B) Creative Diagnostics at Ramsey Road Shirley, NY 11967, USA. In embodiments, the antibody paired with HgBSA is HgAb and has Product Name: RHA anti-$Hg^{2+}$ monoclonal antibody, clone Hg2 (Cat. No: HMABPY007) also available from Creative Diagnostics.

In one or more of the preceding embodiments, the polymer coating is a crosslinked PEG-PHEMA polymer.

In some embodiments, there are provided methods of detecting the presence of a metal ion in a query sample comprising providing a sensor comprising a biomolecule disposed on a functionalized surface of a giant magnetoresistance (GMR) sensor, the biomolecule comprising a binding region configured to bind a detection protein, the detection protein also being capable of binding the metal ion; wherein when the detection protein binds the metal ion, it prevents binding of the detection protein to the binding region of the biomolecule; passing the detection protein over the sensor; passing the query sample over the sensor; passing a reporter protein over the sensor after passing the query sample over the sensor, the reporter protein being capable of binding the detection protein and the reporter protein configured to bind to magnetic nanoparticles; passing magnetic particles over the sensor after passing the reporter protein over the sensor; and detecting the presence of the metal ion by measuring a magnetoresistance change of the GMR sensor based on determining magnetoresistance before and after passing magnetic particles over the GMR sensor.

In some such embodiments, the methods may further comprise calculating a concentration of metal ion in the query sample based on the magnetoresistance change of the GMR sensor.

In one or more of the preceding embodiments, the methods may further comprise performing one or more buffer washes.

In one or more of the preceding embodiments, the detection protein and query sample are mixed prior to passing them over the sensor.

In one or more of the preceding embodiments, the query sample is passed over the sensor after the detection protein is passed over the sensor.

In one or more of the preceding embodiments, the metal ion is arsenic.

In one or more of the preceding embodiments, the metal ion is cadmium.

In one or more of the preceding embodiments, the query sample is water.

In one or more of the preceding embodiments, the query sample is derived from the blood of a subject.

In one or more of the preceding embodiments, the detection protein is an arsenic-binding regulatory protein comprising a tag.

In one or more of the preceding embodiments, the detection protein is a cadmium-binding regulatory protein comprising a tag.

In one or more of the preceding embodiments, wherein the tag is glutathione S-transferase.

In one or more of the preceding embodiments, the tag is a poly-histidine.

In one or more of the preceding embodiments, the biomolecule is double stranded DNA (dsDNA).

In one or more of the preceding embodiments, a forward strand of the dsDNA has a sequence 5'-CTT ACA CAT TCG TTA AGT CAT ATA TGT TTTATGA CTT ATC CGC TTC GAA GA/3AmMC6T/-3' SEQ ID NO. 1.

In one or more of the preceding embodiments, a reverse strand of the dsDNA has a sequence 5'-TCT TCG AAG CGG ATA AGT CAA AAA CAT ATA TG ACTT AAC GAA TGT GTA AG-3' SEQ ID NO. 2.

In one or more of the preceding embodiments, a forward strand of the dsDNA has a sequence 5'-TGA GTC GAA AAT GGT TAT AAT ACA CTC AAA TAA ATA TTT GAA TGA AGA TG/3AmMC6T/-3' SEQ ID NO. 3.

In one or more of the preceding embodiments, a reverse strand of the dsDNA has a sequence 5'-CAT CTT CAT TCA AAT ATT TAT TTG AGT GTA TTA TAA CCA TTT TCG ACT CA-3'SEQ ID NO. 4.

In one or more of the preceding embodiments, the reporter protein is a biotinylated antibody.

In one or more of the preceding embodiments, the magnetic particles comprise streptavidin-linked nanoparticles.

In one or more of the preceding embodiments, determining magnetoresistance change of the GMR sensor comprises using at least one reference resistor to perform phase-sensitive solution of magnetoresistance change of the GMR sensor.

In one or more of the preceding embodiments, a plurality of biomolecules are attached on the surface of the sensor in a density of about $1\times10^9$ to about $5\times10^{10}$ biomolecules per $mm^2$ on the biosensor.

In one or more of the preceding embodiments, Pcad-Ocad-F-Amine strand may be printed on the surface in a concentration of between 10 uM and 25 uM.

In one or more of the preceding embodiments, a sensitivity limit of detection is in a range from about 1 nanomolar to about 10 nanomolar in the metal ion.

In one or more of the preceding embodiments, passing the query sample over the detector comprises a flow rate of the query sample over the sensor at a rate of about 1 ul/min and 5 ul/min. In some such embodiments, reaction duration may be about 30 minutes. In some embodiments, this reaction time was determined to be sufficient by testing flow of biotinylated Pcad-Ocad-R over printed Pcad-Ocad-F. Signal was obtained when streptavidin-labeled magnetic nanoparticles were introduced, which confirmed that hybridization of the two Pcad-Ocad strands was occurring. In some embodiments, R-strand hybridization is always done in concentrations at least equal to the highest available F-strand concentration.

In some embodiments, there are provided sensors for detecting a metal ion comprising a biomolecule disposed on a functionalized surface of the giant magnetoresistance (GMR) sensor, the biomolecule comprising a binding region configured to bind a detection protein, the detection protein also being capable of binding the metal ion; wherein when the detection protein binds the metal ion, it prevents binding of the detection protein to the binding region of the biomolecule.

In some such embodiments, the biomolecule is double stranded DNA (dsDNA).

In one or more of the preceding embodiments, a forward strand of the dsDNA has a sequence 5'-CTT ACA CAT TCG TTA AGT CAT ATA TGT TTTATGA CTT ATC CGC TTC GAA GA/3AmMC6T/-3' SEQ ID NO. 1.

In one or more of the preceding embodiments, a reverse strand of the dsDNA has a sequence 5'-TCT TCG AAG CGG ATA AGT CAA AAA CAT ATA TG ACTT AAC GAA TGT GTA AG-3' SEQ ID NO. 2.

In one or more of the preceding embodiments, a forward strand of the dsDNA has a sequence 5'-TGA GTC GAA AAT GGT TAT AAT ACA CTC AAA TAA ATA TTT GAA TGA AGA TG/3AmMC6T/-3' SEQ ID NO. 3.

In one or more of the preceding embodiments, a reverse strand of the dsDNA has a sequence 5'-CAT CTT CAT TCA AAT ATT TAT TTG AGT GTA TTA TAA CCA TTT TCG ACT CA-3'SEQ ID NO. 4.

In one or more of the preceding embodiments, a plurality of biomolecules are attached on the surface of the sensor in a density of about $1\times10^9$ to about $5\times10^{10}$ biomolecules per/$mm^2$ on the biosensor.

In one or more of the preceding embodiments, the surface of the GMR sensor comprises a polymer comprising a crosslinked PEG-PHEMA.

In one or more of the preceding embodiments, the polymer of the functionalized surface is overcoated with a surfactant. the surfactant is cetyl trimethylammonium bromide.

In one or more embodiments, sensors may further comprise a plurality of wires connected to a plurality of contact pads configured to carry an electronic signal from the sensor to a processor.

In one or more of the preceding embodiments, the metal ion comprises arsenic or cadmium.

In some embodiments, there are provided cartridges for use in detecting metal ions in a query sample, the cartridge comprising (a) a sensor comprising a biomolecule disposed on a functionalized surface of a giant magnetoresistance (GMR) sensor, the biomolecule comprising a binding region configured to bind a detection protein, the detection protein also being capable of binding the metal ion; wherein when the detection protein binds the metal ion, it prevents binding of the detection protein to the binding region of the biomolecule; (b) one or more ports to introduce a query sample, magnetic nanoparticles, and optional wash buffers into the cartridge; and (c) a microfluidics system for moving the query sample, magnetic nanoparticles, and optional wash buffers from the one or more ports to the sensor.

In some such embodiments, the cartridges may further comprise a waste collection area.

In one or more of the preceding embodiments, the biomolecule is double stranded DNA (dsDNA).

In one or more of the preceding embodiments, a forward strand of the dsDNA has a sequence 5'-CTT ACA CAT TCG TTA AGT CAT ATA TGT TTTATGA CTT ATC CGC TTC GAA GA/3AmMC6T/-3' SEQ ID NO. 1.

In one or more of the preceding embodiments, a reverse strand of the dsDNA has a sequence 5'-TCT TCG AAG CGG ATA AGT CAA AAA CAT ATA TG ACTT AAC GAA TGT GTA AG-3' SEQ ID NO. 2.

In one or more of the preceding embodiments, a forward strand of the dsDNA has a sequence 5'-TGA GTC GAA AAT GGT TAT AAT ACA CTC AAA TAA ATA TTT GAA TGA AGA TG/3AmMC6T/-3' SEQ ID NO. 3.

In one or more of the preceding embodiments, a reverse strand of the dsDNA has a sequence 5'-CAT CTT CAT TCA AAT ATT TAT TTG AGT GTA TTA TAA CCA TTT TCG ACT CA-3'SEQ ID NO. 4.

In one or more of the preceding embodiments, a plurality of biomolecules are attached on the surface of the sensor in a density of about $1\times10^9$ to about $5\times10^{10}$ biomolecules per/$mm^2$ on the biosensor.

In one or more of the preceding embodiments, the surface of the GMR sensor comprises a crosslinked PEG-PHEMA polymer.

In one or more of the preceding embodiments, the polymer is coated with a surfactant. In some such embodiments, the surfactant may be cetyl trimethylammonium bromide.

In one or more of the preceding embodiments, sensors in a cartridge may further comprise a plurality of wires connected to a plurality of contact pads configured to carry an electronic signal from the sensor to a processor.

In one or more of the preceding embodiments, cartridges may comprise one or more filters to filter the query sample.

In one or more of the preceding embodiments, the metal ion comprises arsenic or cadmium.

In one or more of the preceding embodiments, the microfluidics system is pneumatically controlled.

In one or more of the preceding embodiments, the cartridge further comprises one or more hardware chips to control flowrate throughout the microfluidics system.

In some embodiments, there are provided methods of making a sensor for the detection of arsenic or cadmium ions in a query sample comprising (a) printing double stranded DNA (dsDNA) on a surface of a giant magnetoresistance (GMR) sensor; the dsDNA comprising a binding region configured to bind a detection protein, the detection protein also being capable of binding the arsenic or cadmium ions; wherein when the detection protein binds the metal ion, it prevents binding of the detection protein to the binding region of the biomolecule; the GMR sensor comprising a polymer coating onto which the dsDNA is printed; and (b) modifying the surface of the polymer coating by: adding one or more blocking agents to the polymer coating after the printing step; and optionally adding a surfactant to the polymer coating after adding the one or more blocking agents.

In one or more of the preceding embodiments, a forward strand of the dsDNA has a sequence 5'-CTT ACA CAT TCG TTA AGT CAT ATA TGT TTTATGA CTT ATC CGC TTC GAA GA/3AmMC6T/-3' SEQ ID NO. 1.

In one or more of the preceding embodiments, a reverse strand of the dsDNA has a sequence 5'-TCT TCG AAG CGG ATA AGT CAA AAA CAT ATA TG ACTT AAC GAA TGT GTA AG-3' SEQ ID NO. 2.

In one or more of the preceding embodiments, a forward strand of the dsDNA has a sequence 5'-TGA GTC GAA AAT GGT TAT AAT ACA CTC AAA TAA ATA TTT GAA TGA AGA TG/3AmMC6T/-3' SEQ ID NO. 3.

In one or more of the preceding embodiments, a reverse strand of the dsDNA has a sequence 5'-CAT CTT CAT TCA AAT ATT TAT TTG AGT GTA TTA TAA CCA TTT TCG ACT CA-3'SEQ ID NO. 4.

In one or more of the preceding embodiments, a plurality of biomolecules are attached on the surface of the sensor in a density of about $1\times10^9$ to about $5\times10^{10}$ biomolecules per/mm$^2$ on the biosensor.

In one or more of the preceding embodiments, Pcad-Ocad-F-Amine strand is printed on the surface in a concentration of between 10 uM and 25 uM.

In one or more of the preceding embodiments, the polymer coating comprises a crosslinked PEG-PHEMA polymer.

Subjects

In some embodiments, a subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is a mammal suspected of ingesting a metal. In certain embodiments, a subject is suspected of being exposed to a metal. In some embodiments, a subject is suspected of having a disease or condition associated with a metal.

Provided herein are methods and compositions for analyzing a sample. In some embodiments, a sample is a liquid sample. In some embodiments a liquid sample is an aqueous sample. A liquid sample may comprise, in some embodiments, fine particulate matter suspended in a liquid. Solid samples (such as soil or tissues) can be washed or extracted with a liquid to obtain a liquid sample suitable for conducting a method described herein.

A sample can be obtained from any suitable environmental source or from a suitable subject. A sample isolated from an environmental source is sometimes referred to as an environmental sample, non-limiting examples of which include liquid samples obtained from a lake, stream, river, ocean, well, run-off, tap water, bottled water, purified or treated water, waste water, irrigation water, ice, snow, dirt, soil, waste, the like, and combinations thereof. In some embodiments, a sample is isolated, obtained or extracted from a product of manufacture, non-limiting examples of which include recycled materials, polymers, plastics, pesticides, wood, textiles, fabric, synthetic fibers, clothes, food, beverages, rubber, detergents, oils, fuels, the like, or combinations thereof.

In some embodiments, a sample is a biological sample, for example a sample obtained from a living organism or a subject. A sample can be isolated or obtained directly or indirectly from a subject or part thereof. In some embodiments, a sample is obtained indirectly from an individual or medical professional who then provides the sample for analysis. A sample can be any specimen that is isolated or obtained from a subject or part thereof. A sample can be any specimen that is isolated or obtained from multiple subjects. Non-limiting examples of biological samples include blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. In some embodiments, a sample is a cell free sample. In some embodiments, a liquid sample is obtained from cells or tissues using a suitable method. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. In some embodiments, a sample is filtered to remove insoluble matter or debris to obtain a liquid sample suitable for analysis by a method described herein.

In certain embodiments, a sample comprises a metal. In certain embodiments, a sample does not comprise a metal. In some embodiments, a sample is suspected of comprising a metal. In some embodiments a sample has a pH in a range of 4 to 10, 6 to 10, 7 to 10 or about 6 to 8.5. In some embodiments, a pH of a sample is adjusted to a pH in a range of 4 to 10, 6 to 10, 7 to 10 or about 6 to 8.5, or to prior to contacting the sample with a sensor.

Nucleic Acids

The term "nucleic acid" refers to one or more nucleic acids (e.g., a set or subset of nucleic acids), non-limiting examples of which include DNA, RNA, combinations thereof, and nucleic acids comprising ribonucleotides (e.g., ribonucleotide monophosphate monomers), deoxyribonucleotides (e.g., deoxyribonucleotide monophosphate monomers, e.g., dA, dT, dG, dC), mixtures thereof, ribonucleotides and/or deoxyribonucleotides analogues (e.g., base analogs, sugar analogs and/or a non-native backbones and the like), polyamide nucleic acids (PNAs), locked nucleic acids (LNAs), the like or combinations thereof. In some embodiments, a nucleic acid is a single strand or single stranded nucleic acid. In some embodiments, a nucleic acid is a double stranded nucleic acid, sometimes referred to as a nucleic acid duplex. A nucleic acid can be of any length of, for example, 2 or more, 3 or more, 4 or more, 5 or more, 10 or more, 50 or more or 100 or more contiguous nucleotides. In certain embodiments, a nucleic acid comprises a length of 4 to 200, 4 to 100, 4 to 50, 4 to 30, 4 to 20 or 4 to 10 nucleotides. A nucleic acid typically comprises a specific 5' to 3' order of nucleotides known in the art as a sequence (e.g., a nucleic acid sequence, e.g., a sequence). Accordingly, a single stranded nucleic acid often has a 3'-end and a 5'-end determined according to the location of the 3'-hydroxyl group and the 5'-hydroxyl group of the nucleic acid, respectively. Similarly, the terms "3' of", "3' to", "5' of" or "5' to" refer to a location on a single stranded nucleic acid with reference to the opposing end of the strand. For example, for a single stranded nucleic acid comprising a target cleavage site and a biotin, the phrase, "the biotin is attached 3' of the target cleavage site" means that the biotin can be attached at any suitable location between the target cleavage site and the 3'-end of the nucleic acid, which includes attachment to the 3' hydroxyl group of the nucleic acid.

Oligonucleotides are relatively short nucleic acids. In some embodiments, a nucleic acid is an oligonucleotide. In some embodiments, an oligonucleotide is a single stranded nucleic acid having a length of about 4 to 150, 4 to 100, 5 to 50, or 5 to about 15 nucleic acids in length, or intermediate lengths thereof. In certain embodiments, an oligonucleotide comprises DNA (e.g., an oligonucleotide consisting essentially of deoxyribonucleotides). An oligonucleotide consisting essentially of deoxyribonucleotides may comprise one or more target cleavage sites, or one, two or three ribonucleotides.

In some embodiments, a nucleic acid comprises one or more target cleavage sites. A target cleavage site is a specific location, nucleotide or sequence within a nucleic acid that can be cleaved by a metal-dependent DNAzyme when a suitable metal is present. In some embodiments, a target cleavage site comprises one or two ribonucleotides located within a DNA strand (e.g., a nucleic acid comprising or consisting essentially of deoxyribonucleotides). In some embodiments, a target cleavage site comprises an adenosine ribonucleotide located within a DNA strand (e.g., a nucleic acid comprising or consisting essentially of deoxyribonucleotides). An oligonucleotide comprising a target cleavage site is sometimes referred to as a substrate strand.

In some embodiments, a nucleic acid comprises one or more repressor binding sites. A repressor binding site is a specific sequence within a nucleic acid or duplex that is recognized by a metalloregulatory repressor protein. In certain embodiments, a metalloregulatory repressor protein specifically binds to its cognate repressor binding site in the absence of a heavy metal.

In certain embodiments, a nucleic acid comprises a double stranded nucleic acid or a DNA duplex. In some embodiments, a nucleic acid duplex comprises a first nucleic acid and a second nucleic acid, wherein a portion of, or all of the first nucleic acid is complementary to a portion of, or all of the second nucleic acid. In some embodiments, one or both strands of a nucleic acid duplex comprises a repressor binding site. In some embodiments, a double stranded nucleic acid comprises 1 to 10, 1 to 5, or 1 to 3 unpaired nucleotides. In some embodiments, a double stranded nucleic acid comprises 1, 2, 3, 4 or 5 unpaired nucleotides. The term "unpaired" means that the indicated nucleotide does not complement or pair with a corresponding nucleotide in another nucleic acid strand (e.g., the enzyme strand). In certain embodiments, a double stranded nucleic acid comprises a 5' or 3' overhang which comprises a nucleic acid sequence that is not hybridized to the opposing strand.

In certain embodiment, a nucleic acid is attached to a surface of a magnetic sensor. In some embodiments a nucleic acid is attached non-covalently or covalently to a suitable solid substrate (e.g., a surface, e.g., a surface of a magnetic sensor) In some embodiments, a first stand of a double stranded nucleic acid is attached to a surface of a magnetic sensor. In some embodiments, a second strand of a double stranded nucleic acid is attached to a surface of a magnetic sensor. Any suitable portion of a nucleic acid can be attached to a surface of a magnetic sensor. In some embodiments, a 5'-end or a 3'-end of a nucleic acid is attached to a surface of a magnetic sensor. A nucleic acid can be attached to a surface of a magnetic sensor using a suitable chemistry.

In some embodiments, a nucleic acid comprises a suitable 3' or 5' modifier that facilitates attachments of a nucleic acid to a surface (e.g., a polymer surface of a magnetic sensor). In some embodiments a modifier is an amino modifier. In some embodiment a modifier comprises a 3' amino modifier C6 dT.

Metals

In some embodiments, a method or device described herein detects the presence, absence, or amount of a metal in a sample. Non-limiting examples of metals that can be detected by a method herein include lead, magnesium, manganese, mercury, arsenic, cadmium, nickel, cobalt, and zinc. In some embodiments, a method or device described herein detects the presence, absence, or amount of cadmium, arsenic, mercury, and/or lead in a sample. In some embodiments, a method or device described herein detects the presence, absence, or amount of arsenic or cadmium in a sample. In some embodiments, a method or device described herein detects the presence, absence, or amount of lead in a sample. In some embodiments, a method or device described herein detects the presence, absence, or amount of lead in a sample In some embodiments, a method or device described herein detects the presence, absence, or amount of a metal in a sample comprising using a metal binding protein that is attached to the surface of a magnetic sensor, such as a GMR, and that binds to the metal to be assayed or detected in a sample. In some embodiments, a method or device described herein detects the presence, absence, or amount of a metal in a sample comprising using a DNAzyme that is attached to the surface of a magnetic sensor, such as a GMR, the cleavage activity of which is mediated by the binding or chelating of the metal ion that is to be assayed or detected in a sample.

In some embodiments, a method or device described herein detects the presence, absence, or amount lead in a sample. In some embodiments, a method or device described herein detects the presence, absence, or amount lead in a sample using a DNAzyme attached to a magnetic sensor, such as a GMR.

In some embodiments, a method or device described herein detects the presence, absence, or amount of mercury in a sample. In some embodiments, a method or device described herein detects the presence, absence, or amount mercury in a sample using a metal binding protein, such as a mercury binding bovine serum albumin (Hg-BSA). In some embodiments, a method or device described herein detects the presence, absence, or amount mercury in a sample using a metal binding protein, such as a mercury binding bovine serum albumin (Hg-BSA), and a mercury binding antibody.

DNAzymes and Metal Detection Using DNAzymes

In some embodiments a method comprises the use of a metal-dependent DNAzyme. In some embodiments, a microfluidic device comprises a metal-dependent DNAzyme. In some embodiments, a metal-dependent DNAzyme is a lead-dependent DNAzyme (e.g., a DNAzyme that is activated by the presence of lead). In some embodiments, a metal-dependent DNAzyme is configured to bind to a metal selected from lead, magnesium, manganese, and zinc. In some embodiments, a metal-dependent DNAzyme binds to lead or lead ions. In certain embodiments, a metal-dependent DNAzyme comprises an endonuclease activity that is activated when the metal-dependent DNAzyme binds to a metal (e.g., lead).

In some embodiments, a metal-dependent DNAzyme comprises a first nucleic acid and a second nucleic acid, wherein a portion of the first nucleic acid is complementary to a portion of the second nucleic acid. In certain embodiments, a metal-dependent DNAzyme comprises a double stranded nucleic acid or a DNA duplex. In certain embodiments, a metal-dependent DNAzyme comprises a double stranded nucleic acid primarily comprising DNA, where one strand of the DNA duplex (e.g., the enzyme strand) can cleave the other strand of the DNA duplex (e.g., the substrate strand) at a specific location (e.g., a target cleavage site) when a metal is associated with, or bound to, the DNA duplex. In some embodiments, a DNAzyme comprises a first nucleic acid comprising one or more target cleavage sites (e.g., sometimes referred to as the "substrate strand"), and a second nucleic acid comprising a catalytic domain (e.g., sometimes referred to as the "enzyme strand").

In some embodiments, a substrate strand and/or target cleavage site comprises at least one paired or unpaired purine ribonucleotide monophosphate which serves as the target cleavage site for the enzyme strand of a DNAzyme. The term "unpaired" means that the indicated nucleotide does not complement or pair with a corresponding nucleotide in another nucleic acid strand (e.g., the enzyme strand). In some embodiments, a substrate strand and/or target cleavage site comprises at least one paired or unpaired purine ribonucleotide monophosphate which is followed by a 3' unpaired deoxyguanosine monophosphate (dG). In some embodiments, a substrate strand and/or target cleavage site comprises at least one paired or unpaired adenosine monophosphate which is followed by a 3' unpaired dG. In some embodiments, a substrate strand and/or target cleavage site comprises the sequence AdGdG, where A is a paired or unpaired adenosine monophosphate and both of the dG nucleotides are unpaired. In some embodiments, a substrate strand and/or target cleavage site comprises the sequence dTAdGdG, where A is a paired or unpaired adenosine monophosphate, both of the dG nucleotides are unpaired, and the deoxythymidine monophosphate (dT) is paired with a corresponding dA (deoxyadenosine monophosphate) in the enzyme strand. In some embodiments, a substrate strand comprises a sequence at least 50%, at least 70%, or at least 80% identical to 5'-CTCACTATAGGAAGAGAT-GATGTCTGTAAATT-3' (SEQ ID NO:1) where the underlined A residue is an adenosine. In some embodiments, a substrate strand comprises the nucleotide sequence of SEQ ID NO:1. In some embodiments, a substrate strand comprises a sequence at least 50%, at least 70%, or at least 80% identical to 5'-ACTCACTATAGGAAGAGATG-3' (SEQ ID NO:6) where the underlined A residue is an adenosine. In some embodiments, a substrate strand comprises the nucleotide sequence of SEQ ID NO:6. In some embodiments, an substrate strand comprises a nucleic acid sequence 5' of a target cleavage site that is substantially complementary to a portion of the enzyme strand and a nucleic sequence 3' of a target cleavage site that is substantially complementary to a portion of the enzyme strand. In some embodiments, a nucleic acid sequence 5' of a target cleavage site that is substantially complementary to a portion of the enzyme strand is at least 4 nucleotides in length, or has a length in a range of 4 to 50, or 4 to 20 nucleotides, or intervening ranges thereof. In some embodiments, a nucleic acid sequence 3' of a target cleavage site that is substantially complementary to a portion of the enzyme strand is at least 4 nucleotides in length, or has a length in a range of 4 to 50, or 4 to 20 nucleotides, or intervening ranges thereof.

In certain embodiments, an enzyme strand of a DNAzyme comprises a catalytic domain. In some embodiments, a catalytic domain comprising a sequence that is not complementary to the substrate strand. In some embodiments, a catalytic domain is flanked by 5' sequence (i.e., 5' arm) that is complementary to a portion of the substrate strand and a 3' sequence (i.e., 3' arm) that is complementary to another portion of the substrate strand. In some embodiments, a catalytic domain sequence comprises 5-25, 8-23, 10-23 or 8-17 consecutive deoxyribonucleotides, or intervening ranges thereof. In some embodiments, a catalytic domain sequence comprises 8-17 consecutive deoxyribonucleotides. In some embodiments, a catalytic domain sequence comprises 15 consecutive deoxyribonucleotides. In some embodiments, a catalytic domain sequence comprises the nucleotide sequence of 5'-GAAGTAGCGCCGCCG-3' (SEQ ID NO:3). In some embodiments, a catalytic domain sequence comprises the nucleotide sequence of 5'-TCCGAGCCGGTCGAA-3' (SEQ ID NO:4). In some embodiments, an enzyme strand comprises a sequence at least 50%, at least 70%, or at least 80% identical to 5'-ACA-GACATCATCTCTGAAGTAGCGCCGCCGTATAGT-GAG-3' (SEQ ID NO:2). In some embodiments, an enzyme strand comprises the nucleotide sequence of SEQ ID NO:2. In some embodiments, an enzyme strand comprises a sequence at least 50%, at least 70%, or at least 80% identical to 5'-CATCTCTTCTCCGAGCCGGTCGAAATAGT-GAGT-3' (SEQ ID NO:5). In some embodiments, an enzyme strand comprises the nucleotide sequence of SEQ ID NO:5.

In some embodiments, a DNAzyme comprises a substrate strand comprising the nucleotide sequence of SEQ ID NO:3 and an enzyme strand comprising a nucleotide sequence at least 50%, at least 70%, at least 80%, or at least 90% identical to SEQ ID NO:2. In some embodiments, a DNAzyme comprises a substrate strand comprising the nucleotide sequence of SEQ ID NO:3 and an enzyme strand comprising a nucleotide sequence of SEQ ID NO:2. In some embodiments, a DNAzyme comprises a substrate strand comprising a nucleotide sequence at least 50%, at least 70%, at least 80%, or at least 90% identical to SEQ ID NO:1 and an enzyme strand comprising a nucleotide sequence at least 50%, at least 70%, at least 80%, or at least 90% identical to SEQ ID NO:2. In some embodiments, a DNAzyme comprises a substrate strand comprising the nucleotide sequence of SEQ ID NO:1 and an enzyme strand comprising the nucleotide sequence of SEQ ID NO:2.

In some embodiments, a DNAzyme comprises a substrate strand comprising the nucleotide sequence of SEQ ID NO:4 and an enzyme strand comprising a nucleotide sequence at least 50%, at least 70%, at least 80%, or at least 90% identical to SEQ ID NO:5. In some embodiments, a DNAzyme comprises a substrate strand comprising the nucleotide sequence of SEQ ID NO:4 and an enzyme strand comprising a nucleotide sequence of SEQ ID NO:5. In some embodiments, a DNAzyme comprises a substrate strand comprising a nucleotide sequence at least 50%, at least 70%, at least 80%, or at least 90% identical to SEQ ID NO:6 and an enzyme strand comprising a nucleotide sequence at least 50%, at least 70%, at least 80%, or at least 90% identical to SEQ ID NO:5. In some embodiments, a DNAzyme comprises a substrate strand comprising the nucleotide sequence of SEQ ID NO:6 and an enzyme strand comprising the nucleotide sequence of SEQ ID NO:5.

In some embodiments, a DNAzyme comprises a substrate strand comprising the nucleotide sequence of the "17E" lead DNAzyme (e.g., 5'-ACTCACTATAGGAAGAGATG-3'; see, e.g., Brown, et al., *Biochemistry,* 42(23), pp. 7152-7161 (2003)) and an enzyme strand comprising a nucleotide sequence at least 50%, at least 70%, at least 80%, or at least 90% identical to the enzyme strand of the "17E" DNAzyme (e.g., 5'-CATCTCTTCTCCGAGCCGGTCGAAATAGT-GAGT-3').

In some embodiments, a DNAzyme comprises a substrate strand comprising the nucleotide sequence of the "8-17" lead DNAzyme (e.g., 5'-AAGUAACUAGAGAUGGA-3'; see, e.g., Lan, et al., *Chemical Communication,* 46(22), pp. 3896-3898 (2010)) and an enzyme strand comprising a nucleotide sequence at least 50%, at least 70%, at least 80%, or at least 90% identical to the enzyme strand of the "8-17" DNAzyme (i.e., 5'-CGCACCCTCCGAGCCG-GAACGAAGTTACTT-3').

In some embodiments, a DNAzyme comprises a substrate strand comprising the nucleotide sequence of the "Ce13d" DNAzyme (e.g., 5'-rAGGAAG-3'; see, e.g., Zhou, Wenhu et al.) and an enzyme strand comprising a nucleotide sequence at least 50%, at least 70%, at least 80%, or at least 90% identical to the enzyme strand of the "Ce13d" DNAzyme (e.g., 5'-AGGTCAAAGGTGGGTGCGAGTITTT-TACTCGTT-3').

In some embodiments a substrate strand comprises a detectable label. In some embodiments a substrate strand comprises a magnetic particle or magnetic nanoparticle. A detectable label can be attached to a suitable location of a substrate strand as long as the detectable label can dissociate from the DNAzyme upon cleavage of the substrate strand by the enzyme strand. In some embodiments, a detectable label is attached (e.g., covalently or non-covalently) to a 5'-end or a 3'-end of a substrate strand. In some embodiments, a 5'-end of a substrate strand is attached to a surface of a sensor and a detectable label is attached at a suitable location located 3' of a target cleavage site. In some embodiments, a 5'-end of a substrate strand is attached to a surface of a sensor and a detectable label is attached to the 3'-end of the substrate strand. In some embodiments, a 3'-end of a substrate strand is attached to a surface of a sensor and a detectable label is attached at a suitable location located 5' of a target cleavage site. In some embodiments, a 3'-end of a substrate strand is attached to a surface of a sensor and a detectable label is attached to the 5'-end of the substrate strand.

In some embodiments a substrate strand comprises a member of a binding pair. In some embodiments a substrate strand comprises biotin. A member of a binding pair can be attached to a suitable location of a substrate strand as long as the member of a binding pair can dissociate from the DNAzyme upon cleavage of the substrate strand by the enzyme strand. In some embodiments, a member of a binding pair is attached (e.g., covalently or non-covalently) to a 5'-end or a 3'-end of a substrate strand. In some embodiments, a 5'-end or a 3'-end of a substrate strand of a DNAzyme is attached to a surface of a sensor. In some embodiments, a 5'-end of a substrate strand is attached to a surface of a sensor and a member of a binding pair is attached at a suitable location located 3' of a target cleavage site. In some embodiments, a 5'-end of a substrate strand is attached to a surface of a sensor and a member of a binding pair is attached to the 3'-end of the substrate strand. In some embodiments, a 3'-end of a substrate strand is attached to a surface of a sensor and a member of a binding pair is attached at a suitable location located 5' of a target cleavage site. In some embodiments, a 3'-end of a substrate strand is attached to a surface of a sensor and a member of a binding pair is attached to the 5'-end of the substrate strand.

In some embodiments a nucleic acid is attached non-covalently or covalently to a suitable solid substrate (e.g., a surface, e.g., a surface of a sensor) In certain embodiment, a DNAzyme is attached to a surface of a sensor. In some embodiments, an enzyme strand of a DNAzyme is attached to a surface of a sensor. In some embodiments, a substrate strand of a DNAzyme is attached to a surface of a sensor. Any suitable portion of an enzyme strand and/or a substrate strand can be attached to a surface of a sensor. In some embodiments, a 5'-end or a 3'-end of an enzyme strand of a DNAzyme is attached to a surface of a sensor. A substrate strand and/or an enzyme strand of a DNAzyme can be attached to a surface of a sensor using a suitable chemistry.

Delectable Labels/Particles/Binding Pairs

In some embodiments, a method or process described herein comprises a use of one or more detectable labels. In some embodiments, a composition or device described herein comprises one or more detectable labels. In some embodiments a nucleic acid, primer, particle, nanoparticle, magnetic particle, magnetic nanoparticle, or bead, comprises one or more detectable labels. In some embodiments a member of a binding pair comprises a detectable label. In some embodiments, a detectable label is attached to a member of a binding pair. Any suitable detectable label can be used for a composition, device or method described herein. In some embodiments, a detectable label can be detected by a suitable sensor Any suitable fluorophore or light emitting material can be used as a label. Non-limiting examples of a detectable label include a radiolabel (e.g., an isotope, radioisotopes or radionuclides (e.g., 3H, 14C, 15N, 35S, 90Y, 99Tc, 125I, 131I), a metallic label, a magnetic label, a fluorescent label, a chromophore, a chemilumines-cent label, an electro-chemiluminescent label, a phospho-rescent label, a quencher (e.g., a fluorophore quencher), a fluorescence resonance energy transfer (FRET) pair (e.g., donor and acceptor), a dye, an enzyme (e.g., horseradish peroxidase, p-galactosidase, luciferase, alkaline phosphatase and the like), an enzyme substrate, a mass tag, quantum dots, the like or combinations thereof.

Detectable labels can be detected and/or quantitated by a suitable sensor comprising one or more of a camera (e.g., a digital camera, a coupled-charge device (CCD) camera), a light sensing diode or photocell, mass spectrometer, a fluo-rescence microscope, a confocal laser scanning microscope, laser scanning cytometer, a magnetic sensor (e.g., a giant magnetoresistance (GMR) sensor), the like and combina-tions thereof. In some embodiments, a sensor comprises one or more of a camera (e.g., digital camera, a coupled-charge device (CCD) camera), a light sensing diode, a photocell, mass spectrometer, a fluorescence microscope, a confocal laser scanning microscope, laser scanning cytometer, a mag-netic sensor (e.g., a giant magnetoresistance (GMR) sensor), the like and combinations thereof. In some embodiments, a sensor comprises a surface.

In certain embodiments a detectable label is directly or indirectly attached to (e.g., bound to, e.g., covalently or non-covalently) a nucleic acid (e.g., a primer), a protein, a member of a binding pair, a substrate (e.g., a bead, a particle), or the like.

In some embodiments a detectable label comprises a magnetic particle, non-limiting examples of which include paramagnetic beads, magnetic beads, metallic microbeads, nanobeads), metallic microparticles, and metallic nanopar-ticles. Any suitable magnetic particle can be used for a method or device herein. In certain embodiments, a mag-netic particle comprises a member of a binding pair. In some embodiments, a magnetic particle comprises streptavidin, or a variant thereof. In some embodiments, a magnetic particle comprises an average or absolute diameter of about 1 to about 1000 nanometers (nm), 1 nm to about 500 nm, about 5 nm to about 1000 nm, about 10 nm to about 1000 nm, about 5 nm to about 500 nm, about 5 nm to about 400 nm, about 5 nm to about 300 nm, about 5 nm to about 300 nm, about 5 nm to about 200 nm, about 5 nm to about 100 nm, about 2 to about 50 nm, about 5 to about 20 nm, or about 5 to about 10 nm, and/or ranges in between. In some embodi-ments, a magnetic particle is coated to facilitate covalent attachment to a member of a binding pair or to a nucleic acid. In other embodiments a magnetic particle is coated to facilitate electrostatic association with molecules. In some embodiments magnetic particles comprises different shapes, sizes and/or diameters to facilitate different amounts of magnetism. In some embodiments, magnetic particles are substantially uniform (e.g., all are substantially the same; e.g., same size, same diameter, same shape and/or same magnetic properties) to facilitate more accurate detections and/or quantitation at the surface of the magnetic sensor. In some embodiments, magnetic beads comprise the same or different members of a binding pair to allow multiplex detection of multiple genetic variants. In some embodiments, magnetic particles comprising different members of a binding pair are configured to interact with different metal-dependent DNAzymes disposed on different GMR sensors or on a single sensor in which different metal-dependent DNAzymes are spatially organized to create addressable locations and signals.

In some embodiments a nucleic acid or oligonucleotide comprises one or more members of a binding pair. In some embodiments a binding pair comprises at least two members (e.g., molecules) that bind non-covalently and specifically to each other Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair include antibody/ antigen, antibody/antibody receptor, antibody/protein A or protein G, hapten/anti-hapten, sulfhydryl/maleimide, sulf-hydryl/haloacetyl derivative, amine/isotriocyanate, amine/ succinimidyl ester, amine/sulfonyl halides, biotin/avidin, biotin/streptavidin, folic acid/folate binding protein, recep-tor/ligand, vitamin B12/intrinsic factor, analogues thereof, derivatives thereof, binding portions thereof, the like or combinations thereof. Non-limiting examples of a member of a binding pair include an antibody or antibody fragment, antibody receptor, an antigen, hapten, a peptide, protein, a fatty acid, a glyceryl moiety (e.g., a lipid), a phosphoryl moiety, a glycosyl moiety, a ubiquitin moiety, lectin, aptamer, receptor, ligand, metal ion, avidin, neutravidin, streptavidin, biotin, B12, intrinsic factor, analogues thereof, derivatives thereof, binding portions thereof, the like or combinations thereof. In some embodiments, a nucleic acid is covalently attached to member of a binding pair. In some embodiments, a nucleic acid comprises biotin. In some embodiments, a nucleic acid is covalently attached to biotin.

DNAzyme-Based Devices

Figure 22:
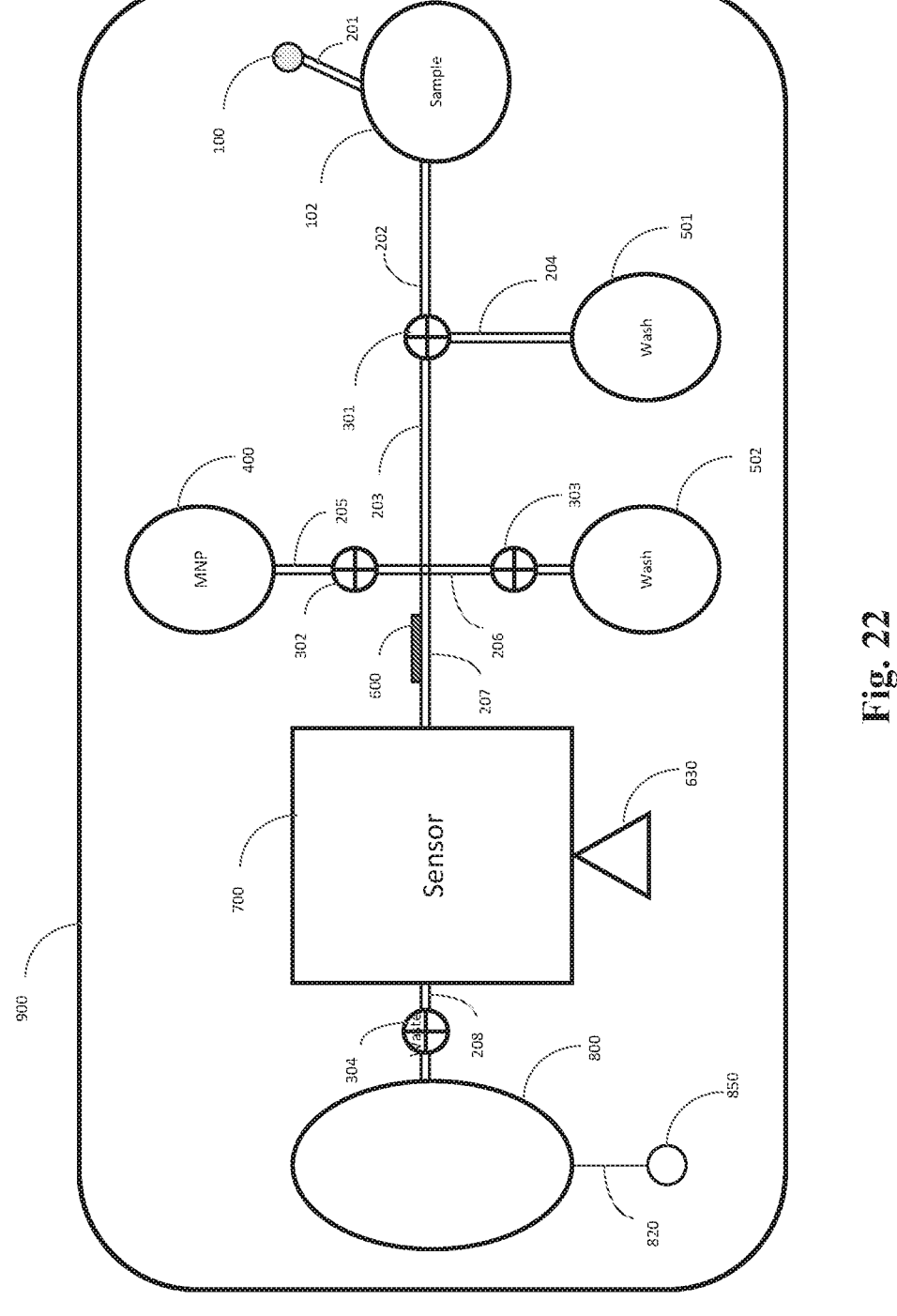
FIG. 22 shows an example of a microfluidic device 900 comprising a DNAzyme and a sensor 700, and: either the cleavage of the substrate strand in the presence of lead ion; or the noncleavage of the substrate strand in the absence of lead ion; in accordance with an embodiment of the present teaching.

Presented herein, in some embodiments, is a microfluidic DNAzyme-comprising device configured to detect a metal in a target nucleic acid that is present in a sample. In some embodiments, the device comprises one or more compo-nents shown in FIG. 22. In some embodiments, a device comprises a configuration, or a variation thereof, shown in FIG. 22. In some embodiments, a DNAzyme device com-prises one or more microfluidic channels that are operably and/or fluidically connected to each of the components of the device.

Components or parts that are "fluidically connected" are components and parts of a device that are in contact with and/or can be contacted with (e.g., by opening or closing a valve) a liquid or fluid disposed within the device. A well of a 96-well plate is not considered to be fluidically connected to another well in a 96-well plate. Similarly, an Eppendorf tube is not fluidically connected to another Eppendorf tube even when fluid can be transferred from one tube to another. The term "operably connected" means that the particular components or parts of the device can communicate, are attached, or are connected in such a way that they cooperate to achieve their intended function or functions. An operable "connection" may be direct, indirect, physical, or remote.

In some embodiments, a microfluidic device (e.g., 900) comprises one or more components selected from a micro-fluidic channel (e.g., 201-208), a chamber (e.g., 102, 400, 501, 502, & 800), one or more valves (e.g., 301-304), a sensor (e.g., 700, e.g., a magnetic sensor), lyophilized reagents, solubilized reagents, a heating source (e.g., 600), a pump, and a port (e.g., a flow control port 850, a sample loading port 100). In some embodiments, some or all of the components of the device are operably and/or fluidically connected (e.g., by associated microfluidic channels and valves). In some embodiments, a device comprises one or more chambers selected from a sample chamber (e.g., 102), wash chamber (e.g., 501 and 502), reagents chambers (e.g., 400), waste chamber (e.g., 800), or combinations thereof. In some embodiments, a microfluid device comprises a camera (e.g., 630) and optionally a radiation source (e.g., a light source, a UV light source).

In some embodiments, a microfluidic device comprises one or more microfluidic channels (e.g., 201-208). A micro-fluidic channel may comprise a suitable geometry in cross-section non-limiting examples of which include circular, oval, rectangular, triangular, the like or combinations thereof. A microfluidic channel may comprise a suitable structure non-liming examples of which include straight, curved, serpentine, and/or elevated, and may include one or more junctions that fluidically connect one or more micro-fluidic channels and associated components of a microfluidic device described herein. In some embodiments, a microflu-idic channel has an average, mean or absolute inside diam-eter of about 10 nanometers to 1000 micrometers, 50 nano-meters to 500 micrometers, 100 nanometers to 500 micrometers, or 100 nanometers to 100 micrometers. In some embodiments, one or more of a valve (e.g., 301-304), chamber, and/or sensor 700 are disposed within a channel body of a microfluidic channel. In some embodiments, a sensor 700 are disposed within a chamber that is operably and/or fluidically connected to one or more microfluidic channels. In some embodiments, a microfluidic channel comprises a sample port 100 for introduction of a sample, or one or more reagents, into a microfluidic device. In some embodiments, a sample port is operably and/or fluidically connected to a sample chamber (e.g., 102) by a microfluidic channel (e.g., 201).

In some embodiments, a microfluidic device comprises a sample chamber and a sensor that are operably and/or fluidically connected by one or more microfluidic channels and valves such that a direction of flow of a fluid disposed within the device is generally in a direction from the sample chamber toward the sensor, and/or towards a waste chamber (e.g., 800). Accordingly, for reference, a first component that is proximal to second component, is a component this is upstream of the second component with reference to the direction of flow toward the sensor. Similarly, a first com-ponent that is distal to a second component is a component this is downstream of the second component with reference to the direction of flow toward the sensor or waste chamber (e.g., 800) In some embodiments, a direction of flow through a microfluidic device is controlled in part by a vacuum pump or syringe pump that is operably connected to a port (e.g., flow control port 850). In some embodiments, a pump is disposed on a microfluid device 900. In some embodiments, one or more pumps can be operably connected to device 900 by a port (e.g., 850), for example when the microfluidic device is in the form of a removable cartridge. In some embodiments a flow control port is operably connected to a chamber (e.g., waste chamber 800) such that when a negative pressure is applied to port 850, fluid is directed (e.g., by one or more valves) from one or more chambers (e.g., 102, 501, 502, and/or 400) to waste chamber 800, such that a flow of fluid can be regulated and/or maintained across a surface of the sensor (e.g., 700). In some embodiments a flow control port is operably connected to a chamber by a microfluidic channel (e.g., 820).

Any suitable valve can be used for a microfluidic device. In some embodiments, a valve is a miniature piloting solenoid valve (e.g., a Lee valves) that can be controlled off-card. Accordingly, a device may comprise a plurality of valves, each of which can be controlled independently. In some embodiments, one or more valves are operably connected to one or more electrical pad connections, so that a microfluidic device can be integrated with a controller or computer that directs flow of fluid through the device.

In some embodiments, a chamber is a sample chamber (e.g., 102). In some embodiments, a sample chamber comprises a sample or is configured to contain a sample. In some embodiments, a sample chamber comprises one or more reagents (e.g., dehydrated salts or buffers). In some embodiments, a microfluidic device comprises a sample port configured for introduction of a sample into the device. In certain embodiments, a sample port is operably connected and/or fluidically connected to one or more chambers. In some embodiments, a device comprises a sample port 100 and a sample chamber 102, where the sample port is proximal to the sample chamber. In some embodiments, a sample port 100 is configured for introduction of a sample into the sample chamber 102. In some embodiments, a sample port is located proximal to a sample chamber. In some embodiments, a sample port is a sample injection port.

In some embodiments, a chamber is a wash chamber (e.g., 510, 502). A wash chamber is configured to contain a suitable wash solution. In some embodiments, a wash solution is disposed within a wash chamber. A wash solution is often used to hydrate or wash a surface of a sensor (e.g., 700). In some embodiments, a wash solution comprises a buffer (e.g., Tris), an alcohol, a detergent, or a salt. In some embodiments a wash chamber provides a solution (e.g., a buffer) that helps maintain flow of fluid over the surface of the sensor, for example during detection. A wash solution may comprise any suitable buffer. In some embodiments, a buffer comprises HEPES (4-(2-hydroxyethyl)-1-piperazineethanesulfonic acid). For example, a solution disposed within chamber 501 can be diverted by valve 301 to microfluid channels 203 and 207, such that fluid flows over sensor 700 and into waste chamber 800.

In some embodiments, a sample chamber (e.g., 102), a reagent chamber (e.g., 400) and/or one or more wash chambers (e.g., 501, 502) are located proximal to a sensor (e.g., 700). In some embodiments, a sample chamber (e.g., 102) and/or one or more wash chambers (e.g., 501, 502) are operably and/or fluidically connected, in parallel to a microfluid channel (e.g., 202, 203, 207), where the microfluid channel comprises one or more valves (e.g., 301, 302, 303) operably connected to the one or more chambers.

In certain embodiments, reagents are disposed within a reagent chamber (e.g., 400). Reagents disposed within a reagent chamber may be dried and/or lyophilized. In some embodiments, reagents disposed within a reagent chamber are solubilized or dispersed in a liquid (e.g., a wash solution). In certain embodiments, dried or lyophilized reagents located within a reagent chamber are substantially solubilized when contacted with a fluid when a fluid enters a reagent chamber. In some embodiments, a reagent chamber (e.g., 400) is located proximal to a sensor. In certain embodiment, a reagent chamber comprises magnetic particles (MNP), where each of the particles are attached to a member of a binding pair (e.g., streptavidin). In some embodiments, a reagent chamber is operably and/or fluidically connected to a valve (e.g., 302) that when open, disperses reagents or particles into a microfluidic channel (e.g., 207) such the particles proceed to contact and/or flow over the sensor.

In certain embodiments, a microfluidic device comprises a heating source (e.g., 600). Any suitable heating source can be used in a device described herein. In some embodiments, a sensor comprises a heating source. In some embodiments, a heating source is located proximal to a sensor, such that a temperature of a fluid flowing over a sensor can be heated.

In some embodiments, a microfluidic device comprises a sensor (e.g., 300, e.g., a magnetic sensor). In some embodiments, a microfluidic device comprises a plurality of sensors (e.g., a magnetic sensors). In some embodiments, a microfluidic device comprises a first sensor that is contacted with a sample, and a second control sensor that is not contacted with a sample. In some embodiments, a microfluidic device comprises an array of sensors with addressable locations. Any suitable sensor can be used for a device or method described herein, non-limiting examples of which include a camera (e.g., a digital camera, a coupled-charge device (CCD) camera), a light sensing diode, a photocell, mass spectrometer, a fluorescence microscope, a confocal laser scanning microscope, laser scanning cytometer, a magnetic sensor (e.g., a giant magnetoresistance (GMR) sensor), the like and combinations thereof. In some embodiments, a sensor comprises a camera (e.g., 630, e.g., a digital camera, a coupled-charge device (CCD) camera), a light sensing diode, a photocell, mass spectrometer, a fluorescence microscope, a confocal laser scanning microscope, laser scanning cytometer, a magnetic sensor (e.g., a giant magnetoresistance (GMR) sensor), the like and combinations thereof. In some embodiments a sensor is a magnetic sensor. In some embodiments a magnetic sensor is a magnetoresistance sensor. In some embodiments a magnetic sensor is a giant magnetoresistance (GMR) sensor. In some embodiments a magnetic sensor is an anisotropic magnetoresistance (AMR) sensor and/or a magnetic tunnel junction (MTJ) sensor.

In some embodiments, a magnetic sensor detects magnetoresistance, current and/or voltage potential, or changes thereof. In some embodiments, a magnetic sensor detects magnetoresistance, current and/or voltage potential, or changes thereof on the surface of the sensor. In some embodiments, a magnetic sensor detects magnetoresistance, current and/or voltage potential, or changes thereof over a period of time non-limiting examples of which include 1 nanosecond to 1 hour, 1 second to 60 minutes, 1 second to 10 minutes, 1 second to 1000 seconds or intervening periods thereof. In some embodiments, a magnetic sensor detects the presence, absence or amount of magnetic particles that are bound to (e.g., indirectly bound to) or associated with a surface of the magnetic sensor according to a magnetoresistance, current and/or voltage potential, or changes thereof, that are detected by the magnetic sensor. In some embodiments, a magnetic sensor detects the presence, absence or amount of a metal present in a sample according to a presence, absence or amount of magnetic particles that are bound to (e.g., indirectly bound to) or associated with a surface of the magnetic sensor. Accordingly, in some embodiments, a magnetic sensor detects the presence, absence or amount of a metal present in a sample according to a magnetoresistance, current and/or voltage potential, or changes thereof, that are detected or measured at the surface of the magnetic sensor.

GMR sensors can have sensitivities that exceed those of anisotropic magnetoresistance (AMR) or Hall sensors. This characteristic enables detection of stray fields from magnetic materials at nanometer scales. For example, stray fields from magnetic nanoparticles that are bound on a sensor surface will alter the magnetization in the magnetic layers, and thus change the magnetoresistance of a GMR sensor. Accordingly, changes in the amount of magnetic nanoparticles bound to a GMR sensor per unit area can be reflected in changes of the magnetoresistance value of a GMR sensor. Accordingly, in some embodiments, a magnetic sensor comprises a GMR sensor.

In some embodiments, a sensor comprises a surface. A surface of a sensor may comprise a suitable material, non-limiting examples of which include glass, modified or functionalized glass (e.g., controlled-pore glass (CPG)), quartz, mica, polyformaldehyde, cellulose, cellulose acetate, ceramics, metals, metalloids, semi-conductive materials, plastic (including acrylics, polystyrene, copolymers of styrene or other materials, polybutylene, polyurethanes, TEFLON™, polyethylene, polypropylene, polyamide, polyester, polyvinylidenedifluoride (PVDF), and the like), resins, silica or silica-based materials including silicon, silica gel, and modified silicon, Sephadex®, SEPHAROSE®, carbon, metals (e.g., steel, gold, silver, aluminum, silicon and copper), conducting polymers (including polymers such as polypyrrole and polyindole); micro or nanostructured surfaces, nanotube, nanowire, or nanoparticulate decorated surfaces, or porous surfaces or gels such as methacrylates, acrylamides, sugar polymers, cellulose, silicates, or other fibrous or stranded polymers. In some embodiments, a surface is coated using passive or chemically-derivatized coatings with any number of materials, including polymers, such as dextrans, acrylamides, gelatins or agarose. In some embodiments a surface of a sensor is non-covalently and/or reversibly attached to an oligonucleotide.

In some embodiments, a surface of a sensor comprises and/or is coated with a crosslinked PEG-PHEMA polymer. A PEG-PH EMA polymer surface can be prepared by mixing a PEG solution comprising N-Hydroxysuccinimide (NHS)-PEG-NHS (MW 600) dissolved in a suitable solvent (e.g., isopropyl alcohol, acetone or methanol, and/or water), a PHEMA solution comprising polyhydroxyethyl methacrylate (MW 20,000) dissolved in a suitable solvent (e.g., isopropyl alcohol, acetone or methanol, and/or water), and an optional crosslinker. The resulting solution can be coated on a sensor surface using a suitable coating process (e.g., micro-printing, dip coating, spin coating or aerosol coating) After coating a surface with the PEG-PHEMA solution, the surface can be cured using UV light followed by washing with a suitable solvent, such as isopropyl alcohol and/or water. In some embodiments a surface of a sensor is covalently attached to one or more nucleic acids. In some embodiments, the coated surface can be used to bind with primary amines (e.g., to attach a protein). A PEG-PHEMA A coating can protect a sensor surface against corrosion. In some embodiments, a surface of a sensor comprises a surface described in International Patent Application No. PCT/US2019/043766.

In some embodiments, a surface of a sensor comprises a coating. In some embodiments a coating comprises a suitable surfactant. In some embodiments, a surfactant comprises cetyl trimethylammonium bromide (CTAB). In some embodiments, a surface of a sensor is coated with, or contacted with a suitable surfactant prior to contacting a sensor with a sample.

In some embodiments, a sensor comprises a metal-dependent DNAzyme. In some embodiments, a metal-dependent DNAzyme, a substrate strand of a DNAzyme or an enzyme strand of a DNAzyme is attached (e.g., covalently) to a surface of a sensor using a suitable chemistry, non-limiting examples of which include a chemistry described in Cha et al. (2004) "Immobilization of oriented protein molecules on poly(ethylene glycol)-coated Si(111)" *Proteomics* 4:1965-1976 and Zellander et al. (2014) "Characterization of Pore Structure in Biologically Functional Poly(2-hydroxyethyl methacrylate)-Poly(ethylene glycol) Diacrylate (PHEMA-PEGDA)," *PLOS ONE* 9(5):e96709. In some embodiments, a surface of a sensor comprises a plurality of DNAzymes at a density of about $1 \times 10^9$ to about $5 \times 10^{10}$ DNAzyme molecules per/mm$^2$.

In some embodiments a device comprises two or more sensors, each comprising a surface comprising a different DNAzyme. In some embodiments, a surface of a sensor comprises addressable locations, each comprising a different DNAzyme configured to bind to a different metal. In some embodiments, a microfluidic device comprises a negative control sensor. In certain embodiments, a negative control sensor is a magnetic sensor (e.g., a GMR). In some embodiments of a method described herein, a negative control sensor is not contacted with a sample. In some embodiments of a method described herein, a negative control sensor is contacted with a suitable control solution, wash buffer or control buffer.

In certain embodiments, a microfluidic device 900 is disposed on a card or cartridge. Accordingly, in some embodiments, a microfluidic device, or a card or cartridge comprising a microfluidic device described herein has a length of 3 to 10 cm, a width of 1 to 10 cm, and a thickness of 0.1 to 1 cm.

In some embodiments, a microfluidic device comprises a printed circuit board (PSB). In some embodiments, a microfluidic device or a PSB comprises one or more memory chips. In some embodiments a microfluid device or a PSB comprises one or more electrical pad connections. In some embodiments the one or more electrical pad connections are operably (e.g., electronically) connected to a memory chip, one or more valves, a sensor and/or one or more pumps of a microfluid device. In some embodiments one or more components of a microfluidic device are disposed on a PSB.

In some embodiments, a microfluidic device is disposed on a cartridge or card that comprises a PSB. In some embodiments, a cartridge is configured for insertion or attachment to a controller, a computer, or larger device that integrates with a microfluidic device. In some embodiments a controller comprises pumps (e.g., diaphragm or syringe type pumps) that operably connect to one or more flow control ports 850 located on a cartridge. In some embodiments, one or more components of a microfluidic device are disposed on a substrate comprising a polymer plastic. In some embodiments, one or more components of a microfluidic device are disposed on a substantially flat substrate comprising a polymer plastic.

In some embodiments, a microfluidic device, PSB or cartridge described herein comprises one or more components, subcomponents or parts described in International Patent Application No. PCT/US2019/043720, entitled "SYSTEM AND METHOD FOR GMR-BASED DETECTION OF BIOMARKERS" filed Jul. 26, 2019, International Patent Application No. PCT/US2019/043753, entitled "SYSTEM AND METHOD FOR SAMPLE PREPARA-TION IN GMR-BASED DETECTION OF BIOMARK-ERS" filed Jul. 26, 2019, International Patent Application No. PCT/US2019/043766, entitled "SYSTEM AND METHOD FOR SENSING ANALYTES IN GMR-BASED DETECTION OF BIOMARKERS" filed Jul. 26, 2019 or, International Patent Application No. PCT/US2019/043791, entitled "SYSTEM AND METHOD FOR PROCESSING ANALYTE SIGNALS IN GMR-BASED DETECTION OF BIOMARKERS" filed Jul. 26, 2019, all of which are hereby incorporated by reference herein in their entirety. In some embodiments, a method described herein utilizes one or more components, subcomponents or parts described in International Patent Application No. PCT/US2019/043720, PCT/US2019/043753, PCT/US2019/043766, or PCT/US2019/043791. In some embodiments, a microfluidic device described herein comprises a magnetic sensor and/or magnetic sensor assembly described in International Patent Application No. PCT/US2019/043720, PCT/US2019/043753, PCT/US2019/043766, or PCT/US2019/043791.

In some embodiments, any one chamber (e.g., 102, 501, 502, 400, 800) and/or a chamber housing a sensor comprises a volume independently selected from 1 µl to 20 ml, 1 µl to 15 ml, 1 µl to 5 ml, 1 µl to 1 ml, 1 µl to 500 µl, 1 µl to 100 µl, and intermediate volumes thereof.

GMR sensors have sensitivities that exceed those of anisotropic magnetoresistance (AMR) or Hall sensors. This characteristic enables detection of stray fields from magnetic materials at nanometer scales. For example, stray fields from magnetic nanoparticles that bound on sensor surface will alter the magnetization in the magnetic layers, and thus change the magnetoresistance of the GMR sensor. Accordingly, changes in the number of magnetic nanoparticles bound to the GMR sensor per unit area can be reflected in changes of the magnetoresistance response of the GMR sensor.

DNAzyme-Based Methods

Figure 21:
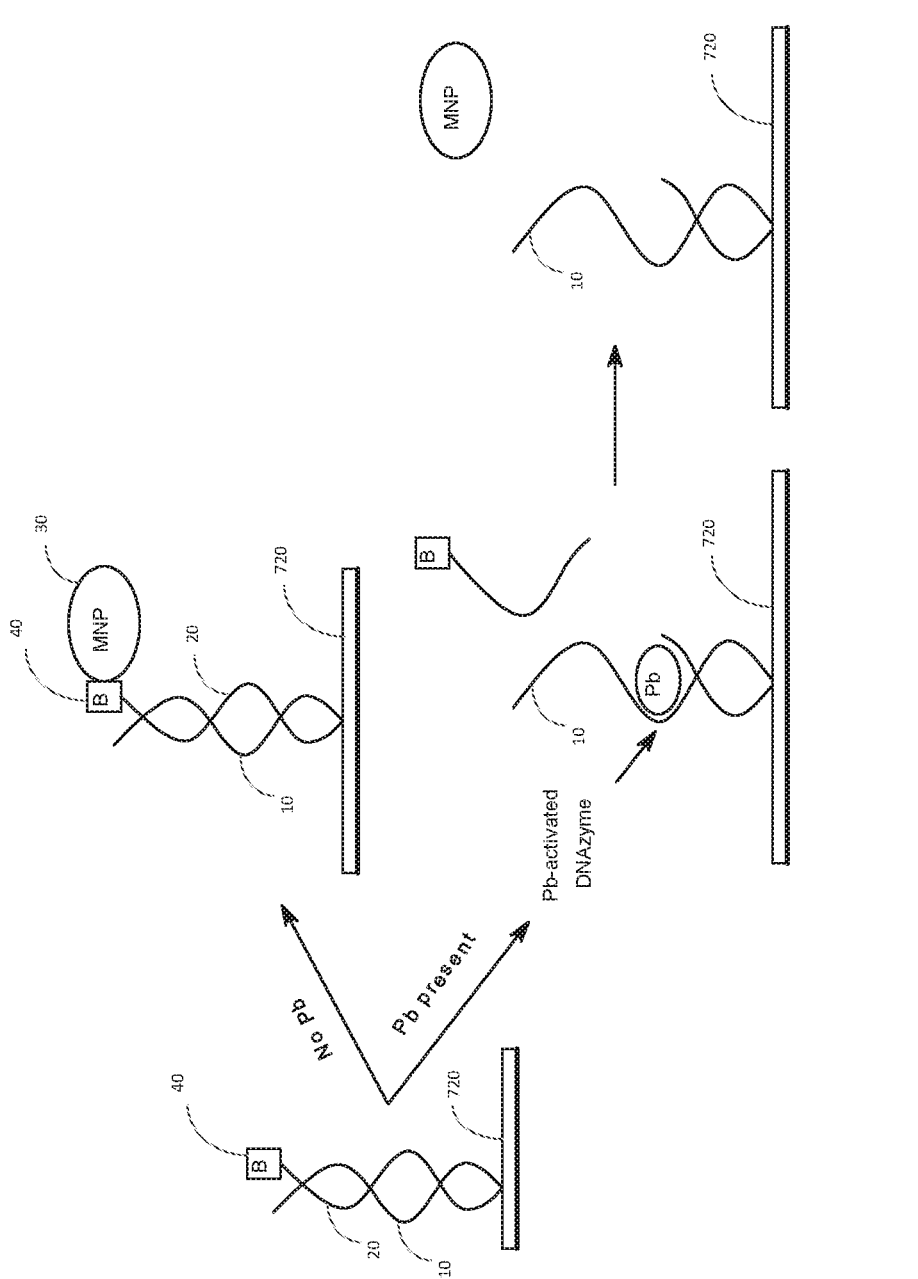
FIG. 21 shows an illustration of an exemplary metal detection method using a surface-bound lead-dependent DNAzyme, in accordance with an embodiment.

Presented herein, in certain embodiments, is a method of detecting the presence, absence, or amount of a metal in a sample. FIG. 21 shows an illustration of an exemplary method described herein where a DNAzyme is attached to the surface of a sensor 720 (e.g., a magnetic sensor). In this example, the DNAzyme comprises a first nucleic acid strand 20 (i.e., the substrate strand) and a second nucleic acid strand 10 (i.e., the enzyme strand), which are hybridized together to form a nucleic acid duplex. The substrate strand 20 is attached to a first member of a binding pair 40 (e.g., biotin (B)). The DNAzyme is then contacted with a sample and a detectable label 30 (e.g., a magnetic particle; MNP), which comprises a second member of a binding pair (e.g., streptavidin). In the absence of lead, the detectable label 30 binds to the substrate strand 20 and the presence or amount of the detectable label 30 is detected at the surface of the sensor 720 (illustrated in top panel, FIG. 21). In the presence of lead (FIG. 21, bottom panels), the substrate strand 20 is cleaved by virtue of lead (Pb) binding to the DNAzyme. When the substrate strand 20 is cleaved, the portion of the substrate strand comprising biotin dissociates from the surface-bound DNAzyme, and the detectable label 30 is washed away from the sensor surface. The presence, absence or amount of lead in a sample can then be determined by detecting the presence, absence or amount of a detectable label that is associated with the surface of the sensor.

In some embodiments, a method comprises contacting a sensor comprising a surface, and a metal-dependent DNAzyme attached to the surface, with a sample suspected of comprising a metal. In some embodiments, a surface of a sensor is contacted with a detergent or a surfactant (e.g., CTAB) prior to contacting the sensor with the sample. In some embodiments, a substrate strand of a DNAzyme comprises a detectable label or a first member of a binding pair (e.g., biotin). In some embodiments, the detectable label comprises one or more magnetic particles. In some embodiments when a DNAzyme comprises a first member of a binding pair (e.g., biotin), a method further comprises contacting the sensor with a detectable label comprising a second member of the binding pair (e.g., streptavidin), such that the first member of the binding pair binds to the second member of the binding pair. In some embodiments, the presence, absence or amount of a detectable label that is at, near or associated with (e.g., indirectly by non-covalent interactions) a sensor is detected. The detecting is sometimes performed after a sample is contacted with a sensor. In certain embodiments, the detecting is performed before, during and/or after contacting a sensor with a sample or with a detectable label. In some embodiments, a detecting process is a dynamic detection process such that a detectable label can be detected before, during and/or after contacting a sensor with a sample while changing one or more conditions at the surface of the sensor.

In some embodiments, the process of contacting a sensor with a sample and/or detectable label comprises flowing a fluid across the surface of the sensor. Non-limiting examples of a fluid include a liquid sample, a blocking solution, a hybridization solution, a wash solution, a buffer solution, water, a solution comprising magnetic particles, a solution containing a blocking reagent, a solution comprising a suitable reagent, a solution comprising a detectable label, the like, combinations thereof or mixtures thereof. In some embodiments, a sensor or surface thereof is continually and/or continuously in contact with a fluid (e.g., a sample, wash solution, buffer, detectable labels and the like) when conducting a method herein. In certain embodiments, a flow rate over the surface of a sensor during a contacting, blocking, hybridization, washing or detecting process is about 0.1 µl/minute to 500 µl/minute, 1 µl/minute to 500 µl/minute, 1 µl/minute to 100 µl/minute, 1 µl/minute to 10 µl/minute, or intervening ranges therein. In certain embodiments, a blocking process occurs at about 1 µl/minute to 50 µl/minute, about 1 µl/minute to 40 µl/minute, about 1 µl/minute to 30 µl/minute, about 1 µl/minute to 20 µl/minute, 1 µl/minute to 10 µl/minute, or intervening ranges therein. In certain embodiments, a hybridization process occurs at about 1 µl/minute to 50 µl/minute, about 1 µl/minute to 40 µl/minute, about 1 µl/minute to 30 µl/minute, about 1 µl/minute to 20 µl/minute, 1 µl/minute to 10 µl/minute, or intervening ranges therein. In certain embodiments, a flow rate over the surface of a sensor during a contacting, washing or detecting process is about 100 Hz to 800 Hz, or about 100 Hz to 300 Hz.

In some embodiments, a volume of a sample that is contacted with a sensor is a volume in a range of 1 µl to 500 µl, 20 µl to 300 µl, or intervening ranges or volumes thereof.

In some embodiments, a sensitivity range of the detection of a metal by a method herein is in a range from about 0.00001 nanomolar to about 100 nanomolar, 0.01 nanomolar to about 10 nanomolar, 0.1 nanomolar to about 10 nanomolar, or about 1 nanomolar to about 10 nanomolar of lead in a sample. In some embodiments, a lower limit of sensitivity of a detection of a metal by a method herein is about 0.01 picomolar, about 0.1 picomolar, about 1.0 picomolar, about 10 picomolar, about 100 picomolar, about 1.0 nanomolar, about 5.0 nanomolar, about 10.0 nanomolar, about 50 nanomolar or about 100 nanomolar of lead in a sample.

In some embodiments, a sensor is washed with a wash solution such that the wash solution flows over the surface of the sensor. A wash solution may comprise any suitable composition. In some embodiments, a wash solution increases the stringency of hybridization conditions to ensure that a cleaved substrate strand dissociates from a surface-bound DNAzyme. Accordingly, in some embodiment, a wash solution comprises one or more of a suitable buffer (e.g., HEPES), a chelating agent (e.g., EDTA), salts, a detergent or surfactant, a chaotropic agent, formamide, combinations thereof and the like. In some embodiments a wash solution does not include a salt. Any suitable wash solution can be used to increase the stringency of hybridization conditions at the surface of a sensor. For example, in some embodiments, the concentration of divalent cations or salt in a wash solution is decreased to increase stringency. In some embodiments, a temperature of a wash solution flowing over the surface of a sensor is increased during a wash step.

In some embodiments, a wash solution is configured to maintain a flow of fluid over a sensor. In such embodiments, a wash solution may comprise the same, or a similar composition (e.g., buffers and salts), as a sample or detectable label (e.g., a suspension of magnetic particles).

In some embodiments, a temperature of fluid flowing over the surface of a sensor is increased before, during and/or after (i) contacting a sensor with a sample, (ii) contacting a sensor with a detectable label, and/or (iii) detecting the presence, absence, or amount a detectable label bound to, or associated with, a sensor surface.

In some embodiments, a temperature of a fluid in contact with the surface of a sensor is increased by at least 10° C., by at least 15° C., by at least 20° C., by at least 25° C., by at least 30° C., by at least 40° C., by at least 60° C., or by at least 80° C. over a period of 1 second to 30 minutes, 1 second to 10 minutes, 1 second to 5 minutes, 1 second to 1 minute, or intervening ranges thereof. In some embodiments, a temperature of a fluid in contact with the surface of a sensor is increased from about 10° C. to about 120° C., from about 10° C. to about 80° C., from about 10° C. to about 70° C., from about 10° C. to about 65° C., from about 10° C. to about 60° C., from about 20° C. to about 120° C., from about 20° C. to about 80° C., from about 20° C. to about 70° C., from about 20° C. to about 65° C., from about 20° C. to about 60° C., from about 25° C. to about 80° C., from about 25° C. to about 70° C., from about 25° C. to about 65° C., from about 25° C. to about 60° C., or intervening ranges thereof, In some embodiments, a temperature of a fluid in contact with the surface of a sensor is increased over a period of 1 second to 30 minutes, 1 second to 10 minutes, 1 second to 5 minutes, 1 second to 1 minute, or intervening ranges thereof.

In some embodiments, a method or detecting process comprises detecting a presence, absence, amount, or change thereof, of a detectable label. In certain embodiments, a presence, absence, amount, or change thereof, of a detectable label is detected by a sensor. In certain embodiments, a presence, absence, amount, or change thereof, of a detectable label is detected at or near a surface of a sensor. In some embodiments, a presence, absence, amount, or change thereof, of a detectable label bound to a surface of a sensor is detected. In certain embodiments, a detection process or detection step comprises detecting a change in an amount of a detectable label at, near, or on the surface of a sensor over time.

In some embodiments, a detection process comprises a dynamic detection process. In certain embodiments, a dynamic detection process comprises detecting a presence, absence, amount, or change in an amount of a detectable label at, near, or on the surface of a sensor over time, while conditions at, near or on the surface of a sensor are changed. Non-limiting examples of conditions that can be changed during a dynamic detection process include temperature, salt concentration, cation concentration, ion concentration, pH, detergent concentration, chaotropic agent concentration, ionic kosmotrope concentration, the like or combinations thereof. Often, conditions are changed during a dynamic detection process to increase stringency of hybridization conditions at, on or near a surface of a sensor.

In some embodiments, a dynamic detection process comprises detecting a change in an amount of a detectable label at, near, or on a surface of a sensor over time, while temperature is increased over a period of time. In some embodiments, a dynamic detection process comprises detecting a change in an amount of a detectable label at, near, or on the surface of a sensor over a period of time, while a concentration of cations (e.g., Na, Ca, Mg, Zn and the like) is decreased. In some embodiments, a dynamic detection process comprises detecting a change in an amount of a detectable label at, near, or on a surface of a sensor over a period of time, while temperature is increased and/or while a concentration of cations (e.g., Na, Ca, Mg, Zn and the like) is decreased.

In some embodiments, a method comprises detecting or determining a magnetoresistance, current, voltage potential, or change thereof on, near or at the surface of a magnetic sensor. In some embodiments, a method comprises detecting or determining a change in a local magnetic field on, near, or at the surface of a magnetic sensor, such as a GMR sensor. In some embodiments, a magnetoresistance, current, voltage potential, or change thereof, on, near or at the surface of a magnetic sensor is determined or detected once, continuously (e.g., during a predetermined period of time), or periodically (e.g., two or more times) before, during and/or after a DNAzyme is contacted with magnetic particles as described herein. In some embodiments, a magnetoresistance, current, voltage potential, or change thereof, on, near or at the surface of a magnetic sensor is determined or detected continuously (e.g., during a predetermined period of time), or periodically (at two or more times) while a temperature is increased at the surface of a magnetic sensor.

In some embodiments, the presence, absence or amount of a metal in a sample is determined according to a magnetoresistance, current, voltage potential, or change thereof, that is detected or measured on, near or at the surface of a magnetic sensor when performing a method described herein.

In some embodiments, a positive control is referenced. In some embodiments, the positive control, a positive control comprises a positive control DNA strand that is printed on a positive control DNA sensor. In some embodiments, the positive control DNA does not contain an RNA base required for DNA cleavage by DNAzyme, but the positive control DNA strand has the same base makeup as a functional substrate strand and is also biotinylated on its 5' end. In some embodiments, a signal change in a functional substrate strand is compared to the signal of the positive control to DNA determine a concentration of a metal, such as lead, in a sample.

In some embodiments, lead ion-mediated signal reduction of functional substrate strand produces a standard curve, where X is the concentration of lead ion in the sample and Y is magnetic sensor, such as a GMR, signal. As the lead ion concentration increases, the magnetic sensor signal decreases.

In some embodiments, lead ion concentrations are determined based on GMR signal when a controlled substrate concentration is used.

In some embodiments, a substrate strand and/or a positive control strand can have 3' modifications to the DNA. Such modifications allow for different functional levels of the DNAzyme and increasing or decreasing overall sensor signal, such as a GMR signal. In some embodiments the length of a substrate strand and/or a positive control strand is modified, for example, by adding additional bases, such as poly-T tails, poly-A tails, poly A/T tails, and the like, to the 3' end.

In some embodiments, a positive control strand nucleic acid sequence is as follows: 5'-CTC ACT ATA GGA AGA GAT GAT GTC TG (functional amine)-3'. In some embodiments, the 5' end of the strand is biotinylated.

In some embodiments, a Poly-T tail substrate strand composition is as follows: 5'-CTC ACT ATA GGA AGA GAT GAT GTC TGT TTT TTT TTT (functional amine)-3', where A (underlined and bold) represents the target cleavage site.

In some embodiments, a poly-T tail substrate strand composition is as follows: 5'-CTC ACT ATA GGA AGA GAT GAT GTC TGT AAA TT (functional amine)-3', where A (underlined and bold) represents the target cleavage site. In some embodiments, the 5' end of the strand is biotinylated.

In some embodiments, sample sensors are compared to other functional substrate strand sensors that are not introduced to a lead ion containing sample. This can be achieved by having multiple flow channels on a magnetic sensor cartridge, such as a GMR cartridge, and only introducing one of them to test sample. By having identically printed magnetic sensors, such as GMR sensors (i.e. having the same functional substrate concentrations), but only introducing a portion of them to a test sample, the test sample sensor can be directly compared to the control, non-patient sample sensors. This allows for a second curve to be developed and a second quantification method of Pb to be conducted.

Detection of Mercury

Mercury Binding Protein

In some embodiments, a magnetic sensor comprises one or more, or a plurality of mercury binding proteins, each of which is configured to bind to one or more mercury ions. In some embodiments, a mercury binding protein is attached to a surface of a magnetic sensor. A mercury binding protein can be covalently or non-covalently attached to a surface of a magnetic sensor. In some embodiments, a mercury binding protein is covalently attached to a polymer coated on the surface of a magnetic sensor. In certain embodiments, a primary amine of a mercury binding protein is crosslinked to the surface of a magnetic sensor. In some embodiments, a surface of a magnetic sensor comprises a plurality of mercury binding proteins at a density of at least about $5 \times 10^3$, at least about $5 \times 10^4$, at least about $5 \times 10^5$, at least about $5 \times 10^6$, at least about $5 \times 10^7$, at least about $5 \times 10^8$, at least about $5 \times 10^9$, at least about $5 \times 10^{10}$, at least about $5 \times 10^{11}$, at least about $5 \times 10^{12}$, at least about $5 \times 10^{13}$, or at least about $5 \times 10^{14}$, molecules per/mm². In some embodiments, a surface of a magnetic sensor comprises a plurality of mercury binding proteins at a density in a range of about $1 \times 10^8$ to about $5 \times 10^{12}$, about $1 \times 10^9$ to about $5 \times 10^{12}$, about $1 \times 10^9$ to about $1 \times 10^{11}$, or about $1 \times 10^9$ to about $1 \times 10^{10}$ molecules per/mm².

In some embodiments, a mercury binding protein is a protein that binds to a mercury ion with an affinity (kD) of at least about $1 \times 10^{-6}$, at least about $1 \times 10^{-7}$, at least about $1 \times 10^{-8}$, at least about $1 \times 10^{-9}$, or at least about $1 \times 10^{-10}$. In some embodiments, a mercury binding protein comprises a protein that binds to a mercury ion with an affinity (kD) of at least about $1 \times 10^{-8}$ to about $1 \times 10^{-12}$.

In some embodiments, a mercury binding protein comprises one or more mercury ions. In some embodiments, a mercury binding protein is bound to one or more mercury ions. In some embodiments, a mercury binding protein is bound to one or more mercury ions with an affinity (kD) of at least about $1 \times 10^{-6}$, at least about $1 \times 10^{-7}$, at least about $1 \times 10^{-8}$, at least about $1 \times 10^{-9}$, or at least about $1 \times 10^{-10}$. In some embodiments, a mercury binding protein is bound to one or more mercury ions with an affinity (kD) of at least about $1 \times 10^{-8}$ to about $1 \times 10^{-12}$. In some embodiments, a mercury binding protein is bound to one or more mercury ions prior to conducting a method herein. In some embodiments, a mercury binding protein is bound to one or more mercury ions prior to contacting a sensor, a surface of a sensor or a mercury binding protein with a sample.

A suitable naturally occurring or recombinant mercury binding protein can be used for a method or device described herein. A mercury binding protein may be a naturally occurring protein, a genetically modified protein, a synthetic protein, or mercury binding portion thereof. In some embodiments, a mercury binding protein comprises a binding agent (e.g., an antibody) or an antigen binding portion thereof. Other non-limiting examples of a mercury binding protein includes HgBP20 and HgBP10 (e.g., as described in Roesijadi (1986) *Environ Health Perspect* 65:45-48; a suitable MerP protein (e.g., a merP of *Bacillus cereus* (e.g., UniProtKB—Q7DHE4); merP of *Pseudomonas* (e.g., UniProtKB—P04131 or Q51770), or merP of *Stenotrophomonas* (e.g., UniProtKB—Q7BRH6)), a suitable MerTP protein, a suitable MerF protein, a suitable MerC protein, a suitable MerC protein, a suitable MerE protein, a suitable serum albumin, the like, a mercury binding portion thereof, variants thereof, and combinations thereof. In certain embodiments, a mercury binding protein is a suitable albumin (e.g., a serum albumin or ovalbumin). In some embodiments an albumin is a mammalian serum albumin. In some embodiments, an albumin is an ovalbumin. In certain embodiments, a mercury binding protein is a bovine serum albumin. In some embodiments, a mercury binding protein comprises a modified protein that is genetically modified and/or configured to bind to mercury or modified to bind more tightly to mercury compared to its corresponding unmodified naturally occurring protein. In some embodiments, a mercury binding protein comprises a serum albumin protein modified to bind to mercury. In some embodiments, a mercury binding protein comprises a bovine serum albumin protein modified to bind to mercury. In certain embodiments, a mercury binding protein comprises HgBSA (Cat. No: DAGA-007B—obtained from Creative Diagnostics at Ramsey Road Shirley, NY 11967, USA).

Mercury Binding Agent

In some embodiments a mercury binding agent comprises an antibody, an antibody-like molecule, or an antigen binding portion thereof, that binds specifically to one or more mercury ions. A suitable mercury binding agent can be used for a method described herein. In some embodiments, a mercury binding agent binds to a mercury ion with an affinity (kD) of at least about $1 \times 10^{-6}$, at least about $1 \times 10^{-7}$, at least about $1 \times 10^{-8}$, at least about $1 \times 10^{-9}$, or at least about $1 \times 10^{-10}$. In some embodiments, a mercury binding agent binds to a mercury ion with an affinity (kD) of at least about $1 \times 10^{-8}$ to about $1 \times 10^{-12}$. In some embodiments, a mercury binding agent binds to mercury with a kD that is 10-fold higher than the kD of a surface-bound mercury binding protein for mercury. In some embodiments, a mercury binding agent binds to mercury with a kD that is 10-fold lower than the kD of a surface-bound mercury binding protein for mercury.

In some embodiments, a mercury binding agent is an antibody, or antigen binding portion thereof, that binds specifically to one or more mercury ions. An antibody can be monoclonal or polyclonal. An antibody can be obtained from any suitable species. In some embodiments, a mercury binding agent comprises or consists of one or more variable regions of an antibody, or a portion thereof. In some embodiments a mercury binding agent comprises a Fab, Fab', F(ab')2, Fv fragment, single-chain Fv (scFv), diabody (Dab), synbody, the like and/or a combination or portion thereof. In some embodiments a mercury binding agent is a Fab, Fab', F(ab')2, Fv fragment, single-chain Fv (scFv), diabody (Dab), synbody, the like and/or a combination, or antigen binding portion thereof (see, e.g., U.S. Pat. Nos. 6,099,842 and 5,990,296). In some embodiments a mercury binding agent comprises an antibody-like molecule, non-limiting examples of which include aptamers, nanobodies, BiTEs, SMIPs, DARPins, DNLs, affibodies, Duocalins, adnectins, fynomers, Kunitz Domains AlbudAbs, DARTs, DVD-IG, Covx-bodies, peptibodies, scFv-Igs, SVD-Igs, dAb-Igs, Knob-in-Holes, triomAbs, the like, and combinations thereof. In certain embodiments, a mercury binding agent comprises monoclonal antibody Hg2 (Cat. No.: HMABPY007—obtained from Creative Diagnostics at Ramsey Road Shirley, NY 11967, USA)

In some embodiments, a mercury binding agent comprises a suitable member of a binding pair. In some embodiments, a mercury binding agent is attached (e.g., covalently) to a member of a binding pair. In some embodiments, a mercury binding agent comprises biotin. In some embodiments, a mercury binding agent is attached (covalently or non-covalently) to a magnetic particle.

The term "specifically binds" refers to an antibody binding agent binding to a target peptide in preference to binding other molecules or other peptides as determined by, for example, a suitable in vitro assay (e.g., an Elisa, Immunoblot, Flow cytometry, and the like). A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more.

Magnetic Particles/Binding Pairs

In some embodiments, a method or process described herein comprises a use of one or more, or a plurality of magnetic particles. In some embodiments, a composition or device described herein comprises one or more magnetic particles. In some embodiments a mercury binding protein, a mercury binding agent, a substrate, a protein, an antibody, a secondary reagent, a bead, and/or a surface comprises one or more magnetic particles. In some embodiments a member of a binding pair comprises one or more magnetic particles. In some embodiments, a magnetic particle is attached to a member of a binding pair. In some embodiments, a magnetic particle comprises a first member of a binding pair. In some embodiments, a magnetic particle comprises a second member of a binding pair. In some embodiments, a first magnetic particle comprises a first member of a binding pair. In some embodiments, a second magnetic particle comprises a second member of a binding pair. In some embodiments, a first plurality of magnetic particles comprises magnetic particles, wherein each member of the first plurality comprises a first member of a binding pair. In some embodiments, a second plurality of magnetic particles comprises magnetic particles, wherein each member of the second plurality comprise a second member of a binding pair.

In some embodiments, a magnetic particle, or each member of a first or a second plurality of magnetic particles, comprises a member of a binding pair comprising streptavidin. In some embodiments, a magnetic particle, or each member of a first or a second plurality of magnetic particles, comprises a member of a binding pair comprising biotin. In some embodiments, a magnetic particle, or each member of a first or a second plurality of magnetic particles, comprises a member of a binding pair comprising biotin. In some embodiments, a magnetic particle, or each member of a first plurality of magnetic particles, comprises a member of a binding pair comprising biotin. In some embodiments, a magnetic particle, or each member of a first plurality of magnetic particles, comprises a member of a binding pair comprising streptavidin. In some embodiments, a magnetic particle, or each member of a second plurality of magnetic particles, comprises a member of a binding pair comprising biotin. In some embodiments, a magnetic particle, or each member of a second plurality of magnetic particles, comprises a member of a binding pair comprising streptavidin.

In some embodiments, a magnetic particle comprises streptavidin, or a variant thereof. In certain embodiments a magnetic particle is directly or indirectly attached to (e.g., bound to, e.g., covalently or non-covalently) a mercury binding protein, a mercury binding agent, a substrate, an antibody, a secondary reagent, a bead, a surface, a member of a binding pair, or the like.

A suitable magnetic particle can be used for a composition, device or method described herein. Non-limiting examples of magnetic particles include paramagnetic beads, magnetic beads, magnetic nanoparticles, heavy metallic microbeads, metallic nanobeads, heavy metallic microparticles, heavy metallic nanoparticles, the like or combinations thereof. In some embodiments, a magnetic particle comprises an average or absolute diameter of about 1 to about 1000 nanometers (nm), 1 nm to about 500 nm, about 5 nm to about 1000 nm, about 10 nm to about 1000 nm, about 5 nm to about 500 nm, about 5 nm to about 400 nm, about 5 nm to about 300 nm, about 5 nm to about 300 nm, about 5 nm to about 200 nm, about 5 nm to about 100 nm, about 2 to about 50 nm, about 5 to about 20 nm, or about 5 to about 10 nm, and/or ranges in between. In some embodiments, a magnetic particle is coated to facilitate covalent attachment to a member of a binding pair or to a mercury binding agent. In other embodiments a magnetic particle is coated to facilitate electrostatic association with molecules. In some embodiments magnetic particles comprises different shapes, sizes and/or diameters to facilitate different amounts of magnetism. In some embodiments, magnetic particles are substantially uniform (e.g., all are substantially the same; e.g., same size, same diameter, same shape and/or same magnetic properties) to facilitate more accurate detections and/or quantitation at the surface of the magnetic sensor. In some embodiments, magnetic beads comprise the same or different members of a binding pair to allow multiplex detection of multiple different analytes in the same query sample or in different query samples. In some embodiments, such analytes in the same sample or in different samples comprise one or more heavy metals. In some embodiments, the presence, absence and/or number of magnetic particles can be detected and/or quantitated by a suitable magnetic sensor. In some embodiments, a magnetic sensor comprises a surface.

In some embodiments a substrate, a particle (e.g., a magnetic particle), a bead, a protein, an antibody, a surface, or a mercury binding agent comprises one or more members of a binding pair. In certain embodiments, a first member of a binding pair can bind, and/or binds to, a second member of a binding pair. In certain embodiments, a first member of a binding pair is configured to bind specifically to a second member of a binding pair. In some embodiments a binding pair comprises at least two members (e.g., molecules) that bind non-covalently and specifically to each other Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair (e.g., first member/second member) include antibody/antigen, antibody/antibody receptor, antibody/protein A or protein G, antibody/GST, hapten/anti-hapten, sulfhydryl/maleimide, sulfhydryl/haloacetyl derivative, amine/isotriocyanate, amine/succinimidyl ester, amine/sulfonyl halides, biotin/avidin, biotin/streptavidin, folic acid/folate binding protein, receptor/ligand, GST/GT, vitamin B12/intrinsic factor, analogues thereof, derivatives thereof, binding portions thereof, the like or combinations thereof. Non-limiting examples of a member of a binding pair include an antibody or antibody fragment, antibody receptor, an antigen, hapten, a peptide, protein, a fatty acid, a glyceryl moiety (e.g., a lipid), a phosphoryl moiety, a glycosyl moiety, a ubiquitin moiety, lectin, aptamer, receptor, ligand, heavy metal ion, avidin, neutravidin, streptavidin, biotin, B12, intrinsic factor, analogues thereof, derivatives thereof, binding portions thereof, the like or combinations thereof. In some embodiments, a mercury binding agent or magnetic particles is covalently attached to member of a binding pair.

Mercury Detection Devices

Figure 26:
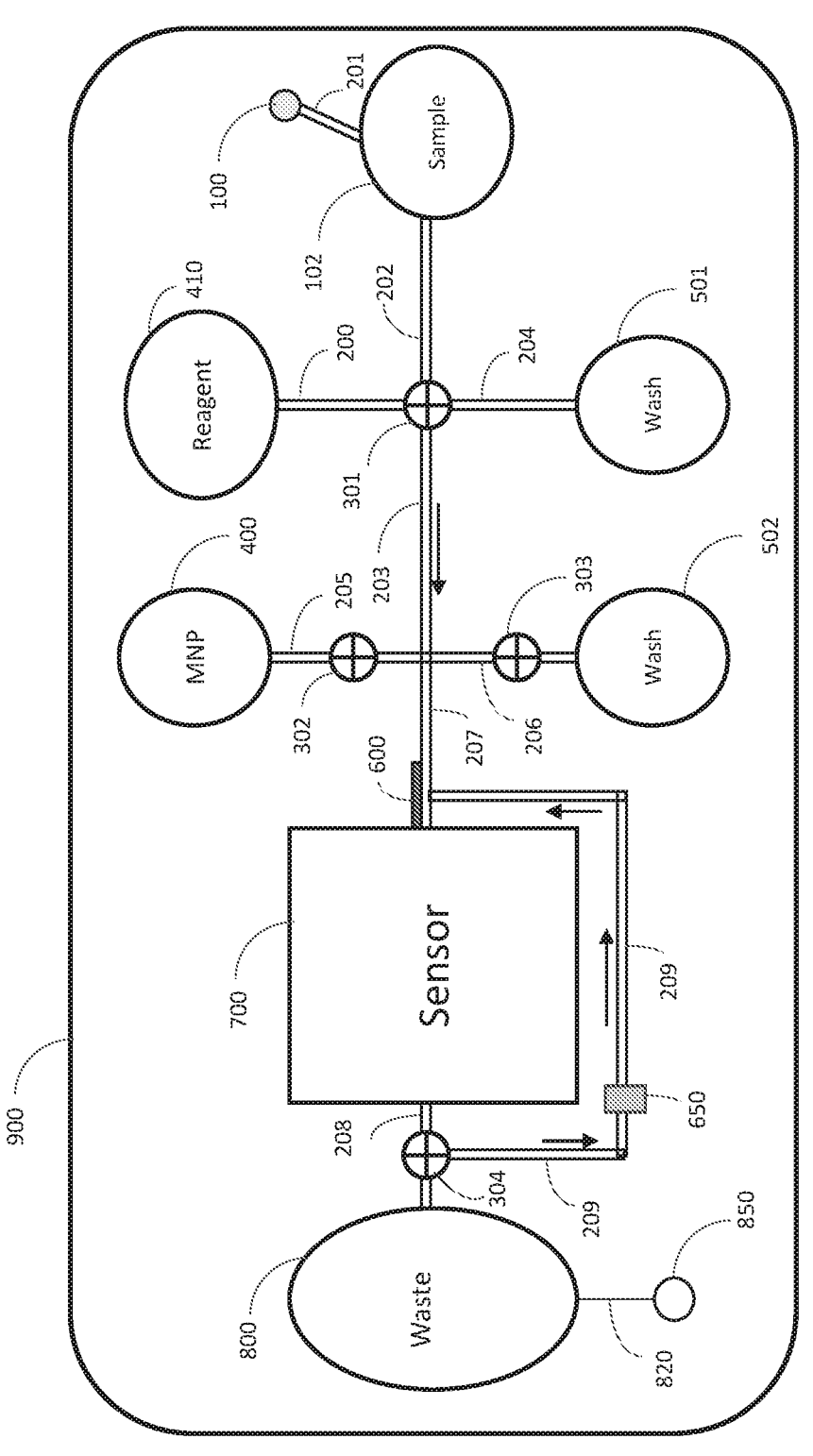
FIG. 26 shows an example of a microfluidic device 900 configured to detect mercury in a sample, in accordance with an embodiment of the present teaching.

Presented herein, in some embodiments, is a microfluidic device configured to detect mercury in a sample. In some embodiments, the device comprises one or more components shown in FIG. 26. In some embodiments, a device comprises a configuration, or a variation thereof, as shown in FIG. 26. In some embodiments, a device comprises one or more microfluidic channels that are operably and/or fluidically connected to each of the components of the device.

Components or parts that are "fluidically connected" are components and parts of a device that are in contact with and/or can be contacted with (e.g., by opening or closing a valve) a liquid or fluid disposed within the device. A well of a 96-well plate is not considered to be fluidically connected to another well in a 96-well plate. Similarly, an Eppendorf tube is not fluidically connected to another Eppendorf tube even when fluid can be transferred from one tube to another. The term "operably connected" means that the particular components or parts of the device can communicate, are attached, or are connected in such a way that they cooperate to achieve their intended function or functions. An operable "connection" may be direct, indirect, physical, or remote.

In some embodiments, a microfluidic device (e.g., 900) comprises one or more components selected from a microfluidic channel (e.g., 200-208 & 209), a chamber (e.g., 102, 400, 410, 501, 502, & 800), one or more valves (e.g., 301-304), a magnetic sensor (e.g., 700), lyophilized reagents, solubilized reagents, a heating source (e.g., 600), a pump, and a port (e.g., a flow control port 850, a sample loading port 100). In some embodiments, some or all of the components of the device are operably and/or fluidically connected (e.g., by associated microfluidic channels and valves). In some embodiments, a device comprises one or more chambers selected from a sample chamber (e.g., 102), wash chamber (e.g., 501 and 502), reagents chambers (e.g., 400, 410), waste chamber (e.g., 800), or combinations thereof.

In some embodiments, a microfluidic device comprises one or more microfluidic channels (e.g., 201-208 & 209). A microfluidic channel may comprise a suitable geometry in cross-section non-limiting examples of which include circular, oval, rectangular, triangular, the like or combinations thereof. A microfluidic channel may comprise a suitable structure non-liming examples of which include straight, curved, serpentine, and/or elevated, and may include one or more junctions that fluidically connect one or more microfluidic channels and associated components of a microfluidic device described herein. In some embodiments, a microfluidic channel has an average, mean or absolute inside diameter of about 10 nanometers to 1000 micrometers, 50 nanometers to 500 micrometers, 100 nanometers to 500 micrometers, or 100 nanometers to 100 micrometers. In some embodiments, one or more of a valve (e.g., 301-304), chamber, and/or sensor 700 are disposed within a channel body of a microfluidic channel. In some embodiments, a magnetic sensor 700 is disposed within a chamber that is operably and/or fluidically connected to one or more microfluidic channels. In some embodiments, a microfluidic channel comprises a sample port 100 for introduction of a sample, or one or more reagents, into a microfluidic device. In some embodiments, a sample port is operably and/or fluidically connected to a sample chamber (e.g., 102) by a microfluidic channel (e.g., 201).

In some embodiments, a microfluidic device comprises a sample chamber and a magnetic sensor that are operably and/or fluidically connected by one or more microfluidic channels and valves such that a direction of flow of a fluid disposed within the device is generally in a direction from the sample chamber toward the sensor, and/or towards a waste chamber (e.g., 800). Accordingly, for reference, a first component that is proximal to second component, is a component this is upstream of the second component with reference to the direction of flow toward the sensor. Similarly, a first component that is distal to a second component is a component this is downstream of the second component with reference to the direction of flow toward the sensor or waste chamber (e.g., 800) In some embodiments, a direction of flow through a microfluidic device is controlled in part by one or more of a vacuum pump or syringe pump that is operably connected to a port (e.g., flow control port 850). In some embodiments, a direction of flow through a microfluidic device is controlled in part by one or more relay pumps (e.g., 650) that are operably connected to a microfluidic channel of a microfluidic device). In some embodiments, a pump 650 is disposed on a microfluidic device 900. In some embodiments, one or more pumps can be operably connected to device 900 by a port (e.g., 850), for example when the microfluidic device is in the form of a removable cartridge. In some embodiments a flow control port is operably connected to a chamber (e.g., waste chamber 800) such that when a negative pressure is applied to port 850, fluid is directed (e.g., by one or more valves) from one or more chambers (e.g., 102, 501, 502, and/or 400/410) to sensor 700 and/or to waste chamber 800, such that a flow of fluid can be regulated and/or maintained across a surface of the sensor (e.g., 700). In some embodiments a flow control port is operably connected to a chamber by a microfluidic channel (e.g., 820). In certain embodiments, a sensor is operably and/or fluidically connected to one or more microfluidic channels (e.g., 207, 209 and 208), a valve 304 and a pump 650, such that fluid can be circulated through sensor 700, and/or over the surface of a sensor.

Any suitable valve can be used for a microfluidic device. In some embodiments, a valve is a miniature piloting solenoid valve (e.g., a Lee valves) that can be controlled on or off-card. Accordingly, a device may comprise a plurality of valves, each of which can be controlled independently. In some embodiments, one or more valves are operably connected to one or more electrical pad connections, so that a microfluidic device can be integrated with a controller or computer that directs flow of fluid through the device.

In some embodiments, a chamber is a sample chamber (e.g., 102). In some embodiments, a sample chamber comprises a sample or is configured to contain a sample. In some embodiments, a sample chamber comprises one or more reagents (e.g., dehydrated salts or buffers). In some embodiments, a microfluidic device comprises a sample port configured for introduction of a sample into the device. In certain embodiments, a sample port is operably connected and/or fluidically connected to one or more chambers. In some embodiments, a device comprises a sample port 100 and a sample chamber 102, where the sample port is proximal to the sample chamber. In some embodiments, a sample port 100 is configured for introduction of a sample into the sample chamber 102. In some embodiments, a sample port is located proximal to a sample chamber. In some embodiments, a sample port is a sample injection port.

In some embodiments, a chamber is a wash chamber (e.g., 510, 502). A wash chamber is configured to contain a suitable wash solution. In some embodiments, a wash solution is disposed within a wash chamber. A wash solution is often used to hydrate or wash a surface of a magnetic sensor (e.g., 700). In some embodiments, a wash solution comprises a buffer (e.g., Tris), an alcohol, a detergent, or a salt. In some embodiments a wash chamber provides a solution (e.g., a buffer) that helps maintain flow of fluid over the surface of the sensor, for example during detection. A wash solution may comprise any suitable buffer. In some embodiments, a buffer comprises HEPES (4-(2-hydroxyethyl)-1-piperazineethanesulfonic acid). For example, a solution disposed within chamber 501 can be diverted by valve 301 to microfluidic channels 203 and 207, such that fluid flows over sensor 700 and into waste chamber 800.

In some embodiments, a sample chamber (e.g., 102), a reagent chamber (e.g., 400/410) and/or one or more wash chambers (e.g., 501, 502) are located proximal to a magnetic sensor (e.g., 700). In some embodiments, a sample chamber (e.g., 102) and/or one or more wash chambers (e.g., 501, 502) are operably and/or fluidically connected, in parallel to a microfluidic channel (e.g., 202, 203, 207), where the microfluidic channel comprises one or more valves (e.g., 301, 302, 303) operably connected to the one or more chambers.

In certain embodiments, reagents are disposed within a reagent chamber (e.g., 400 or 410). Reagents disposed within a reagent chamber may be dried and/or lyophilized. In some embodiments, reagents disposed within a reagent chamber are solubilized or dispersed in a liquid (e.g., a wash solution). In certain embodiments, dried or lyophilized reagents located within a reagent chamber are substantially solubilized when contacted with a fluid when a fluid enters a reagent chamber. In some embodiments, a reagent chamber (e.g., 400/410) is located proximal to a magnetic sensor. In certain embodiment, a reagent chamber (e.g., 400) comprises magnetic particles (MNP), where each of the particles are attached to a member of a binding pair (e.g., streptavidin). In certain embodiment, a reagent chamber (e.g., 410) comprises a mercury binding agent. In some embodiments, a reagent chamber is operably and/or fluidically connected to a valve (e.g., 301 or 302) that when open, disperses reagents or particles into a microfluidic channel (e.g., 207) such the particles proceed to contact and/or flow over a magnetic sensor 700. In certain embodiments, valve 304 can divert fluids leaving sensor 700 to microfluidic channel 209, where pump 650 can be actuated thereby cycling reagents, sample and/or wash solutions over the surface of sensor 700.

In certain embodiments, a microfluidic device comprises a heating source (e.g., 600). Any suitable heating source can be used in a device described herein. In some embodiments, a magnetic sensor comprises a heating source. In some embodiments, a heating source is located proximal to a magnetic sensor, such that a temperature of a fluid flowing over a magnetic sensor can be heated.

In some embodiments, a microfluidic device comprises a magnetic sensor (e.g., 700). In some embodiments, a microfluidic device comprises a plurality of magnetic sensors (e.g., GMRs). In some embodiments, a microfluidic device comprises a first magnetic sensor that is for contacting with a sample, and a second "control" magnetic sensor that is not contacted with a sample. A control sensor is often for establishing a baseline of magnetoresistance for a magnetic sensor that is not contacted with a sample or mercury. For example, a device may comprise duplicate sensors, wherein one sensor is contacted with a sample suspected of containing mercury, and the other sensor is not contacted with the sample. The magnetoresistance at the surface of each of the two sensors can be compared to determine a presence, absence or amount of mercury in the sample. In some embodiments, a microfluidic device comprises an array of sensors with addressable locations. In some embodiments a magnetic sensor is a magnetoresistance sensor. In some embodiments a magnetic sensor is a giant magnetoresistance (GMR) sensor. In some embodiments a magnetic sensor is an anisotropic magnetoresistance (AMR) sensor and/or a magnetic tunnel junction (MTJ) sensor.

In some embodiments, a magnetic sensor detects magnetoresistance, current and/or voltage potential, or changes thereof, at a surface of the sensor. In some embodiments, a magnetic sensor detects magnetoresistance, current and/or voltage potential, or changes thereof on the surface of the sensor. In some embodiments, a magnetic sensor detects magnetoresistance, current and/or voltage potential, or changes thereof over a period of time non-limiting examples of which include 1 nanosecond to 1 hour, 1 second to 60 minutes, 1 second to 10 minutes, 1 second to 1000 seconds or intervening periods thereof. In some embodiments, a magnetic sensor detects the presence, absence or amount of magnetic particles that are bound to (e.g., indirectly bound to) or associated with a surface of the magnetic sensor according to a magnetoresistance, current and/or voltage potential, or changes thereof, that are detected by the magnetic sensor. In some embodiments, a magnetic sensor detects the presence, absence or amount of mercury present in a sample according to a presence, absence or amount of magnetic particles that are bound to (e.g., indirectly bound to) or associated with a surface of the magnetic sensor. Accordingly, in some embodiments, a magnetic sensor detects the presence, absence or amount of mercury present in a sample according to a magnetoresistance, current and/or voltage potential, or changes thereof, that are detected or measured at the surface of the magnetic sensor.

GMR sensors can have sensitivities that exceed those of anisotropic magnetoresistance (AMR) or Hall sensors. This characteristic enables detection of stray fields from magnetic materials at nanometer scales. For example, stray fields from magnetic nanoparticles that are bound on a magnetic sensor surface will alter the magnetization in the magnetic sensor layers, and thus change the magnetoresistance of a GMR sensor. Accordingly, changes in the amount of magnetic nanoparticles bound to a GMR sensor per unit area can be reflected in changes of the magnetoresistance value of a GMR sensor. In some embodiments, a magnetic sensor comprises a GMR sensor.

In some embodiments, a magnetic sensor comprises a surface. A surface of a magnetic sensor may comprise a suitable material, non-limiting examples of which include glass, modified or functionalized glass (e.g., controlled-pore glass (CPG)), quartz, mica, polyformaldehyde, cellulose, cellulose acetate, ceramics, heavy metals, heavy metalloids, semi-conductive materials, plastic (including acrylics, polystyrene, copolymers of styrene or other materials, polybutylene, polyurethanes. TEFLON™, polyethylene, polypropylene, polyamide, polyester, polyvinylidenedifluoride (PVDF), and the like), resins, silica or silica-based materials including silicon, silica gel, and modified silicon, Sephadex®, SEPHAROSE®, carbon, heavy metals (e.g., steel, gold, silver, aluminum, silicon and copper), conducting polymers (including polymers such as polypyrrole and polyindole); micro or nanostructured surfaces, nanotube, nanowire, or nanoparticulate decorated surfaces; or porous surfaces or gels such as methacrylates, acrylamides, sugar polymers, cellulose, silicates, or other fibrous or stranded polymers. In some embodiments, a surface is coated using passive or chemically-derivatized coatings with any number of materials, including polymers, such as dextrans, acrylamides, gelatins or agarose. In some embodiments a surface of a magnetic sensor is non-covalently and/or reversibly attached to an oligonucleotide.

In some embodiments, a surface of a magnetic sensor comprises and/or is coated with a crosslinked PEG-PHEMA polymer. A PEG-PHEMA polymer surface can be prepared by mixing a PEG solution comprising N-Hydroxysuccinimide(NHS)-PEG-NHS (MW 600) dissolved in a suitable solvent (e.g., isopropyl alcohol, acetone or methanol, and/or water), a PHEMA solution comprising polyhydroxyethyl methacrylate (MW 20,000) dissolved in a suitable solvent (e.g., isopropyl alcohol, acetone or methanol, and/or water), and an optional crosslinker. The resulting solution can be coated on a magnetic sensor surface using a suitable coating process (e.g., micro-printing, dip coating, spin coating or aerosol coating). After coating a surface with the PEG-PHEMA solution, the surface can be cured using UV light followed by washing with a suitable solvent, such as isopropyl alcohol and/or water. In some embodiments a surface of a magnetic sensor is covalently attached to one or more mercury binding proteins. In some embodiments a surface of a magnetic sensor is covalently attached to one or more BSA molecules (e.g., a Hg-BSA). In some embodiments, the coated surface can be used to bind with primary amines (e.g., to attach a protein). A PEG-PHEMA coating can protect a magnetic sensor surface against corrosion. In some embodiments, a surface of a magnetic sensor comprises a surface described in International Patent Application No. PCT/US2019/043766.

In some embodiments, a surface of a magnetic sensor comprises a coating. In some embodiments a coating comprises a suitable surfactant. In some embodiments, a surfactant comprises cetyl trimethylammonium bromide (CTAB). In some embodiments, a surface of a magnetic sensor is coated with, or contacted with a suitable surfactant prior to contacting a magnetic sensor with a sample.

In some embodiments, a magnetic sensor or surface of a magnetic sensor comprises a mercury binding protein. In some embodiments, a magnetic sensor or surface of a magnetic sensor comprises a plurality of mercury binding proteins. In some embodiments, a mercury binding protein is attached non-covalently to a surface of a magnetic sensor. In some embodiments, a mercury binding protein is attached covalently to a surface of a magnetic sensor using a suitable chemistry, non-limiting examples of which include a chemistry described in Cha et al. (2004) "Immobilization of oriented protein molecules on poly(ethylene glycol)-coated Si(111)" *Proteomics* 4:1965-1976 and Zellander et al. (2014) "Characterization of Pore Structure in Biologically Functional Poly(2-hydroxyethyl methacrylate)-Poly(ethylene glycol) Diacrylate (PHEMA-PEGDA)," *PLOS ONE* 9(5):e96709. In some embodiments, a surface of a magnetic sensor comprises a plurality of a mercury binding protein at a density of about $1 \times 10^9$ to about $5 \times 10^{10}$ molecules per/ $mm^2$.

In some embodiments a device comprises two or more magnetic sensors, each comprising a surface comprising the same nucleic acid comprising the same MRP binding site and/or the same MRP. For example, in some embodiments a device comprises a first magnetic sensor configured to contact a sample and a second control magnetic sensor that does not contact a sample, where the first and the second sensors comprise the same nucleic acid comprising the same MRP binding site and/or the same MRP. In some embodiments a device comprises two or more magnetic sensors, each comprising a surface comprising a different nucleic acid comprising a different MRP binding site and/or a different MRP. In some embodiments, a surface of a magnetic sensor comprises a plurality of addressable locations, each comprising a different nucleic acid comprising a different MRP binding site and/or a different MRP.

In some embodiments, a microfluidic device comprises a negative control sensor. In certain embodiments, a negative control sensor is a magnetic sensor (e.g., a GMR). In some embodiments of a method described herein, a negative control sensor is not contacted with a sample. In some embodiments of a method described herein, a negative control sensor is contacted with a suitable control solution, wash buffer or control buffer.

In certain embodiments, a microfluidic device 900 is disposed on a card or cartridge. Accordingly, in some embodiments, a microfluidic device, or a card or cartridge comprising a microfluidic device described herein has a length of 3 to 10 cm, a width of 1 to 10 cm, and a thickness of 0.1 to 1 cm.

In some embodiments, a microfluidic device comprises a printed circuit board (PSB). In some embodiments, a microfluidic device or a PSB comprises one or more memory chips. In some embodiments a microfluidic device or a PSB comprises one or more electrical pad connections. In some embodiments the one or more electrical pad connections are operably (e.g., electronically) connected to a memory chip, one or more valves, a magnetic sensor and/or one or more pumps of a microfluidic device. In some embodiments one or more components of a microfluidic device are disposed on a PSB.

In some embodiments, a microfluidic device is disposed on a cartridge or card that comprises a PSB. In some embodiments, a cartridge is configured for insertion or attachment to a controller, a computer, or larger device that integrates with a microfluidic device. In some embodiments a controller comprises pumps (e.g., diaphragm or syringe type pumps) that operably connect to one or more flow control ports 850 located on a cartridge. In some embodiments, one or more components of a microfluidic device are disposed on a substrate comprising a polymer plastic. In some embodiments, one or more components of a microfluidic device are disposed on a substantially flat substrate comprising a polymer plastic.

In some embodiments, a microfluidic device, PSB or cartridge described herein comprises one or more components, subcomponents or parts described in International Patent Application No. PCT/US2019/043720, entitled "SYSTEM AND METHOD FOR GMR-BASED DETECTION OF BIOMARKERS" filed Jul. 26, 2019, International Patent Application No. PCT/US2019/043753, entitled "SYSTEM AND METHOD FOR SAMPLE PREPARATION IN GMR-BASED DETECTION OF BIOMARKERS" filed Jul. 26, 2019, International Patent Application No. PCT/US2019/043766, entitled "SYSTEM AND METHOD FOR SENSING ANALYTES IN GMR-BASED DETECTION OF BIOMARKERS" filed Jul. 26, 2019 or, International Patent Application No. PCT/US2019/043791, entitled "SYSTEM AND METHOD FOR PROCESSING ANALYTE SIGNALS IN GMR-BASED DETECTION OF BIOMARKERS" filed Jul. 26, 2019, all of which are hereby incorporated by reference herein in their entirety. In some embodiments, a method described herein utilizes one or more components, subcomponents or parts described in International Patent Application No. PCT/US2019/043720, PCT/US2019/043753, PCT/US2019/043766, or PCT/US2019/043791. In some embodiments, a microfluidic device described herein comprises a magnetic sensor and/or magnetic sensor assembly described in International Patent Application No. PCT/US2019/043720, PCT/US2019/043753, PCT/US2019/043766, or PCT/US2019/043791.

In some embodiments, any one chamber (e.g., 102, 501, 502, 400, 410, 800) and/or a chamber housing a magnetic sensor comprises a volume independently selected from 1 µl to 20 ml, 1 µl to 15 ml, 1 µl to 5 ml, 1 µl to 1 ml, 1 µl to 500 µl, 1 µl to 100 µl, and intermediate volumes thereof.

Methods

Presented herein, in certain embodiments, is a method of detecting the presence, absence, or amount of mercury in a sample (e.g., a liquid sample). In some embodiments, a method comprises contacting a magnetic sensor comprising a surface 720, and a mercury binding protein 40 attached to the surface, with a sample suspected of comprising mercury (Hg). A mercury binding protein (e.g., 40) is often bound to one or more mercury ions prior to contacting a sensor with a sample. In some embodiments, a sensor comprises a plurality of mercury binding proteins, each of which comprises one or more mercury ions. In some embodiments, each mercury binding protein is bound to, or attached to one or more mercury ions. In some embodiments, a surface of a magnetic sensor is contacted with a detergent or a surfactant (e.g., CTAB) prior to contacting the sensor with a sample. In some embodiments, a surface of a magnetic sensor is blocked with a suitable blocking solution prior to contacting a sensor with a sample. A blocking solution may one comprise one or more of a detergent or a surfactant (e.g., CTAB, polysorbate, Triton X-100), a suitable buffer and/or a blocking agent (e.g., BSA, yeast extract, gelatin, and/or amino acids).

Figure 25:
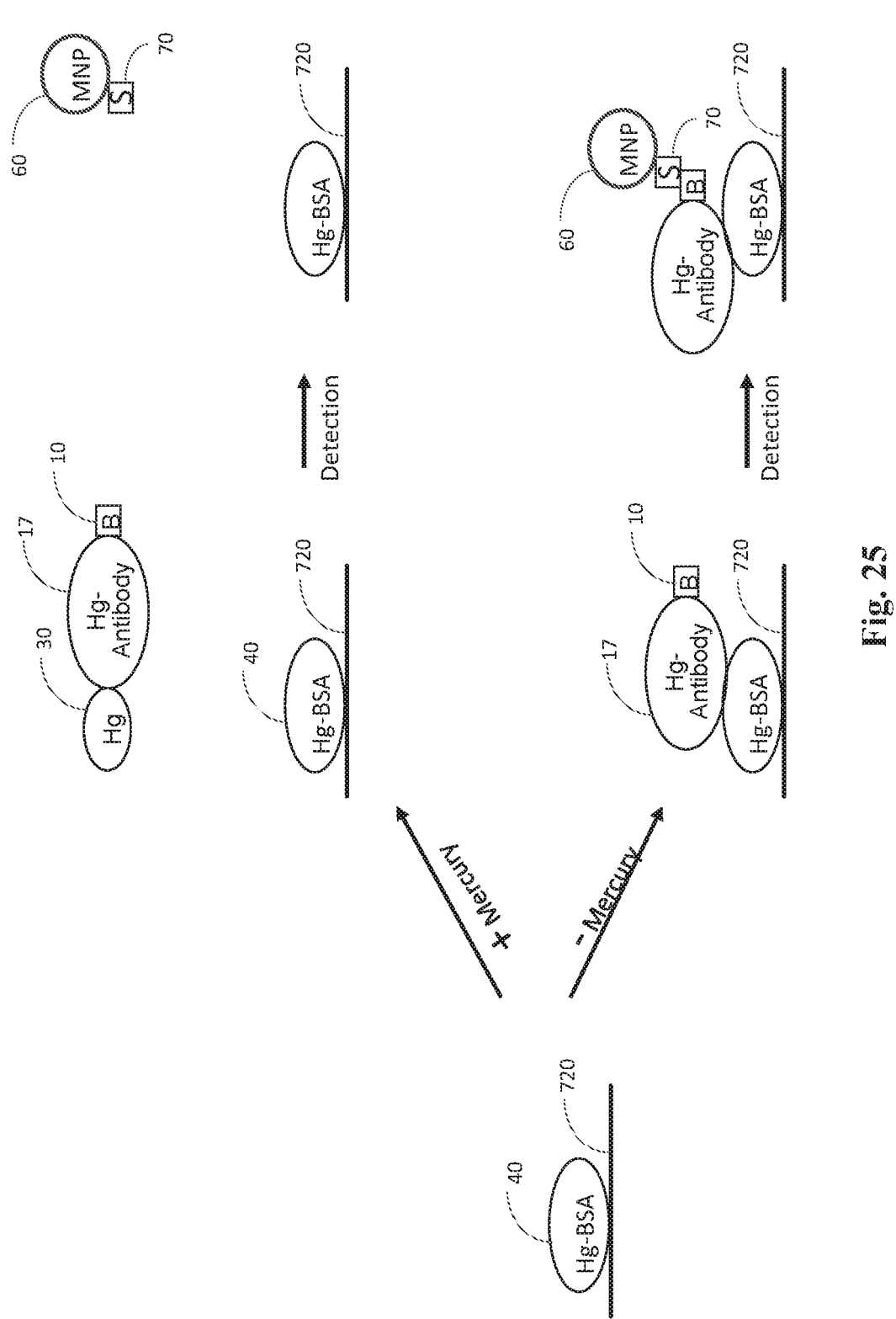
FIG. 25 shows an illustration of an exemplary detection method using a sensor surface 720 attached to a mercury binding protein 40 that is bound to mercury (e.g., a modified BSA bound to mercury (Hg-BSA)); and either: in the presence of mercury ion, the biotinylated mercury-binding antibody 17 binds the mercury ion and does not bind to the mercury binding protein 40; in the absence of mercury ion the biotinylated mercury-binding antibody 17 binds the mercury binding protein 40; in accordance with an embodiment of the present teaching.

In some embodiments, a sensor 700 or surface of a sensor 720 is contacted with a mercury binding agent (e.g., 17). A mercury binding agent, in some embodiments, comprises a first member of a binding pair (e.g., 10, e.g., biotin). In some embodiments, a mercury binding agent comprises a magnetic particle (e.g., 60). In some embodiments, a sensor is contacted with a mercury binding agent prior to contacting a sample with a sensor. In such embodiments, the mercury binding agent is allowed to bind to mercury ions that are bound by a surface-attached mercury binding protein, thereby forming a surface bound complex (e.g., see FIG. 25, bottom panel). In some embodiments, a sample is contacted with a mercury binding agent to form a mixture, and the sample mixture is contacted with a magnetic sensor. In some embodiments, a sample comprising mercury is contacted with a sensor in the presence of a mercury binding agent. In such an embodiment, the mercury binding agent 17 binds to free mercury 30 in the sample instead of to the sensor surface 720 and the mercury-bound mercury binding agent is washed away from the sensor surface (e.g., FIG. 25, upper panel). In certain embodiments, a sensor comprising a mercury binding protein is first contacted with a sample, and the sensor is then contacted with a mercury binding agent.

In some embodiments, a mercury binding agent comprises magnetic particles or a first member of a binding pair (e.g., biotin). In some embodiments when an mercury binding agent comprises a first member of a binding pair (e.g., biotin), a method comprises contacting a sensor or a mercury binding agent with magnetic particles comprising a second member of the binding pair (e.g., streptavidin), such that the first member of the binding pair binds to the second member of the binding pair. In some embodiments, the presence, absence or amount of magnetic particles that are at, on, near or associated with (e.g., indirectly by non-covalent interactions) a magnetic sensor are detected by a method herein. The detecting is sometimes performed after a magnetic sensor is contacted with a sample. In certain embodiments, the detecting is performed before, during and/or after contacting a magnetic sensor with a sample or with magnetic particles. In some embodiments, a detecting process is a dynamic detection process such that one or more magnetic particles can be detected before, during and/or after contacting a magnetic sensor with a sample while changing one or more conditions at the surface of the sensor.

In some embodiments, a process of contacting a magnetic sensor with a sample, a mercury binding agent and/or magnetic particles comprises flowing a fluid across the surface of the sensor. Non-limiting examples of a fluid include a liquid sample, a wash solution, a buffer solution, water, a solution comprising magnetic particles, a solution comprising a suitable reagent, a solution comprising a mercury binding agent, the like, combinations thereof or mixtures thereof. In some embodiments, a magnetic sensor or surface thereof is continually and/or continuously in contact with a fluid (e.g., a sample, wash solution, buffer, magnetic particles and the like) when conducting a method herein. In certain embodiments, a flow rate over the surface of a magnetic sensor during a contacting, washing or detecting process is about 0 to about 500 µl/minute, 0.1 µl/minute to 500 µl/minute, 1 µl/minute to 500 µl/minute, 1 µl/minute to 100 µl/minute, 1 µl/minute to 10 µl/minute, or intervening ranges therein. In certain embodiments, a flow rate over the surface of a magnetic sensor during a contacting, washing or detecting process is about 100 Hz to 800 Hz, or about 100 Hz to 300 Hz.

In some embodiments, a volume of a sample that is contacted with a magnetic sensor is a volume in a range of 1 μl to 500 μl, 20 μl to 300 μl, or intervening ranges or volumes thereof.

In some embodiments, a sensitivity range of the detection of mercury by a method herein is in a range from about 0.00001 nanomolar (nM) to about 100 nM, 0.01 nM to about 100 nM, 0.1 nM to about 100 nM, about 1 nM to about 100 nM, or about 1 nM to about 50 nM of mercury (Hg) in a sample. In some embodiments, a lower limit of sensitivity of a detection of mercury by a method herein is about 0.01 picomolar, about 0.1 picomolar, about 1.0 picomolar, about 10 picomolar, about 0.1 nM, about 1.0 nM, about 5.0 nM, or about 7.5 nM of mercury in a sample.

In some embodiments, a magnetic sensor is washed with a wash solution such that the wash solution flows over the surface of the sensor. A wash solution may comprise any suitable composition. In some embodiments, a wash solution stabilizes interactions between a repressor protein and its cognate repressor binding site. In some embodiments, a wash solution stabilizes binding of a mercury binding agent to a sensor. In some embodiments a wash solution increases affinity of a first member of a binding pair to a second member of a binding pair. In some embodiments, a wash solution is configured to dissociate non-specific binding interaction between a member of a binding pair and another molecule. In some embodiments, a wash solution is configured to dissociate non-specific binding interaction between a surface-bound mercury binding protein and other molecules or proteins present in a sample. In some embodiments, a wash solution is configured to dissociate non-specific binding interaction between a mercury binding agent and other molecules or proteins present in a sample. Accordingly, in some embodiment, a wash solution comprises one or more of a suitable buffer (e.g., HEPES, or Tris), a chelating agent (e.g., EDTA), salts, a detergent or surfactant, a chaotropic agent, formamide, a blocking agent, combinations thereof and the like. In some embodiments a wash solution does not include a salt. Any suitable wash solution can be used to increase the stringency of protein binding conditions at the surface of a magnetic sensor. In some embodiments, a temperature of a wash solution flowing over the surface of a magnetic sensor is increased during a wash step or during a detection step.

In some embodiments, a wash solution is configured to maintain a flow of fluid over a magnetic sensor. In such embodiments, a wash solution may comprise the same, or a similar composition (e.g., buffers and salts), as a sample or a reagent (e.g., a suspension of magnetic particles or a mercury binding agent).

In some embodiments, a sample, one or more reagents, or a wash solution is flowed over a sensor in a loop (e.g., see microfluidic channel 209, FIG. 26). In some embodiments, a sample, one or more reagents, or a wash solution is flowed over the sensor providing a constant supply of fresh sample, fresh reagents or wash solution. In some embodiments, a biotinylated anti-Hg antibody is added to a sample prior flowing the sample over the sensor. In some embodiments, a biotinylated anti-Hg antibody is added to a sample while flowing the sample over the sensor. In some embodiments, a biotinylated anti-Hg antibody is contacted with a sensor prior to flowing the sample over the sensor. In some embodiments, a sample is contacted with a sensor for a duration of 1 to 60 minutes, or in some embodiments, for about 30 minutes.

In some embodiments, a temperature of fluid flowing over the surface of a magnetic sensor is increased before, during and/or after (i) contacting a magnetic sensor with a sample, (ii) contacting a magnetic sensor with a mercury binding agent, (iii) contacting a sensor with a magnetic particle, and/or (iv) detecting a presence, absence, or amount of magnetic particles bound to, or associated with, a magnetic sensor surface.

In some embodiments, a temperature of a fluid in contact with the surface of a magnetic sensor is increased by at least 10° C., by at least 15° C., by at least 20° C., by at least 25° C., by at least 30° C., by at least 40° C., by at least 60° C., or by at least 80° C. over a period of 1 second to 30 minutes, 1 second to 10 minutes, 1 second to 5 minutes, 1 second to 1 minute, or intervening ranges thereof. In some embodiments, a temperature of a fluid in contact with the surface of a magnetic sensor is increased from about 10° C. to about 120° C., from about 10° C. to about 80° C., from about 10° C. to about 70° C., from about 10° C. to about 65° C., from about 10° C. to about 60° C., from about 20° C. to about 120° C., from about 20° C. to about 80° C., from about 20° C. to about 70° C., from about 20° C. to about 65° C., from about 20° C. to about 60° C., from about 25° C. to about 80° C., from about 25° C. to about 70° C., from about 25° C. to about 65° C., from about 25° C. to about 60° C., or intervening ranges thereof, In some embodiments, a temperature of a fluid in contact with the surface of a magnetic sensor is increased over a period of 1 second to 30 minutes, 1 second to 10 minutes, 1 second to 5 minutes, 1 second to 1 minute, or intervening ranges thereof.

In some embodiments, a temperature of a fluid in contact with the surface of a magnetic sensor is increased to a temperature in a range of about 30° C. to 90° C., about 30° C. to 80° C., about 30° C. to 75° C., about 30° C. to 70° C., about 30° C. to 65° C., about 30° C. to 60° C., about 30° C. to 55° C., or about 30° C. to 50° C. In some embodiments, a temperature of a fluid in contact with the surface of a magnetic sensor is increased to a temperature in a range of about 30° C. to 90° C., about 30° C. to 80° C., about 30° C. to 75° C., about 30° C. to 70° C., about 30° C. to 65° C., about 30° C. to 60° C., about 30° C. to 55° C., or about 30° C. to 50° C. over a period of 1 second to 30 minutes, 1 second to 10 minutes, 1 second to 5 minutes, 1 second to 30 minutes, or intervening ranges thereof.

In some embodiments, a method or detecting process comprises detecting a presence, absence, amount, or change thereof, of magnetic particles at, on, near or associated with a surface of a magnetic sensor. In some embodiments, a presence, absence, amount, or change thereof, of magnetic particles bound to a surface of a magnetic sensor is detected. In certain embodiments, a detection process or detection step comprises detecting a change in an amount of magnetic particles at, near, or on the surface of a magnetic sensor over a period of time.

In some embodiments, a detection process comprises a dynamic detection process. In certain embodiments, a dynamic detection process comprises detecting a presence, absence, amount, or change in an amount of magnetic particles at, near, or on the surface of a magnetic sensor over time, while conditions at, near or on the surface of a magnetic sensor are changed. Non-limiting examples of conditions that can be changed during a dynamic detection process include temperature, salt concentration, cation concentration, ion concentration, pH, detergent concentration, chaotropic agent concentration, ionic kosmotrope concentration, the like or combinations thereof. Often, conditions are changed during a dynamic detection process to increase stringency of protein-protein interactions or protein-DNA interactions at, on or near a surface of a magnetic sensor.

In some embodiments, a dynamic detection process comprises detecting a change in an amount of magnetic particles at, near, or on a surface of a magnetic sensor over time, while temperature is increased over a period of time. In some embodiments, a dynamic detection process comprises detecting a change in an amount of magnetic particles at, near, or on the surface of a magnetic sensor over a period of time, while a concentration of cations (e.g., Na, Ca, Mg, Zn and the like) is increases or decreased. In some embodiments, a dynamic detection process comprises detecting a change in an amount of magnetic particles at, near, or on a surface of a magnetic sensor over a period of time, while temperature is increased and/or while a concentration of salt is increased or decreased.

In some embodiments, a method comprises detecting or determining a magnetoresistance, current, voltage potential, or change thereof on, near or at the surface of a magnetic sensor. In some embodiments, a magnetoresistance, current, voltage potential, or change thereof, on, near or at the surface of a magnetic sensor is determined or detected once, continuously (e.g., during a predetermined period of time), or periodically (e.g., two or more times) before, during and/or after a magnetic sensor is contacted with magnetic particles as described herein. In some embodiments, a magnetoresistance, current, voltage potential, or change thereof, on, near or at the surface of a magnetic sensor is determined or detected continuously (e.g., during a predetermined period of time), or periodically (at two or more times) while a temperature is increased at the surface of a magnetic sensor.

In some embodiments, some or all aspects of a method and/or some or all steps of a method described herein are performed in a microfluidic device described herein.

It will be understood that all embodiments disclosed herein may be combined in any manner to carry out a method of detecting an analyte and that such methods may be carried out using any combination of embodiments disclosed herein describing the various system components. Detection of Arsenic, Cadmium, and Other Metals Metalloregulatory Repressor Proteins In some embodiments a method comprises the use of a metalloregulatory repressor protein (MPR). In some embodiments, a microfluidic device comprises an MPR. In certain embodiments, a MRP binds specifically to a repressor binding site. An MPR may bind to single or double stranded nucleic acid. In certain embodiments, an MPR comprises a suitable arsenical resistance operon repressor (arsR), non-limiting examples of which include an arsR of *E. coli*, strain K12 (UniProtKB accession no. P37309), an arsR of *B. subtilis* (UniProtKB accession no. P45949), an arsR of *S. aureus* (UniProtKB accession no. P30338), an arsR of *Pseudomonas putida* (UniProtKB accession no. Q88LK1), the like, homologues thereof, and functional variants thereof. In some embodiments, an arsR comprises an arsR protein described in Busenlelhner et al., (2003) *FEMS Microbiology Reviews,* 27 (2-3): p. 131-143, or a functional variant thereof. In some embodiments, an arsR comprises the amino acid sequence MSFLLPIQLFKILADETRLGIVLLLSELGELCVCDLC-TALDQSQPKISRHLALLRESGLLLD RKQGKWVHY-RLSPHIPAWAAKIIDEAWRCEQEKVQAIVRNLAR-QNCSGDSKNICS (SEQ ID NO:1), or a functional variant thereof. In some embodiments, an arsR binds to a specific repressor binding site comprising a specific recognition sequence when the arsR protein is not bound to arsenic. In certain embodiments, an arsR protein dissociates from its cognate repressor binding site when the arsR protein is bound to arsenic. Accordingly, in certain embodiments, an arsR protein does not bind to a nucleic acid when the arsR is bound to arsenic.

In certain embodiments, an MPR comprises a suitable cadmium resistance transcriptional regulatory protein (cadC), non-limiting examples of which include a cadC of *S. aureus* (UniProtKB accession no. P20047), a cadC of *E. coli* (UniProtKB accession no. P23890), a cadC of *Bacillus pseudofirmus* (UniProtKB accession no. P30339), a cadC of *Listeria monocytogenes* (UniProtKB accession no. Q56405), a cadC of *Klebsiella pneumoniae* (UniProtKB accession no. W9BEV1) the like, homologues thereof, and functional variants thereof. In some embodiments, a cadC comprises a cadC protein described in Busenlelhner et al., (2003) *FEMS Microbiology Reviews,* 27 (2-3): p. 131-143, or a functional variant thereof. In some embodiments, an cadC comprises the amino acid sequence of MKKKDTCE-IFCYDEEKVNRIQGDLQTVDISGVSQILKAIADEN-RAKITYALCQDEELCVC DIANILGVTIANASHHLRT-LYKQGVVNFRKEGKLALYSLGDEHIRQIMMIALAHKKEVK VNV (SEQ ID NO:2), or a functional variant thereof. In some embodiments, a cadC binds to a specific repressor binding site comprising a specific recognition sequence when the cadC protein is not bound to cadmium. In certain embodiments, a cadC protein dissociates from its cognate repressor binding site when the cadC protein is bound to cadmium. Accordingly, in certain embodiments, an cadC protein does not bind to a nucleic acid when the cadC is bound to cadmium.

Repressor Binding Sites

In certain embodiments, a nucleic acid comprises a suitable repressor binding site that is recognized by a specific MRP. In certain embodiments, a nucleic acid comprises a repressor binding site that is recognized by a suitable MRP. A repressor binding site is often a specific nucleotide sequence, and/or complement thereof, that an MRP recognizes and binds to. Different MRPs often recognize different repressor binding sites. Many MRPs are known and their cognate repressor binding sites are known. Accordingly, a specific arsenic or cadmium responsive MRP can be paired with its cognate repressor binding site for use in a method or device described herein.

In certain embodiments, a nucleic acid comprises a repressor binding site of an arsR. In some embodiments, an arsR disclosed herein recognizes and can bind to a repressor binding site selected from one or more of the nucleic acid sequences of 5'-CATTCGTTAAGT-CATATATGTTTTTGAC-3' (SEQ ID NO:3), 5'-CTTACA CATTCGTTAAGTCATATATGTTTTTGAC-3' (SEQ ID NO:4), 5'-TCTGCACTTACACATTCGTTAAGT-CATATATGTTTTTGAC-3' (SEQ ID NO:5), 5'-CATTCGT-TAAGTCATATATGTTTTTGACTT-3' (SEQ ID NO:6), 5'-CATTCGTTAAGTCATATATGTTTTTGACT-TATCCGCTTCGAAGA-3' (SEQ ID NO:7), 5'-CTTACA CATTCGTTAAGTCATATATGTTTTTGACT-TATCCGCTTCGAAGA-3' (SEQ ID NO:8), and 5'-TCTGCACTTACACATTCGTTAAGT-CATATATGTTTTTGACTT ATCCGCTTCGAAGA-3' (SEQ ID NO:9), and/or a reverse complement thereof. In some embodiments, a repressor binding site of an arsR comprises a nucleic acid sequence selected from SEQ ID NO:3, SEQ ID NO:4, SEQ ID NO:5, SEQ ID NO:6, SEQ ID NO:7, SEQ ID NO:8 and SEQ ID NO:9. In some embodiments, a repressor binding site of an arsR comprises a nucleic acid sequence that is the reverse complement of a nucleic acid sequence selected from SEQ ID NO:3, SEQ ID NO:4, SEQ ID NO:5, SEQ ID NO:6, SEQ ID NO:7, SEQ ID NO:8 and SEQ ID NO:9. In some embodiments, a repressor binding site of an arsR comprises a double stranded nucleic acid sequence comprising a first strand comprising a nucleic acid sequence selected from SEQ ID NO:3, SEQ ID NO:4, SEQ ID NO:5, SEQ ID NO:6, SEQ ID NO:7, SEQ ID NO:8 and SEQ ID NO:9, and a second strand comprising a nucleic acid sequence that is the reverse complement of a nucleic acid sequence selected from SEQ ID NO:3, SEQ ID NO:4, SEQ ID NO:5, SEQ ID NO:6, SEQ ID NO:7, SEQ ID NO:8 and SEQ ID NO:9.

In certain embodiments, a nucleic acid comprises a repressor binding site of a cadC. In some embodiments, a cadC disclosed herein recognizes and can bind to the nucleic acid sequence 5'-ATAATACACTCAAATAAATATTT-GAATGAAGATG-3' (SEQ ID NO:10), the nucleic acid 5'-TGAGTCGAAAATGGTTATAATACACT-CAAATAAATATTTGAATGAAGATG-3' (SEQ ID NO:13), a subsequence thereof, and/or a reverse complement thereof. In some embodiments, a cadC disclosed herein recognizes and can bind to a nucleic acid sequence at least 80%, at least 90%, at least 95%, or at least 98% identical to the nucleic acid sequence of SEQ ID NO:10, SEQ ID NO: 13, and/or a subsequence thereof, or a reverse complement thereof. In some embodiments, a repressor binding site of cadC comprises the nucleic acid sequence of SEQ ID NO:10 or SEQ ID NO:13. In some embodiments, a repressor binding site of cadC comprises a nucleic acid sequence that is the reverse complement of SEQ ID NO:10 or SEQ ID NO:13. In some embodiments, a repressor binding site of cadC comprises a double stranded nucleic acid sequence comprising a first strand comprising a nucleic acid sequence selected from SEQ ID NO:10 and SEQ ID NO:13, and a second strand comprising a nucleic acid sequence that is the reverse complement of a nucleic acid sequence selected from SEQ ID NO:10 and SEQ ID NO:13.

Magnetic Particles/Binding Pairs

In some embodiments, a method or process described herein comprises a use of one or more, or a plurality of magnetic particles. In some embodiments, a composition or device described herein comprises one or more magnetic particles. In some embodiments a nucleic acid, a substrate, a protein, an antibody, a secondary reagent, a bead, a surface, and/or an MPR comprises one or more magnetic particles. In some embodiments a member of a binding pair comprises one or more a magnetic particle. In some embodiments, a magnetic particle is attached to a member of a binding pair. In some embodiments, a magnetic particle comprises streptavidin, or a variant thereof. In certain embodiments a magnetic particle is directly or indirectly attached to (e.g., bound to, e.g., covalently or non-covalently) a nucleic acid, a substrate, an antibody, a secondary reagent, a bead, a surface, a member of a binding pair, and/or an MPR, or the like.

Any suitable magnetic particle can be used for a composition, device or method described herein. Non-limiting examples of magnetic particles include paramagnetic beads, magnetic beads, magnetic nanoparticles, heavy metallic microbeads, metallic nanobeads, heavy metallic micropar-ticles, heavy metallic nanoparticles, the like or combinations thereof.

In some embodiments, magnetic particles comprise iron oxide particles. In some embodiments, magnetic particles comprise iron oxide magnetic particles and streptavidin. In some embodiments, magnetic particles comprise iron oxide magnetic particles and biotin.

In some embodiments, a magnetic particle comprises an average or absolute diameter of about 1 to about 1000 nanometers (nm), 1 nm to about 500 nm, about 5 nm to about 1000 nm, about 10 nm to about 1000 nm, about 5 nm to about 500 nm, about 5 nm to about 400 nm, about 5 nm to about 300 nm, about 5 nm to about 300 nm, about 5 nm to about 200 nm, about 5 nm to about 100 nm, about 2 to about 50 nm, about 5 to about 20 nm, or about 5 to about 10 nm, and/or ranges in between. In some embodiments, a magnetic particle comprises an average or absolute diameter of about 2 to about 50 nm, or about 5 to about 20 nm, or about 5 to about 10 nm. In some embodiments, a magnetic particle is coated to facilitate covalent attachment to a member of a binding pair or to a nucleic acid. In other embodiments a magnetic particle is coated to facilitate electrostatic asso-ciation with molecules. In some embodiments magnetic particles comprises different shapes, sizes and/or diameters to facilitate different amounts of magnetism. In some embodiments, magnetic particles are substantially uniform (e.g., all are substantially the same; e.g., same size, same diameter, same shape and/or same magnetic properties) to facilitate more accurate detections and/or quantitation at the surface of the magnetic sensor. In some embodiments, magnetic beads comprise the same or different members of a binding pair to allow multiplex detection of multiple analytes, such as one or more heavy metals, in the same query sample or in different query samples. In some embodi-ments, magnetic particles comprising different members of a binding pair are configured to interact with different MRPs disposed on different GMR sensors or on a single sensor in which different MRPs are spatially organized to create addressable locations and signals. In some embodiments, the presence, absence and/or amount of magnetic particles can be detected and/or quantitated by a suitable magnetic sensor. In some embodiments, a magnetic sensor comprises a sur-face.

In some embodiments a nucleic acid, a substrate, a particle (e.g., a magnetic particle), a secondary reagent, a bead, a protein, an antibody, a surface, and/or an MPR comprises one or more members of a binding pair. In certain embodiments, a first member of a binding pair can bind, and/or binds to, a second member of a binding pair. In certain embodiments, a first member of a binding pair is configured to bind specifically to a second member of a binding pair. In some embodiments a binding pair comprises at least two members (e.g., molecules) that bind non-covalently and specifically to each other. Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair (e.g., first member/second member) include antibody/antigen, antibody/antibody receptor, antibody/pro-tein A or protein G, antibody/GST, hapten/anti-hapten, sulf-hydryl/maleimide, sulfhydryl/haloacetyl derivative, amine/isotriocyanate, amine/succinimidyl ester, amine/sulfonyl halides, biotin/avidin, biotin/streptavidin, folic acid/folate binding protein, receptor/ligand, GST/GT, vitamin B12/intrinsic factor, analogues thereof, derivatives thereof, bind-ing portions thereof, the like or combinations thereof. Non-limiting examples of a member of a binding pair include an antibody or antibody fragment, antibody receptor, an anti-gen, hapten, a peptide, protein, a fatty acid, a glyceryl moiety (e.g., a lipid), a phosphoryl moiety, a glycosyl moiety, a ubiquitin moiety, lectin, aptamer, receptor, ligand, heavy metal ion, avidin, neutravidin, streptavidin, biotin, B12, intrinsic factor, analogues thereof, derivatives thereof, binding portions thereof, the like or combinations thereof. In some embodiments, a MRP is covalently attached to member of a binding pair.

Figure 30:
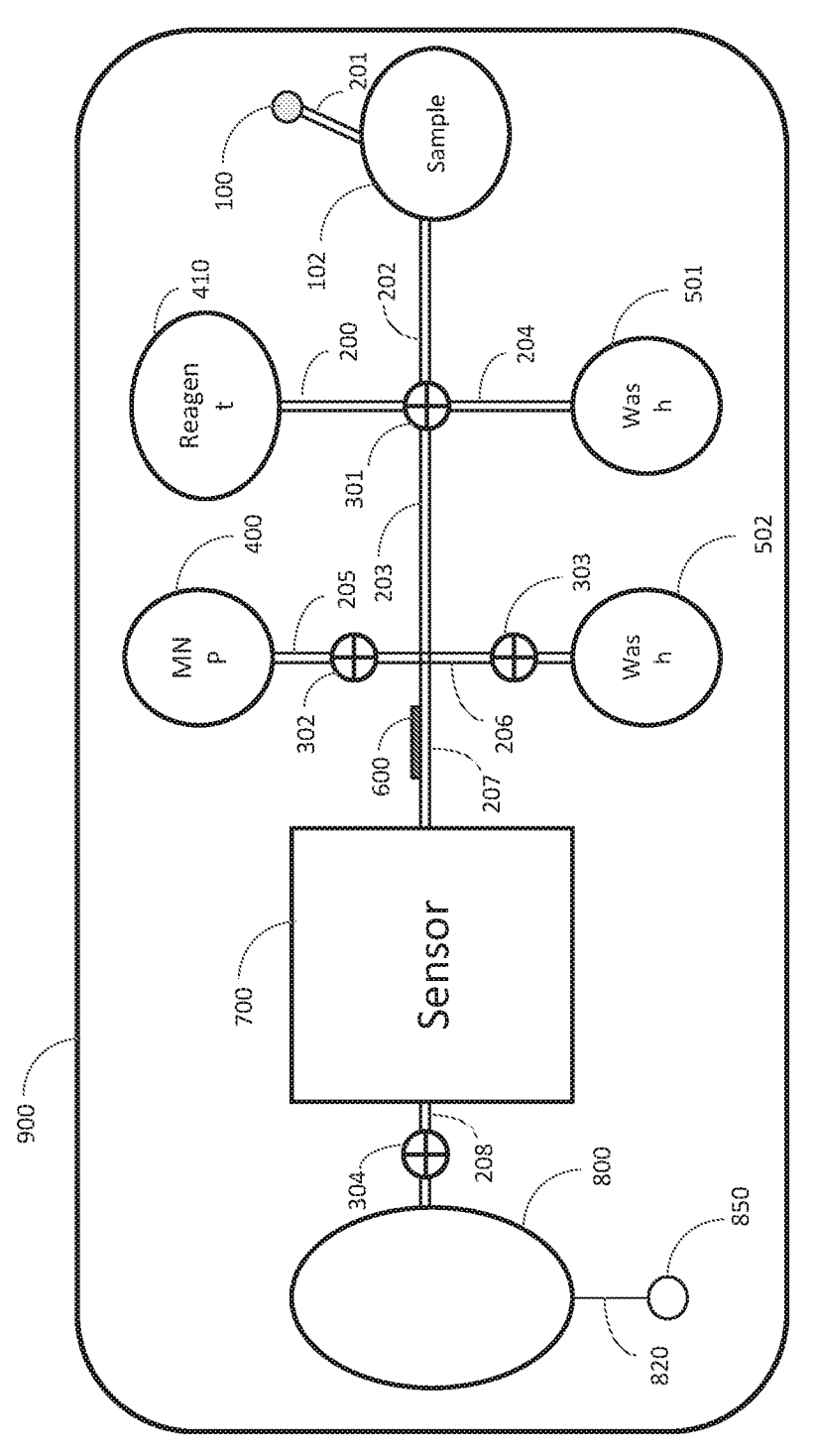
FIG. 30 shows an example of a microfluidic device 900 configured to detect a heavy metal in a sample, in accordance with an embodiment of the present teaching.

In some embodiments, a method comprises the use of a secondary reagent. In some embodiments, a device comprises one or more secondary reagents. In certain embodiments, a secondary reagent is used to bind a first molecule and a second molecule thereby indirectly attaching the first molecule to the second molecule. Accordingly, a secondary reagent often comprises at least two members of a binding pair. In some embodiments, a secondary reagent comprises two members of a binding pair, each of which are different, and where each of the two members of the binding pair do not bind to each other. For example, a secondary reagent may comprise a bead or particle comprising a member of a first binding pair (e.g., glutathione, which is configured to bind to GST), and a member of a second binding pair (e.g., biotin, which is configured to bind to streptavidin). In yet another example, a secondary reagent may comprise an antibody (i.e., a member of a first binding pair. e.g., an antibody configured to bind to GST), and a member of a second binding pair (e.g., biotin, which is configured to bind to streptavidin). A secondary reagent may comprise any suitable member of a binding pair. In some embodiments, a secondary reagent comprises a suitable substrate (e.g., a bead or particle). In some embodiments, a secondary reagent comprises a suitable substrate (e.g., a bead or particle), a member of a first binding pair and a member of a second binding pair Metalloregulatory Protein-Based Devices Presented herein, in some embodiments, is a microfluidic device configured to detect a heavy metal in a sample using devices that employ metalloregulatory protein binding sites, such as repressor protein binding sites. In some embodiments, the device comprises one or more components shown in FIG. 30. In some embodiments, a device comprises a configuration, or a variation thereof, as shown in FIG. 30. In some embodiments, a device comprises one or more microfluidic channels that are operably and/or fluidically connected to each of the components of the device.

Components or parts that are "fluidically connected" are components and parts of a device that are in contact with and/or can be contacted with (e.g., by opening or closing a valve) a liquid or fluid disposed within the device. A well of a 96-well plate is not considered to be fluidically connected to another well in a 96-well plate. Similarly, an Eppendorf tube is not fluidically connected to another Eppendorf tube even when fluid can be transferred from one tube to another. The term "operably connected" means that the particular components or parts of the device can communicate, are attached, or are connected in such a way that they cooperate to achieve their intended function or functions. An operable "connection" may be direct, indirect, physical, or remote.

In some embodiments, a microfluidic device (e.g., 900) comprises one or more components selected from a microfluidic channel (e.g., 200-208), a chamber (e.g., 102, 400, 410, 501, 502, & 800), one or more valves (e.g., 301-304), a magnetic sensor (e.g., 700), lyophilized reagents, solubilized reagents, a heating source (e.g., 600), a pump, and a port (e.g., a flow control port 850, a sample loading port 100). In some embodiments, some or all of the components of the device are operably and/or fluidically connected (e.g., by associated microfluidic channels and valves). In some embodiments, a device comprises one or more chambers selected from a sample chamber (e.g., 102), wash chamber (e.g., 501 and 502), reagents chambers (e.g., 400, 410), waste chamber (e.g., 800), or combinations thereof.

In some embodiments, a microfluidic device comprises one or more microfluidic channels (e.g., 201-208). A microfluidic channel may comprise a suitable geometry in cross-section non-limiting examples of which include circular, oval, rectangular, triangular, the like or combinations thereof. A microfluidic channel may comprise a suitable structure non-liming examples of which include straight, curved, serpentine, and/or elevated, and may include one or more junctions that fluidically connect one or more microfluidic channels and associated components of a microfluidic device described herein. In some embodiments, a microfluidic channel has an average, mean or absolute inside diameter of about 10 nanometers to 1000 micrometers, 50 nanometers to 500 micrometers, 100 nanometers to 500 micrometers, or 100 nanometers to 100 micrometers. In some embodiments, one or more of a valve (e.g., 301-304), chamber, and/or sensor 700 are disposed within a channel body of a microfluidic channel. In some embodiments, a magnetic sensor 700 is disposed within a chamber that is operably and/or fluidically connected to one or more microfluidic channels. In some embodiments, a microfluidic channel comprises a sample port 100 for introduction of a sample, or one or more reagents, into a microfluidic device. In some embodiments, a sample port is operably and/or fluidically connected to a sample chamber (e.g., 102) by a microfluidic channel (e.g., 201).

In some embodiments, a microfluidic device comprises a sample chamber and a magnetic sensor that are operably and/or fluidically connected by one or more microfluidic channels and valves such that a direction of flow of a fluid disposed within the device is generally in a direction from the sample chamber toward the sensor, and/or towards a waste chamber (e.g., 800). Accordingly, for reference, a first component that is proximal to second component, is a component this is upstream of the second component with reference to the direction of flow toward the sensor. Similarly, a first component that is distal to a second component is a component this is downstream of the second component with reference to the direction of flow toward the sensor or waste chamber (e.g., 800) In some embodiments, a direction of flow through a microfluidic device is controlled in part by one or more of a vacuum pump or syringe pump that is operably connected to a port (e.g., flow control port 850). In some embodiments, a pump is disposed on a microfluidic device 900. In some embodiments, one or more pumps can be operably connected to device 900 by a port (e.g., 850), for example when the microfluidic device is in the form of a removable cartridge. In some embodiments a flow control port is operably connected to a chamber (e.g., waste chamber 800) such that when a negative pressure is applied to port 850, fluid is directed (e.g., by one or more valves) from one or more chambers (e.g., 102, 501, 502, and/or 400/410) to sensor 700 and/or to waste chamber 800, such that a flow of fluid can be regulated and/or maintained across a surface of the sensor (e.g., 700). In some embodiments a flow control port is operably connected to a chamber by a microfluidic channel (e.g., 820).

Any suitable valve can be used for a microfluidic device. In some embodiments, a valve is a miniature piloting solenoid valve (e.g., a Lee valves) that can be controlled off-card. Accordingly, a device may comprise a plurality of valves, each of which can be controlled independently. In some embodiments, one or more valves are operably connected to one or more electrical pad connections, so that a microfluidic device can be integrated with a controller or computer that directs flow of fluid through the device.

In some embodiments, a chamber is a sample chamber (e.g., 102). In some embodiments, a sample chamber comprises a sample or is configured to contain a sample. In some embodiments, a sample chamber comprises one or more reagents (e.g., dehydrated salts or buffers). In some embodiments, a microfluidic device comprises a sample port configured for introduction of a sample into the device. In certain embodiments, a sample port is operably connected and/or fluidically connected to one or more chambers. In some embodiments, a device comprises a sample port 100 and a sample chamber 102, where the sample port is proximal to the sample chamber. In some embodiments, a sample port 100 is configured for introduction of a sample into the sample chamber 102. In some embodiments, a sample port is located proximal to a sample chamber. In some embodiments, a sample port is a sample injection port.

In some embodiments, a chamber is a wash chamber (e.g., 510, 502). A wash chamber is configured to contain a suitable wash solution. In some embodiments, a wash solution is disposed within a wash chamber. A wash solution is often used to hydrate or wash a surface of a magnetic sensor (e.g., 700). In some embodiments, a wash solution comprises a buffer (e.g., Tris), an alcohol, a detergent, or a salt. In some embodiments a wash chamber provides a solution (e.g., a buffer) that helps maintain flow of fluid over the surface of the sensor, for example during detection. A wash solution may comprise any suitable buffer. In some embodiments, a buffer comprises HEPES (4-(2-hydroxyethyl)-1-piperazineethanesulfonic acid). For example, a solution disposed within chamber 501 can be diverted by valve 301 to microfluidic channels 203 and 207, such that fluid flows over sensor 700 and into waste chamber 800.

In some embodiments, a sample chamber (e.g., 102), a reagent chamber (e.g., 400/410) and/or one or more wash chambers (e.g., 501, 502) are located proximal to a magnetic sensor (e.g., 700). In some embodiments, a sample chamber (e.g., 102) and/or one or more wash chambers (e.g., 501, 502) are operably and/or fluidically connected, in parallel to a microfluidic channel (e.g., 202, 203, 207), where the microfluidic channel comprises one or more valves (e.g., 301, 302, 303) operably connected to the one or more chambers.

In certain embodiments, reagents are disposed within a reagent chamber (e.g., 400 or 410). Reagents disposed within a reagent chamber may be dried and/or lyophilized. In some embodiments, reagents disposed within a reagent chamber are solubilized or dispersed in a liquid (e.g., a wash solution). In certain embodiments, dried or lyophilized reagents located within a reagent chamber are substantially solubilized when contacted with a fluid when a fluid enters a reagent chamber. In some embodiments, a reagent chamber (e.g., 400/410) is located proximal to a magnetic sensor. In certain embodiment, a reagent chamber (e.g., 400) comprises magnetic particles (MNP), where each of the particles are attached to a member of a binding pair (e.g., streptavidin). In certain embodiment, a reagent chamber (e.g., 410) comprises a secondary reagent), where each secondary reagent is attached to one or more members of a binding pair (e.g., an antibody and/or biotin or streptavidin). In some embodiments, a reagent chamber is operably and/or fluidically connected to a valve (e.g., 301 or 302) that when open, disperses reagents or particles into a microfluidic channel (e.g., 207) such the particles proceed to contact and/or flow over a magnetic sensor 700.

In certain embodiments, a microfluidic device comprises a heating source (e.g., 600). Any suitable heating source can be used in a device described herein. In some embodiments, a magnetic sensor comprises a heating source. In some embodiments, a heating source is located proximal to a magnetic sensor, such that a temperature of a fluid flowing over a magnetic sensor can be heated.

In some embodiments, a microfluidic device comprises a magnetic sensor (e.g., 700). In some embodiments, a microfluidic device comprises a plurality of magnetic sensors (e.g., GMRs). In some embodiments, a microfluidic device comprises a first magnetic sensor that is for contacting with a sample, and a second "control" magnetic sensor that is not contacted with a sample. A control sensor is often for establishing a baseline of magnetoresistance for a magnetic sensor that is not contacted with a sample or a heavy metal. For example, a device may comprise duplicate sensors, wherein one sensor is contacted with a sample suspected of containing a heavy metal, and the other sensor is not contacted with the sample. The magnetoresistance at the surface of each of the two sensors can be compared to determine a presence, absence or amount of a heavy metal in the sample. In some embodiments, a microfluidic device comprises an array of sensors with addressable locations. In some embodiments a magnetic sensor is a magnetoresistance sensor. In some embodiments a magnetic sensor is a giant magnetoresistance (GMR) sensor. In some embodiments a magnetic sensor is an anisotropic magnetoresistance (AMR) sensor and/or a magnetic tunnel junction (MTJ) sensor.

In some embodiments, a magnetic sensor detects magnetoresistance, current and/or voltage potential, or changes thereof, at a surface of the sensor. In some embodiments, a circuit detects current and/or voltage, or changes thereof due to magnetoresistance changes of the sensor. In some embodiments, the circuit detects current and/or voltage, or changes thereof over a period of time non-limiting examples of which include 1 nanosecond to 1 hour, 1 second to 60 minutes, 1 second to 10 minutes, 1 second to 1000 seconds or intervening periods thereof. In some embodiments, a magnetic sensor detects the presence, absence or amount of magnetic particles that are bound to (e.g., indirectly bound to) or associated with a surface of the magnetic sensor according to a current and/or voltage, or changes thereof, that are detected by the magnetic sensor. In some embodiments, a magnetic sensor detects the presence, absence or amount of a heavy metal present in a sample according to a presence, absence or amount of magnetic particles that are bound to (e.g., indirectly bound to) or associated with a surface of the magnetic sensor. Accordingly, in some embodiments, a magnetic sensor detects the presence, absence or amount of a heavy metal present in a sample according to a current and/or voltage, or changes thereof, that are detected or measured due to magnetic particles on the surface of the magnetic sensor.

GMR sensors can have sensitivities that exceed those of anisotropic magnetoresistance (AMR) or Hall sensors. This characteristic enables detection of stray fields from magnetic materials at nanometer scales. For example, stray fields from magnetic nanoparticles that are bound on a magnetic surface will alter the magnetization in the magnetic layers, and thus change the magnetoresistance of a GMR sensor. Accordingly, changes in the amount of magnetic nanoparticles bound to a GMR sensor per unit area can be reflected in changes of the magnetoresistance value of a GMR sensor. Accordingly, in some embodiments, a magnetic sensor comprises a GMR sensor.

In some embodiments, a magnetic sensor comprises a surface A surface of a magnetic sensor may comprise a suitable material, non-limiting examples of which include glass, modified or functionalized glass (e.g., controlled-pore glass (CPG)), quartz, mica, polyformaldehyde, cellulose, cellulose acetate, ceramics, heavy metals, heavy metalloids, semi-conductive materials, plastic (including acrylics, polystyrene, copolymers of styrene or other materials, polybutylene, polyurethanes, TEFLON™, polyethylene, polypropylene, polyamide, polyester, polyvinylidenedifluoride (PVDF), and the like), resins, silica or silica-based materials including silicon, silica gel, and modified silicon, Sephadex®, SEPHAROSE®, carbon, heavy metals (e.g., steel, gold, silver, aluminum, silicon and copper), conducting polymers (including polymers such as polypyrrole and polyindole), micro or nanostructured surfaces, nanotube, nanowire, or nanoparticulate decorated surfaces; or porous surfaces or gels such as methacrylates, acrylamides, sugar polymers, cellulose, silicates, or other fibrous or stranded polymers. In some embodiments, a surface is coated using passive or chemically-derivatized coatings with any number of materials, including polymers, such as dextrans, acrylamides, gelatins or agarose. In some embodiments a surface of a magnetic sensor is non-covalently and/or reversibly attached to an oligonucleotide.

In some embodiments, a surface of a magnetic sensor comprises and/or is coated with a crosslinked PEG-PHEMA polymer. A PEG-PHEMA polymer surface can be prepared by mixing a PEG solution comprising N-Hydroxysuccinimide(NHS)-PEG-NHS (MW 600) dissolved in a suitable solvent (e.g., isopropyl alcohol, acetone or methanol, and/or water), a PHEMA solution comprising polyhydroxyethyl methacrylate (MW 20,000) dissolved in a suitable solvent (e.g., isopropyl alcohol, acetone or methanol, and/or water), and an optional crosslinker. The resulting solution can be coated on a magnetic surface using a suitable coating process (e.g., micro-printing, dip coating, spin coating or aerosol coating). After coating a surface with the PEG-PHEMA solution, the surface can be cured using UV light followed by washing with a suitable solvent, such as isopropyl alcohol and/or water. In some embodiments a surface of a magnetic sensor is covalently attached to one or more nucleic acids. In some embodiments, the coated surface can be used to bind with primary amines (e.g., to attach a protein). A PEG-PHEMA coating can protect a magnetic sensor surface against corrosion. In some embodiments, a surface of a magnetic sensor comprises a surface described in International Patent Application No. PCT/US2019/043766.

In some embodiments, a surface of a magnetic sensor comprises a coating. In some embodiments a coating comprises a suitable surfactant. In some embodiments, a surfactant comprises cetyl trimethylammonium bromide (CTAB). In some embodiments, a surface of a magnetic sensor is coated with, or contacted with a suitable surfactant prior to contacting a magnetic sensor with a sample.

In some embodiments, a magnetic sensor or surface of a magnetic sensor comprises a nucleic acid. In some embodiments, a magnetic sensor or surface of a magnetic sensor comprises a doubled stranded nucleic acid (e.g., a DNA duplex). In some embodiments, a magnetic sensor or surface of a magnetic sensor comprises a nucleic acid comprising one or more repressor binding sites for an MRP. In some embodiments, a nucleic acid is attached non-covalently to a surface of a magnetic sensor. In some embodiments, a nucleic acid is attached covalently to a surface of a magnetic sensor using a suitable chemistry, non-limiting examples of which include a chemistry described in Cha et al. (2004) "Immobilization of oriented protein molecules on poly(ethylene glycol)-coated Si(111)" *Proteomics* 4:1965-1976 and Zellander et al. (2014) "Characterization of Pore Structure in Biologically Functional Poly(2-hydroxyethyl methacrylate)-Poly(ethylene glycol) Diacrylate (PHEMA-PEGDA)," *PLOS ONE* 9(5):e96709. In some embodiments, a surface of a magnetic sensor comprises a plurality of nucleic acids (e.g., nucleic acids comprising a repressor binding site) at a density of about $1\times10^9$ to about $5\times10^{10}$ nucleic acid molecules per/mm$^2$. In some embodiments, a magnetic sensor or surface of a magnetic sensor comprises a nucleic acid comprising a repressor binding site and an MRP In some embodiments, a magnetic sensor or surface of a magnetic sensor comprises a plurality of nucleic acids each comprising a repressor binding site and each attached to an MRP. In some embodiments, a magnetic sensor or surface of a magnetic sensor comprises a plurality of nucleic acids each comprising a repressor binding site and a plurality of MRPs, where the MRPs are bound to the nucleic acids.

In some embodiments, a magnetic sensor or surface of a magnetic sensor comprises a plurality of nucleic acids each comprising a binding site for an arsenical resistance operon repressor (arsR). In some embodiments, a magnetic sensor or surface of a magnetic sensor comprises a plurality of nucleic acids each comprising a binding site for an arsR, and a plurality of arsR proteins. In some embodiments, a magnetic sensor or surface of a magnetic sensor comprises a plurality of nucleic acids each comprising a binding site for an arsR, and a plurality of arsR proteins, each bound to a repressor binding site of the nucleic acids. In some embodiments, a magnetic sensor or surface of a magnetic sensor comprises a nucleic acid attached to the sensor or sensor surface, and an arsR, where (i) the nucleic acid comprises a repressor binding site for the arsR, and (ii) the arsR is bound to the repressor binding site of the nucleic acid. In some embodiments, a magnetic sensor or surface of a magnetic sensor comprises a double stranded nucleic acid duplex attached to the sensor or sensor surface, and an arsR, wherein (i) the duplex comprises a repressor binding site for the arsR, and (ii) the arsR is bound to the repressor binding site. In some embodiments, a magnetic sensor or surface of a magnetic sensor comprises a nucleic acid attached to the sensor or sensor surface, and an arsR, wherein (i) the nucleic acid comprises a repressor binding site for the arsR, (ii) the arsR is bound to the repressor binding site, and (iii) the arsR comprises a member of a binding pair or a magnetic particle.

In some embodiments, a magnetic sensor or surface of a magnetic sensor comprises a plurality of nucleic acids each comprising a binding site for a cadmium resistance operon repressor (cadC). In some embodiments, a magnetic sensor or surface of a magnetic sensor comprises a plurality of nucleic acids each comprising a binding site for a cadC, and a plurality of cadC proteins. In some embodiments, a magnetic sensor or surface of a magnetic sensor comprises a plurality of nucleic acids each comprising a binding site for a cadC, and a plurality of cadC proteins, each bound to a repressor binding site of the nucleic acids. In some embodiments, a magnetic sensor or surface of a magnetic sensor comprises a nucleic acid attached to the sensor or sensor surface, and a cadC, where (i) the nucleic acid comprises a repressor binding site for the cadC, and (ii) the cadC is bound to the repressor binding site of the nucleic acid. In some embodiments, a magnetic sensor or surface of a magnetic sensor comprises a double stranded nucleic acid duplex attached to the sensor or sensor surface, and a cadC, wherein (i) the duplex comprises a repressor binding site for the cadC, and (ii) the cadC is bound to the repressor binding site. In some embodiments, a magnetic sensor or surface of a magnetic sensor comprises a nucleic acid attached to the sensor or sensor surface, and a cadC, wherein (i) the nucleic acid comprises a repressor binding site for the cadC, (ii) the cadC is bound to the repressor binding site, and (iii) the cadC comprises a member of a binding pair or a magnetic particle.

In some embodiments a device comprises two or more magnetic sensors, each comprising a surface comprising the same nucleic acid comprising the same MRP binding site and/or the same MRP. For example, in some embodiments a device comprises a first magnetic sensor configured to contact a sample and a second control magnetic sensor that does not contact a sample, where the first and the second sensors comprise the same nucleic acid comprising the same MRP binding site and/or the same MRP. In some embodiments a device comprises two or more magnetic sensors, each comprising a surface comprising a different nucleic acid comprising a different MRP binding site and/or a different MRP. In some embodiments, a surface of a magnetic sensor comprises a plurality of addressable locations, each comprising a different nucleic acid comprising a different MRP binding site and/or a different MRP.

In some embodiments, a microfluidic device comprises a negative control sensor. In certain embodiments, a negative control sensor is a magnetic sensor (e.g., a GMR). In some embodiments of a method described herein, a negative control sensor is not contacted with a sample. In some embodiments of a method described herein, a negative control sensor is contacted with a suitable control solution, wash buffer or control buffer.

In certain embodiments, a microfluidic device 900 is disposed on a card or cartridge. Accordingly, in some embodiments, a microfluidic device, or a card or cartridge comprising a microfluidic device described herein has a length of 3 to 10 cm, a width of 1 to 10 cm, and a thickness of 0.1 to 1 cm.

In some embodiments, a microfluidic device comprises a printed circuit board (PSB). In some embodiments, a microfluidic device or a PSB comprises one or more memory chips. In some embodiments a microfluidic device or a PSB comprises one or more electrical pad connections. In some embodiments the one or more electrical pad connections are operably (e.g., electronically) connected to a memory chip, one or more valves, a magnetic sensor and/or one or more pumps of a microfluidic device. In some embodiments one or more components of a microfluidic device are disposed on a PSB.

In some embodiments, a microfluidic device is disposed on a cartridge or card that comprises a PSB. In some embodiments, a cartridge is configured for insertion or attachment to a controller, a computer, or larger device that integrates with a microfluidic device. In some embodiments a controller comprises pumps (e.g., diaphragm or syringe type pumps) that operably connect to one or more flow control ports 850 located on a cartridge. In some embodiments, one or more components of a microfluidic device are disposed on a substrate comprising a polymer plastic. In some embodiments, one or more components of a microfluidic device are disposed on a substantially flat substrate comprising a polymer plastic.

In some embodiments, a microfluidic device, PSB or cartridge described herein comprises one or more components, subcomponents or parts described in International Patent Application No. PCT/US2019/043720, entitled "SYSTEM AND METHOD FOR GMR-BASED DETECTION OF BIOMARKERS" filed Jul. 26, 2019, International Patent Application No. PCT/US2019/043753, entitled "SYSTEM AND METHOD FOR SAMPLE PREPARATION IN GMR-BASED DETECTION OF BIOMARK- ERS" filed Jul. 26, 2019, International Patent Application No. PCT/US2019/043766, entitled "SYSTEM AND METHOD FOR SENSING ANALYTES IN GMR-BASED DETECTION OF BIOMARKERS" filed Jul. 26, 2019 or, International Patent Application No. PCT/US2019/043791, entitled "SYSTEM AND METHOD FOR PROCESSING ANALYTE SIGNALS IN GMR-BASED DETECTION OF BIOMARKERS" filed Jul. 26, 2019, all of which are hereby incorporated by reference herein in their entirety. In some embodiments, a method described herein utilizes one or more components, subcomponents or parts described in International Patent Application No. PCT/US2019/043720, PCT/US2019/043753, PCT/US2019/043766, or PCT/US2019/043791. In some embodiments, a microfluidic device described herein comprises a magnetic sensor and/or magnetic sensor assembly described in International Patent Application No. PCT/US2019/043720, PCT/US2019/043753, PCT/US2019/043766, or PCT/US2019/043791.

In some embodiments, any one chamber (e.g., 102, 501, 502, 400, 410, 800) and/or a chamber housing a magnetic sensor comprises a volume independently selected from 1 µl to 20 ml, 1 µl to 15 ml, 1 µl to 5 ml, 1 µl to 1 ml, 1 µl to 500 µl, 1 µl to 100 µl, and intermediate volumes thereof.

GMR sensors have sensitivities that exceed those of anisotropic magnetoresistance (AMR) or Hall sensors. This characteristic enables detection of stray fields from magnetic materials at nanometer scales. For example, stray fields from magnetic nanoparticles that bound on sensor surface will alter the magnetization in the magnetic layers, and thus change the magnetoresistance of the GMR sensor. Accordingly, changes in the number of magnetic nanoparticles bound to the GMR sensor per unit area can be reflected in changes of the magnetoresistance value of the GMR sensor.

Methods

Presented herein, in certain embodiments, is a method of detecting the presence, absence, or amount of a heavy metal (e.g., arsenic and/or cadmium) in a sample (e.g., a liquid sample). In some embodiments, a method comprises contacting a magnetic sensor comprising a surface, and a nucleic acid and/or an MPR attached to the surface, with a sample suspected of comprising a heavy metal. In some embodiments, a surface of a magnetic sensor is contacted with a detergent or a surfactant (e.g., CTAB) prior to contacting the sensor with the sample. In some embodiments, MPR comprises magnetic particles or a first member of a binding pair (e.g., biotin). In some embodiments when an MRP comprises a first member of a binding pair (e.g., biotin), a method comprises contacting the sensor or MRP with a magnetic particles comprising a second member of the binding pair (e.g., streptavidin), such that the first member of the binding pair binds to the second member of the binding pair. In some embodiments, the presence, absence or amount of magnetic particles that are at, on, near or associated with (e.g., indirectly by non-covalent interactions) a magnetic sensor are detected by a method herein. The detecting is sometimes performed after a sample is contacted with a magnetic sensor. In certain embodiments, the detecting is performed before, during and/or after contacting a magnetic sensor with a sample or with magnetic particles. In some embodiments, a detecting process is a dynamic detection process such that one or more magnetic particles can be detected before, during and/or after contacting a magnetic sensor with a sample while changing one or more conditions at the surface of the sensor.

Figure 28:
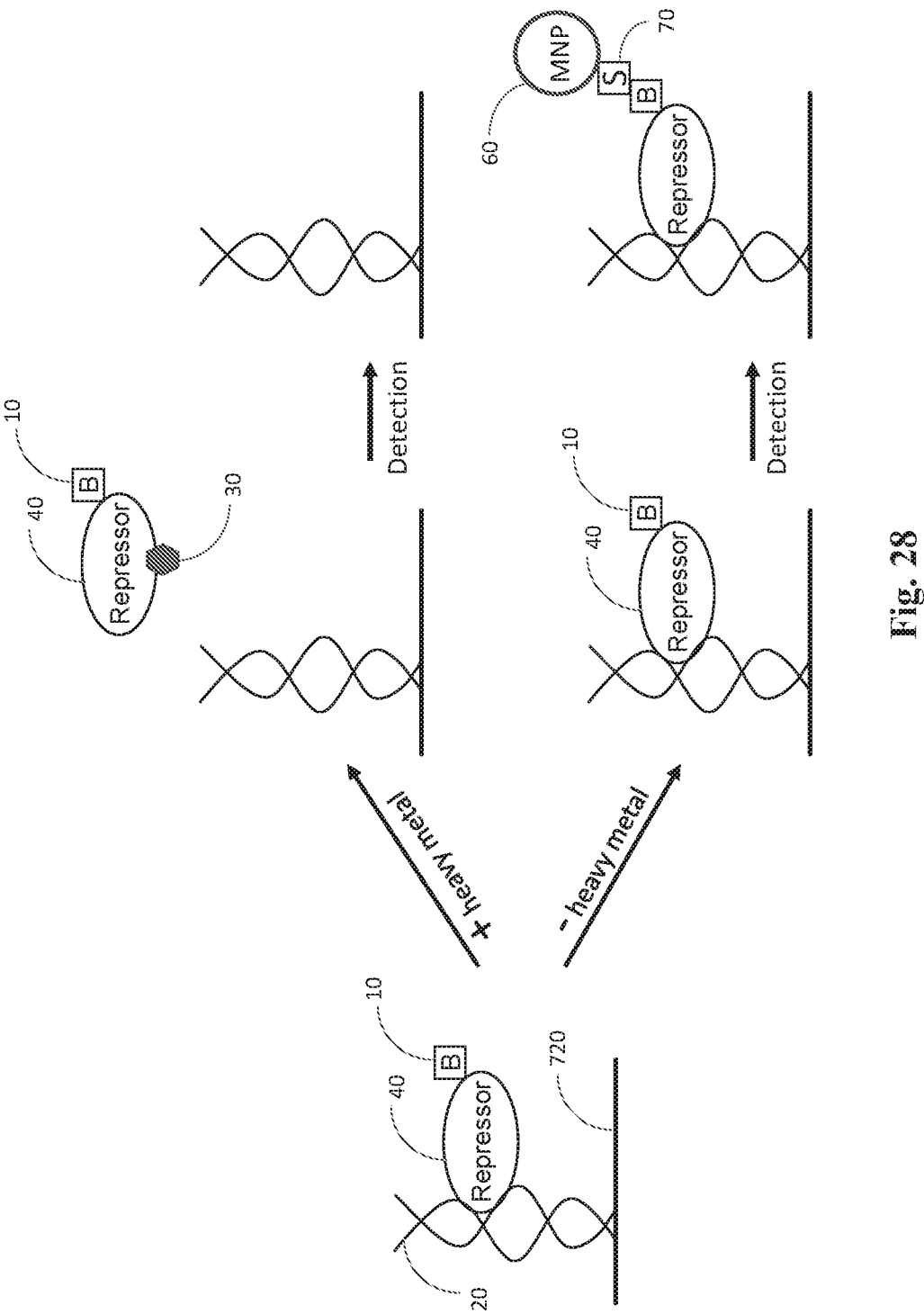
FIG. 28 shows an illustration of an exemplary detection method using a surface-bound nucleic acid duplex 20 comprising a metalloregulatory repressor protein 40, in accordance with an embodiment of the present teaching.

FIG. 28 shows an embodiment of an exemplary detection method using a surface-bound nucleic acid duplex 20 comprising a metalloregulatory repressor protein 40. The nucleic acid duplex is attached to the surface of a magnetic sensor 720. In this example, the nucleic acid duplex comprises a first nucleic acid strand and a second nucleic acid strand, which are hybridized together to form the nucleic acid duplex. The nucleic acid duplex also comprises a repressor binding site. In the absence of a heavy metal 30, the metalloregulatory repressor protein 40 binds to the repressor binding site of the nucleic acid duplex. In some embodiments, the metalloregulatory repressor protein 40 comprises a first member of a binding pair 10 which in this example is biotin (B). In the upper right scenario, the sensor is contacted with a sample comprising a heavy metal 30. Upon binding to the heavy metal 30, the metalloregulatory repressor protein 40 dissociates from the nucleic acid duplex 20 and is washed away from the surface of the sensor 720. In the lower right scenario, the sensor is contacted with a sample that does not contain a heavy metal. In this scenario, the metalloregulatory repressor protein remains bound to the nucleic acid duplex. After contacting the sensor with a sample, the sensor is contacted with a magnetic particle 60 comprising a second member of a binding pair 70, which in this example is streptavidin (S). The streptavidin of the magnetic particle binds tightly to the biotin of the metalloregulatory repressor protein, when present. The presence, absence or amount of the magnetic particles that are associated with the surface of the sensor can then be detected by measuring magnetoresistance, or a change thereof, due to magnetic particles on the surface of the magnetic sensor. Accordingly, the presence, absence or amount of arsenic or cadmium in a sample can be determined by detecting the presence, absence or amount of magnetic particles associated with the surface of the sensor.

Figure 29:
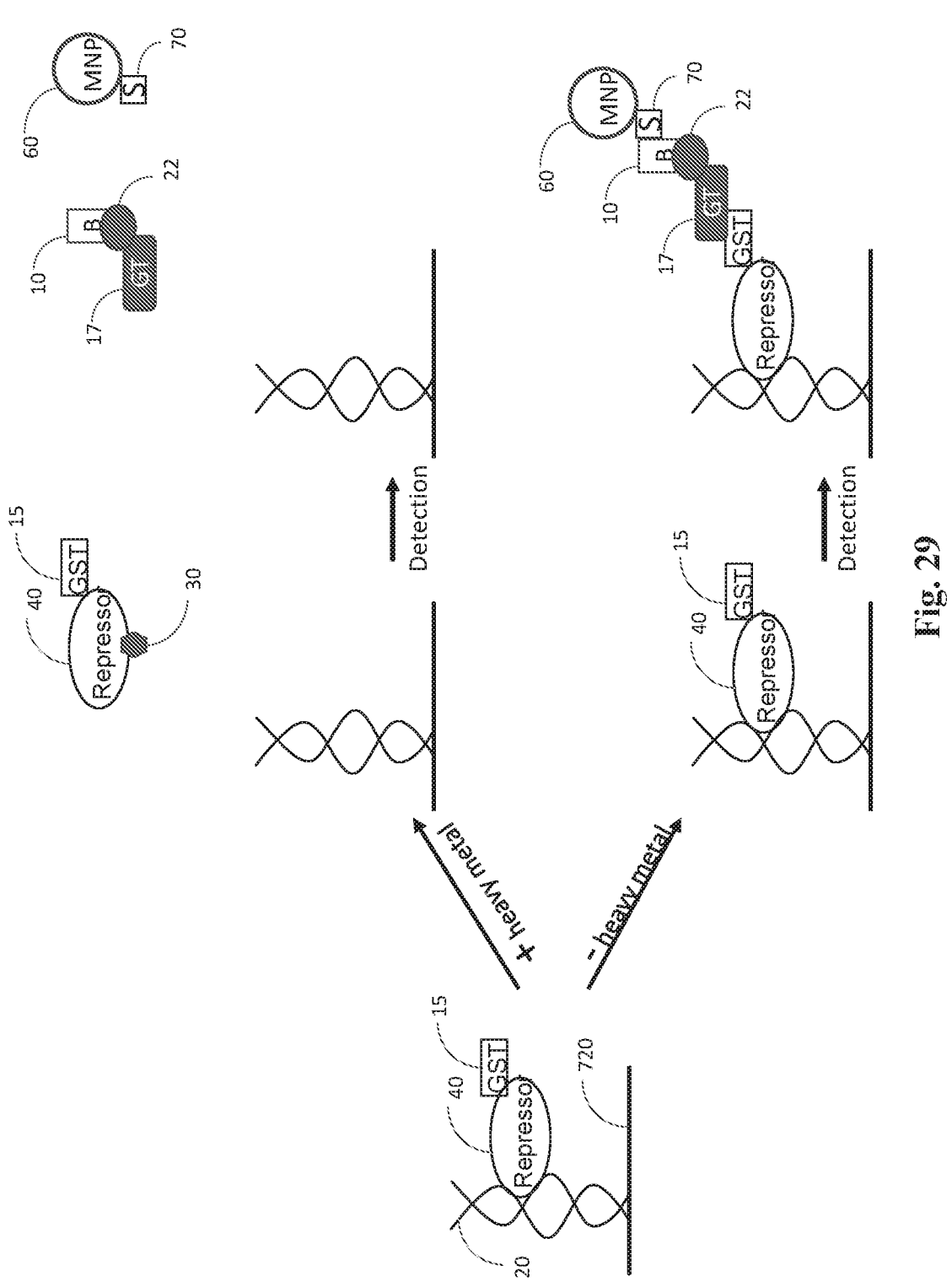
FIG. 29 shows an illustration of another embodiment of a detection method using a surface-bound nucleic acid duplex 20, comprising a metalloregulatory repressor protein 40, in accordance with an embodiment of the present teaching.

FIG. 29 shows another embodiment of an exemplary detection method using a surface-bound nucleic acid duplex 20 comprising a metalloregulatory repressor protein 40. The nucleic acid duplex is attached to the surface of a magnetic sensor 720. In this example, the nucleic acid duplex comprises a first nucleic acid strand and a second nucleic acid strand, which are hybridized together to form the nucleic acid duplex. The nucleic acid duplex also comprises a repressor binding site. In the absence of a heavy metal 30, the metalloregulatory repressor protein 40 binds to the repressor binding site of the nucleic acid duplex. In this embodiment, the metalloregulatory repressor protein 40 comprises a first member of a binding pair 15 which in this example is glutathione S-transferase (GST). In the upper right scenario of FIG. 28, the sensor is contacted with a sample comprising a heavy metal 30. Upon binding to the heavy metal 30, the metalloregulatory repressor protein 40 dissociates from the nucleic acid duplex 20 and is washed away from the surface of the sensor 720. In the lower right scenario of FIG. 28, the sensor is contacted with a sample that does not contain a heavy metal. In this scenario, the metalloregulatory repressor protein remains bound to the nucleic acid duplex. After contacting the sensor with a sample, the sensor is contacted with a secondary reagent 22 which in this embodiment is a bead comprising a second member of a binding pair 17 (e.g., glutathione (GT)), which binds tightly to GST when present. The secondary reagent also comprises a first member of a second binding pair 10 (e.g., biotin (B)). After contacting the sensor with a sample, and the secondary reagent, the sensor is contacted with a magnetic particle 60 comprising a second member of the second binding pair 70, which in this example is streptavidin (S). The streptavidin of the magnetic particle binds tightly to the biotin of the secondary reagent, when present. The presence, absence or amount of the magnetic particles that are associated with the surface of the sensor can then be detected by measuring magnetoresistance, or a change thereof, at the surface of the magnetic sensor. Accordingly, the presence, absence or amount of arsenic or cadmium in a sample can be determined by detecting the presence, absence or amount of magnetic particles associated with the surface of the sensor.

In some embodiments, a MRP comprises a first member of a first binding pair (e.g., GST) and a method comprises contacting the MRP (e.g., a surface of a magnetic sensor comprising the MRP) with a secondary reagent and magnetic particles where the secondary reagent comprises a second member of the first binding pair (e.g., an antibody that binds GST) and a first member of a second binding pair (e.g., biotin), and the magnetic particles comprise a second member of the second binding pair (e.g., streptavidin).

In some embodiments, a process of contacting a magnetic sensor with a sample and/or magnetic particles comprises flowing a fluid across the surface of the sensor. Non-limiting examples of a fluid include a liquid sample, a wash solution, a buffer solution, water, a solution comprising magnetic particles, a solution comprising a suitable reagent, a solution comprising a MRP, the like, combinations thereof or mixtures thereof. In some embodiments, a magnetic sensor or surface thereof is continually and/or continuously in contact with a fluid (e.g., a sample, wash solution, buffer, magnetic particles and the like) when conducting a method herein. In certain embodiments, a flow rate over the surface of a magnetic sensor during a contacting, washing or detecting process is about 0.1 μl/minute to 500 μl/minute, 1 μl/minute to 500 μl/minute, 1 μl/minute to 100 μl/minute, 1 μl/minute to 10 μl/minute, or intervening ranges therein. In certain embodiments, a flow rate over the surface of a magnetic sensor during a contacting, washing or detecting process is about 100 Hz to 800 Hz, or about 100 Hz to 300 Hz.

In some embodiments, a volume of a sample that is contacted with a magnetic sensor is a volume in a range of 1 μl to 500 μl, 20 μl to 300 μl, or intervening ranges or volumes thereof.

In some embodiments, a sensitivity range of the detection of a heavy metal by a method herein is in a range from about 0.00001 nanomolar to about 100 nanomolar, 0.01 nanomolar to about 10 nanomolar, 0.1 nanomolar to about 10 nanomolar, or about 1 nanomolar to about 10 nanomolar of arsenic or cadmium in a sample. In some embodiments, a lower limit of sensitivity of a detection of a heavy metal by a method herein is about 0.01 picomolar, about 0.1 picomolar, about 1.0 picomolar, about 10 picomolar, about 100 picomolar, about 1.0 nanomolar, about 5.0 nanomolar, about 10.0 nanomolar, about 50 nanomolar or about 100 nanomolar of arsenic or cadmium in a sample.

In some embodiments, a magnetic sensor is washed with a wash solution such that the wash solution flows over the surface of the sensor. A wash solution may comprise any suitable composition. In some embodiments, a wash solution stabilizes interactions between a repressor protein and its cognate repressor binding site. In some embodiments, a wash solution stabilizes binding of a heavy metal to an MRP. In some embodiments a wash solution increases affinity of a first member of a binding pair to a second member of a binding pair. In some embodiments, a wash solution is configured to dissociate non-specific binding interaction between a member of a binding pair and another molecule. In some embodiments, a wash solution is configured to dissociate non-specific binding interaction between a surface-bound nucleic acid and other molecules or proteins present in a sample. In some embodiments, a wash solution is configured to dissociate non-specific binding interaction between an antibody and other molecules or proteins present in a sample. Accordingly, in some embodiment, a wash solution comprises one or more of a suitable buffer (e.g., HEPES), a chelating agent (e.g., EDTA), salts, a detergent or surfactant, a chaotropic agent, formamide, combinations thereof and the like. In some embodiments a wash solution does not include a salt. Any suitable wash solution can be used to increase the stringency of hybridization conditions at the surface of a magnetic sensor. In some embodiments, a temperature of a wash solution flowing over the surface of a magnetic sensor is increased during a wash step or during a detection step.

In some embodiments, a wash solution is configured to maintain a flow of fluid over a magnetic sensor. In such embodiments, a wash solution may comprise the same, or a similar composition (e.g., buffers and salts), as a sample or a reagent (e.g., a suspension of magnetic particles or a secondary reagent).

In some embodiments, a temperature of fluid flowing over the surface of a magnetic sensor is increased before, during and/or after (i) contacting a magnetic sensor with a sample, (ii) contacting a magnetic sensor with a magnetic particle, and/or (iii) detecting a presence, absence, or amount of magnetic particles bound to, or associated with, a magnetic sensor surface.

In some embodiments, a temperature of a fluid in contact with the surface of a magnetic sensor is increased by at least 10° C., by at least 15° C., by at least 20° C., by at least 25° C., by at least 30° C., by at least 40° C., by at least 60° C., or by at least 80° C. over a period of 1 second to 30 minutes, 1 second to 10 minutes, 1 second to 5 minutes, 1 second to 1 minute, or intervening ranges thereof. In some embodiments, a temperature of a fluid in contact with the surface of a magnetic sensor is increased from about 10° C. to about 120° C., from about 10° C. to about 80° C., from about 10° C. to about 70° C., from about 10° C. to about 65° C., from about 10° C. to about 60° C., from about 20° C. to about 120° C., from about 20° C. to about 80° C., from about 20° C. to about 70° C., from about 20° C. to about 65° C., from about 20° C. to about 60° C., from about 25° C. to about 80° C., from about 25° C. to about 70° C., from about 25° C. to about 65° C., from about 25° C. to about 60° C., or intervening ranges thereof, In some embodiments, a temperature of a fluid in contact with the surface of a magnetic sensor is increased over a period of 1 second to 30 minutes, 1 second to 10 minutes, 1 second to 5 minutes, 1 second to 1 minute, or intervening ranges thereof.

In some embodiments, a temperature of a fluid in contact with the surface of a magnetic sensor is increased to a temperature in a range of about 30° C. to 90° C., about 30° C. to 80° C., about 30° C. to 75° C., about 30° C. to 70° C., about 30° C. to 65° C., about 30° C. to 60° C., about 30° C. to 55° C., or about 30° C. to 50° C. In some embodiments, a temperature of a fluid in contact with the surface of a magnetic sensor is increased to a temperature in a range of about 30° C. to 90° C., about 30° C. to 80° C., about 30° C. to 75° C., about 30° C. to 70° C., about 30° C. to 65° C., about 30° C. to 60° C., about 30° C. to 55° C., or about 30° C. to 50° C. over a period of 1 second to 30 minutes, 1 second to 10 minutes, 1 second to 5 minutes, 1 second to 30 minutes, or intervening ranges thereof.

In some embodiments, a method or detecting process comprises detecting a presence, absence, amount, or change thereof, of magnetic particles at, on, near or associated with a surface of a magnetic sensor. In some embodiments, a presence, absence, amount, or change thereof, of magnetic particles bound to a surface of a magnetic sensor is detected. In certain embodiments, a detection process or detection step comprises detecting a change in an amount of magnetic particles at, near, or on the surface of a magnetic sensor over a period of time.

In some embodiments, a detection process comprises a dynamic detection process. In certain embodiments, a dynamic detection process comprises detecting a presence, absence, amount, or change in an amount of magnetic particles at, near, or on the surface of a magnetic sensor over time, while conditions at, near or on the surface of a magnetic sensor are changed. Non-limiting examples of conditions that can be changed during a dynamic detection process include temperature, salt concentration, cation concentration, ion concentration, pH, detergent concentration, chaotropic agent concentration, ionic kosmotrope concentration, the like or combinations thereof. Often, conditions are changed during a dynamic detection process to increase stringency of protein-protein interactions or protein-DNA interactions at, on or near a surface of a magnetic sensor.

In some embodiments, a dynamic detection process comprises detecting a change in an amount of magnetic particles at, near, or on a surface of a magnetic sensor over time, while temperature is increased over a period of time. In some embodiments, a dynamic detection process comprises detecting a change in an amount of magnetic particles at, near, or on the surface of a magnetic sensor over a period of time, while a concentration of cations (e.g., Na, Ca, Mg, Zn and the like) is increases or decreased. In some embodiments, a dynamic detection process comprises detecting a change in an amount of magnetic particles at, near, or on a surface of a magnetic sensor over a period of time, while temperature is increased and/or while a concentration of salt is increased or decreased.

In some embodiments, a method comprises detecting or determining a magnetoresistance, current, voltage potential, or change thereof on, near or at the surface of a magnetic sensor. In some embodiments, a magnetoresistance, current, voltage potential, or change thereof, on, near or at the surface of a magnetic sensor is determined or detected once, continuously (e.g., during a predetermined period of time), or periodically (e.g., two or more times) before, during and/or after a magnetic sensor is contacted with magnetic particles as described herein. In some embodiments, a magnetoresistance, current, voltage potential, or change thereof, on, near or at the surface of a magnetic sensor is determined or detected continuously (e.g., during a predetermined period of time), or periodically (at two or more times) while a temperature is increased at the surface of a magnetic sensor.

In some embodiments, the presence, absence or amount of a heavy metal in a sample is determined according to a magnetoresistance, current, voltage potential, or change thereof, that is detected or measured on, near or at the surface of a magnetic sensor when performing a method described herein.

EXAMPLES

Example 1—Preparation of DNAzyme Magnetic Sensor and Detection of Lead

A substrate strand was synthesized having a 5' conjugated biotin moiety (Biosg) and a 3' Amino Modifier C6 dT (3AmMC6T, Integrated DNA Technologies, Iowa, USA) to facilitate attachment of the substrate strand to the sensor surface. The substrate strand also contains a single adenosine (A, underlined and bold) residue which represents the target cleavage site. The remaining nucleotides are deoxyribonucleotides. The sequence of the substrate strand used in this example is shown below.

(SEQ ID NO: 1)
5'-CTCACTATAGGAAGAGATGATGTCTGTAAATT-3'

The substrate strand of SEQ ID NO:1 was hybridized to an enzyme strand to form the DNAzyme. The enzyme strand used in this example is shown below.

(SEQ ID NO: 2)
5'-ACAGACATCATCTCTGAAGTAGCGCCGCCGTATAGTGAG-3'

For hybridization, the substrate strand and the enzyme strand were mixed in hybridization buffer at a flow rate of 10 μl/minute for 30 minutes at a ratio of 1:2 (1 part substrate strand:2 parts enzyme strand) in 25 mM Na3PO4, 0.1% polyvinyl alcohol (PVA, 40K MW), heated to 80° C. for 10 minutes, then cooled to room temperature. The resulting DNAzyme was attached to the surface of a GMR sensor using Scienion printer (SCIENION US, Inc.).

Following attachment, the surface of the sensor was blocked by washing the surface with a $1^{st}$ blocking solution comprising PBS (phosphate buffered saline), 50 mM ethanolamine, and 0.05% Tween 20, pH 8.4, which was flowed at a flow rate of 10 μl/minute for 30 minutes. After the $1^{st}$ blocking step, the surface of the sensor was treated with $2^{nd}$ blocking solution (25 mM HEPES, 1% hexadecyltrimethylammonium bromide (CTAB), pH 7.25), which was flowed at a flow rate of 10 μl/minute for 30 minutes. This step neutralizes the net-negative charge of the polymer coated surface of the sensor. After the $2^{nd}$ blocking step, the sensor was washed with 25 mM HEPES.

Figure 23:
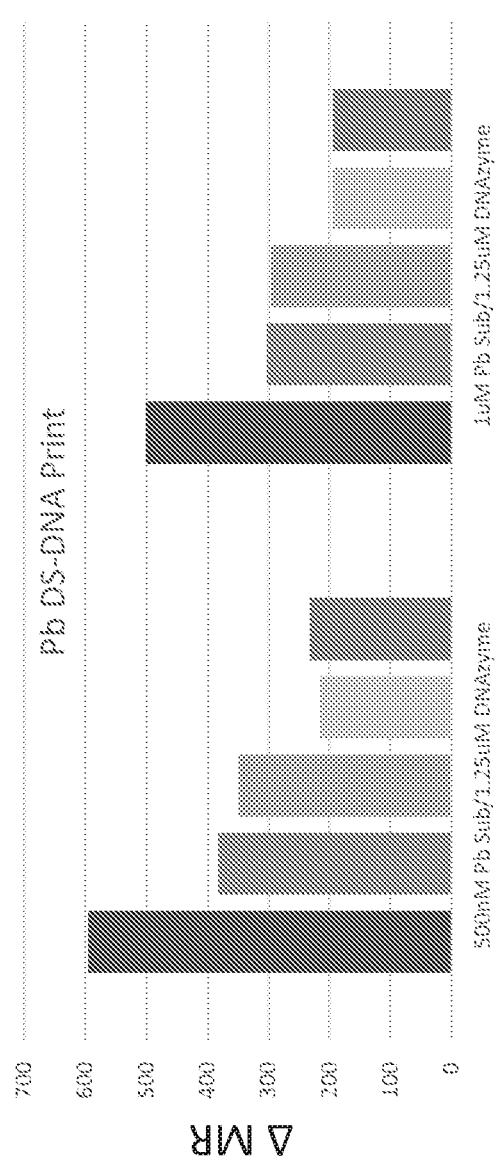
FIG. 23 shows results of GMR-based detection of the indicated concentrations of lead ion using a surface-bound lead-dependent DNAzyme, in accordance with an embodiment. Pb=lead ion; MR="magnetoresistance"; ∆MR="change in magnetoresistance, which is the difference between: the magnetoresistance measured in the absence of magnetic particles; and the magnetoresistance measured in the presence of magnetic particles and the indicated concentrations of lead ion.
Figure 24:
FIG. 24 shows results of GMR-based detection of the indicated concentrations of lead ion using a surface-bound lead-dependent DNAzyme in which various concentrations biotinylated substrate strand of the DNAzyme comprising a polyT linker ("PolyT Substrate"). MR="magnetoresistance"; ∆MR="change in magnetoresistance, which is the difference between: the magnetoresistance measured in the absence of magnetic particles; and the magnetoresistance measured in the presence of magnetic particles and the indicated concentrations of lead ion.
Figure 24:

The results, depicted in FIG. 23, demonstrate a dose-dependent decrease in the change in magnetoresistance divided by control magnetoresistance with increasing lead ion concentration was observed by using the DNAzyme attached to the surface of the magnetic sensor.

Example 2—Magnetic Sensor Preparation and Detection of Mercury

HgBSA (Hg$^{2+}$ [BSA] (Cat. No: DAGA-007B) Creative Diagnostics) at a concentration of 250 μg/ml in 0.1% Polyvinyl Alcohol (PVA, 90,000 MW) was attached (i.e., printed) to the surface of a GMR sensor using a Scienion printer. Attachment of the HgBSA to the surface of the GMR sensor was performed using a polymer composition comprising two hydrophilic polymers and a crosslinking agent as described above and as described in, e.g., in U.S. provisional application No. 62/958,510, the disclosure of which is hereby incorporated by reference. The surface of the sensor was then blocked with a solution comprising PBS (phosphate buffered saline), 50 mM ethanolamine, and 0.05% Tween 20, pH 8.4, which was flowed at a flow rate of 10 μl/minute for 30 minutes. After blocking, the sensor was washed with 200 μl of MOPST (10 mM MOPS, 100 mM NaNO₃, 0.05% Tween 20, pH 7.2.

The antibody used was a mouse anti-Hg2+ monoclonal antibody (RHA™ anti-Hg$^{2+}$ monoclonal antibody, clone Hg2 (Cat. No: HMABPY007) from Creative Diagnostics). The biotinylated Hg-antibody was added to the sample, and the Hg-antibody/sample composition was flowed over the GMR sensor at a rate of 10 microliters/minute for 30 minutes. Samples containing mercury at various concentrations at neutral pH in a volume of 200 μl, was contacted with the sensor using a micro-peristaltic pump (RPTX). Single GMR mode was then selected and allowed to run for 60 seconds, after which a negative control sensor was selected to serve as a zero Mux2 Sensor. Dual GMR mode was selected and a magnetic bead solution was contacted with the GMR sensors at a flow rate of 5 microliters/minute.

This sensor assay and format was designed to detect mercury in query samples as follows. The Hg-antibody bound to either the printed Hg-BSA substrate or a free Hg ion in solution. When there was no Hg present in solution, Hg-BSA had no competition for binding Hg-antibody, and all available Hg-antibodies were bound to the Hg-BSA. However, when Hg was present, some of the Hg-antibodies bound to Hg in solution instead of binding Hg-BSA. As the concentration of Hg in solution increased, it was more likely for Hg-antibody to bind to solution Hg and less likely for Hg-antibody to bind to Hg-BSA. Therefore, the more Hg in solution, the fewer Hg-antibodies were bound to the Hg-BSA-covered GMR surface.

Figure 27:
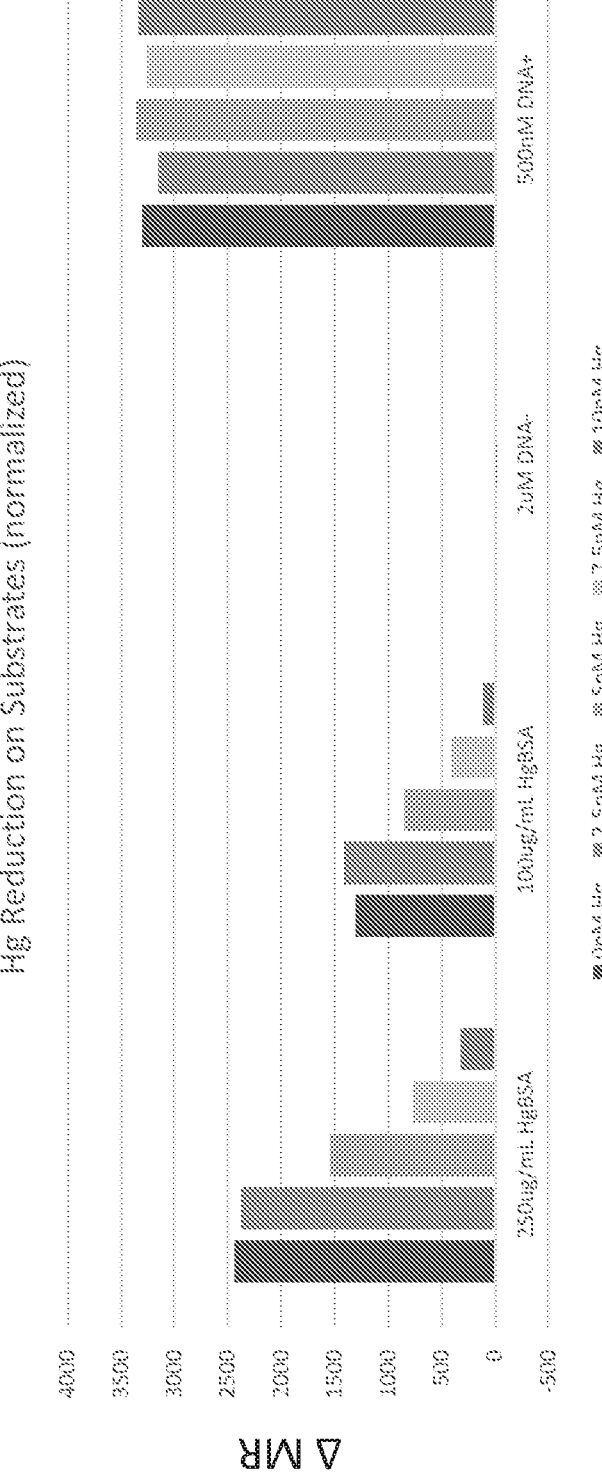
FIG. 27 shows results of GMR-based detection of the indicated concentrations of mercury ion ("Hg") using the indicated concentrations a surface-bound mercury binding protein ("Hg-BSA"). Detection using unbiotinylated DNA (DNA−) served as a negative control, and detection using biotinylated DNA (DNA+) served as a positive control. HgBSA=mercury-bound bovine serum albumin. MR="magnetoresistance"; ∆MR="change in magnetoresistance, which is the difference between: the magnetoresistance measured in the absence of magnetic particles; and the magnetoresistance measured in the presence of magnetic particles and the indicated concentrations of mercury ion.

The Hg-antibodies are biotinylated, which allowed them to bind to the streptavidin-conjugated magnetic nanoparticles (MNPs). As depicted in FIG. 27, the Hg concentration was increased from sample to sample, and less biotinylated Hg-antibodies was observed to bind to the Hg-BSA surface with increased amounts of Hg in each given tested sample; as a result, less MNPs bound and interacted with the GMR sensor. This allowed for a gradient/standard curve to be developed that corresponded to the concentration of Hg in solution. This standard was compared from sample to sample to quantify Hg concentrations. The results demonstrate a dose-dependent decrease in the change in magnetoresistance divided by control magnetoresistance with increasing mercury ion concentration.

Example 3—Magnetic Sensor Preparation and Detection of Cadmium and Arsenic

A Pars-Oars-F strand (forward strand) was mixed with Pars-Oars-R strand (reverse strand) by adding each strand at a 1:1 ratio in 25 mM Na₃PO₄, 0.1% Polyvinyl Alcohol (PVA, 40,000 MW). The Pars-Oars-F strand has the sequence 5'-CCTACACATTCGTTAAGT-CATATATGTTTTGACTT ATCCGCTTCGAAGA-3' (SEQ ID NO:11). The 3' hydroxyl of SEQ ID NO:11 contains a 3' amino modifier C6 dT (i.e., 3AmMC6t) which facilitated attachment to the surface of the GMR sensor.

The Pars-Oars-R strand has the sequence 5'-TCTTCGAAGCGGATAAGTCAAAAA-CATATATGACTTAACGAATGTGTAAG-3' (SEQ ID NO:12). The DNA mixture was heated to 80° C. for 10 minutes, then cooled to room temperature to allow the two strands to hybridize into a double-stranded duplex by slowing the Pars-Oars-R strand over the Pars-Oars-F strand-attached GMR sensor at 5-25 microliters/minute for 30 minutes. The duplex was then attached (e.g., printed) to the surface of a GMR sensor using a Scienion printer. Several duplicate GMR sensors were prepared.

After attachment of the DNA duplex to the surface of the GMR sensor, 200 μl of ethanolamine in PBS containing 0.05% Tween 20, pH 8.4 was flowed over the surface of the sensor at between 5-25 microliters/minute for 30 minutes. The sensor was then washed with 100 μl of 50 mM potassium phosphate buffer with 0.05% Tween 20 (KPBT buffer).

Recombinant Glutathione S-transferase(GST)-arsR protein was expressed in *E. coli* and cell lysates were prepared. GST-arsR lysate (2 µl) diluted to 200 µl in KPBT, was then flowed over the sensor.

An array of sensors prepared as described above, as well as positive control sensors (biotinylated DNA strands that do not participate in the protein-binding steps of the assay and bind SA-MNPs independent of the arsenic detection assay) and negative control sensors (DNA strands that were generic DNA strands (about 20 bp in length) that weren't biotinylated, and thus cannot bind streptavidin-MNPs), was washed by flowing wash buffer into the array (KPBT) such that it flowed over the sensors. A patient sample containing arsenic was then introduced into the array and thus flowed over the sensors. A biotinylated antibody that specifically binds to GST was also flowed into the array, and thus over the sensors, at 5-25 microliters/minute for 30 minutes. Detection of magnetoresistance at the surface of the sensors was initiated and magnetic particles that were conjugated to streptavidin were then flowed into the array, and thus over the sensors.

Example 4—GMR Sensor Signal Amplification

Amplification of GMR signal in a sandwich immunoassay format as depicted, for example, in FIG. 16A, was performed. Biotinylated-troponin I capture antibodies were flowed over independent GMR sensors to create a series of troponin I biosurface-attached sensors (via crosslinking of the biotin moiety to a polymer composition on the sensor) in order to test varying concentrations of Troponin I. Each of the query samples containing the different concentrations of Troponin I as indicated in Table 2, below, was flowed over a Troponin I capture antibody-printed sensor. Other biotinylated-anti-troponin I antibodies where then flowed over the sensors. Subsequently, streptavidin-coated magnetic nanoparticles were then flowed over each sensor surface and bound to the biotinylated-anti-troponin I antibodies that were bound to the surface via biotin-streptavidin interaction. Sensor signal readings (change in magnetoresistance) were recorded as indicated in Table 2 ("Primary signal").

Subsequently, biotin-coated magnetic nanoparticles were flowed over the sensors; these biotin-coated magnetic nanoparticles then bound to the free streptavidin groups on the streptavidin-coated magnetic nanoparticles. Sensor signal readings (change in magnetoresistance) were recorded as indicated in Table 2 ("$1^{st}$ enhanced signal signal").

Subsequently, another sample of streptavidin-coated magnetic nanoparticles were flowed over the sensors; these streptavidin-coated magnetic nanoparticles then bound to the free biotin groups on the biotin-coated magnetic nanoparticles. Sensor signal readings (change in magnetoresistance) were recorded as indicated in Table 2 ("$2^{st}$ enhanced signal signal").

TABLE 2

| Human troponin I test data without and with signal enhancement | | | |
|---|---|---|---|
| Troponin I (ng/L) | Primary signal (ppm) | $1^{st}$ enhanced signal (ppm) | $2^{nd}$ enhanced signal (ppm) |
| 0 | 0.8 | 2.4 | 4.4 |
| 7.8 | 4.8 | 60 | 94.7 |
| 31.5 | 11.7 | 178 | 373.9 |
| 125 | 39.5 | 266.2 | 554.9 |

Figure 31:
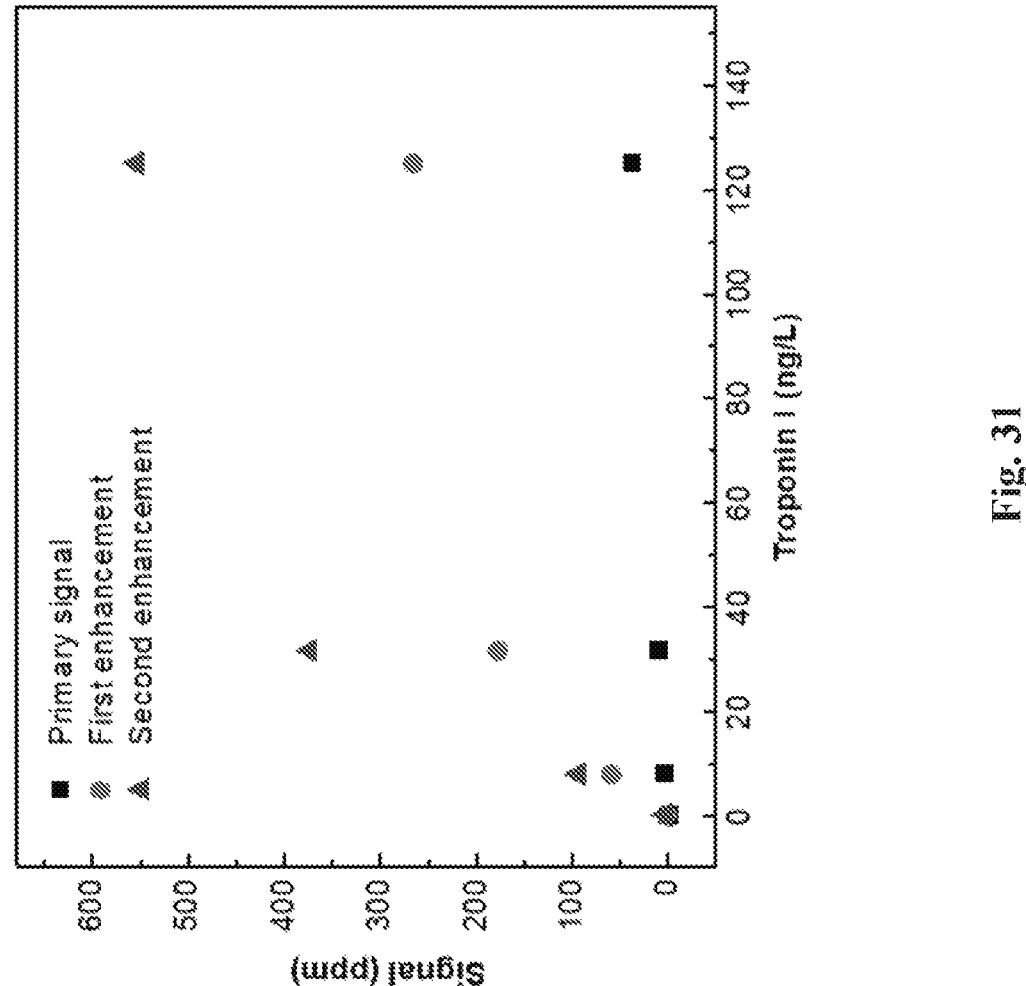
FIG. 31 shows an example of amplification of a GMR signal, in accordance with an embodiment of the present teaching.

The results, shown in Table 2 and in FIG. 31, demonstrate that for low levels (0-125 ng/L) of tropinin I tests, all signals were significantly increased after 1st and 2nd signal enhancement processes. For blank sample (0 ng/L troponin I), the signal modestly increased (from 0.8 ppm to 2.4 and 4.4) after each enhancement, indicating that assay "noise" was slightly increase. However, for 7.8 ng/L, the SNR (signal to noise ratio) increased from 6 to 25 and 21.5 after each subsequent enhancement. Significant signal enhancements were also achieved at the 31.5 and 125 nh/mL Troponin I concentrations, as well.

The magnetic (GMR) sensor measures bound magnetic beads which are proportional to the concentration of analytes in the sample. In situations where the amount of bound beads is very low, the GMR sensor signal to noise ratio may be lower than desired. The results described herein demonstrate that the signal to noise ratio can be markedly enhanced in such by flowing magnetic beads coated with biotin (MB-Biotin) which was captured by the initial magnetic beads coated with streptavidin (MB-SA) that was captured on the surface of sensors that had been previously exposed to samples containing troponin I on surface. Then MB-SA flowed again over sensor surface and additional signal enhancement was generated due to MB-SA subsequent binding by MB-Biotin on the sensor. The altering of MB-Biotin and MB-SA can be repeated for multiple rounds of enhancement to further increase the GMR signals.

In some embodiments, all aspects of a method and/or all steps of a method described herein are performed in a microfluidic device described herein.

It will be understood that all embodiments disclosed herein may be combined in any manner to carry out a method of detecting an analyte and that such methods may be carried out using any combination of embodiments disclosed herein describing the various system components.

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

What is claimed is:

1. A method of amplifying a detection signal for detecting the presence of an analyte in a query sample, the method comprising:
   (a) providing a sensor comprising double stranded DNA molecules disposed on a functionalized surface of a giant magnetoresistance (GMR) sensor, the double stranded DNA molecules comprising a first nucleic acid and a second nucleic acid bound to the first nucleic acid and being bound to a first member of a binding pair,
   (b) passing the query sample over the sensor,
   (c) passing a plurality of magnetic particles over the sensor after passing the query sample over the sensor, and
   (d) detecting the presence of the analyte in the query sample by measuring magnetoresistance change of the GMR sensor based on determining magnetoresistance before and after passing the plurality of magnetic particles over the sensor, wherein determining magnetoresistance change of the GMR sensor comprises using at least one reference resistor to perform phase-sensitive solution of magnetoresistance change of the GMR sensor, thereby amplifying the detection signal.

2. The method of amplifying a detection signal for detecting the presence of an analyte in a query sample according to claim 1, wherein:
   (a) the second nucleic acid comprises: a removable portion covalently bound to the second nucleic acid, removal of the removable portion being actualized by the presence of the analyte in the query sample; and the first member of the binding pair is coupled with the removable portion of the second nucleic acid, the first member of the binding pair being capable of binding a second member of the binding pair that comprises a magnetic nanoparticle; and
   (b) passing the query sample over the sensor allows removal of the removable portion with the first member of the binding pair from the second nucleic acid if the analyte is present.

3. The method of amplifying a detection signal for detecting the presence of an analyte in a query sample according to claim 1, wherein:
   (a) the second nucleic acid comprises: a protein binding portion that binds a protein at a protein binding site, the protein further comprising a portion separate from the protein binding site configured to bind the first member of the binding pair; and
   (b) wherein the protein binding site of the protein binds the analyte if present in the query sample, thereby preventing binding of the protein to the protein binding portion of the second nucleic acid.

4. The method of amplifying a detection signal for detecting the presence of an analyte in a query sample according to claim 3, wherein:
   the first member of the binding pair includes biotin; and
   a second member of the binding pair includes streptavidin.

5. The method of amplifying a detection signal for detecting the presence of an analyte in a query sample according to claim 3, wherein:
   the first member of the binding pair includes glutathione S-transferase; and
   a second member of the binding pair includes glutathione.

6. The method of amplifying a detection signal for detecting the presence of an analyte in a query sample according to claim 5 comprising:

before contacting the sensor with the plurality of magnetic
particles, contacting the sensor with a secondary
reagent that includes the second member of the binding
pair and a first additional member of an additional
binding pair;

wherein a second additional member of the additional
binding pair includes a magnetic particle.

7. The method according to claim 1, wherein the first
member of the binding pair comprises biotin and a second
member of the binding pair comprises streptavidin.

8. The method according to claim 1, wherein the magne-
toresistance change of the GMR sensor comprises an ampli-
fied magnetoresistance change.

9. The method according to claim 1, wherein the analyte
comprises one or more heavy metals.

10. The method according to claim 9, wherein the one or
more heavy metals include at least one of mercury, cad-
mium, lead, or arsenic.

11. A method of detecting the presence of one or more
analytes in one or more query samples in a multiplex
detection scheme, the method comprising:

(a) providing at least two spatially disposed giant mag-
netoresistance (GMR) sensors, wherein at least two of
the GMR sensors comprise a first GMR sensor with a
first number of double-stranded DNA molecules dis-
posed on a functionalized surface of the first GMR
sensor and a second GMR sensor with a second number
of double-stranded DNA molecules disposed on a func-
tionalized surface of the second GMR sensor, wherein:
the first number of double-stranded DNA molecules
includes a first nucleic acid and a second nucleic acid
bound to the first nucleic acid and being bound to a
first member of a first binding pair; and
the second number of double-stranded DNA molecules
includes a first additional nucleic acid and a second
additional nucleic acid bound to the first additional
nucleic acid and being bound to a first additional
member of a second binding pair different from the
first binding pair;

(b) passing magnetic particles over the at least two GMR
sensors after passing the one or more query samples
over the at least two GMR sensors; and (c) detecting the presence of at least one of the one or
more analytes in the one or more query samples by
measuring magnetoresistance change of at least one of
the at least two GMR sensors based on determining
magnetoresistance before and after passing magnetic
particles over the at least two GMR sensors.

12. The method of detecting the presence of one or more
analytes in one or more query samples in a multiplex
detection scheme according to claim 11, wherein:

(a) individual second nucleic acids and second additional
nucleic acids comprise: a removable portion covalently
bound to the individual second nucleic acids or the
second additional nucleic acids, removal being actual-
ized by the presence of at least one of the one or more
analytes in the one or more query samples; and the first
member of the first binding pair and the first additional
member of the second binding pair being capable of
binding a magnetic nanoparticle; and (b) passing the one or more query samples over the at least
two GMR sensors allows removal of the removable
portion with the first member of the first binding pair or
the first additional member of the second binding pair
from one or more second nucleic acids or one or more
second additional nucleic acids if at least one of the one
or more analytes is present.

13. The method of detecting the presence of one or more
analytes in one or more query samples in a multiplex
detection scheme according to claim 11, wherein:

(a) the second nucleic acid and the second additional
nucleic acid comprises: a portion that binds protein at
a protein binding site, the protein further comprising a
portion separate from the protein binding site config-
ured to bind the first member of the first binding pair or
the first additional member of the second binding pair;
and (b) the one or more query samples are passed as a mixture
with the protein over the at least two GMR sensors,
wherein the protein binding site of the protein binds the
one or more analytes if present in the one or more query
samples, thereby preventing binding of the protein to
the protein binding site of the second nucleic acid or the
second additional nucleic acid.

14. The method of detecting the presence of one or more
analytes in one or more query samples in a multiplex
detection scheme according to claim 13, wherein:

the first member of the first binding pair includes a first
metalloregulatory repressor protein;

a second member of the first binding pair includes a first
substance that binds to the first metalloregulatory
repressor protein;

the first additional member of the second binding pair
includes a second metalloregulatory repressor protein;
and a second additional member of the second binding pair
includes a second substance that binds to the second
metalloregulatory repressor protein.

15. The method according to claim 11, wherein the at least
two spatially disposed GMR sensors are disposed in a
channel of a GMR sensor chip, wherein the GMR sensor
chip comprises at least one channel.

16. The method according to claim 11, wherein the at least
two spatially disposed GMR sensors are disposed in a
channel of a GMR sensor chip, wherein the GMR sensor
chip comprises a plurality of channels or the least two
spatially disposed GMR sensors are each disposed different
channels of a GMR sensor chip, wherein the GMR sensor
chip comprises a plurality of channels.

17. The method according to claim 14, wherein the first
metalloregulatory repressor protein includes glutathione
S-transferase and the second metalloregulatory repressor
protein include a poly-histidine.

18. The method according to claim 11, wherein at least
one of the one or more analytes includes a heavy metal.

19. The method according to claim 18, wherein the heavy
metal includes mercury, cadmium, lead, or arsenic.

20. A method of amplifying a detection signal for detect-
ing the presence of an analyte in a query sample, the method
comprising:

providing a sensor comprising double stranded DNA
molecules disposed on a functionalized surface of a
giant magnetoresistance (GMR) sensor, the double
stranded DNA molecules comprising a first nucleic acid
and a second nucleic acid bound to the first nucleic acid
and being configured to bind a detection protein, the
detection protein also being capable of binding the
analyte, passing the detection protein over the sensor;

passing the query sample over the sensor, passing a reporter protein over the sensor after passing the
query sample over the sensor, the reporter protein capable of binding the detection protein and the reporter protein configured to bind to magnetic nanoparticles;

passing a plurality of magnetic particles comprising a first member of a binding pair over the sensor after passing the query sample over the sensor, then passing a plurality of magnetic particles comprising a second member of the binding pair over the sensor; and detecting the presence of the analyte by measuring amplified magnetoresistance change of the GMR sensor based on determining magnetoresistance before and after passing magnetic particles over the sensor; thereby amplifying the detection signal.

* * * * *